United States Patent
Kantardzhieva et al.

(10) Patent No.: US 10,662,425 B2
(45) Date of Patent: May 26, 2020

(54) MATERIALS AND METHODS FOR TREATMENT OF AUTOSOMAL DOMINANT RETINITIS PIGMENTOSA

(71) Applicants: CRISPR THERAPEUTICS AG, Zug (CH); Bayer Healthcare LLC, Whippany, NJ (US)

(72) Inventors: Albena Kantardzhieva, Cambridge, MA (US); Akiko Noma, Cambridge, MA (US); Abraham Scaria, Cambridge, MA (US); Ryo Takeuchi, Cambridge, MA (US)

(73) Assignees: CRISPR THERAPEUTICS AG, Zug (CH); Bayer Healthcare LLC, Whippany, NJ (US)

( * ) Notice: Subject to any disclaimer, the term of this patent is extended or adjusted under 35 U.S.C. 154(b) by 0 days.

(21) Appl. No.: 16/198,361

(22) Filed: Nov. 21, 2018

(65) Prior Publication Data

US 2019/0153441 A1    May 23, 2019

Related U.S. Application Data

(60) Provisional application No. 62/589,111, filed on Nov. 21, 2017, provisional application No. 62/649,133, filed on Mar. 28, 2018, provisional application No. 62/693,080, filed on Jul. 2, 2018, provisional application No. 62/724,319, filed on Aug. 29, 2018.

(51) Int. Cl.
| | |
|---|---|
| *C12N 15/11* | (2006.01) |
| *A61K 31/7088* | (2006.01) |
| *A61K 38/46* | (2006.01) |
| *C12N 9/22* | (2006.01) |
| *C12N 15/90* | (2006.01) |
| *A61P 27/02* | (2006.01) |
| *C12N 15/113* | (2010.01) |

(52) U.S. Cl.
CPC .......... *C12N 15/11* (2013.01); *A61K 31/7088* (2013.01); *A61K 38/465* (2013.01); *A61P 27/02* (2018.01); *C12N 9/22* (2013.01); *C12N 15/1138* (2013.01); *C12N 15/907* (2013.01); *C12N 2310/20* (2017.05); *C12N 2320/34* (2013.01); *C12N 2800/80* (2013.01)

(58) Field of Classification Search
CPC .............. A61K 31/7088; A61K 38/435; C12N 15/1138; C12N 15/11; C12N 18/907; C12N 9/22
See application file for complete search history.

(56) References Cited

U.S. PATENT DOCUMENTS

| | | |
|---|---|---|
| 9,624,498 B2 | 4/2017 | Froelich et al. |
| 9,701,964 B2 | 7/2017 | Clube et al. |
| 9,834,791 B2 | 12/2017 | Zhang et al. |
| 9,873,894 B2 | 1/2018 | Conway et al. |
| 9,902,974 B2 | 2/2018 | Conway et al. |
| 9,963,719 B1 | 5/2018 | Friedland et al. |
| 10,006,054 B1 | 6/2018 | Friedland et al. |
| 2015/0056705 A1 | 2/2015 | Conway et al. |
| 2015/0267205 A1 | 9/2015 | Froelich et al. |
| 2015/0353917 A1 | 12/2015 | Miller |
| 2016/0074535 A1 | 3/2016 | Ranganathan et al. |
| 2016/0090607 A1 | 3/2016 | Conway et al. |
| 2016/0175462 A1 | 6/2016 | Zhang et al. |
| 2016/0186213 A1 | 6/2016 | Zhang et al. |
| 2016/0237455 A1 | 8/2016 | Glucksmann et al. |
| 2016/0324987 A1 | 11/2016 | Wang et al. |
| 2016/0340661 A1 | 11/2016 | Cong et al. |
| 2016/0354487 A1 | 12/2016 | Zhang et al. |
| 2016/0355796 A1 | 12/2016 | Davidson et al. |
| 2017/0073674 A1 | 3/2017 | Maeder et al. |
| 2017/0096683 A1 | 4/2017 | Scaria et al. |

(Continued)

FOREIGN PATENT DOCUMENTS

| | | |
|---|---|---|
| EP | 2982758 | 2/2016 |
| EP | 3011029 | 4/2016 |

(Continued)

OTHER PUBLICATIONS

Burnight et al., "Using CRISPR-Cas9 to Generate Gene-Corrected Autologous iPSCs for the Treatment of Inherited Retinal Degeneration", Molecular Therapy: The Journal of the American Society of Gene Therapy, vol. 25, No. 9, Jun. 12, 2017 (Jun. 12, 2017), pp. 1999-2013.

(Continued)

*Primary Examiner* — Antonio Galisteo Gonzalez

(74) *Attorney, Agent, or Firm* — Nelson Mullins Riley & Scarborough LLP; Amy E. Mandragouras, Esq.; Ariana D. Harris

(57) ABSTRACT

The present application provides materials and methods for treating a patient with autosomal dominant RP, both ex vivo and in vivo; materials and methods for editing a RHO gene in a human cell; and materials and methods for editing a P23H mutation in a RHO gene in a human cell. In addition, the present application provides one or more gRNAs or sgRNAs for editing a RHO gene; one or more gRNAs or sgRNAs for editing a P23H mutation in a RHO gene; and a therapeutic comprising at least one or more gRNAs or sgRNAs for editing a P23H mutation in a RHO gene. The present application provides a therapeutic for treating a patient with autosomal dominant RP. The present application provides a kit for treating a patient with autosomal dominant RP. In addition, the present application provides a self-inactivating CRISPR-Cas system.

30 Claims, 20 Drawing Sheets

Specification includes a Sequence Listing.

(56) References Cited

U.S. PATENT DOCUMENTS

| | | |
|---|---|---|
| 2017/0114413 A1 | 4/2017 | Hahn et al. |
| 2017/0196225 A1 | 7/2017 | Clube et al. |
| 2017/0224843 A1 | 8/2017 | Deglon et al. |
| 2017/0246221 A1 | 8/2017 | Clube et al. |
| 2017/0260547 A1 | 9/2017 | Dombrowski et al. |
| 2017/0283831 A1 | 10/2017 | Zhang et al. |
| 2017/0306307 A1 | 10/2017 | Zhang et al. |
| 2017/0321214 A1 | 11/2017 | Zhang et al. |
| 2017/0349894 A1 | 12/2017 | Dahlman et al. |
| 2017/0349914 A1 | 12/2017 | Cox et al. |
| 2018/0064114 A1 | 3/2018 | Clube |
| 2018/0064115 A1 | 3/2018 | Clube et al. |
| 2018/0070594 A1 | 3/2018 | Clube et al. |
| 2018/0084785 A1 | 3/2018 | Clube |
| 2018/0084786 A1 | 3/2018 | Clube |
| 2018/0100201 A1 | 4/2018 | Garraway et al. |
| 2018/0112234 A9 | 4/2018 | Dombrowski et al. |
| 2018/0127783 A1 | 5/2018 | Zhang et al. |
| 2018/0142259 A1 | 5/2018 | Davidson et al. |
| 2018/0148711 A1 | 5/2018 | Finer et al. |
| 2018/0169131 A1 | 6/2018 | Murray et al. |
| 2018/0171357 A1 | 6/2018 | Jantz et al. |
| 2018/0187172 A1 | 7/2018 | Bleris et al. |
| 2018/0200388 A1 | 7/2018 | Jaskula-Ranga et al. |
| 2018/0201956 A1 | 7/2018 | Friedland et al. |
| 2018/0251792 A1 | 9/2018 | Friedland et al. |
| 2018/0258424 A1 | 9/2018 | Greenberg et al. |
| 2018/0369420 A1 | 12/2018 | Jaskula-Ranga et al. |
| 2019/0022192 A1 | 1/2019 | Ruan et al. |

FOREIGN PATENT DOCUMENTS

| | | |
|---|---|---|
| EP | 3011034 | 4/2016 |
| EP | 3079725 | 10/2016 |
| EP | 3080257 | 10/2016 |
| EP | 3080258 | 10/2016 |
| EP | 3119878 | 1/2017 |
| EP | 3129393 | 2/2017 |
| EP | 3137497 | 3/2017 |
| EP | 2997146 | 4/2017 |
| EP | 3151846 | 4/2017 |
| EP | 3152319 | 4/2017 |
| EP | 3155101 | 4/2017 |
| EP | 3177726 | 6/2017 |
| EP | 3230451 | 10/2017 |
| EP | 3230452 | 10/2017 |
| EP | 3261440 | 1/2018 |
| EP | 3261643 | 1/2018 |
| EP | 3066201 | 3/2018 |
| EP | 3289080 | 3/2018 |
| EP | 3298134 | 3/2018 |
| EP | 3302575 | 4/2018 |
| EP | 3310369 | 4/2018 |
| EP | 3363903 | 8/2018 |
| EP | 3374494 | 9/2018 |
| WO | WO2014186585 | 11/2014 |
| WO | WO2014204724 | 12/2014 |
| WO | WO2014204729 | 12/2014 |
| WO | WO2015048577 | 4/2015 |
| WO | WO2015070083 | 5/2015 |
| WO | WO2015089351 | 6/2015 |
| WO | WO2015089462 | 6/2015 |
| WO | WO2015143046 | 9/2015 |
| WO | WO2015168666 | 11/2015 |
| WO | WO2015188056 | 12/2015 |
| WO | WO2015188065 | 12/2015 |
| WO | WO2015195621 | 12/2015 |
| WO | WO2016004010 | 1/2016 |
| WO | WO2016020399 | 2/2016 |
| WO | WO2016094867 | 6/2016 |
| WO | WO2016094872 | 6/2016 |
| WO | WO2016094874 | 6/2016 |
| WO | WO2016094880 | 6/2016 |
| WO | WO2016106244 | 6/2016 |
| WO | WO2016115632 | 7/2016 |
| WO | WO2016134375 | 8/2016 |
| WO | WO2016138353 | 9/2016 |
| WO | WO2016176690 | 11/2016 |
| WO | WO2016177682 | 11/2016 |
| WO | WO2016186772 | 11/2016 |
| WO | WO2016187717 | 12/2016 |
| WO | WO2016191684 | 12/2016 |
| WO | WO2016205613 | 12/2016 |
| WO | WO2016205728 | 12/2016 |
| WO | WO2016205825 | 12/2016 |
| WO | WO2017004153 | 1/2017 |
| WO | WO 2017/044649 A1 | 3/2017 |
| WO | WO2017062855 | 4/2017 |
| WO | WO2017069958 | 4/2017 |
| WO | WO2017074788 | 5/2017 |
| WO | WO2017075451 | 5/2017 |
| WO | WO2017075465 | 5/2017 |
| WO | WO2017075478 | 5/2017 |
| WO | WO2017083722 | 5/2017 |
| WO | WO2017106290 | 6/2017 |
| WO | WO2017117395 | 7/2017 |
| WO | WO2017132291 | 8/2017 |
| WO | WO2017136335 | 8/2017 |
| WO | WO2017160752 | 9/2017 |
| WO | WO2017182468 | 10/2017 |
| WO | WO2018005873 | 1/2018 |
| WO | WO2018009534 | 1/2018 |
| WO | WO2018009562 | 1/2018 |
| WO | WO2018035387 | 2/2018 |
| WO | WO2018049025 | 3/2018 |
| WO | WO2018064208 | 4/2018 |
| WO | WO2018067991 | 4/2018 |
| WO | WO2018069474 | 4/2018 |
| WO | WO2015089354 | 6/2018 |
| WO | WO2018106693 | 6/2018 |

OTHER PUBLICATIONS

Latella et al., "In vivo Editing of the Human Mutant *Rhodopsin* Gene by Electroporation of Plasmid-based CRISPR/Cas9 in the Mouse Retina", Molecular Therapy—Nucleic Acids, vol. 5, Nov. 22, 2016 (Nov. 22, 2016), p. e389 (12 pages).

Li et al., "Allele-specific CRISPR/Cas9 genome editing of the single-base P23H mutation for rhodopsin associated dominant retinitis pigmentosa", bioRxiv, Oct. 3, 2017 (Oct. 3, 2017), 15 pages.

International Search Report and Written Opinion of the International Searching Authority for International Application No. PCT/IB2018/059190 dated Apr. 30, 2019.

Epstein, Benjamin E and Schaffer, David V. "Engineering a Self-Inactivating Crispr system for AAV Vectors." Molecular Therapy. vol. 24, Supplement 1, May 2016, p. S50. Abstract presented at the American Society of Gene & Cell Therapy 19th Annual Meeting on May 4-7, 2016.

Li, Fan, et al. "Efficacy and dynamics of self-targeting CRISPR/Cas constructs for gene editing in the retina." Posted to bioRxiv server on Jan. 5, 2018. Not peer reviewed.

Moore, R. et al., "CRISPR-based self-cleaving mechanism for controllable gene delivery in human cells," Nucleic Acids Research. Jan. 2015, vol. 43, Issue 2, pp. 1297-1303. Published online Dec. 18, 2014.

Vachey, G., et al. "Genome editing with a self-inactivating CRISPR/Cas9 system for neurodegenerative diseases." Human Gene Therapy. vol. 27, No. 11, p. A48. Published online Oct. 18, 2016.

FIGURE 2A

| Sequence name | Cas9 | Target DNA sequence (5' - 3') | |
|---|---|---|---|
| 1. Rho WT SpCas9 20 | Sp | GGTGTGGTACGCAGCCCCTT | (SEQ ID NO: 5272) |
| 2. Rho WT SpCas9 19 | Sp | GTGTGGTACGCAGCCCCTT | (SEQ ID NO: 5273) |
| 3. Rho WT SpCas9 18 | Sp | TGTGGTACGCAGCCCCTT | (SEQ ID NO: 5274) |
| 4. Human Rhodopsin WT 20mer | Sa | GGGTGTGGTACGCAGCCCCT | (SEQ ID NO: 5275) |
| 5. Human Rhodopsin WT19mer | Sa | GGTGTGGTACGCAGCCCCT | (SEQ ID NO: 5276) |
| 6. Rho Mut SpCas9 20mer | Sp | GGTGTGGTACGCAGCCACTT | (SEQ ID NO: 5277) |
| 7. Rho Mut SpCas9 19mer | Sp | GTGTGGTACGCAGCCACTT | (SEQ ID NO: 5278) |
| 8. Rho Mut SpCas9 18mer | Sp | TGTGGTACGCAGCCACTT | (SEQ ID NO: 5279) |
| 9. Human Rhodopsin P23H 20mer | Sa | GGGTGTGGTACGCAGCCACT | (SEQ ID NO: 5280) |
| 10. Human Rhodopsin P23H 19mer | Sa | GGTGTGGTACGCAGCCACT | (SEQ ID NO: 5281) |

FIGURE 2B

| Sequence name | Cas9 | Single guide RNA (sgRNA) sequence | |
|---|---|---|---|
| 1. Rho WT SpCas9 20 | Sp | GGUGUGGUACGCAGCCCCUU | (SEQ ID NO: 5282) |
| 2. Rho WT SpCas9 19 | Sp | GUGUGGUACGCAGCCCCUU | (SEQ ID NO: 5283) |
| 3. Rho WT SpCas9 18 | Sp | UGUGGUACGCAGCCCCUU | (SEQ ID NO: 5284) |
| 4. Human Rhodopsin WT 20mer | Sa | GGGUGUGGUACGCAGCCCCU | (SEQ ID NO: 5285) |
| 5. Human Rhodopsin WT19mer | Sa | GGUGUGGUACGCAGCCCCU | (SEQ ID NO: 5286) |
| 6. Rho Mut SpCas9 20mer | Sp | GGUGUGGUACGCAGCCACUU | (SEQ ID NO: 5287) |
| 7. Rho Mut SpCas9 19mer | Sp | GUGUGGUACGCAGCCACUU | (SEQ ID NO: 5288) |
| 8. Rho Mut SpCas9 18mer | Sp | UGUGGUACGCAGCCACUU | (SEQ ID NO: 5289) |
| 9. Human Rhodopsin P23H 20mer | Sa | GGGUGUGGUACGCAGCCACU | (SEQ ID NO: 5290) |
| 10. Human Rhodopsin P23H 19mer | Sa | GGUGUGGUACGCAGCCACU | (SEQ ID NO: 5291) |

FIGURE 2C

| Sequence name | Cas9 | Reverse strand of Target DNA sequence to which the sgRNA will bind (5' - 3') | |
|---|---|---|---|
| 1. Rho WT SpCas9 20 | Sp | AAGGGGCTGCGTACCACACC | (SEQ ID NO: 5292) |
| 2. Rho WT SpCas9 19 | Sp | AAGGGGCTGCGTACCACAC | (SEQ ID NO: 5293) |
| 3. Rho WT SpCas9 18 | Sp | AAGGGGCTGCGTACCACA | (SEQ ID NO: 5294) |
| 4. Human Rhodopsin WT 20mer | Sa | AGGGGCTGCGTACCACACCC | (SEQ ID NO: 5295) |
| 5. Human Rhodopsin WT19mer | Sa | AGGGGCTGCGTACCACACC | (SEQ ID NO: 5296) |
| 6. Rho Mut SpCas9 20mer | Sp | AAGTGGCTGCGTACCACACC | (SEQ ID NO: 5297) |
| 7. Rho Mut SpCas9 19mer | Sp | AAGTGGCTGCGTACCACAC | (SEQ ID NO: 5298) |
| 8. Rho Mut SpCas9 18mer | Sp | AAGTGGCTGCGTACCACA | (SEQ ID NO: 5299) |
| 9. Human Rhodopsin P23H 20mer | Sa | AGTGGCTGCGTACCACACCC | (SEQ ID NO: 5300) |
| 10. Human Rhodopsin P23H 19mer | Sa | AGTGGCTGCGTACCACACC | (SEQ ID NO: 5301) |

FIGURE 2D

| Sequence Name | Cas9 | Target DNA Sequence (5'-3') |
|---|---|---|
| 1. Rho-P23HMut-24mer | Sa | CGACGGGTGTGGTACGCAGCCACT (SEQ ID NO: 5315) |
| 2. Rho-P23HMut-23mer | Sa | GACGGGTGTGGTACGCAGCCACT (SEQ ID NO: 5316) |
| 3. Rho-P23HMut-22mer | Sa | ACGGGTGTGGTACGCAGCCACT (SEQ ID NO: 5317) |
| 4. Rho-P23HMut-21mer | Sa | CGGGTGTGGTACGCAGCCACT (SEQ ID NO: 5318) |

FIGURE 2E

| Sequence Name | Cas9 | Single-guide RNA (sgRNA) sequence |
|---|---|---|
| 1. Rho-P23HMut-24mer | Sa | CGACGGGUGUGGUACGCAGCCACU (SEQ ID NO: 5319) |
| 2. Rho-P23HMut-23mer | Sa | GACGGGUGUGGUACGCAGCCACU (SEQ ID NO: 5320) |
| 3. Rho-P23HMut-22mer | Sa | ACGGGUGUGGUACGCAGCCACU (SEQ ID NO: 5321) |
| 4. Rho-P23HMut-21mer | Sa | CGGGUGUGGUACGCAGCCACU (SEQ ID NO: 5322) |

FIGURE 2F

| Sequence Name | Cas9 | Reverse Strand of Target DNA sequence to which the sgRNA will bind (5'-3') |
|---|---|---|
| 1. Rho-P23HMut-24mer | Sa | AGTGGCTGCGTACCACACCCGTCG (SEQ ID NO: 5323) |
| 2. Rho-P23HMut-23mer | Sa | AGTGGCTGCGTACCACACCCGTC (SEQ ID NO: 5324) |
| 3. Rho-P23HMut-22mer | Sa | AGTGGCTGCGTACCACACCCGT (SEQ ID NO: 5325) |
| 4. Rho-P23HMut-21mer | Sa | AGTGGCTGCGTACCACACCCG (SEQ ID NO: 5326) |

FIGURE 2G

| Sequence Name | Cas9 | Target DNA Sequence (5'-3') |
|---|---|---|
| 1. Rho-P23HMut-18mer | Sa | GTGTGGTACGCAGCCACT    (SEQ ID NO: 5357) |

FIGURE 2H

| Sequence Name | Cas9 | Single-guide RNA (sgRNA) sequence |
|---|---|---|
| 1. Rho-P23HMut-18mer | Sa | GUGUGGUACGCAGCCACU    (SEQ ID NO: 5358) |

FIGURE 2I

| Sequence Name | Cas9 | Reverse Strand of Target DNA sequence to which the sgRNA will bind (5'-3') |
|---|---|---|
| 1. Rho-P23HMut-18mer | Sa | AGTGGCTGCGTACCACAC    (SEQ ID NO: 5359) |

Samples

1. Human Rhodopsin  WT    20mer  (SEQ ID NO: 5285) - on-target editing
2. Human Rhodopsin  WT    19mer  (SEQ ID NO: 5286) - on-target editing
3. Human Rhodopsin  P23H  20mer  (SEQ ID NO: 5290) - off-target editing
4. Human Rhodopsin  P23H  19mer  (SEQ ID NO: 5291) - off-target editing
5. Control cells

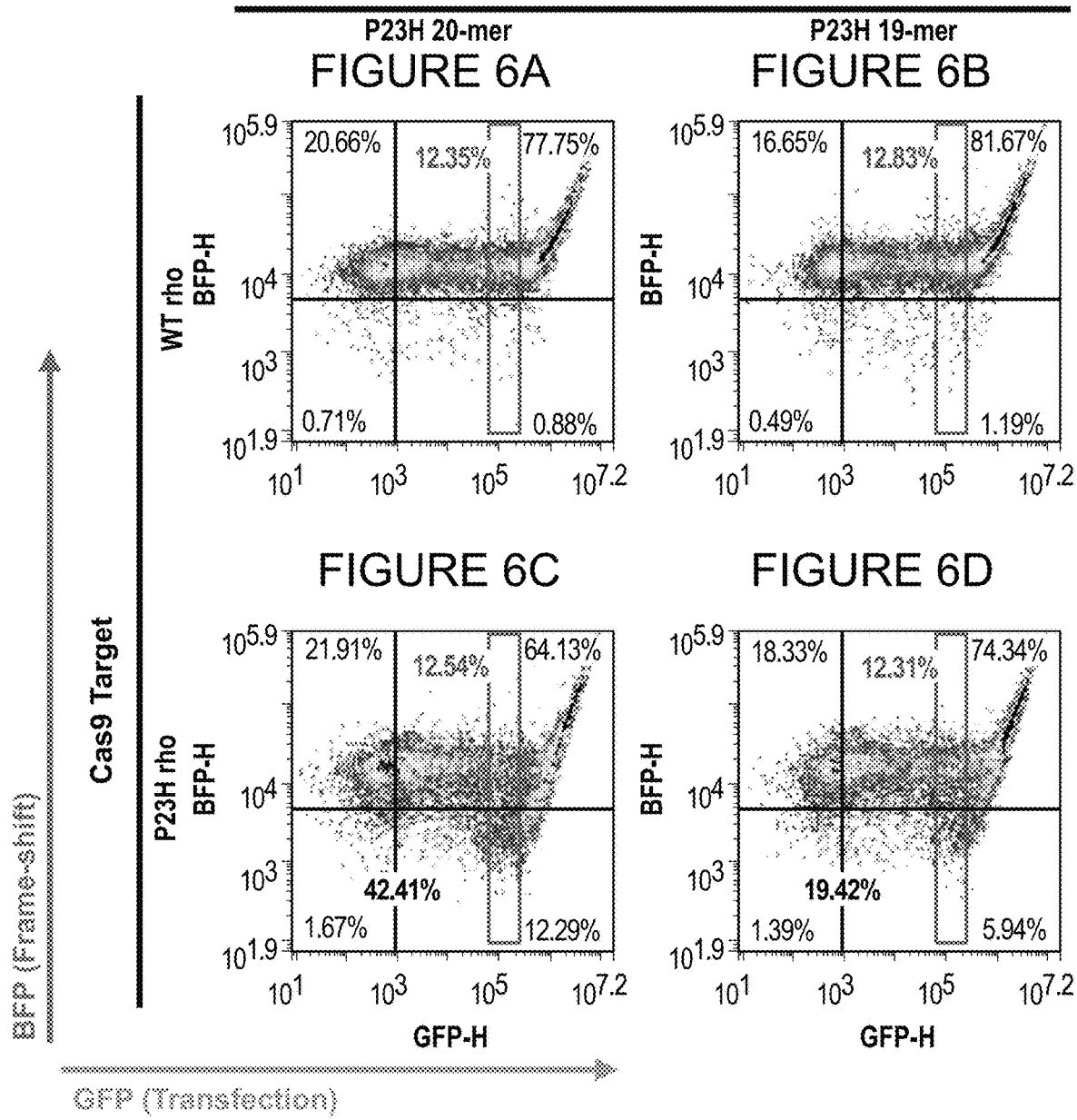
| Guide name | SEQ ID NO: | | P23H target site | SEQ ID NO: |
|---|---|---|---|---|
| Human Rhodopsin P23H 20-mer | 5290 | edits → | agtggctgcgtaccacaccc (located in 5' SIN site) | 5300 |
| | | | gggtgtggtacgcagccact (located in 3' SIN site) | 5280 |
| Human Rhodopsin P23H 19-mer | 5291 | edits → | agtggctgcgtaccacacc (located in 5' SIN site) | 5301 |
| | | | ggtgtggtacgcagccact (located in 3' SIN site) | 5281 |

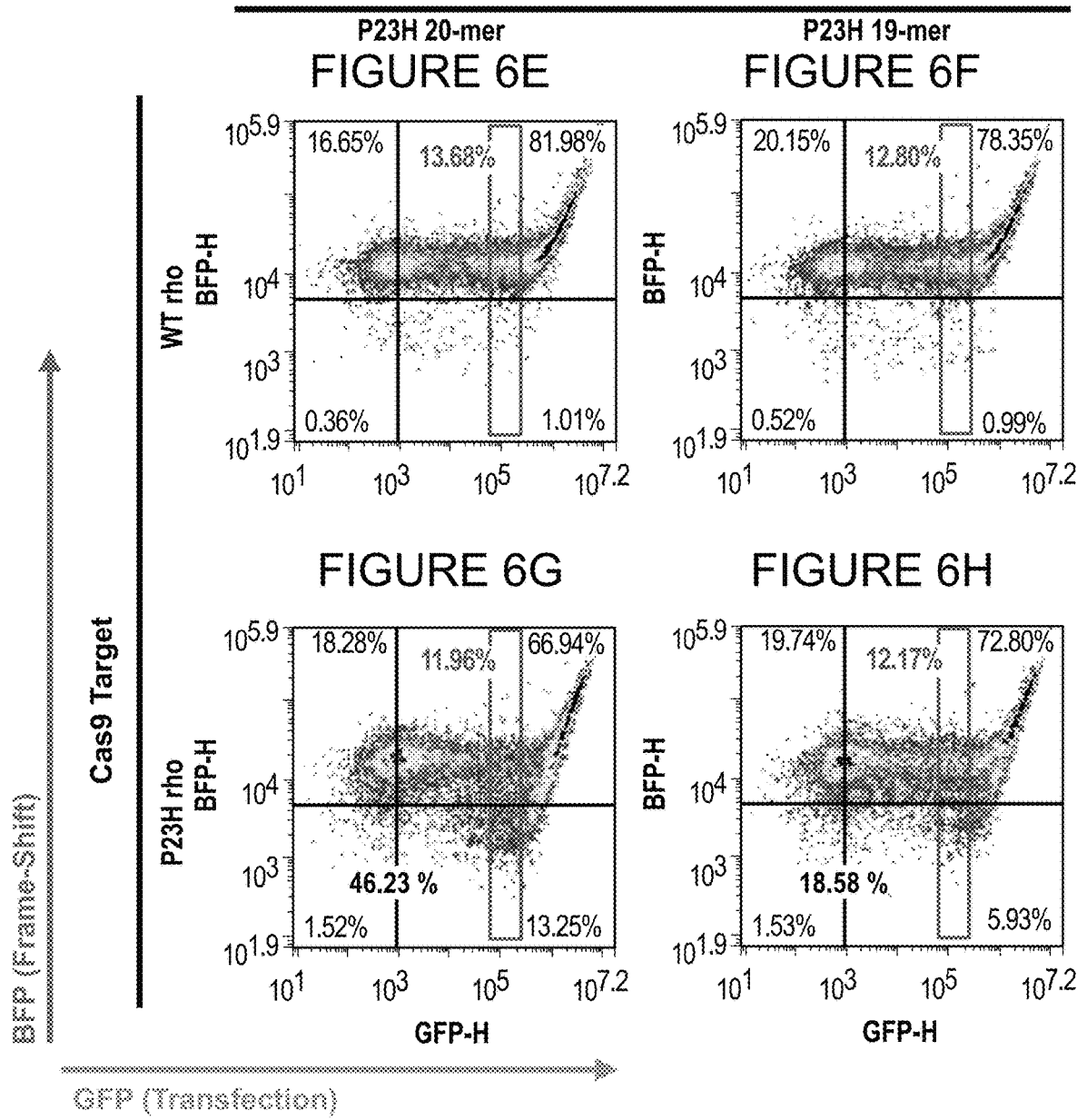
| Guide name | SEQ ID NO: | | P23H target site | SEQ ID NO: |
|---|---|---|---|---|
| Human Rhodopsin P23H 20-mer | 5290 | edits → | agtggctgcgtaccacaccc (located in 5' SIN site) | 5300 |
| | | | gggtgtggtacgcagccact (located in 3' SIN site) | 5280 |
| Human Rhodopsin P23H 19-mer | 5291 | edits → | agtggctgcgtaccacacc (located in 5' SIN site) | 5301 |
| | | | ggtgtggtacgcagccact (located in 3' SIN site) | 5281 |

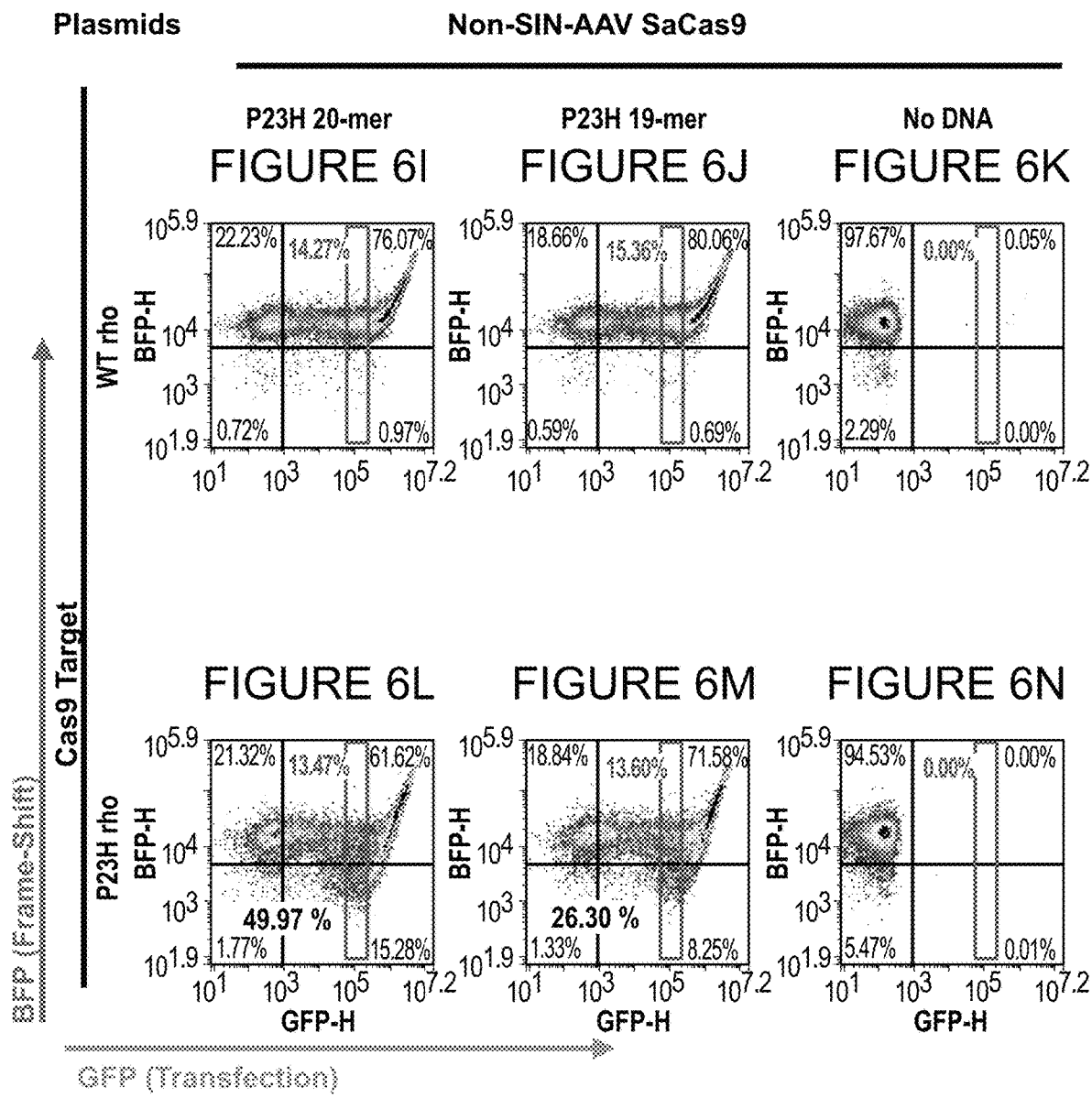
| Guide name | SEQ ID NO: | | P23H target site | SEQ ID NO: |
|---|---|---|---|---|
| Human Rhodopsin P23H 20-mer | 5290 | edits → | agtggctgcgtaccacaccc (located in 5' SIN site) | 5300 |
| | | | gggtgtggtacgcagccact (located in 3' SIN site) | 5280 |
| Human Rhodopsin P23H 19-mer | 5291 | edits → | agtggctgcgtaccacacc (located in 5' SIN site) | 5301 |
| | | | ggtgtggtacgcagccact (located in 3' SIN site) | 5281 |

| Guide name | SEQ ID NO: | | P23H target site | SEQ ID NO: |
|---|---|---|---|---|
| Human Rhodopsin P23H 20-mer | 5290 | edits → | agtggctgcgtaccacaccc (located in 5' SIN site) | 5300 |
| | | | gggtgtggtacgcagccact (located in 3' SIN site) | 5280 |
| Human Rhodopsin P23H 19-mer | 5291 | edits → | agtggctgcgtaccacacc (located in 5' SIN site) | 5301 |
| | | | ggtgtggtacgcagccact (located in 3' SIN site) | 5281 |

| Guide name | SEQ ID NO: | | P23H target site | SEQ ID NO: |
|---|---|---|---|---|
| Human Rhodopsin P23H 20-mer | 5290 | edits → | agtggctgcgtaccacaccc (located in 5' SIN site) | 5300 |
| | | | gggtgtggtacgcagccact (located in 3' SIN site) | 5280 |
| Human Rhodopsin P23H 19-mer | 5291 | edits → | agtggctgcgtaccacacc (located in 5' SIN site) | 5301 |
| | | | ggtgtggtacgcagccact (located in 3' SIN site) | 5281 |

P23H mutation introduced to the genomic DNA

1. Non-SIN AAV-SaCas9 and pSIA010 in P23H-*hRHO*-RFP mice (n=10)
2. Non-SIN AAV-SaCas9 and pSIA010 in control *hRHO*-GFP mice (n=6)

MATERIALS AND METHODS FOR TREATMENT OF AUTOSOMAL DOMINANT RETINITIS PIGMENTOSA

RELATED APPLICATIONS

This application claims the benefit of U.S. Provisional Application No. 62/589,111 filed Nov. 21, 2017; U.S. Provisional Application No. 62/649,133 filed Mar. 28, 2018; U.S. Provisional Application No. 62/693,080 filed Jul. 2, 2018; and U.S. Provisional Application No. 62/724,319 filed Aug. 29, 2018, all of which are incorporated herein in their entirety by reference.

FIELD

The present application provides materials and methods for treating a patient with autosomal dominant Retinitis Pigmentosa (RP), both ex vivo and in vivo.

INCORPORATION BY REFERENCE OF SEQUENCE LISTING

This application contains a Sequence Listing in computer readable form (filename: 170621-2 Sequence Listing: 10,127,342 bytes—ASCII text file; created Nov. 15, 2018), which is incorporated by reference in its entirety and forms part of the disclosure.

BACKGROUND

Retinitis pigmentosa (RP) is a rare, genetic disorder that involves a breakdown and loss of cells in the retina, the light sensitive tissue that lines the back of the eye. Common symptoms include difficulty seeing at night and a loss of peripheral vision.

A number of services and devices are available to help people with vision loss associated with RP carry out daily activities and maintain their independence. However, even with these services and devices, life can be challenging for an individual with RP.

Despite efforts from researchers and medical professionals worldwide who have been trying to address RP, there still remains a critical need for developing safe and effective treatments for RP.

SUMMARY

The present disclosure presents a novel approach to ameliorate autosomal dominant RP. The novel approach targets a mutation in the RHO gene, such as a P23H mutation, and the novel approach can reduce or eliminate expression of the P23H mutant allele at the protein level with as few as a single treatment. The resulting therapy can ameliorate the effects of or completely eliminate autosomal dominant RP.

Provided herein is a method for editing a RHO gene in a human cell. The method comprises introducing into the human cell one or more deoxyribonucleic acid (DNA) endonucleases to effect one or more single-strand breaks (SSBs) or double-strand breaks (DSBs) within or near the RHO gene or other DNA sequences that encode regulatory elements of the RHO gene that results in a permanent deletion, insertion, correction, or modulation of expression or function of one or more mutations within or near or affecting the expression or function of the RHO gene thereby creating an edited human cell.

Also provided herein is a method for editing a P23H mutation in a RHO gene in a human cell. The method comprises: introducing into the human cell one or more DNA endonucleases to effect one or more SSBs or DSBs within or near the P23H mutation in a RHO gene that results in a permanent deletion, insertion, correction, or modulation of expression or function of the P23H mutation thereby creating an edited human cell.

Also provided herein is an in vivo method for treating a patient with autosomal dominant RP. The method comprises: editing a P23H mutation in a RHO gene in a cell of the patient.

Also provided herein is one or more guide ribonucleic acids (gRNAs) for editing a P23H mutation in a RHO gene in a cell from a patient with autosomal dominant RP. The one or more gRNAs comprises a spacer sequence selected from the group consisting of nucleic acid sequences in SEQ ID NOs: 5287-5291, 5319-5322, and 5358 of the Sequence Listing.

Also provided herein is a therapeutic for treating a patient with autosomal dominant Retinitis Pigmentosa, the therapeutic comprising at least one or more gRNAs for editing a P23H mutation in a RHO gene. The one or more gRNAs comprises a spacer sequence selected from the group consisting of nucleic acid sequences in SEQ ID NOs: 5287-5291, 5319-5322, and 5358 of the sequence listing.

Also provided herein is a therapeutic for treating a patient with autosomal dominant RP, the therapeutic formed by a method comprising: introducing one or more DNA endonucleases; introducing one or more gRNA or one or more sgRNA for editing a P23H mutation in a RHO gene; and optionally introducing one or more donor template. The one or more gRNAs or sgRNAs comprises a spacer sequence selected from the group consisting of nucleic acid sequences in SEQ ID NOs: 5287-5291, 5319-5322, and 5358 of the Sequence Listing.

Also provided herein is a kit for treating a patient with autosomal dominant RP in vivo. The kit comprises one or more gRNAs or sgRNAs for editing a P23H mutation in a RHO gene, one or more DNA endonucleases; and optionally, one or more donor template. The one or more gRNAs or sgRNAs comprises a spacer sequence selected from the group consisting of nucleic acid sequences in SEQ ID NOs: 5287-5291, 5319-5322, and 5358 of the Sequence Listing.

Also provided herein is a single-molecule guide RNA (sgRNA) comprising the nucleic acid sequence of SEQ ID NO: 5287.

Also provided herein is a single-molecule guide RNA (sgRNA) comprising the nucleic acid sequence of SEQ ID NO: 5288.

Also provided herein is a single-molecule guide RNA (sgRNA) comprising the nucleic acid sequence of SEQ ID NO: 5289.

Also provided herein is a single-molecule guide RNA (sgRNA) comprising the nucleic acid sequence of SEQ ID NO: 5290.

Also provided herein is a single-molecule guide RNA (sgRNA) comprising the nucleic acid sequence of SEQ ID NO: 5291.

Also provided herein is a single-molecule guide RNA (sgRNA) comprising the nucleic acid sequence of SEQ ID NO: 5319.

Also provided herein is a single-molecule guide RNA (sgRNA) comprising the nucleic acid sequence of SEQ ID NO: 5320.

Also provided herein is a single-molecule guide RNA (sgRNA) comprising the nucleic acid sequence of SEQ ID NO: 5321.

Also provided herein is a single-molecule guide RNA (sgRNA) comprising the nucleic acid sequence of SEQ ID NO: 5322.

Also provided herein is a single-molecule guide RNA (sgRNA) comprising the nucleic acid sequence of SEQ ID NO: 5358.

Also provided herein is a single-molecule guide RNA (sgRNA) comprising the nucleic acid sequence of SEQ ID NO: 5290 and any one of SEQ ID NOs: 5327-5338.

Also provided herein is a single-molecule guide RNA (sgRNA) comprising the nucleic acid sequence of SEQ ID NO: 5291 and any one of SEQ ID NOs: 5327-5338.

Also provided herein is a single-molecule guide RNA (sgRNA) comprising the nucleic acid sequence of SEQ ID NO: 5319 and any one of SEQ ID NOs: 5327-5338.

Also provided herein is a single-molecule guide RNA (sgRNA) comprising the nucleic acid sequence of SEQ ID NO: 5320 and any one of SEQ ID NOs: 5327-5338.

Also provided herein is a single-molecule guide RNA (sgRNA) comprising the nucleic acid sequence of SEQ ID NO: 5321 and any one of SEQ ID NOs: 5327-5338.

Also provided herein is a single-molecule guide RNA (sgRNA) comprising the nucleic acid sequence of SEQ ID NO: 5322 and any one of SEQ ID NOs: 5327-5338.

Also provided herein is a single-molecule guide RNA (sgRNA) comprising the nucleic acid sequence of SEQ ID NO: 5358 and any one of SEQ ID NOs: 5327-5338.

Also provided herein is a method for editing a P23H mutation within a RHO gene, the method comprising administering a gRNA or sgRNA comprising SEQ ID NO: 5287.

Also provided herein is a method for editing a P23H mutation within a RHO gene, the method comprising administering a gRNA or sgRNA comprising SEQ ID NO: 5288.

Also provided herein is a method for editing a P23H mutation within a RHO gene, the method comprising administering a gRNA or sgRNA comprising SEQ ID NO: 5289.

Also provided herein is a method for editing a P23H mutation within a RHO gene, the method comprising administering a gRNA or sgRNA comprising SEQ ID NO: 5290.

Also provided herein is a method for editing a P23H mutation within a RHO gene, the method comprising administering a gRNA or sgRNA comprising SEQ ID NO: 5291.

Also provided herein is a method for editing a P23H mutation within a RHO gene, the method comprising administering a gRNA or sgRNA comprising SEQ ID NO: 5319.

Also provided herein is a method for editing a P23H mutation within a RHO gene, the method comprising administering a gRNA or sgRNA comprising SEQ ID NO: 5320.

Also provided herein is a method for editing a P23H mutation within a RHO gene, the method comprising administering a gRNA or sgRNA comprising SEQ ID NO: 5321.

Also provided herein is a method for editing a P23H mutation within a RHO gene, the method comprising administering a gRNA or sgRNA comprising SEQ ID NO: 5322.

Also provided herein is a method for editing a P23H mutation within a RHO gene, the method comprising administering a gRNA or sgRNA comprising SEQ ID NO: 5358.

Also provided herein is a method for editing a P23H mutation within a RHO gene, the method comprising administering a gRNA or sgRNA comprising SEQ ID NO: 5290 and any one of SEQ ID NOs: 5327-5338.

Also provided herein is a method for editing a P23H mutation within a RHO gene, the method comprising administering a gRNA or sgRNA comprising SEQ ID NO: 5291 and any one of SEQ ID NOs: 5327-5338.

Also provided herein is a method for editing a P23H mutation within a RHO gene, the method comprising administering a gRNA or sgRNA comprising SEQ ID NO: 5319 and any one of SEQ ID NOs: 5327-5338.

Also provided herein is a method for editing a P23H mutation within a RHO gene, the method comprising administering a gRNA or sgRNA comprising SEQ ID NO: 5320 and any one of SEQ ID NOs: 5327-5338.

Also provided herein is a method for editing a P23H mutation within a RHO gene, the method comprising administering a gRNA or sgRNA comprising SEQ ID NO: 5321 and any one of SEQ ID NOs: 5327-5338.

Also provided herein is a method for editing a P23H mutation within a RHO gene, the method comprising administering a gRNA or sgRNA comprising SEQ ID NO: 5322 and any one of SEQ ID NOs: 5327-5338.

Also provided herein is a method for editing a P23H mutation within a RHO gene, the method comprising administering a gRNA or sgRNA comprising SEQ ID NO: 5358 and any one of SEQ ID NOs: 5327-5338.

Also provided herein is a method for treating a patient with a P23H mutation within a RHO gene, the method comprising administering a gRNA or sgRNA comprising SEQ ID NO: 5287 to the patient.

Also provided herein is a method for treating a patient with a P23H mutation within a RHO gene, the method comprising administering a gRNA or sgRNA comprising SEQ ID NO: 5288 to the patient.

Also provided herein is a method for treating a patient with a P23H mutation within a RHO gene, the method comprising administering a gRNA or sgRNA comprising SEQ ID NO: 5289 to the patient.

Also provided herein is a method for treating a patient with a P23H mutation within a RHO gene, the method comprising administering a gRNA or sgRNA comprising SEQ ID NO: 5290 to the patient.

Also provided herein is a method for treating a patient with a P23H mutation within a RHO gene, the method comprising administering a gRNA or sgRNA comprising SEQ ID NO: 5291 to the patient.

Also provided herein is a method for treating a patient with a P23H mutation within a RHO gene, the method comprising administering a gRNA or sgRNA comprising SEQ ID NO: 5319 to the patient.

Also provided herein is a method for treating a patient with a P23H mutation within a RHO gene, the method comprising administering a gRNA or sgRNA comprising SEQ ID NO: 5320 to the patient.

Also provided herein is a method for treating a patient with a P23H mutation within a RHO gene, the method comprising administering a gRNA or sgRNA comprising SEQ ID NO: 5321 to the patient.

Also provided herein is a method for treating a patient with a P23H mutation within a RHO gene, the method comprising administering a gRNA or sgRNA comprising SEQ ID NO: 5322 to the patient.

Also provided herein is a method for treating a patient with a P23H mutation within a RHO gene, the method comprising administering a gRNA or sgRNA comprising SEQ ID NO: 5358 to the patient.

Also provided herein is a method for treating a patient with a P23H mutation within a RHO gene, the method comprising administering a gRNA or sgRNA to the patient, wherein the sgRNA comprises SEQ ID NO: 5290 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5291 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5319 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5320 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5321 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5322 and any one of SEQ ID NOs: 5327-5338.

Also provided herein is a method for treating a patient with a P23H mutation within a RHO gene, the method comprising administering a gRNA or sgRNA to the patient, wherein the sgRNA comprises SEQ ID NO: 5358 and any one of SEQ ID NOs: 5327-5338.

Also provided herein is a self-inactivating CRISPR-Cas system. The self-inactivating CRISPR-Cas system comprises a first segment, a second segment, and one or more third segments. The first segment comprises a nucleotide sequence that encodes a polypeptide inducing site-directed mutagenesis. The second segment comprises a nucleotide sequence that encodes a guide RNA (gRNA) or a single-molecule guide RNA (sgRNA) wherein the gRNA or sgRNA comprise SEQ ID NO: 5290. The one or more third segments comprise a self-inactivating (SIN) site. The gRNA or sgRNA is substantially complementary to the SIN site. The gRNA or sgRNA is substantially complementary to a genomic target sequence.

Also provided herein is a self-inactivating CRISPR-Cas system. The self-inactivating CRISPR-Cas system comprises a first segment, a second segment, and one or more third segments. The first segment comprises a nucleotide sequence that encodes a polypeptide inducing site-directed mutagenesis. The second segment comprises a nucleotide sequence that encodes a guide RNA (gRNA) or a single-molecule guide RNA (sgRNA) wherein the gRNA or sgRNA comprise SEQ ID NO: 5291. The one or more third segments comprise a self-inactivating (SIN) site. The gRNA or sgRNA is substantially complementary to the SIN site. The gRNA or sgRNA is substantially complementary to a genomic target sequence.

Also provided herein is a self-inactivating CRISPR-Cas system. The self-inactivating CRISPR-Cas system comprises a first segment, a second segment, and one or more third segments. The first segment comprises a nucleotide sequence that encodes a SaCas9 or any variants thereof. The second segment comprises a nucleotide sequence that encodes a gRNA or sgRNA. The one or more third segments comprise a self-inactivating (SIN) site. The gRNA or sgRNA is substantially complementary to the SIN site. The gRNA or sgRNA is substantially complementary to a genomic target sequence. The SIN site comprises a sequence selected from the group consisting of SEQ ID NOs: 5313-5314.

It is understood that the inventions described in this specification are not limited to the examples summarized in this Summary. Various other aspects are described and exemplified herein.

BRIEF DESCRIPTION OF THE DRAWINGS

Various aspects of materials and methods for treatment of RP disclosed and described in this specification can be better understood by reference to the accompanying figures, in which:

FIG. 1A depicts the type II CRISPR/Cas system including gRNA.

FIG. 1B depicts the type II CRISPR/Cas system including sgRNA.

FIGS. 2A-C show the target DNA sequence, the single guide RNA (sgRNA) sequence, and the reverse strand of the target DNA sequence to which the sgRNA binds, for each of 10 sgRNA sequences.

FIG. 2A shows the target DNA sequence, for each of 10 sgRNA sequences.

FIG. 2B shows the single guide RNA (sgRNA) sequence, for each of 10 sgRNA sequences.

FIG. 2C shows the reverse strand of the target DNA sequence to which the sgRNA binds, for each of 10 sgRNA sequences.

FIGS. 2D-F show the target DNA sequence, the single guide RNA (sgRNA) sequence, and the reverse strand of the target DNA sequence to which the sgRNA binds, for each of 4 sgRNA sequences.

FIG. 2D shows the target DNA sequence, for each of 4 sgRNA sequences.

FIG. 2E shows the single guide RNA (sgRNA) sequence, for each of 4 sgRNA sequences.

FIG. 2F shows the reverse strand of the target DNA sequence to which the sgRNA binds, for each of 4 sgRNA sequences.

FIGS. 2G-I show the target DNA sequence, the single guide RNA (sgRNA) sequence, and the reverse strand of the target DNA sequence to which the sgRNA binds for 1 sgRNA sequence.

FIG. 2G shows the target DNA sequence for 1 sgRNA sequence.

FIG. 2H shows the single guide RNA (sgRNA) sequence for 1 sgRNA sequence.

FIG. 2I shows the reverse strand of the target DNA sequence to which the sgRNA binds for 1 sgRNA sequence.

FIG. 5A depicts the structural arrangement of SIN-AAV SaCas9 version 1 (sEF1α promoter).

FIG. 5B depicts the structural arrangement of SIN-AAV SaCas9 version 2 (sEF1α promoter).

FIG. 5C depicts the structural arrangement of Non-SIN-AAV SaCas9 (sEF1α promoter).

FIG. 5D depicts the structural arrangement of an AAV sequence of pSIA010 and pSIA011. pSIA010 is a plasmid comprising an AAV sequence that encodes a sgRNA comprising SEQ ID NO: 5290. pSIA011 is a plasmid comprising an AAV sequence that encodes a sgRNA comprising SEQ ID NO: 5291.

FIGS. 6A-N show flow cytometry data for 2 different HEK 293FT reporter cell lines that are co-transfected with pSIA010, a plasmid comprising an AAV sequence that encodes P23H 20-mer sgRNA (a sgRNA comprising SEQ ID NO: 5290) or pSIA011, a plasmid comprising an AAV sequence that encodes P23H 19-mer sgRNA (a sgRNA comprising SEQ ID NO: 5291), and either (1) a SIN-AAV SaCas9 version 1 (sEF1α promoter), (2) a SIN-AAV SaCas9 version 2 (sEF1α promoter), or (3) a Non-SIN-AAV SaCas9 (sEF1α promoter).

FIG. 6A shows flow cytometry data for HEK 293FT reporter cells that have the wild-type RHO gene as the Cas9 target site and that are co-transfected with (1) pSIA010 and (2) a SIN-AAV SaCas9 version 1 (sEF1α).

FIG. 6B shows flow cytometry data for HEK 293FT reporter cells that have the wild-type RHO gene as the Cas9 target site and that are co-transfected with (1) pSIA011 and (2) a SIN-AAV SaCas9 version 1 (sEF1α).

FIG. 6C shows flow cytometry data for HEK 293FT reporter cells that have the P23H mutation as the Cas9 target site and that are co-transfected with (1) pSIA010 and (2) a SIN-AAV SaCas9 version 1 (sEF1α).

FIG. 6D shows flow cytometry data for HEK 293FT reporter cells that have the P23H mutation as the Cas9 target site and that are co-transfected with (1) pSIA011 and (2) a SIN-AAV SaCas9 version 1 (sEF1α).

FIG. 6E shows flow cytometry data for HEK 293FT reporter cells that have the wild-type RHO gene as the Cas9 target site and that are co-transfected with (1) pSIA010 and (2) a SIN-AAV SaCas9 version 2 (sEF1α).

FIG. 6F shows flow cytometry data for HEK 293FT reporter cells that have the wild-type RHO gene as the Cas9 target site and that are co-transfected with (1) pSIA011 and (2) a SIN-AAV SaCas9 version 2 (sEF1α).

FIG. 6G shows flow cytometry data for HEK 293FT reporter cells that have the P23H mutation as the Cas9 target site and that are co-transfected with (1) pSIA010 and (2) a SIN-AAV SaCas9 version 2 (sEF1α).

FIG. 6H shows flow cytometry data for HEK 293FT reporter cells that have the P23H mutation as the Cas9 target site and that are co-transfected with (1) pSIA011 and (2) a SIN-AAV SaCas9 version 2 (sEF1α).

FIG. 6I shows flow cytometry data for HEK 293FT reporter cells that have the wild-type RHO gene as the Cas9 target site and that are co-transfected with (1) pSIA010 and (2) a Non-SIN-AAV SaCas9 (sEF1α).

FIG. 6J shows flow cytometry data for HEK 293FT reporter cells that have the wild-type RHO gene as the Cas9 target site and that are co-transfected with (1) pSIA011 and (2) a Non-SIN-AAV SaCas9 (sEF1α).

FIG. 6K shows flow cytometry data for HEK 293FT reporter cells that have the wild-type RHO gene as the Cas9 target site and that are not transfected with any DNA.

FIG. 6L shows flow cytometry data for HEK 293FT reporter cells that have the P23H mutation as the Cas9 target site and that are co-transfected with (1) pSIA010 and (2) a Non-SIN-AAV SaCas9 (sEF1α).

FIG. 6M shows flow cytometry data for HEK 293FT reporter cells that have the P23H mutation as the Cas9 target site and that are co-transfected with (1) pSIA011 and (2) a Non-SIN-AAV SaCas9 (sEF1α).

FIG. 6N shows flow cytometry data for HEK 293FT reporter cells that have the P23H mutation as the Cas9 target site and that are not transfected with any DNA.

FIG. 7A is a western blot showing SaCas9, Actin, and GFP expression in HEK 293FT reporter cells that have the wild-type RHO gene as the Cas9 target site. These HEK 293FT reporter cells are transfected with either pSIA010 or pSIA011. The HEK 293FT reporter cells are also transfected with either (1) a SIN-AAV SaCas9 version 1 (sEF1α promoter), (2) a SIN-AAV SaCas9 version 2 (sEF1α promoter), or (3) a Non-SIN-AAV SaCas9 (sEF1α promoter).

FIG. 7B is a western blot showing SaCas9, Actin, and GFP expression in HEK 293FT reporter cells that have the P23H mutation as the Cas9 target site. These HEK 293FT reporter cells are transfected with pSIA010 or pSIA011. The HEK 293FT reporter cells are also transfected with either (1) a SIN-AAV SaCas9 version 1 (sEF1α promoter), (2) a SIN-AAV SaCas9 version 2 (sEF1α promoter), or (3) a Non-SIN-AAV SaCas9 (sEF1α promoter).

FIG. 9A shows a P23H mutation introduced into genomic DNA via HDR.

FIG. 9B shows a single nucleotide mutation in codon 23 of the human rhodopsin gene.

BRIEF DESCRIPTION OF THE SEQUENCE LISTING

SEQ ID NOs: 1-612 are Cas endonuclease ortholog sequences.
SEQ ID NOs: 613-4696 are microRNA sequences.
SEQ ID NOs: 4697-5265 are AAV serotype sequences.
SEQ ID NO: 5266 is a RHO nucleotide sequence.
SEQ ID NOs: 5267-5269 show sample sgRNA backbone sequences that SpCas9 is complexed with.

SEQ ID NO: 5270 is a sample guide RNA (gRNA) for a *Streptococcus pyogenes* Cas9 endonuclease.

SEQ ID NO: 5271 shows a known family of homing endonuclease, as classified by its structure.

SEQ ID NOs: 5272-5281 are sequences that represent the target DNA sequences, for each of 10 sgRNA sequences.

SEQ ID NOs: 5282-5284 are 18-20 bp spacer sequences for targeting within or near a RHO gene or other DNA sequence that encodes a regulatory element of the RHO gene with a *S. pyogenes* Cas9 endonuclease.

SEQ ID NOs: 5285-5286 are 19-20 bp spacer sequences for targeting within or near a RHO gene or other DNA sequence that encodes a regulatory element of the RHO gene with a *Staphylococcus aureus* Cas9 endonuclease.

SEQ ID NOs: 5287-5289 are 18-20 bp spacer sequences for targeting within or near a P23H mutation in a RHO gene with a *S. pyogenes* Cas9 endonuclease.

SEQ ID NOs: 5290-5291 are 19-20 bp spacer sequences for targeting within or near a P23H mutation in a RHO gene with a *S. aureus* Cas9 endonuclease.

SEQ ID NOs: 5292-5301 are sequences that represent the reverse strands of the target DNA sequence to which the sgRNA will bind, for each of 10 sgRNA sequences.

SEQ ID NO: 5302 is a full-length sgRNA comprising SEQ ID NOs: 5287 and 5267.

SEQ ID NO: 5303 is a full-length sgRNA comprising SEQ ID NOs: 5288 and 5267.

SEQ ID NO: 5304 is a full-length sgRNA comprising SEQ ID NOs: 5289 and 5267.

SEQ ID NO: 5305-5307 do not include sequences.

SEQ ID NO: 5308 is pSIA010, a plasmid sequence comprising an AAV sequence that encodes for a sgRNA comprising SEQ ID NOs: 5290 and 5327.

SEQ ID NO: 5309 is pSIA011, a plasmid sequence comprising an AAV sequence that encodes for a sgRNA comprising SEQ ID NOs: 5291 and 5327.

Figure 5A:
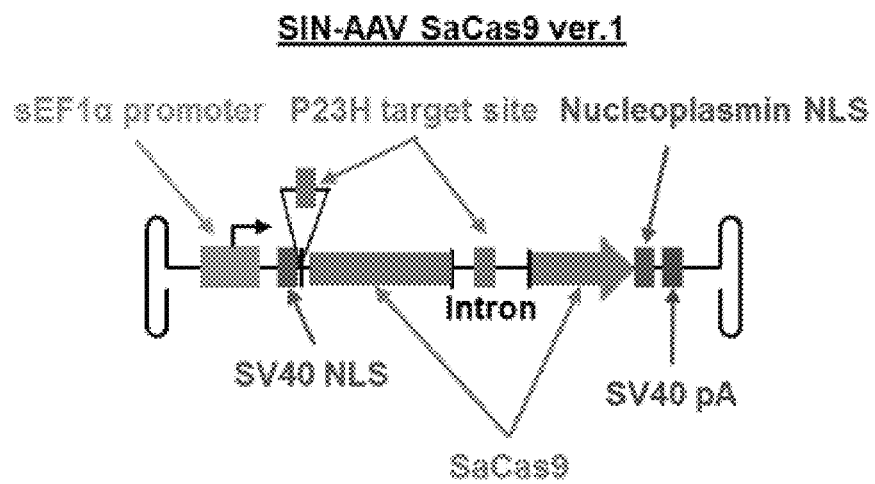
FIGS. 5A-D depict the structural arrangement of SIN-AAV SaCas9 version 1 (sEF1α promoter), SIN-AAV SaCas9 version 2 (sEF1α promoter), Non-SIN-AAV SaCas9 (sEF1α promoter), and the AAV sequence of pSIA010 and pSIA011.

SEQ ID NO: 5310 is a plasmid sequence comprising SIN-AAV SaCas9 ver. 1 (sEF1α promoter), depicted in FIG. 5A.

Figure 5B:
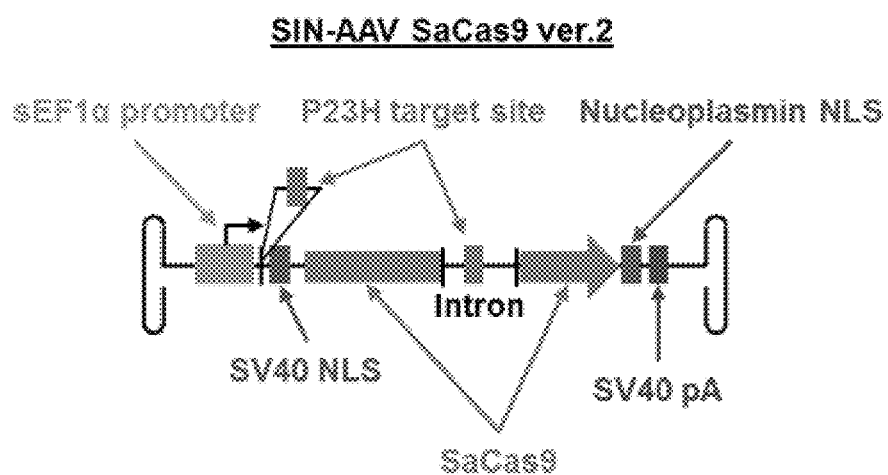

SEQ ID NO: 5311 is a plasmid sequence comprising SIN-AAV SaCas9 ver. 2 (sEF1α promoter), depicted in FIG. 5B.

Figure 5C:
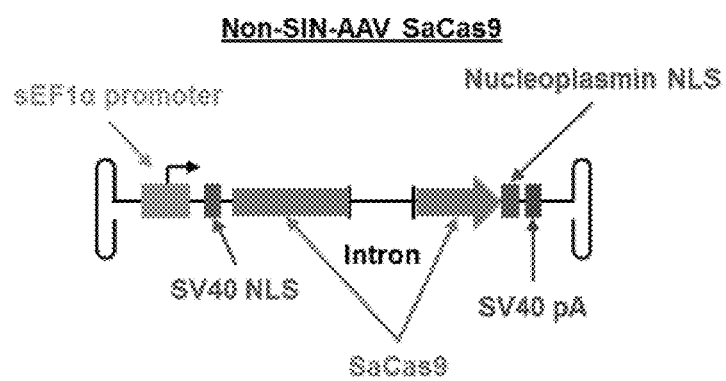

SEQ ID NO: 5312 is a plasmid sequence comprising Non-SIN-AAV SaCas9 (sEF1α promoter), depicted in FIG. 5C.

SEQ ID NO: 5313 is a possible SIN site (also called P23H target site) located upstream of the SaCas9 ORF in the SIN-AAV SaCas9 ver. 1, depicted in FIG. 5A and upstream of the SaCas9 ORF in the SIN-AAV SaCas9 ver. 2, depicted in FIG. 5B.

SEQ ID NO: 5314 is a possible SIN site (also called P23H target site) located within a naturally occurring or chimeric inserted intron located within the SaCas9 ORF in SIN-AAV SaCas9 ver. 1 depicted in FIG. 5A or SIN-AAV SaCas9 ver. 2 depicted in FIG. 5B.

SEQ ID NOs: 5315-5318 are sequences that represent the target DNA sequences, for each of 4 sgRNA sequences.

SEQ ID NOs: 5319-5322 are 21-24 bp protospacer sequences for targeting genome sequences across a P23H mutation in a RHO gene with a *S. aureus* Cas9 endonuclease.

SEQ ID NOs: 5323-5326 are sequences that represent the reverse strands of the target DNA sequence to which the sgRNA will bind, for each of 4 sgRNA sequences.

SEQ ID NOs: 5327-5338 show sample sgRNA backbone sequences that SaCas9 is complexed with.

SEQ ID NO: 5339 is the AAV sequence in pSIA010.

SEQ ID NO: 5340 is the AAV sequence in pSIA011.

SEQ ID NO: 5341 is the AAV sequence in SIN-AAV-SaCas9 version 1 (GRK1).

SEQ ID NO: 5342 is the AAV sequence in SIN-AAV-SaCas9 version 2 (GRK1).

SEQ ID NO: 5343 is an RNA protospacer sequence for targeting within or near the RHO gene with a *S. pyogenes* Cas9 endonuclease to generate the P23H mutant RHO cell line.

SEQ ID NO: 5344 is the target DNA sequence located within or near the RHO gene, which was targeted to generate the P23H mutant RHO cell line.

SEQ ID NO: 5345 is the reverse strand of the target DNA sequence located within or near the RHO gene to which the sgRNA will bind.

SEQ ID NO: 5346 is a single-stranded DNA oligonucleotide used as a template for homology directed repair. The single-stranded DNA oligonucleotide is used to generate the P23H mutant RHO cell line.

SEQ ID NO: 5347 is a forward primer used to amplify around codon 23 of the RHO gene.

SEQ ID NO: 5348 is a reverse primer used to amplify around codon 23 of the RHO gene.

SEQ ID NO: 5349 is a full-length sgRNA comprising SEQ ID NOs: 5285 and 5332.

SEQ ID NO: 5350 is a full-length sgRNA comprising SEQ ID NOs: 5286 and 5332.

SEQ ID NO: 5351 is a full-length sgRNA comprising SEQ ID NOs: 5290 and 5332.

SEQ ID NO: 5352 is a full-length sgRNA comprising SEQ ID NOs: 5291 and 5332.

SEQ ID NO: 5353 is a full-length sgRNA comprising SEQ ID NOs: 5319 and 5332.

SEQ ID NO: 5354 is a full-length sgRNA comprising SEQ ID NOs: 5320 and 5332.

SEQ ID NO: 5355 is a full-length sgRNA comprising SEQ ID NOs: 5321 and 5332.

SEQ ID NO: 5356 is a full-length sgRNA comprising SEQ ID NOs: 5322 and 5332.

SEQ ID NO: 5357 is a sequence that represents the target DNA sequence for 1 sgRNA sequence.

SEQ ID NO: 5358 is an 18 bp RNA protospacer sequence for targeting genome sequences comprising a P23H mutation in a RHO gene with a *S. aureus* Cas9 endonuclease.

SEQ ID NO: 5359 is a sequence that represents the reverse strand of the target DNA sequence to which the sgRNA will bind for 1 sgRNA sequence.

SEQ ID NO: 5360 is a full-length sgRNA comprising SEQ ID NOs: 5358 and 5332.

SEQ ID NO: 5361 is a plasmid sequence that encodes for a sgRNA comprising SEQ ID NO: 5358.

SEQ ID NO: 5362 is a plasmid sequence that encodes for a sgRNA comprising SEQ ID NO: 5291.

SEQ ID NO: 5363 is a plasmid sequence that encodes for a sgRNA comprising SEQ ID NO: 5290.

SEQ ID NO: 5364 is a plasmid sequence that encodes for a sgRNA comprising SEQ ID NO: 5322.

SEQ ID NO: 5365 is a plasmid sequence that encodes for a sgRNA comprising SEQ ID NO: 5321.

SEQ ID NO: 5366 is a plasmid sequence that encodes for a sgRNA comprising SEQ ID NO: 5320.

SEQ ID NO: 5367 is a plasmid sequence that encodes for a sgRNA comprising SEQ ID NO: 5319.

DETAILED DESCRIPTION

Therapeutic Approach

The methods provided herein, regardless of whether a cellular, ex vivo or in vivo method can involve one or a combination of the following: 1) reducing or eliminating expression of the P23H mutant allele at the protein level via introduction of a frameshift mutation in the P23H mutant allele in the RHO gene by an insertion or deletion that arises due to non-homologous end joining (NHEJ); 2) correcting a P23H mutation in a RHO gene by HDR; or 3) knocking-in RHO cDNA into the RHO gene locus or a safe harbor locus.

The NHEJ frameshifting strategy can involve inducing one single stranded break or double stranded break within or near the P23H mutation in the RHO gene with one or more CRISPR endonucleases and a gRNA (e.g., crRNA+tracrRNA, or sgRNA), or two or more single stranded breaks or double stranded breaks within or near the P23H mutation in the RHO gene with two or more CRISPR endonucleases and two or more sgRNAs. This approach can prevent the transcription/synthesis of the P23H mutant allele by causing a frameshift in the P23H mutant allele. This method utilizes gRNAs or sgRNAs specific for the P23H mutation in the RHO gene.

The HDR correction strategy can involve inducing one single stranded break or double stranded break within or near the P23H mutation in the RHO gene with one or more CRISPR endonucleases and a gRNA (e.g., crRNA+tracrRNA, or sgRNA), or two or more single stranded breaks or double stranded breaks within or near the P23H mutation in the RHO gene with one or more CRISPR endonucleases (Cas9, Cpf1 and the like) and two or more gRNAs, in the presence of a donor DNA template introduced exogenously to direct the cellular DSB response to Homology-Directed Repair. The donor DNA template can be a short single stranded oligonucleotide, a short double stranded oligonucleotide, a long single or double stranded DNA molecule. The methods can provide gRNA pairs that make a deletion by cutting the gene twice, one gRNA cutting at the 5' end of the P23H mutation and the other gRNA cutting at the 3' end of the P23H mutation that facilitates insertion of a new sequence from a polynucleotide donor template to replace the P23H mutation in the RHO gene. The cutting can be accomplished by a pair of DNA endonucleases that each makes a DSB (one DSB on each end of the P23H mutation), or by multiple nickases that together make a DSB (one DSB on each end of the P23H mutation). This method utilizes gRNAs or sgRNAs specific for the P23H mutation in the RHO gene and donor DNA molecules.

The knock-in strategy involves knocking-in RHO cDNA into the RHO gene locus using a gRNA (e.g., crRNA+tracrRNA, or sgRNA) or a pair of gRNAs targeting upstream of or in the first or other exon and/or intron of the RHO gene, or in a safe harbor site (such as AAVS1). The donor DNA can be single or double stranded DNA.

The advantages for the above strategies (frameshift, correction, and knock-in strategies) are similar, including in principle both short and long term beneficial clinical and laboratory effects. The knock-in approach provides at least one advantage over the frameshift and correction approach—the ability to treat all patients versus only a subset of patients.

Such methods use endonucleases, such as CRISPR-associated (Cas, Cpf1 and the like) nucleases, to stably correct the P23H mutation within the genomic locus of the RHO gene. Any CRISPR endonuclease can be used in the methods of the present disclosure, each CRISPR endonuclease having its own associated PAM, which can or cannot be disease specific. For example, gRNA spacer sequences for targeting the P23H mutation in the RHO gene with a CRISPR/Cas9 endonuclease from *S. pyogenes* have been identified in SEQ ID NOs. 5287-5289 of the Sequence Listing. gRNA spacer sequences for targeting the P23H mutation in the RHO gene with a CRISPR/Cas9 endonuclease from *S. aureus* have been identified in SEQ ID NOs. 5290-5291 of the Sequence Listing.

Examples set forth in the present disclosure can induce single stranded breaks or double stranded breaks within or near the P23H mutation in the RHO gene to introduce a frameshift or correct the P23H mutation within the RHO gene with as few as a single treatment (rather than deliver potential therapies for the lifetime of the patient).

Retinitis Pigmentosa (RP)

Retinitis pigmentosa (RP) refers to a group of inherited diseases causing retinal degeneration. More than 60 genes have been identified that are associated with RP; and are autosomal recessive (50-60%), autosomal dominant (30-40%), or X-linked (5-15%). In a number of cases, RP is caused by mutations in a RHO gene. A P23H mutation in RHO accounts for 10% of all advanced retinitis pigmentosa representing approximately 2500 patients in the US, with approximately 30 new patients per year. The mutation leads to an accumulation of unfolded, mutated rhodopsin associated with photoreceptor degradation. The disorder is characterized by abnormalities of the photoreceptors (rods and cones) or the retinal pigment epithelium of the retina, and pigment deposits in the peripheral retina that lead to progressive visual loss. Typical RP is a rod-cone dystrophy with primary degeneration of rods followed by cones. The incidence of this disease is 1:3000 to 1:7000 individuals, or 14 to 33 per 100,000. The incidence in the US and Europe is about 1:3500 to 1:4000 and the age of onset is usually 10-30. RP does not exhibit any ethnic specificity, although the range of pathogenic variants within a given gene can differ between populations.

RP is a long lasting disease that evolves over decades. Individuals affected with the disease first experience night blindness, followed by progressive loss in the peripheral visual field in daylight and eventually to blindness. Clinical manifestations include night blindness, visual acuity, fundus appearance, posterior subcapsular cataracts, dust-like particles in the vitreous, white dots deep in the retina, hyaline bodies of the optic nerve head, exudative vasculopathy, and sector RP. The term "sector RP" has been used to describe changes in one quadrant or one half of each fundus. Most commonly, the inferior and nasal quadrants are symmetrically involved. Such sectoral changes have been observed in autosomal dominant RP, for example in people with the common P23H pathogenic variant in RHO and in females heterozygous for X-linked RP. The retina is assessed by ophthalmoscopy, electroretinography, optical coherence tomography, fluorescein angiography and a functional assessment of vision is performed by visual acuity, visual fields and color vision.

RP caused by a P23H mutation in a RHO gene is a monogenic disorder with autosomal dominant inheritance. If a patient only has one P23H mutant allele, a frameshift can be introduced into one P23H mutant allele per cell to prevent the transcription/synthesis of the one P23H mutant allele. A novel approach has been discovered for ameliorating the effects of autosomal dominant RP by introducing a frameshift into one P23H mutant allele per cell to prevent the transcription/synthesis of the one P23H mutant allele.

Also, if a patient only has one P23H mutant allele, the one P23H mutant allele can be corrected to restore RHO function. If a patient has two P23H mutant alleles, both P23H mutant alleles can be corrected with HDR to restore RHO function.

Introducing a frameshift into a P23H mutant allele or correcting a P23H mutant allele using gene editing provides an important improvement over existing or potential therapies, such as introduction of RHO expression cassettes through lentivirus delivery and integration because of its preciseness and lower adverse effects.

Rhodopsin (RHO) Gene

RHO can also be referred to as Rhodopsin 2; Opsin-2; OPN2; Retinitis Pigmentosa 4, Autosomal Dominant; Opsin 2, Rod Pigment; Rod Pigment; Opsin 2; CSNBAD1; or RP4.

RHO has a cytogenetic location of 3q22.1 and the genomic coordinates as seen on Ensembl database are on Chromosome 3 on the forward strand at position 129,528,640-129,535,169. A nucleotide sequence of RHO is shown as SEQ ID NO: 5266. RHO has 826 SNPs, 4 introns and 5 exons. The exon identifier from Ensembl and the start/stop sites of the introns and exons are shown in Table 1.

TABLE 1

Exons and Introns for RHO

| Exon No. | Exon ID | Start/Stop | Intron No. | Intron based on Exon ID | Start/Stop |
|---|---|---|---|---|---|
| Exon 1 | ENSE00001079597 | 129,528,640-129,529,094 | Intron 1 | Intron ENSE00001079597-ENSE00001152211 | 129,529,095-129,530,875 |
| Exon 2 | ENSE00001079599 | 129,533,608-129,535,169 | Intron 2 | Intron ENSE00001152211-ENSE00001152205 | 129,531,045-129,532,250 |
| Exon 3 | ENSE00001152199 | 129,532,533-129,532,772 | Intron 3 | Intron ENSE00001152205-ENSE00001152199 | 129,532,417-129,532,532 |
| Exon 4 | ENSE00001152205 | 129,532,251-129,532,416 | Intron 4 | Intron ENSE00001152199-ENSE00001079599 | 129,532,773-129,533,607 |
| Exon 5 | ENSE00001152211 | 129,530,876-129,531,044 | | | |

RHO has 826 SNPs and the NCBI rs number and/or UniProt VAR number for the SNPs of the RHO gene are VAR_004765, VAR_004766, VAR_004767, VAR_004768, VAR_004769, VAR_004770, VAR_004771, VAR_004772, rs104893770, VAR_004774, rs149079952, VAR_004776, VAR_004777, rs28933395, rs28933394, VAR_004781, VAR_004782, VAR_004783, VAR_004784, rs144317206, VAR_004786, VAR_004787, VAR_004788, VAR_004789, VAR_004790, VAR_004791, VAR_004792, VAR_004793, VAR_004794, VAR_004795, VAR_004796, VAR_004797, VAR_004798, VAR_004799, VAR_004800, VAR_004801, VAR_004802, VAR_004803, VAR_004804, VAR_004805, VAR_004806, VAR_004807, VAR_004808, VAR_004809, VAR_004810, VAR_004811, VAR_004812, VAR_004813, VAR_004814, VAR_004815, VAR_004816, rs567288669, rs28933993, VAR_004819, VAR_004820, VAR_004821, VAR_004822, VAR_004825, VAR_004826, VAR_004827, rs29001653, VAR_004829, VAR_004830, VAR_004831, VAR_004832, VAR_004833, VAR_004834, VAR_004835, rs29001566, rs29001637, VAR_068359, VAR_068360, rs2410, rs7984, rs2071092, rs2071093, rs2269736, rs2625953, rs2625955, rs2855557, rs2855558, rs3755837, rs6803484, rs11359208, rs55915536, rs55941599, rs35005824, rs35649104, rs34204582, rs60744548, rs58508862, rs35822883, rs61170455, rs72987932, rs62267563, rs74435833, rs75456752, rs73863103, rs74578881, rs73204245, rs73204247, rs77154523, rs77530178, rs78163008, rs75783569, rs76288565, rs113310993, rs113312341, rs111823780, rs139028150, rs115345357, rs142285818, rs142322202, rs113751838, rs139374423, rs113964897, rs140851495, rs117803086, rs144222821, rs144270441, rs104893768, rs104893769, rs104893771, rs104893772, rs104893774, rs104893775, rs104893776, rs104893777, rs104893778, rs104893779, rs104893780, rs104893782, rs104893783, rs104893786, rs104893787, rs104893788, rs104893793, rs104893794, rs104893796, rs104893797, rs139502149, rs145921862, rs118173887, rs144339478, rs121918590, rs104893795, rs104893792, rs104893791, rs104893790, rs142771862, rs139731264, rs141185480, rs104893789, rs104893781, rs104893773, rs143003934, rs146311684, rs112963101, rs146327704, rs144211117, rs139435571, rs112445170, rs144852771, rs80263713, rs113823926, rs145004306, rs116351742, rs112302797, rs111871140, rs149084537, rs138831590, rs145248729, rs141844397, rs78872255, rs79311890, rs76257822, rs141951118, rs143735182, rs141956356, rs79765751, rs181914973, rs147005807, rs60645924, rs56340615, rs145549270, rs143977825, rs149615742, rs60120581, rs187430296, rs56120415, rs190889142, rs55851525, rs34476780, rs12633814, rs6803468, rs2855556, rs2855553, rs2855552, rs3733149, rs181047668, rs3733148, rs148627764, rs2625969, rs2625964, rs2625954, rs188128858, rs139566602, rs148748781, rs181387582, rs199553540, rs199573532, rs137883686, rs112640710, rs142769113, rs185011073, rs183230830, rs112855188, rs138115019, rs138142023, rs369408405, rs371461422, rs369445725, rs146389280, rs375593312, rs200054443, rs146391463, rs141468335, rs200165530, rs200207070, rs367631575, rs367633279, rs143193489, rs144939863, rs145024369, rs189018030, rs192412661, rs143559914, rs145310205, rs200946638, rs200947122, rs367909246, rs376057120, rs373949248, rs369851208, rs147640435, rs146936681, rs376111618, rs369893168, rs146987110, rs147761866, rs151063543, rs184124255, rs532137084, rs368157839, rs528482125, rs372128112, rs376271158, rs386665775, rs192604199, rs374334512, rs186091794, rs148110888, rs370271660, rs149722668, rs148165044, rs192710452, rs201411679, rs191009602, rs368522974, rs148222991, rs376626260, rs370441842, rs374550929, rs372570611, rs182735834, rs376727697, rs376776890, rs150129519, rs187923166, rs376802160, rs398122525, rs150250946, rs188052820, rs527236102, rs527236103, rs374788784, rs368819173, rs531014611, rs370746434, rs372812523, rs376995477, rs374902462, rs368910470, rs189786911, rs186719544, rs368995053, rs184850373, rs184966973, rs529295739, rs377157554, rs531210663, rs369102407, rs199583468, rs148801522, rs529338772, rs199701338, rs373118114, rs369198420, rs369233304, rs529422419, rs529438885, rs191819667, rs531346738, rs183318466, rs375306799, rs371264378, rs531409081, rs202215179, rs375391319, rs537581749, rs373369517, rs527538362, rs373450899, rs529674071, rs541163949, rs200076128, rs541204702, rs544766619, rs200095648, rs533358632, rs200248198, rs200826498, rs367797677, rs548932276, rs534588062, rs200894277, rs371853220, rs192461600, rs201008735, rs373974298, rs553108022, rs541825239, rs368037594, rs372010849, rs556769049, rs534810430, rs377687329, rs376184299, rs528605519, rs368352202, rs561052129, rs528662813, rs553392884, rs372349714, rs538581410, rs201340914, rs549470128, rs565201858, rs538744995, rs549590160, rs370370574, rs538820015, rs535230697, rs370401948, rs545950016, rs557301477, rs368534414, rs376708009, rs569450099, rs374685958, rs542367012, rs565597965, rs370601606, rs546127355, rs527236100, rs527236101, rs554039303, rs535635302, rs531077633, rs539249995, rs529156413, rs377120794, rs375044079, rs371192803, rs569952875, rs371288618, rs554315811, rs566173741, rs552362456, rs532949412, rs532967085, rs201989308, rs541053156, rs548708237, rs543124635, rs558037874, rs554303709, rs566186118, rs546852513, rs562439338, rs552455660, rs554753426, rs562524475, rs543466160, rs570565774, rs558624347, rs554828452, rs533370883, rs531691276, rs545193682, rs556655422, rs534695614, rs570714427, rs534707151, rs560835715, rs558838311, rs545440059, rs560894093, rs534819675, rs534820968, rs564967700, rs562999077, rs564979898, rs569161209, rs536844415, rs538560123, rs569194631, rs571256673, rs553654969, rs544155208, rs567350735, rs538825293, rs544170990, rs537065273, rs553775083, rs569445278, rs546065873, rs547981493, rs538999065, rs542454091, rs571636757, rs539172762, rs548089979, rs548091071, rs535653812, rs548113513, rs548157527, rs544423048, rs544431807, rs541024414, rs571916150, rs559747229, rs565900188, rs747643955, rs569761830, rs564018441, rs552237368, rs568169643, rs548581449, rs556514951, rs542748394, rs568202024, rs539370960, rs542966841, rs755921724, rs747855401, rs564262280, rs560324786, rs751894032, rs543204560, rs572406990, rs760515764, rs564388429, rs570075375, rs756162630, rs568632402, rs566301956, rs562374398, rs752076372, rs558503555, rs566319717, rs570266760, rs568571580, rs560600890, rs560370759, rs543521798, rs764633076, rs760792843, rs756454203, rs551028346, rs756509737, rs773890977, rs551043575, rs543542992, rs558693495, rs558768385, rs756658659, rs536467893, rs570795323, rs562853201, rs769544430, rs558877754, rs764927452, rs764956905, rs536582170, rs562985533, rs574163826, rs547374351, rs574202023, rs566997247, rs540386305, rs769769360, rs551679853, rs536977497, rs551759609, rs540632143, rs555790621, rs551828590, rs559421777, rs765265996, rs774425557, rs779169631, rs752805805, rs769954281, rs563636567, rs765350593, rs774496991, rs556019320, rs748989122, rs761500453, rs556049666, rs548460589, rs577235805, rs573163746, rs757219458, rs779382381, rs560101491, rs572252938, rs756285704, rs756306377, rs748269752, rs560500100, rs765586234, rs760667657, rs748211662, rs753036982, rs761682198, rs573715035, rs774816413, rs779560689, rs757395830, rs745616372, rs761781295, rs779609930, rs761784827, rs749280021, rs574677952, rs764607760, rs765564333, rs779665096, rs765781218, rs749137786, rs749356883, rs774967666, rs765855030, rs752248867, rs760894205, rs748429090, rs745759264, rs765931092, rs761990733, rs775095233, rs769464362, rs745851408, rs762059468, rs766027021, rs753353276, rs757690261, rs770701400, rs748483575, rs756663175, rs775191474, rs761013258, rs761022507, rs762146554, rs752455127, rs762150760, rs752496804, rs761101263, rs746029882, rs748689832, rs749663446, rs766225946, rs753496233, rs748723598, rs762290223, rs766275471, rs780188527, rs756898155, rs770941561, rs575161157, rs765139791, rs766326902, rs766344345, rs753585848, rs771007146, rs779029199, rs752695098, rs774336493, rs775528600, rs746210043, rs746223530, rs775557680, rs766422679, rs762451457, rs775579127, rs765193154, rs746247806, rs780408367, rs756986191, rs761338278, rs752830466, rs749929388, rs780494657, rs757106299, rs779296525, rs771322615, rs749016955, rs765438313, rs775945120, rs761562089, rs765519035, rs746563423, rs776014770, rs770151249, rs754064314, rs758475500, rs774698907, rs758484916, rs758491851, rs779465221, rs750171247, rs758543619, rs776124711, rs766932095, rs749155432, rs750219764, rs750220975, rs774809893, rs746773592, rs771637224, rs771682972, rs754349343, rs767152979, rs745643650, rs776411064, rs758844049, rs758848516, rs750473517, rs781237162, rs757449302, rs750519691, rs776504351, rs758901694, rs763223221, rs781325869, rs747002188, rs776586711, rs754584217, rs770432635, rs774865494, rs576140640, rs759021503, rs781266982, rs781437688, rs754648640, rs781460558, rs781375897, rs772086479, rs766943400, rs763402049, rs763422574, rs779747890, rs754206526, rs763447187, rs750430777, rs757524357, rs775005384, rs745849174, rs747159750, rs776812466, rs767573351, rs754809715, rs772222838, rs763538125, rs770703927, rs745920387, rs749567084, rs757740913, rs766112074, rs780060597, rs766161322, rs766196737, rs750905251, rs775382640, rs772316842, rs576444344, rs746121931, rs759316820, rs759322778, rs749753555, rs575196456, rs746186352, rs753609310, rs759406692, rs759406789, rs759425622, rs747369599, rs751084368, rs755085836, rs753665727, rs771123958, rs772533932, rs747418983, rs751153075, rs746332355, rs767979610, rs751167062, rs763887860, rs771188148, rs746468201, rs762711356, rs780682812, rs796098464, rs759637818, rs751280060, rs780707497, rs766787635, rs751312906, rs780743370, rs780785077, rs766852589, rs776101913, rs768251138, rs767363145, rs777559042, rs776654836, rs764208456, rs768298431, rs781465927, rs576974880, rs576216267, rs772137360, rs759818475, rs777625206, rs781539793, rs759122760, rs750763646, rs751561815, rs759945007, rs773022490, rs764386311, rs768300463, rs755654296, rs763455152, rs773127460, rs781550757, rs759209103, rs773177902, rs768616082, rs777943803, rs747203410, rs773291833, rs773295145, rs773347364, rs767646428, rs778170529, rs778173978, rs768877243, rs776890381, rs769009613, rs747215789, rs763566456, rs773808406, rs767654426, rs781681710, rs778626065, rs781713461, rs763644539, rs754963794, rs750974086, rs759354812, rs763728621, rs763794994, rs772528490, rs755171690, rs755190538, rs777274073, rs777283396, rs768030547, rs576802125, rs751311620, rs796247959, rs755350955, rs768195502, rs768210562, rs747582133, rs576980794, rs751475771, rs747620121, rs777637179, rs755540170, rs764277444, rs773077062, rs755674549, rs777849735, rs777851867, rs764590515, rs768787274, rs778356027, rs778533886, rs778536018, rs778587340, rs778804021, rs769236224, and rs778794165.

The RHO gene provides instructions for making a protein called rhodopsin. This protein is necessary for normal vision, particularly in low-light conditions. Rhodopsin is found in specialized light receptor cells called rods. As part of the light-sensitive tissue at the back of the eye (the retina), rods provide vision in low light. Other light receptor cells in the retina, called cones, are responsible for vision in bright light. The rhodopsin protein is bound to a molecule called 11-cis retinal, which is a form of vitamin A. When this molecule is exposed to light, it activates rhodopsin and sets off a series of chemical reactions that create electrical signals. These signals are transmitted to the brain, where they are interpreted as vision.

There are various mutations associated with retinitis pigmentosa (RP), which can be insertions, deletions, missense, nonsense, frameshift and other mutations, with the common effect of inactivating the RHO gene. Any one or more of the mutations can be repaired to restore RHO protein activity. For example, the pathological variant, P23H, can be restored or corrected (See Table 2).

TABLE 2

| Variant | Location | Variant type |
|---------|----------|--------------|
| P23H | Chromosome 3: 129528801 | missense |

Exon Deletion

Another genome engineering strategy involves exon deletion. Targeted deletion of specific exons can be an attractive strategy for treating a large subset of patients with a single therapeutic cocktail. Deletions can either be single exon deletions or multi-exon deletions. While multi-exon deletions can reach a larger number of patients, for larger deletions the efficiency of deletion greatly decreases with increased size. Therefore, deletions range can be from 40 to 10,000 base pairs (bp) in size. For example, deletions can range from 40-100; 100-300; 300-500; 500-1,000; 1,000-2,000; 2,000-3,000; 3,000-5,000; or 5,000-10,000 base pairs in size.

As stated previously, the RHO gene contains 5 exons. Any one or more of the 5 exons can contain a mutation. Any one or more of the 5 mutated exons, or aberrant intronic splice acceptor or donor sites, can be deleted to restore or partially restore the RHO function. In some embodiments, the methods provide gRNA pairs that can be used to delete any one or more of the mutated exons 1, 2, 3, 4, 5, or any combinations thereof.

To ensure that the pre-mRNA is properly processed following deletion, the surrounding splicing signals can be deleted. Splicing donor and acceptors are generally within 100 base pairs of the neighboring intron. Therefore, in some examples, methods can provide all gRNAs that cut approximately +/−100-3100 bp with respect to each exon/intron junction of interest.

For any of the genome editing strategies, gene editing can be confirmed by sequencing or PCR analysis.

In Vivo Based Therapy

Provided herein are methods for treating a patient with autosomal dominant RP. In some aspects, the method is an in vivo cell-based therapy. Chromosomal DNA of the cells in the RP patient can be edited using the materials and methods described herein. For example, the in vivo method can comprise editing a P23H mutation in a RHO gene in a cell of a patient, such as photoreceptor cells or retinal progenitor cells.

Although certain cells present an attractive target for ex vivo treatment and therapy, increased efficacy in delivery may permit direct in vivo delivery to such cells. Ideally the targeting and editing would be directed to the relevant cells. Cleavage in other cells can also be prevented by the use of promoters only active in certain cells and or developmental stages. Additional promoters are inducible, and therefore can be temporally controlled if the nuclease is delivered as a plasmid. The amount of time that delivered RNA and protein remain in the cell can also be adjusted using treatments or domains added to change the half-life. In vivo treatment would eliminate a number of treatment steps, but a lower rate of delivery can require higher rates of editing. In vivo treatment can eliminate problems and losses from ex vivo treatment and engraftment.

An advantage of in vivo gene therapy can be the ease of therapeutic production and administration. The same therapeutic approach and therapy will have the potential to be used to treat more than one patient, for example a number of patients who share the same or similar genotype or allele. In contrast, ex vivo cell therapy typically requires using a patient's own cells, which are isolated, manipulated and returned to the same patient.

Ex Vivo Based Therapy

Provided herein are methods for treating a patient with autosomal dominant RP. An aspect of such method is an ex vivo cell-based therapy. For example, a patient-specific induced pluripotent stem cell (iPSC) can be created. Then, the chromosomal DNA of these iPSC cells can be edited using the materials and methods described herein. For example, the method can comprise editing within or near a P23H mutation in a RHO gene of the iPSC. Next, the genome-edited iPSCs can be differentiated into other cells, such as photoreceptor cells or retinal progenitor cells. Finally, the differentiated cells, such as photoreceptor cell or retinal progenitor cell, can be implanted into the patient.

Another aspect of such method is an ex vivo cell-based therapy. For example, photoreceptor cells or retinal progenitor cells can be isolated from the patient. Next, the chromosomal DNA of these photoreceptor cells or retinal progenitor cells can be edited using the materials and methods described herein. For example, the method can comprise editing within or near a P23H mutation in a RHO gene of the photoreceptor cells or retinal progenitor cells. Finally, the genome-edited photoreceptor cells or retinal progenitor cells can be implanted into the patient.

Another aspect of such method is an ex vivo cell-based therapy. For example, a mesenchymal stem cell can be isolated from the patient, which can be isolated from the patient's bone marrow or peripheral blood. Next, the chromosomal DNA of these mesenchymal stem cells can be edited using the materials and methods described herein. For example, the method can comprise editing within or near a P23H mutation in a RHO gene of the mesenchymal stem cells. Next, the genome-edited mesenchymal stem cells can be differentiated into any type of cell, e.g., photoreceptor cells or retinal progenitor cells. Finally, the differentiated cells, e.g., photoreceptor cells or retinal progenitor cells can be implanted into the patient.

One advantage of an ex vivo cell therapy approach is the ability to conduct a comprehensive analysis of the therapeutic prior to administration. Nuclease-based therapeutics can have some level of off-target effects. Performing gene correction ex vivo allows one to characterize the corrected cell population prior to implantation. The present disclosure includes sequencing the entire genome of the corrected cells to ensure that the off-target effects, if any, can be in genomic locations associated with minimal risk to the patient. Furthermore, populations of specific cells, including clonal populations, can be isolated prior to implantation.

Another advantage of ex vivo cell therapy relates to genetic correction in iPSCs compared to other primary cell sources. iPSCs are prolific, making it easy to obtain the large number of cells that will be required for a cell-based therapy. Furthermore, iPSCs are an ideal cell type for performing clonal isolations. This allows screening for the correct genomic correction, without risking a decrease in viability. In contrast, other primary cells, such as photoreceptor cells or retinal progenitor cells, are viable for only a few passages and difficult to clonally expand. Thus, manipulation of iPSCs for the treatment of autosomal dominant RP can be much easier, and can shorten the amount of time needed to make the desired genetic correction.

Genome Editing

Genome editing refers to the process of modifying the nucleotide sequence of a genome such as in a precise or pre-determined manner. Examples of methods of genome editing described herein include methods of using site-directed nucleases to cut DNA at precise target locations in the genome, thereby creating single-strand or double-strand DNA breaks at particular locations within the genome. Such breaks can be and regularly are repaired by natural, endogenous cellular processes, such as HDR and NHEJ. These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ (ANHEJ)", in which the genetic outcome is similar to NHEJ in that small deletions and insertions can occur at the cleavage site. MMEJ can make use of homologous sequences of a few base pairs flanking the DNA break site to drive a more favored DNA end joining repair outcome, and recent reports have further elucidated the molecular mechanism of this process. In some instances, it may be possible to predict likely repair outcomes based on analysis of potential microhomologies at the site of the DNA break.

Each of these genome editing mechanisms can be used to create desired genomic alterations. A step in the genome editing process can be to create one or two DNA breaks, the latter as double-strand breaks or as two single-stranded breaks, in the target locus as near the site of intended mutation. This can be achieved via the use of site-directed polypeptides, as described and illustrated herein.

Site-directed polypeptides, such as a DNA endonuclease, can introduce double-strand breaks or single-strand breaks in nucleic acids, e.g., genomic DNA. The double-strand break can stimulate a cell's endogenous DNA-repair pathways [e.g., homology-dependent repair (HDR) or non-homologous end joining (NHEJ) or (ANHEJ) or (MMEJ)]. NHEJ can repair cleaved target nucleic acid without the need for a homologous template. This can sometimes result in small deletions or insertions (indels) in the target nucleic acid at the site of cleavage, and can lead to disruption or alteration of gene expression. The deletions range can be from 40 to 10,000 base pairs (bp) in size. For example, deletions can range from 40-100; 100-300; 300-500; 500-1,000; 1,000-2,000; 2,000-3,000; 3,000-5,000; or 5,000-10,000 base pairs in size. HDR can occur when a homologous repair template, or donor, is available. The homologous donor template can comprise at least a portion of the wild-type RHO gene, or cDNA. The at least a portion of the wild-type RHO gene or cDNA can be exon 1, exon 2, exon 3, exon 4, exon 5, intronic regions, fragments or combinations thereof, or the entire RHO gene or cDNA. The donor template can be either a single or double stranded polynucleotide. The donor template can be up to 5 KB. The donor template can be up to 4 KB. The donor template can be up to 3 KB. The donor template can be up to 2 KB. The donor template can be up to 1 KB. The donor template can be delivered by AAV. The homologous donor template can comprise sequences that can be homologous to sequences flanking the target nucleic acid cleavage site. For example, the donor template can have homologous arms to the 3q22.1 region. The donor template can also have homologous arms to the pathological variant P23H. The sister chromatid can be used by the cell as the repair template. However, for the purposes of genome editing, the repair template can be supplied as an exogenous nucleic acid, such as a plasmid, duplex oligonucleotide, single-strand oligonucleotide, double-stranded oligonucleotide, or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few base pairs flanking the cleavage site to drive a favored end-joining DNA repair outcome. In some instances, it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence or polynucleotide donor template) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The modifications of the target DNA due to NHEJ and/or HDR can lead to, for example, mutations, deletions, alterations, integrations, gene correction, gene replacement, gene tagging, transgene insertion, nucleotide deletion, gene disruption, translocations and/or gene mutation. The processes of deleting genomic DNA and integrating non-native nucleic acid into genomic DNA are examples of genome editing.

CRISPR Endonuclease System

A CRISPR (Clustered Regularly Interspaced Short Palindromic Repeats) genomic locus can be found in the genomes of many prokaryotes (e.g., bacteria and archaea). In prokaryotes, the CRISPR locus encodes products that function as a type of immune system to help defend the prokaryotes against foreign invaders, such as virus and phage. There are three stages of CRISPR locus function: integration of new sequences into the CRISPR locus, expression of CRISPR RNA (crRNA), and silencing of foreign invader nucleic acid. Five types of CRISPR systems (e.g., Type I, Type II, Type III, Type U, and Type V) have been identified.

A CRISPR locus includes a number of short repeating sequences referred to as "repeats." When expressed, the repeats can form secondary structures (e.g., hairpins) and/or comprise unstructured single-stranded sequences. The repeats usually occur in clusters and frequently diverge between species. The repeats are regularly interspaced with unique intervening sequences referred to as "spacers," resulting in a repeat-spacer-repeat locus architecture. The spacers are identical to or have high homology with known foreign invader sequences. A spacer-repeat unit encodes a crisprRNA (crRNA), which is processed into a mature form of the spacer-repeat unit. A crRNA comprises a "seed" or spacer sequence that is involved in targeting a target nucleic acid (in the naturally occurring form in prokaryotes, the spacer sequence targets the foreign invader nucleic acid). A spacer sequence is located at the 5' or 3' end of the crRNA.

A CRISPR locus also comprises polynucleotide sequences encoding CRISPR Associated (Cas) genes. Cas genes encode endonucleases involved in the biogenesis and the interference stages of crRNA function in prokaryotes. Some Cas genes comprise homologous secondary and/or tertiary structures.

Type II CRISPR Systems crRNA biogenesis in a Type II CRISPR system in nature requires a trans-activating CRISPR RNA (tracrRNA). The tracrRNA can be modified by endogenous RNaseIII, and then hybridizes to a crRNA repeat in the pre-crRNA array. Endogenous RNaseIII can be recruited to cleave the pre-crRNA. Cleaved crRNAs can be subjected to exoribonuclease trimming to produce the mature crRNA form (e.g., 5' trimming). The tracrRNA can remain hybridized to the crRNA, and the tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid can activate Cas9 for targeted nucleic acid cleavage. The target nucleic acid in a Type II CRISPR system is referred to as a protospacer adjacent motif (PAM). In nature, the PAM is essential to facilitate binding of a site-directed polypeptide (e.g., Cas9) to the target nucleic acid. Type II systems (also referred to as Nmeni or CASS4) are further subdivided into Type II-A (CASS4) and II-B (CASS4a). Jinek et al., *Science,* 337(6096):816-821 (2012) showed that the CRISPR/Cas9 system is useful for RNA-programmable genome editing, and international patent application publication number WO2013/176772 provides numerous examples and applications of the CRISPR/Cas endonuclease system for site-specific gene editing.

Type V CRISPR Systems

Type V CRISPR systems have several important differences from Type II systems. For example, Cpf1 is a single RNA-guided endonuclease that, in contrast to Type II systems, lacks tracrRNA. In fact, Cpf1-associated CRISPR arrays can be processed into mature crRNAs without the requirement of an additional trans-activating tracrRNA. The Type V CRISPR array can be processed into short mature crRNAs of 42-44 nucleotides in length, with each mature crRNA beginning with 19 nucleotides of direct repeat followed by 23-25 nucleotides of spacer sequence. In contrast, mature crRNAs in Type II systems can start with 20-24 nucleotides of spacer sequence followed by about 22 nucleotides of direct repeat. Also, Cpf1 can utilize a T-rich protospacer-adjacent motif such that Cpf1-crRNA complexes efficiently cleave target DNA preceded by a short T-rich PAM, which is in contrast to the G-rich PAM following the target DNA for Type II systems. Thus, Type V systems cleave at a point that is distant from the PAM, while Type II systems cleave at a point that is adjacent to the PAM. In addition, in contrast to Type II systems, Cpf1 cleaves DNA via a staggered DNA double-stranded break with a 4 or 5 nucleotide 5' overhang. Type II systems cleave via a blunt double-stranded break. Similar to Type II systems, Cpf1 contains a predicted RuvC-like endonuclease domain, but lacks a second HNH endonuclease domain, which is in contrast to Type II systems.

Cas Genes/Polypeptides and Protospacer Adjacent Motifs

Figure 1A:
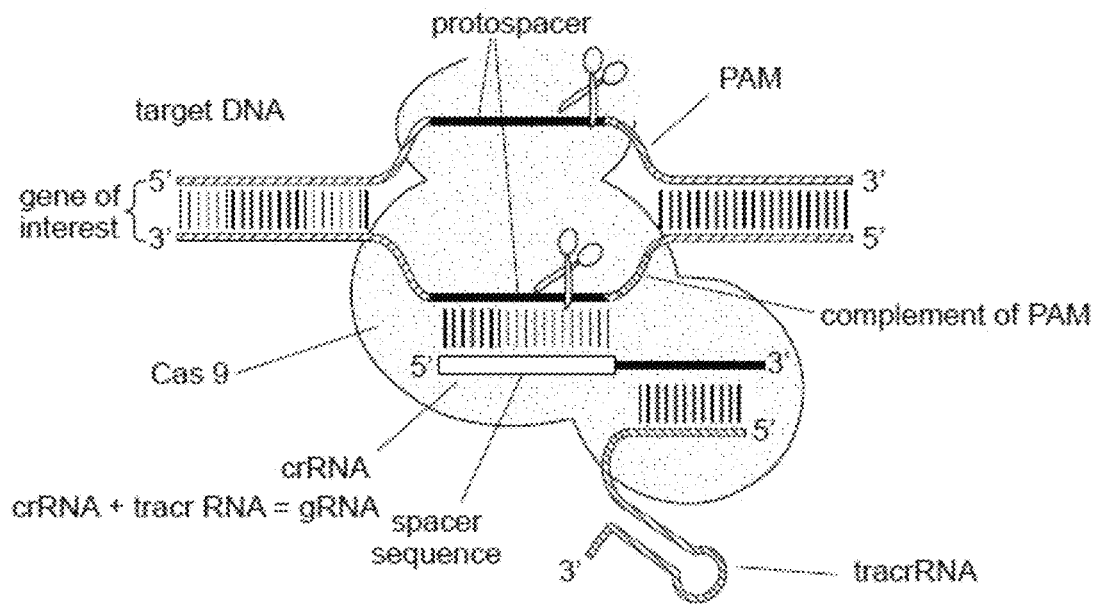
FIGS. 1A-B depict the type II CRISPR/Cas system.
Figure 1B:
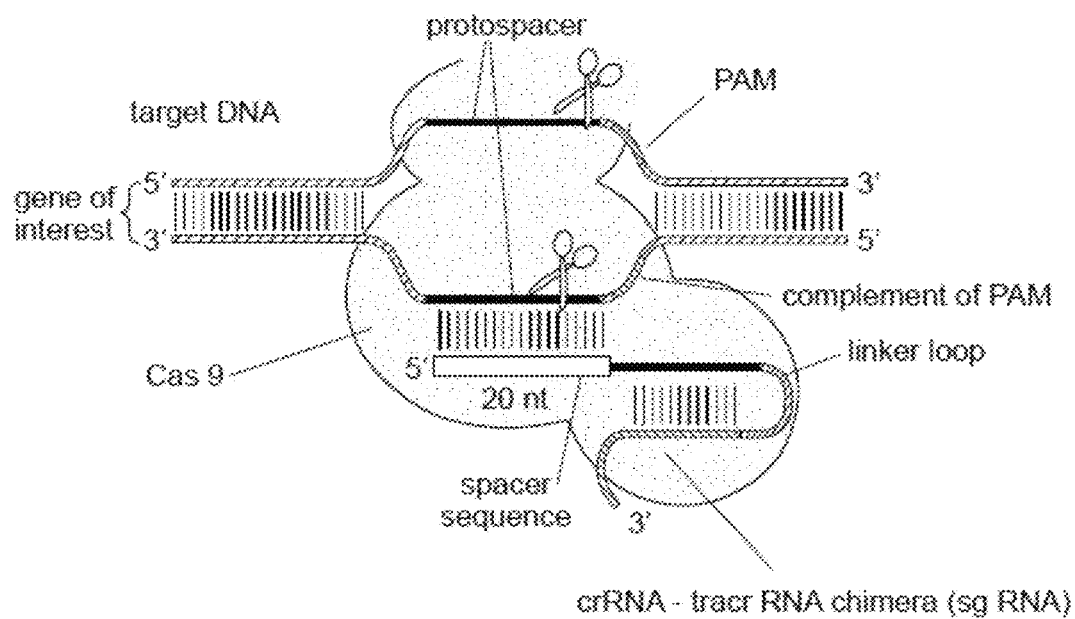

Exemplary CRISPR/Cas polypeptides include the Cas9 polypeptides in FIG. 1 of Fonfara et al., *Nucleic Acids Research,* 42: 2577-2590 (2014). The CRISPR/Cas gene naming system has undergone extensive rewriting since the Cas genes were discovered. FIG. 5 of Fonfara, supra, provides PAM sequences for the Cas9 polypeptides from various species.

Site-Directed Polypeptides

A site-directed polypeptide is a nuclease used in genome editing to cleave DNA and/or induce site-directed mutagenesis. The site-directed nuclease can be administered to a cell or a patient as either: one or more polypeptides, or one or more mRNAs encoding the polypeptide. Any of the enzymes or orthologs listed in SEQ ID NOs. 1-612, or disclosed herein, can be utilized in the methods herein.

In the context of a CRISPR/Cas or CRISPR/Cpf1 system, the site-directed polypeptide can bind to a guide RNA that, in turn, specifies the site in the target DNA to which the polypeptide is directed. In the CRISPR/Cas or CRISPR/Cpf1 systems disclosed herein, the site-directed polypeptide can be an endonuclease, such as a DNA endonuclease.

A site-directed polypeptide can comprise a plurality of nucleic acid-cleaving (i.e., nuclease) domains. Two or more nucleic acid-cleaving domains can be linked together via a linker. For example, the linker can comprise a flexible linker. Linkers can comprise 1, 2, 3, 4, 5, 6, 7, 8, 9, 10, 11, 12, 13, 14, 15, 16, 17, 18, 19, 20, 21, 22, 23, 24, 25, 30, 35, 40 or more amino acids in length.

Naturally-occurring wild-type Cas9 enzymes comprise two nuclease domains, a HNH nuclease domain and a RuvC domain. Herein, the "Cas9" refers to both naturally occurring and recombinant Cas9s. Cas9 enzymes contemplated herein can comprise a HNH or HNH-like nuclease domain, and/or a RuvC or RuvC-like nuclease domain.

HNH or HNH-like domains comprise a McrA-like fold. HNH or HNH-like domains comprises two antiparallel β-strands and an α-helix. HNH or HNH-like domains comprises a metal binding site (e.g., a divalent cation binding site). HNH or HNH-like domains can cleave one strand of a target nucleic acid (e.g., the complementary strand of the crRNA targeted strand).

RuvC or RuvC-like domains comprise an RNaseH or RNaseH-like fold. RuvC/RNaseH domains are involved in a diverse set of nucleic acid-based functions including acting on both RNA and DNA. The RNaseH domain comprises 5 β-strands surrounded by a plurality of α-helices. RuvC/RNaseH or RuvC/RNaseH-like domains comprise a metal binding site (e.g., a divalent cation binding site). RuvC/RNaseH or RuvC/RNaseH-like domains can cleave one strand of a target nucleic acid (e.g., the non-complementary strand of a double-stranded target DNA).

Site-directed polypeptides can introduce double-strand breaks or single-strand breaks in nucleic acids, e.g., genomic DNA. The double-strand break can stimulate a cell's endogenous DNA-repair pathways [e.g., HDR or NHEJ or ANHEJ or MMEJ]. NHEJ can repair cleaved target nucleic acid without the need for a homologous template. This can sometimes result in small deletions or insertions (indels) in the target nucleic acid at the site of cleavage, and can lead to disruption or alteration of gene expression. HDR can occur when a homologous repair template, or donor, is available. The homologous donor template can comprise sequences that are homologous to sequences flanking the target nucleic acid cleavage site. The sister chromatid can be used by the cell as the repair template. However, for the purposes of genome editing, the repair template can be supplied as an exogenous nucleic acid, such as a plasmid, duplex oligonucleotide, single-strand oligonucleotide or viral nucleic acid. With exogenous donor templates, an additional nucleic acid sequence (such as a transgene) or modification (such as a single or multiple base change or a deletion) can be introduced between the flanking regions of homology so that the additional or altered nucleic acid sequence also becomes incorporated into the target locus. MMEJ can result in a genetic outcome that is similar to NHEJ in that small deletions and insertions can occur at the cleavage site. MMEJ can make use of homologous sequences of a few base pairs flanking the cleavage site to drive a favored end-joining DNA repair outcome. In some instances, it may be possible to predict likely repair outcomes based on analysis of potential microhomologies in the nuclease target regions.

Thus, in some cases, homologous recombination can be used to insert an exogenous polynucleotide sequence into the target nucleic acid cleavage site. An exogenous polynucleotide sequence is termed a donor polynucleotide (or donor or donor sequence) herein. The donor polynucleotide, a portion of the donor polynucleotide, a copy of the donor polynucleotide, or a portion of a copy of the donor polynucleotide can be inserted into the target nucleic acid cleavage site. The donor polynucleotide can be an exogenous polynucleotide sequence, i.e., a sequence that does not naturally occur at the target nucleic acid cleavage site.

The site-directed polypeptide can comprise an amino acid sequence having at least 10%, at least 15%, at least 20%, at least 30%, at least 40%, at least 50%, at least 60%, at least 70%, at least 75%, at least 80%, at least 85%, at least 90%, at least 95%, at least 99%, or 100% amino acid sequence identity to a wild-type exemplary site-directed polypeptide [e.g., Cas9 from *S. pyogenes*, US2014/0068797 Sequence ID No. 8 or Sapranauskas et al., *Nucleic Acids Res*, 39(21): 9275-9282 (2011)], and various other site-directed polypeptides. The site-directed polypeptide can comprise at least 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a HNH nuclease domain of the site-directed polypeptide. The site-directed polypeptide can comprise at least: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide. The site-directed polypeptide can comprise at most: 70, 75, 80, 85, 90, 95, 97, 99, or 100% identity to a wild-type site-directed polypeptide (e.g., Cas9 from *S. pyogenes*, supra) over 10 contiguous amino acids in a RuvC nuclease domain of the site-directed polypeptide.

The site-directed polypeptide can comprise a modified form of a wild-type exemplary site-directed polypeptide. The modified form of the wild-type exemplary site-directed polypeptide can comprise a mutation that reduces the nucleic acid-cleaving activity of the site-directed polypeptide. The modified form of the wild-type exemplary site-directed polypeptide can have less than 90%, less than 80%, less than 70%, less than 60%, less than 50%, less than 40%, less than 30%, less than 20%, less than 10%, less than 5%, or less than 1% of the nucleic acid-cleaving activity of the wild-type exemplary site-directed polypeptide (e.g., Cas9 from *S. pyogenes*, supra). The modified form of the site-directed polypeptide can have no substantial nucleic acid-cleaving activity. When a site-directed polypeptide is a modified form that has no substantial nucleic acid-cleaving activity, it is referred to herein as "enzymatically inactive."

The modified form of the site-directed polypeptide can comprise a mutation such that it can induce a SSB on a target nucleic acid (e.g., by cutting only one of the sugar-phosphate backbones of a double-strand target nucleic acid). The mutation can result in less than 90%, less than 80%, less than 70%, less than 60%, less than 50%, less than 40%, less than 30%, less than 20%, less than 10%, less than 5%, or less than 1% of the nucleic acid-cleaving activity in one or more of the plurality of nucleic acid-cleaving domains of the wild-type site directed polypeptide (e.g., Cas9 from *S. pyogenes*, supra). The mutation can result in one or more of the plurality of nucleic acid-cleaving domains retaining the ability to cleave the complementary strand of the target nucleic acid, but reducing its ability to cleave the non-complementary strand of the target nucleic acid. The mutation can result in one or more of the plurality of nucleic acid-cleaving domains retaining the ability to cleave the non-complementary strand of the target nucleic acid, but reducing its ability to cleave the complementary strand of the target nucleic acid. For example, residues in the wild-type exemplary *S. pyogenes* Cas9 polypeptide, such as Asp10, His840, Asn854 and Asn856, are mutated to inactivate one or more of the plurality of nucleic acid-cleaving domains (e.g., nuclease domains). The residues to be mutated can correspond to residues Asp10, His840, Asn854 and Asn856 in the wild-type exemplary *S. pyogenes* Cas9 polypeptide (e.g., as determined by sequence and/or structural alignment). Non-limiting examples of mutations include D10A, H840A, N854A or N856A. Mutations other than alanine substitutions can be suitable.

A D10A mutation can be combined with one or more of H840A, N854A, or N856A mutations to produce a site-directed polypeptide substantially lacking DNA cleavage activity. A H840A mutation can be combined with one or more of D10A, N854A, or N856A mutations to produce a site-directed polypeptide substantially lacking DNA cleavage activity. A N854A mutation can be combined with one or more of H840A, D10A, or N856A mutations to produce a site-directed polypeptide substantially lacking DNA cleavage activity. A N856A mutation can be combined with one or more of H840A, N854A, or D10A mutations to produce a site-directed polypeptide substantially lacking DNA cleavage activity. Site-directed polypeptides that comprise one substantially inactive nuclease domain are referred to as "nickases".

Nickase variants of RNA-guided endonucleases, for example Cas9, can be used to increase the specificity of CRISPR-mediated genome editing. Wild type Cas9 is typically guided by a single guide RNA designed to hybridize with a specified ~20 nucleotide sequence in the target sequence (such as an endogenous genomic locus). However, several mismatches can be tolerated between the guide RNA and the target locus, effectively reducing the length of required homology in the target site to, for example, as little as 13 nt of homology, and thereby resulting in elevated potential for binding and double-strand nucleic acid cleavage by the CRISPR/Cas9 complex elsewhere in the target genome—also known as off-target cleavage. Because nickase variants of Cas9 each only cut one strand, in order to create a double-strand break it is necessary for a pair of nickases to bind in close proximity and on opposite strands of the target nucleic acid, thereby creating a pair of nicks, which is the equivalent of a double-strand break. This requires that two separate guide RNAs—one for each nickase—must bind in close proximity and on opposite strands of the target nucleic acid. This requirement essentially doubles the minimum length of homology needed for the double-strand break to occur, thereby reducing the likelihood that a double-strand cleavage event will occur elsewhere in the genome, where the two guide RNA sites—if they exist—are unlikely to be sufficiently close to each other to enable the double-strand break to form. As described in the art, nickases can also be used to promote HDR versus NHEJ. HDR can be used to introduce selected changes into target sites in the genome through the use of specific donor sequences that effectively mediate the desired changes.

Mutations contemplated can include substitutions, additions, and deletions, or any combination thereof. The mutation converts the mutated amino acid to alanine. The mutation converts the mutated amino acid to another amino acid (e.g., glycine, serine, threonine, cysteine, valine, leucine, isoleucine, methionine, proline, phenylalanine, tyrosine, tryptophan, aspartic acid, glutamic acid, asparagines, glutamine, histidine, lysine, or arginine). The mutation converts the mutated amino acid to a non-natural amino acid (e.g., selenomethionine). The mutation converts the mutated amino acid to amino acid mimics (e.g., phosphomimics). The mutation can be a conservative mutation. For example, the mutation converts the mutated amino acid to amino acids that resemble the size, shape, charge, polarity, conformation, and/or rotamers of the mutated amino acids (e.g., cysteine/serine mutation, lysine/asparagine mutation, histidine/phenylalanine mutation). The mutation can cause a shift in reading frame and/or the creation of a premature stop codon. Mutations can cause changes to regulatory regions of genes or loci that affect expression of one or more genes.

The site-directed polypeptide (e.g., variant, mutated, enzymatically inactive and/or conditionally enzymatically inactive site-directed polypeptide) can target nucleic acid. The site-directed polypeptide (e.g., variant, mutated, enzymatically inactive and/or conditionally enzymatically inactive endoribonuclease) can target DNA. The site-directed polypeptide (e.g., variant, mutated, enzymatically inactive and/or conditionally enzymatically inactive endoribonuclease) can target RNA.

The site-directed polypeptide can comprise one or more non-native sequences (e.g., the site-directed polypeptide is a fusion protein).

The site-directed polypeptide can comprise an amino acid sequence comprising at least 15% amino acid identity to a Cas9 from a bacterium (e.g., *S. pyogenes*), a nucleic acid binding domain, and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain).

The site-directed polypeptide can comprise an amino acid sequence comprising at least 15% amino acid identity to a Cas9 from a bacterium (e.g., *S. pyogenes*), and two nucleic acid cleaving domains, wherein one or both of the nucleic acid cleaving domains comprise at least 50% amino acid identity to a nuclease domain from Cas9 from a bacterium (e.g., *S. pyogenes*).

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), and non-native sequence (for example, a nuclear localization signal) or a linker linking the site-directed polypeptide to a non-native sequence.

The site-directed polypeptide can comprise an amino acid sequence comprising at least 15% amino acid identity to a Cas9 from a bacterium (e.g., *S. pyogenes*), two nucleic acid cleaving domains (i.e., a HNH domain and a RuvC domain), wherein the site-directed polypeptide comprises a mutation in one or both of the nucleic acid cleaving domains that reduces the cleaving activity of the nuclease domains by at least 50%.

The site-directed polypeptide can comprise an amino acid sequence comprising at least 15% amino acid identity to a Cas9 from a bacterium (e.g., *S. pyogenes*), and two nucleic acid cleaving domains (i.e., a HNH domain and a RuvC domain), wherein one of the nuclease domains comprises mutation of aspartic acid 10, and/or wherein one of the nuclease domains can comprise a mutation of histidine 840, and wherein the mutation reduces the cleaving activity of the nuclease domain(s) by at least 50%.

The one or more site-directed polypeptides, e.g. DNA endonucleases, can comprise two nickases that together effect one double-strand break at a specific locus in the genome, or four nickases that together effect or cause two double-strand breaks at specific loci in the genome. Alternatively, one site-directed polypeptide, e.g. DNA endonuclease, can effect or cause one double-strand break at a specific locus in the genome.

Non-limiting examples of Cas9 orthologs from other bacterial strains including but not limited to, Cas proteins identified in *Acaryochloris marina* MBIC11017; *Acetohalobium arabaticum* DSM 5501; *Acidithiobacillus caldus*; *Acidithiobacillus ferrooxidans* ATCC 23270; *Alicyclobacillus acidocaldarius* LAA1; *Alicyclobacillus acidocaldarius* subsp. *acidocaldarius* DSM 446; *Allochromatium vinosum* DSM 180; *Ammonifex degensii* KC4; *Anabaena variabilis* ATCC 29413; *Arthrospira maxima* CS-328; *Arthrospira platensis* str. Paraca; *Arthrospira* sp. PCC 8005; *Bacillus pseudomycoides* DSM 12442; *Bacillus selenitireducens* MLS10; *Burkholderiales bacterium* 1_1_47; *Caldicellulosiruptor becscii* DSM 6725; *Candidatus Desulforudis audaxviator* MP104C; *Caldicellulosiruptor hydrothermalis* 108; *Clostridium* phage c-st; *Clostridium botulinum* A3 str. Loch Maree; *Clostridium botulinum* Ba4 str. 657; *Clostridium difficile* QCD-63q42; *Crocosphaera watsonii* WH 8501; *Cyanothece* sp. ATCC 51142; *Cyanothece* sp. CCY0110; *Cyanothece* sp. PCC 7424; *Cyanothece* sp. PCC 7822; *Exiguobacterium sibiricum* 255-15; *Finegoldia magna* ATCC 29328; *Ktedonobacter racemifer* DSM 44963; *Lactobacillus delbrueckii* subsp. *bulgaricus* PB2003/044-T3-4; *Lactobacillus salivarius* ATCC 11741; *Listeria innocua*; *Lyngbya* sp. PCC 8106; *Marinobacter* sp. ELB17; *Methanohalobium evestigatum* Z-7303; *Microcystis* phage Ma-LMM01; *Microcystis aeruginosa* NIES-843; *Microscilla marina* ATCC 23134; *Microcoleus chthonoplastes* PCC 7420; *Neisseria meningitidis*; *Nitrosococcus* halophilus Nc4; *Nocardiopsis dassonvillei* subsp. *dassonvillei* DSM 43111; *Nodularia spumigena* CCY9414; *Nostoc* sp. PCC 7120; *Oscillatoria* sp. PCC 6506; *Pelotomaculum thermopropionicum* SI; *Petrotoga mobilis* SJ95; *Polaromonas naphthalenivorans* CJ2; *Polaromonas* sp. J5666; *Pseudoalteromonas haloplanktis* TAC125; *Streptomyces pristinaespiralis* ATCC 25486; *Streptomyces pristinaespiralis* ATCC 25486; *Streptococcus thermophilus; Streptomyces viridochromogenes* DSM 40736; *Streptosporangium roseum* DSM 43021; *Synechococcus* sp. PCC 7335; and *Thermosipho africanus* TCF52B (Chylinski et al., *RNA Biol.*, 2013; 10(5): 726-737.

In addition to Cas9 orthologs, other Cas9 variants such as fusion proteins of inactive dCas9 and effector domains with different functions can be served as a platform for genetic modulation. Any of the foregoing enzymes can be useful in the present disclosure.

Further examples of endonucleases that can be utilized in the present disclosure are provided in SEQ ID NOs: 1-612. These proteins can be modified before use or can be encoded in a nucleic acid sequence such as a DNA, RNA or mRNA or within a vector construct such as the plasmids or adeno-associated virus (AAV) vectors taught herein. Further, they can be codon optimized.

Genome-Targeting Nucleic Acid

The present disclosure provides a genome-targeting nucleic acid that can direct the activities of an associated polypeptide (e.g., a site-directed polypeptide) to a specific target sequence within a target nucleic acid. The genome-targeting nucleic acid can be an RNA. A genome-targeting RNA is referred to as a "guide RNA" or "gRNA" herein. A guide RNA can comprise at least a spacer sequence that hybridizes to a target nucleic acid sequence of interest, and a CRISPR repeat sequence. In Type II systems, the gRNA also comprises a second RNA called the tracrRNA sequence. In the Type II gRNA, the CRISPR repeat sequence and tracrRNA sequence hybridize to each other to form a duplex. In the Type V gRNA, the crRNA forms a duplex. In both systems, the duplex can bind a site-directed polypeptide, such that the guide RNA and site-direct polypeptide form a complex. The genome-targeting nucleic acid can provide target specificity to the complex by virtue of its association with the site-directed polypeptide. The genome-targeting nucleic acid thus can direct the activity of the site-directed polypeptide.

Exemplary guide RNAs include the spacer sequences in SEQ ID NOs: 5282-5291 of the Sequence Listing, shown with genome location of their target sequence (See SEQ ID NOs: 5272-5281 in FIG. 2A) and the associated Cas9 cut site, wherein the genome location is based on the GRCh38/hg38 human genome assembly.

Each guide RNA can be designed to include a spacer sequence complementary to its genomic target sequence. For example, each of the spacer sequences in SEQ ID NOs: 5282-5291 of the Sequence Listing can be put into a single RNA chimera or a crRNA (along with a corresponding tracrRNA). See Jinek et al., *Science*, 337, 816-821 (2012) and Deltcheva et al., *Nature*, 471, 602-607 (2011).

The genome-targeting nucleic acid can be a double-molecule guide RNA. The genome-targeting nucleic acid can be a single-molecule guide RNA. The double-molecule guide RNA or single-molecule guide RNA can be modified.

A double-molecule guide RNA can comprise two strands of RNA. The first strand comprises in the 5' to 3' direction, an optional spacer extension sequence, a spacer sequence and a minimum CRISPR repeat sequence. The second strand can comprise a minimum tracrRNA sequence (complementary to the minimum CRISPR repeat sequence), a 3' tracrRNA sequence and an optional tracrRNA extension sequence.

A single-molecule guide RNA (sgRNA) in a Type II system can comprise, in the 5' to 3' direction, an optional spacer extension sequence, a spacer sequence, a minimum CRISPR repeat sequence, a single-molecule guide linker, a minimum tracrRNA sequence, a 3' tracrRNA sequence and an optional tracrRNA extension sequence. The optional tracrRNA extension can comprise elements that contribute additional functionality (e.g., stability) to the guide RNA. The single-molecule guide linker can link the minimum CRISPR repeat and the minimum tracrRNA sequence to form a hairpin structure. The optional tracrRNA extension can comprise one or more hairpins.

The sgRNA can comprise a variable length spacer sequence with 17-30 nucleotides at the 5' end of the sgRNA sequence (Table 3). In other examples, the sgRNA can comprise a variable length spacer sequence with 17-24 nucleotides at the 5' end of the sgRNA sequence.

The sgRNA can comprise a 20 nucleotide spacer sequence at the 5' end of the sgRNA sequence. The sgRNA can comprise a less than 20 nucleotide spacer sequence at the 5' end of the sgRNA sequence. The sgRNA can comprise a 19 nucleotide spacer sequence at the 5' end of the sgRNA sequence. The sgRNA can comprise a 18 nucleotide spacer sequence at the 5' end of the sgRNA sequence. The sgRNA can comprise a 17 nucleotide spacer sequence at the 5' end of the sgRNA sequence. The sgRNA can comprise a more than 20 nucleotide spacer sequence at the 5' end of the sgRNA sequence. The sgRNA can comprise a 21 nucleotide spacer sequence at the 5' end of the sgRNA sequence. The sgRNA can comprise a 22 nucleotide spacer sequence at the 5' end of the sgRNA sequence. The sgRNA can comprise a 23 nucleotide spacer sequence at the 5' end of the sgRNA sequence. The sgRNA can comprise a 24 nucleotide spacer sequence at the 5' end of the sgRNA sequence. The sgRNA can comprise a 25 nucleotide spacer sequence at the 5' end of the sgRNA sequence. The sgRNA can comprise a 26 nucleotide spacer sequence at the 5' end of the sgRNA sequence. The sgRNA can comprise a 27 nucleotide spacer sequence at the 5' end of the sgRNA sequence. The sgRNA can comprise a 28 nucleotide spacer sequence at the 5' end of the sgRNA sequence. The sgRNA can comprise a 29 nucleotide spacer sequence at the 5' end of the sgRNA sequence. The sgRNA can comprise a 30 nucleotide spacer sequence at the 5' end of the sgRNA sequence.

The sgRNA can comprise no uracil at the 3'end of the sgRNA sequence, such as in SEQ ID NOs: 5268, 5328, 5331, 5334, or 5337 of Table 3. The sgRNA can comprise one or more uracil at the 3'end of the sgRNA sequence, such as in SEQ ID NOs: 5267, 5269, 5327, 5329, 5330, 5332, 5333, 5335, 5336, or 5338 in Table 3. For example, the sgRNA can comprise 1 uracil (U) at the 3' end of the sgRNA sequence. The sgRNA can comprise 2 uracil (UU) at the 3' end of the sgRNA sequence. The sgRNA can comprise 3 uracil (UUU) at the 3' end of the sgRNA sequence. The sgRNA can comprise 4 uracil (UUUU) at the 3' end of the sgRNA sequence. The sgRNA can comprise 5 uracil (UUUUU) at the 3' end of the sgRNA sequence. The sgRNA can comprise 6 uracil (UUUUUU) at the 3' end of the sgRNA sequence. The sgRNA can comprise 7 uracil (UUUUUUU) at the 3' end of the sgRNA sequence. The sgRNA can comprise 8 uracil) at the 3' end of the sgRNA sequence.

The sgRNA can be unmodified or modified. For example, modified sgRNAs can comprise one or more 2'-O-methyl phosphorothioate nucleotides.

Spacer Extension Sequence

In some examples of genome-targeting nucleic acids, a spacer extension sequence can modify activity, provide

TABLE 3

| SEQ ID NO. | sgRNA sequence | |
|---|---|---|
| 5267 | n$_{(17-30)}$guuuuagagcuagaaauagcaaguuaaaauaaggcuaguccguuaucaacuugaaaaaguggcaccgagucggugcuuuu | Sp |
| 5268 | n$_{(17-30)}$guuuuagagcuagaaauagcaaguuaaaauaaggcuaguccguuaucaacuugaaaaaguggcaccgagucggugc | Sp |
| 5269 | n$_{(17-30)}$guuuuagagcuagaaauagcaaguuaaaauaaggcuaguccguuaucaacuugaaaaaguggcaccgagucggugcu$_{(1-8)}$ | Sp |
| 5327 | n$_{(17-30)}$guuuaaguacucugugcuggaaacagcacagaaucuacuuaaacaaggcaaaaugccguguuuaucucgucaacuuguuggcgagauuuuuu | Sa |
| 5328 | n$_{(17-30)}$guuuaaguacucugugcuggaaacagcacagaaucuacuuaaacaaggcaaaaugccguguuuaucucgucaacuuguuggcgaga | Sa |
| 5329 | n$_{(17-30)}$guuuaaguacucugugcuggaaacagcacagaaucuacuuaaacaaggcaaaaugccguguuuaucucgucaacuuguuggcgagau$_{(1-8)}$ | Sa |
| 5330 | n$_{(17-30)}$guuuuaguacucuguaaugaaaauuacagaaucuacuaaaacaaggcaaaaugccguguuuaucucgucaacuuguuggcgagauuuuuuuu | Sa |
| 5331 | n$_{(17-30)}$guuuuaguacucuguaaugaaaauuacagaaucuacuaaaacaaggcaaaaugccguguuuaucucgucaacuuguuggcgaga | Sa |
| 5332 | n$_{(17-30)}$guuuuaguacucuguaaugaaaauuacagaaucuacuaaaacaaggcaaaaugccguguuuaucucgucaacuuguuggcgagau$_{(1-8)}$ | Sa |
| 5333 | n$_{(17-30)}$guuuaaguacucugugcuggaaacagcacagaaucuacuuaaacaaggcaaaaugccguguuuaucucgucaacuuguuggcgagauuuuuuu | Sa |
| 5334 | n$_{(17-30)}$guuuaaguacucugugcuggaaacagcacagaaucuacuuaaacaaggcaaaaugccguguuuaucucgucaacuuguuggcgaga | Sa |
| 5335 | n$_{(17-30)}$guuuaaguacucugugcuggaaacagcacagaaucuacuuaaacaaggcaaaaugccguguuuaucucgucaacuuguuggcgagau$_{(1-8)}$ | Sa |
| 5336 | n$_{(17-30)}$guuuuaguacucuggaaacagaaucuacuaaaacaaggcaaaaugccguguuuaucucgucaacuuguuggcgagauuuu | Sa |
| 5337 | n$_{(17-30)}$guuuuaguacucuggaaacagaaucuacuaaaacaaggcaaaaugccguguuuaucucgucaacuuguuggcgaga | Sa |
| 5338 | n$_{(17-30)}$guuuuaguacucuggaaacagaaucuacuaaaacaaggcaaaaugccguguuuaucucgucaacuuguuggcgagau$_{(1-8)}$ | Sa |

A single-molecule guide RNA (sgRNA) in a Type V system can comprise, in the 5' to 3' direction, a minimum CRISPR repeat sequence and a spacer sequence.

By way of illustration, guide RNAs used in the CRISPR/Cas/Cpf1 system, or other smaller RNAs can be readily synthesized by chemical means, as illustrated below and described in the art. While chemical synthetic procedures are continually expanding, purifications of such RNAs by procedures such as high performance liquid chromatography (HPLC, which avoids the use of gels such as PAGE) tends to become more challenging as polynucleotide lengths increase significantly beyond a hundred or so nucleotides. One approach used for generating RNAs of greater length is to produce two or more molecules that are ligated together. Much longer RNAs, such as those encoding a Cas9 or Cpf1 endonuclease, are more readily generated enzymatically. Various types of RNA modifications can be introduced during or after chemical synthesis and/or enzymatic generation of RNAs, e.g., modifications that enhance stability, reduce the likelihood or degree of innate immune response, and/or enhance other attributes, as described in the art.

stability and/or provide a location for modifications of a genome-targeting nucleic acid. A spacer extension sequence can modify on- or off-target activity or specificity. In some examples, a spacer extension sequence can be provided. The spacer extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, or 7000 or more nucleotides. The spacer extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400, 1000, 2000, 3000, 4000, 5000, 6000, 7000 or more nucleotides. The spacer extension sequence can be less than 10 nucleotides in length. The spacer extension sequence can be between 10-30 nucleotides in length. The spacer extension sequence can be between 30-70 nucleotides in length.

The spacer extension sequence can comprise another moiety (e.g., a stability control sequence, an endoribonuclease binding sequence, a ribozyme). The moiety can decrease or increase the stability of a nucleic acid targeting nucleic acid. The moiety can be a transcriptional terminator segment (i.e., a transcription termination sequence). The moiety can function in a eukaryotic cell. The moiety can function in a prokaryotic cell. The moiety can function in both eukaryotic and prokaryotic cells. Non-limiting examples of suitable moieties include: a 5' cap (e.g., a 7-methylguanylate cap (m7 G)), a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like).

Spacer Sequence

The spacer sequence hybridizes to a sequence in a target nucleic acid of interest. The spacer of a genome-targeting nucleic acid can interact with a target nucleic acid in a sequence-specific manner via hybridization (i.e., base pairing). The nucleotide sequence of the spacer can vary depending on the sequence of the target nucleic acid of interest.

In a CRISPR/Cas system herein, the spacer sequence can be designed to hybridize to a target nucleic acid that is located 5' of a PAM of the Cas9 enzyme used in the system. The spacer can perfectly match the target sequence or can have mismatches. Each Cas9 enzyme has a particular PAM sequence that it recognizes in a target DNA. For example, S. pyogenes recognizes in a target nucleic acid a PAM that comprises the sequence 5'-NRG-3', where R comprises either A or G, where N is any nucleotide and N is immediately 3' of the target nucleic acid sequence targeted by the spacer sequence.

The target nucleic acid sequence can comprise 20 nucleotides. The target nucleic acid can comprise less than 20 nucleotides. The target nucleic acid can comprise more than 20 nucleotides. The target nucleic acid can comprise at least: 5, 10, 15, 16, 17, 18, 19, 20, 21, 22, 23, 24, 25, 30 or more nucleotides. The target nucleic acid can comprise at most: 5, 10, 15, 16, 17, 18, 19, 20, 21, 22, 23, 24, 25, 30 or more nucleotides. The target nucleic acid sequence can comprise 20 bases immediately 5' of the first nucleotide of the PAM. For example, in a sequence comprising 5'-G-3' (SEQ ID NO. 5270), the target nucleic acid can comprise the sequence that corresponds to the Ns, wherein N is any nucleotide, and the underlined NRG sequence is the S. pyogenes PAM.

The spacer sequence that hybridizes to the target nucleic acid can have a length of at least about 6 nucleotides (nt). The spacer sequence can be at least about 6 nt, at least about 10 nt, at least about 15 nt, at least about 18 nt, at least about 19 nt, at least about 20 nt, at least about 25 nt, at least about 30 nt, at least about 35 nt or at least about 40 nt, from about 6 nt to about 80 nt, from about 6 nt to about 50 nt, from about 6 nt to about 45 nt, from about 6 nt to about 40 nt, from about 6 nt to about 35 nt, from about 6 nt to about 30 nt, from about 6 nt to about 25 nt, from about 6 nt to about 20 nt, from about 6 nt to about 19 nt, from about 10 nt to about 50 nt, from about 10 nt to about 45 nt, from about 10 nt to about 40 nt, from about 10 nt to about 35 nt, from about 10 nt to about 30 nt, from about 10 nt to about 25 nt, from about 10 nt to about 20 nt, from about 10 nt to about 19 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt. In some examples, the spacer sequence can comprise 20 nucleotides. In some examples, the spacer can comprise 19 nucleotides. In some examples, the spacer can comprise 18 nucleotides. In some examples, the spacer can comprise 22 nucleotides.

In some examples, the percent complementarity between the spacer sequence and the target nucleic acid is at least about 30%, at least about 40%, at least about 50%, at least about 60%, at least about 65%, at least about 70%, at least about 75%, at least about 80%, at least about 85%, at least about 90%, at least about 95%, at least about 97%, at least about 98%, at least about 99%, or 100%. In some examples, the percent complementarity between the spacer sequence and the target nucleic acid is at most about 30%, at most about 40%, at most about 50%, at most about 60%, at most about 65%, at most about 70%, at most about 75%, at most about 80%, at most about 85%, at most about 90%, at most about 95%, at most about 97%, at most about 98%, at most about 99%, or 100%. In some examples, the percent complementarity between the spacer sequence and the target nucleic acid is 100% over the six contiguous 5'-most nucleotides of the target sequence of the complementary strand of the target nucleic acid. The percent complementarity between the spacer sequence and the target nucleic acid can be at least 60% over about 20 contiguous nucleotides. The length of the spacer sequence and the target nucleic acid can differ by 1 to 6 nucleotides, which can be thought of as a bulge or bulges.

The spacer sequence can be designed or chosen using a computer program. The computer program can use variables, such as predicted melting temperature, secondary structure formation, predicted annealing temperature, sequence identity, genomic context, chromatin accessibility, % GC, frequency of genomic occurrence (e.g., of sequences that are identical or are similar but vary in one or more spots as a result of mismatch, insertion or deletion), methylation status, presence of SNPs, and the like.

Minimum CRISPR Repeat Sequence

A minimum CRISPR repeat sequence can be a sequence with at least about 30%, about 40%, about 50%, about 60%, about 65%, about 70%, about 75%, about 80%, about 85%, about 90%, about 95%, or 100% sequence identity to a reference CRISPR repeat sequence (e.g., crRNA from S. pyogenes).

A minimum CRISPR repeat sequence can comprise nucleotides that can hybridize to a minimum tracrRNA sequence in a cell. The minimum CRISPR repeat sequence and a minimum tracrRNA sequence can form a duplex, i.e. a base-paired double-stranded structure. Together, the minimum CRISPR repeat sequence and the minimum tracrRNA sequence can bind to the site-directed polypeptide. At least a part of the minimum CRISPR repeat sequence can hybridize to the minimum tracrRNA sequence. At least a part of the minimum CRISPR repeat sequence can comprise at least about 30%, about 40%, about 50%, about 60%, about 65%, about 70%, about 75%, about 80%, about 85%, about 90%, about 95%, or 100% complementary to the minimum tracrRNA sequence. At least a part of the minimum CRISPR repeat sequence can comprise at most about 30%, about 40%, about 50%, about 60%, about 65%, about 70%, about 75%, about 80%, about 85%, about 90%, about 95%, or 100% complementary to the minimum tracrRNA sequence.

The minimum CRISPR repeat sequence can have a length from about 7 nucleotides to about 100 nucleotides. For example, the length of the minimum CRISPR repeat sequence is from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. In some examples, the minimum CRISPR repeat sequence can be approximately 9 nucleotides in length. The minimum CRISPR repeat sequence can be approximately 12 nucleotides in length.

The minimum CRISPR repeat sequence can be at least about 60% identical to a reference minimum CRISPR repeat sequence (e.g., wild-type crRNA from *S. pyogenes*) over a stretch of at least 6, 7, or 8 contiguous nucleotides. For example, the minimum CRISPR repeat sequence can be at least about 65% identical, at least about 70% identical, at least about 75% identical, at least about 80% identical, at least about 85% identical, at least about 90% identical, at least about 95% identical, at least about 98% identical, at least about 99% identical or 100% identical to a reference minimum CRISPR repeat sequence over a stretch of at least 6, 7, or 8 contiguous nucleotides.

Minimum tracrRNA Sequence

A minimum tracrRNA sequence can be a sequence with at least about 30%, about 40%, about 50%, about 60%, about 65%, about 70%, about 75%, about 80%, about 85%, about 90%, about 95%, or 100% sequence identity to a reference tracrRNA sequence (e.g., wild type tracrRNA from *S. pyogenes*).

A minimum tracrRNA sequence can comprise nucleotides that hybridize to a minimum CRISPR repeat sequence in a cell. A minimum tracrRNA sequence and a minimum CRISPR repeat sequence form a duplex, i.e. a base-paired double-stranded structure. Together, the minimum tracrRNA sequence and the minimum CRISPR repeat can bind to a site-directed polypeptide. At least a part of the minimum tracrRNA sequence can hybridize to the minimum CRISPR repeat sequence. The minimum tracrRNA sequence can be at least about 30%, about 40%, about 50%, about 60%, about 65%, about 70%, about 75%, about 80%, about 85%, about 90%, about 95%, or 100% complementary to the minimum CRISPR repeat sequence.

The minimum tracrRNA sequence can have a length from about 7 nucleotides to about 100 nucleotides. For example, the minimum tracrRNA sequence can be from about 7 nucleotides (nt) to about 50 nt, from about 7 nt to about 40 nt, from about 7 nt to about 30 nt, from about 7 nt to about 25 nt, from about 7 nt to about 20 nt, from about 7 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt or from about 15 nt to about 25 nt long. The minimum tracrRNA sequence can be approximately 9 nucleotides in length. The minimum tracrRNA sequence can be approximately 12 nucleotides. The minimum tracrRNA can consist of tracrRNA nt 23-48 described in Jinek et al., supra.

The minimum tracrRNA sequence can be at least about 60% identical to a reference minimum tracrRNA (e.g., wild type, tracrRNA from *S. pyogenes*) sequence over a stretch of at least 6, 7, or 8 contiguous nucleotides. For example, the minimum tracrRNA sequence can be at least about 65% identical, about 70% identical, about 75% identical, about 80% identical, about 85% identical, about 90% identical, about 95% identical, about 98% identical, about 99% identical or 100% identical to a reference minimum tracrRNA sequence over a stretch of at least 6, 7, or 8 contiguous nucleotides.

The duplex between the minimum CRISPR RNA and the minimum tracrRNA can comprise a double helix. The duplex between the minimum CRISPR RNA and the minimum tracrRNA can comprise at least about 1, 2, 3, 4, 5, 6, 7, 8, 9, or 10 or more nucleotides. The duplex between the minimum CRISPR RNA and the minimum tracrRNA can comprise at most about 1, 2, 3, 4, 5, 6, 7, 8, 9, or 10 or more nucleotides.

The duplex can comprise a mismatch (i.e., the two strands of the duplex are not 100% complementary). The duplex can comprise at least about 1, 2, 3, 4, or 5 or mismatches. The duplex can comprise at most about 1, 2, 3, 4, or 5 or mismatches. The duplex can comprise no more than 2 mismatches.

Bulges

In some cases, there can be a "bulge" in the duplex between the minimum CRISPR RNA and the minimum tracrRNA. A bulge is an unpaired region of nucleotides within the duplex. A bulge can contribute to the binding of the duplex to the site-directed polypeptide. The bulge can comprise, on one side of the duplex, an unpaired 5'-XXXY-3' where X is any purine and Y comprises a nucleotide that can form a wobble pair with a nucleotide on the opposite strand, and an unpaired nucleotide region on the other side of the duplex. The number of unpaired nucleotides on the two sides of the duplex can be different.

In one example, the bulge can comprise an unpaired purine (e.g., adenine) on the minimum CRISPR repeat strand of the bulge. In some examples, the bulge can comprise an unpaired 5'-AAGY-3' of the minimum tracrRNA sequence strand of the bulge, where Y comprises a nucleotide that can form a wobble pairing with a nucleotide on the minimum CRISPR repeat strand.

A bulge on the minimum CRISPR repeat side of the duplex can comprise at least 1, 2, 3, 4, or 5 or more unpaired nucleotides. A bulge on the minimum CRISPR repeat side of the duplex can comprise at most 1, 2, 3, 4, or 5 or more unpaired nucleotides. A bulge on the minimum CRISPR repeat side of the duplex can comprise 1 unpaired nucleotide.

A bulge on the minimum tracrRNA sequence side of the duplex can comprise at least 1, 2, 3, 4, 5, 6, 7, 8, 9, or 10 or more unpaired nucleotides. A bulge on the minimum tracrRNA sequence side of the duplex can comprise at most 1, 2, 3, 4, 5, 6, 7, 8, 9, or 10 or more unpaired nucleotides. A bulge on a second side of the duplex (e.g., the minimum tracrRNA sequence side of the duplex) can comprise 4 unpaired nucleotides.

A bulge can comprise at least one wobble pairing. In some examples, a bulge can comprise at most one wobble pairing. A bulge can comprise at least one purine nucleotide. A bulge can comprise at least 3 purine nucleotides. A bulge sequence can comprise at least 5 purine nucleotides. A bulge sequence can comprise at least one guanine nucleotide. In some examples, a bulge sequence can comprise at least one adenine nucleotide.

Hairpins

In various examples, one or more hairpins can be located 3' to the minimum tracrRNA in the 3' tracrRNA sequence.

The hairpin can start at least about 1, 2, 3, 4, 5, 6, 7, 8, 9, 10, 15, or 20 or more nucleotides 3' from the last paired nucleotide in the minimum CRISPR repeat and minimum tracrRNA sequence duplex. The hairpin can start at most about 1, 2, 3, 4, 5, 6, 7, 8, 9 or 10 or more nucleotides 3' of the last paired nucleotide in the minimum CRISPR repeat and minimum tracrRNA sequence duplex.

The hairpin can comprise at least about 1, 2, 3, 4, 5, 6, 7, 8, 9, 10, 15, or 20 or more consecutive nucleotides. The hairpin can comprise at most about 1, 2, 3, 4, 5, 6, 7, 8, 9, 10, 15, or more consecutive nucleotides.

The hairpin can comprise a CC dinucleotide (i.e., two consecutive cytosine nucleotides).

The hairpin can comprise duplexed nucleotides (e.g., nucleotides in a hairpin, hybridized together). For example, a hairpin can comprise a CC dinucleotide that is hybridized to a GG dinucleotide in a hairpin duplex of the 3' tracrRNA sequence.

One or more of the hairpins can interact with guide RNA-interacting regions of a site-directed polypeptide.

In some examples, there are two or more hairpins, and in other examples there are three or more hairpins.

3' tracrRNA Sequence

A 3' tracrRNA sequence can comprise a sequence with at least about 30%, about 40%, about 50%, about 60%, about 65%, about 70%, about 75%, about 80%, about 85%, about 90%, about 95%, or 100% sequence identity to a reference tracrRNA sequence (e.g., a tracrRNA from *S. pyogenes*).

The 3' tracrRNA sequence can have a length from about 6 nucleotides to about 100 nucleotides. For example, the 3' tracrRNA sequence can have a length from about 6 nucleotides (nt) to about 50 nt, from about 6 nt to about 40 nt, from about 6 nt to about 30 nt, from about 6 nt to about 25 nt, from about 6 nt to about 20 nt, from about 6 nt to about 15 nt, from about 8 nt to about 40 nt, from about 8 nt to about 30 nt, from about 8 nt to about 25 nt, from about 8 nt to about 20 nt, from about 8 nt to about 15 nt, from about 15 nt to about 100 nt, from about 15 nt to about 80 nt, from about 15 nt to about 50 nt, from about 15 nt to about 40 nt, from about 15 nt to about 30 nt, or from about 15 nt to about 25 nt. The 3' tracrRNA sequence can have a length of approximately 14 nucleotides.

The 3' tracrRNA sequence can be at least about 60% identical to a reference 3' tracrRNA sequence (e.g., wild type 3' tracrRNA sequence from *S. pyogenes*) over a stretch of at least 6, 7, or 8 contiguous nucleotides. For example, the 3' tracrRNA sequence can be at least about 60% identical, about 65% identical, about 70% identical, about 75% identical, about 80% identical, about 85% identical, about 90% identical, about 95% identical, about 98% identical, about 99% identical, or 100% identical, to a reference 3' tracrRNA sequence (e.g., wild type 3' tracrRNA sequence from *S. pyogenes*) over a stretch of at least 6, 7, or 8 contiguous nucleotides.

The 3' tracrRNA sequence can comprise more than one duplexed region (e.g., hairpin, hybridized region). The 3' tracrRNA sequence can comprise two duplexed regions.

The 3' tracrRNA sequence can comprise a stem loop structure. The stem loop structure in the 3' tracrRNA can comprise at least 1, 2, 3, 4, 5, 6, 7, 8, 9, 10, 15 or 20 or more nucleotides. The stem loop structure in the 3' tracrRNA can comprise at most 1, 2, 3, 4, 5, 6, 7, 8, 9 or 10 or more nucleotides. The stem loop structure can comprise a functional moiety. For example, the stem loop structure can comprise an aptamer, a ribozyme, a protein-interacting hairpin, a CRISPR array, an intron, or an exon. The stem loop structure can comprise at least about 1, 2, 3, 4, or 5 or more functional moieties. The stem loop structure can comprise at most about 1, 2, 3, 4, or 5 or more functional moieties.

The hairpin in the 3' tracrRNA sequence can comprise a P-domain. In some examples, the P-domain can comprise a double-stranded region in the hairpin.

tracrRNA Extension Sequence

A tracrRNA extension sequence can be provided whether the tracrRNA is in the context of single-molecule guides or double-molecule guides. The tracrRNA extension sequence can have a length from about 1 nucleotide to about 400 nucleotides. The tracrRNA extension sequence can have a length of more than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, or 400 nucleotides. The tracrRNA extension sequence can have a length from about 20 to about 5000 or more nucleotides. The tracrRNA extension sequence can have a length of more than 1000 nucleotides. The tracrRNA extension sequence can have a length of less than 1, 5, 10, 15, 20, 25, 30, 35, 40, 45, 50, 60, 70, 80, 90, 100, 120, 140, 160, 180, 200, 220, 240, 260, 280, 300, 320, 340, 360, 380, 400 or more nucleotides. The tracrRNA extension sequence can have a length of less than 1000 nucleotides. The tracrRNA extension sequence can comprise less than 10 nucleotides in length. The tracrRNA extension sequence can be 10-30 nucleotides in length. The tracrRNA extension sequence can be 30-70 nucleotides in length.

The tracrRNA extension sequence can comprise a functional moiety (e.g., a stability control sequence, ribozyme, endoribonuclease binding sequence). The functional moiety can comprise a transcriptional terminator segment (i.e., a transcription termination sequence). The functional moiety can have a total length from about 10 nucleotides (nt) to about 100 nucleotides, from about 10 nt to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt, from about 15 nt to about 80 nt, from about 15 nt to about 50 nt, from about 15 nt to about 40 nt, from about 15 nt to about 30 nt, or from about 15 nt to about 25 nt. The functional moiety can function in a eukaryotic cell. The functional moiety can function in a prokaryotic cell. The functional moiety can function in both eukaryotic and prokaryotic cells.

Non-limiting examples of suitable tracrRNA extension functional moieties include a 3' poly-adenylated tail, a riboswitch sequence (e.g., to allow for regulated stability and/or regulated accessibility by proteins and protein complexes), a sequence that forms a dsRNA duplex (i.e., a hairpin), a sequence that targets the RNA to a subcellular location (e.g., nucleus, mitochondria, chloroplasts, and the like), a modification or sequence that provides for tracking (e.g., direct conjugation to a fluorescent molecule, conjugation to a moiety that facilitates fluorescent detection, a sequence that allows for fluorescent detection, etc.), and/or a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like). The tracrRNA extension sequence can comprise a primer binding site or a molecular index (e.g., barcode sequence). The tracrRNA extension sequence can comprise one or more affinity tags.

Single-Molecule Guide Linker Sequence

The linker sequence of a single-molecule guide nucleic acid can have a length from about 3 nucleotides to about 100 nucleotides. In Jinek et al., supra, for example, a simple 4 nucleotide "tetraloop" (-GAAA-) was used, Science, 337 (6096):816-821 (2012). An illustrative linker has a length from about 3 nucleotides (nt) to about 90 nt, from about 3 nt to about 80 nt, from about 3 nt to about 70 nt, from about 3 nt to about 60 nt, from about 3 nt to about 50 nt, from about 3 nt to about 40 nt, from about 3 nt to about 30 nt, from about 3 nt to about 20 nt, from about 3 nt to about 10 nt. For example, the linker can have a length from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. The linker of a single-molecule guide nucleic acid can be between 4 and 40 nucleotides. The linker can be at least about 100, 500, 1000, 1500, 2000, 2500, 3000, 3500, 4000, 4500, 5000, 5500, 6000, 6500, or 7000 or more nucleotides. The linker can be at most about 100, 500, 1000, 1500, 2000, 2500, 3000, 3500, 4000, 4500, 5000, 5500, 6000, 6500, or 7000 or more nucleotides.

Linkers can comprise any of a variety of sequences, although in some examples the linker will not comprise sequences that have extensive regions of homology with other portions of the guide RNA, which might cause intra-molecular binding that could interfere with other functional regions of the guide. In Jinek et al., supra, a simple 4 nucleotide sequence -GAAA- was used, Science, 337 (6096):816-821 (2012), but numerous other sequences, including longer sequences can likewise be used.

The linker sequence can comprise a functional moiety. For example, the linker sequence can comprise one or more features, including an aptamer, a ribozyme, a protein-interacting hairpin, a protein binding site, a CRISPR array, an intron, or an exon. The linker sequence can comprise at least about 1, 2, 3, 4, or 5 or more functional moieties. In some examples, the linker sequence can comprise at most about 1, 2, 3, 4, or 5 or more functional moieties.

Complexes of a Genome-Targeting Nucleic Acid and a Site-Directed Polypeptide

A genome-targeting nucleic acid interacts with a site-directed polypeptide (e.g., a nucleic acid-guided nuclease such as Cas9), thereby forming a complex. The genome-targeting nucleic acid guides the site-directed polypeptide to a target nucleic acid.

Ribonucleoprotein Complexes (RNPs)

The site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The site-directed polypeptide can be pre-complexed with one or more sgRNA. The pre-complexed material can then be administered to a cell or a patient. Such pre-complexed material is known as a ribonucleoprotein particle (RNP). The site-directed polypeptide in the RNP can be, for example, a Cas9 endonuclease or a Cpf1 endonuclease. The site-directed polypeptide can be flanked at the N-terminus, the C-terminus, or both the N-terminus and C-terminus by one or more nuclear localization signals (NLSs). For example, a Cas9 endonuclease can be flanked by two NLSs, one NLS located at the N-terminus and the second NLS located at the C-terminus. The NLS can be any NLS known in the art, such as a SV40 NLS. The weight ratio of genome-targeting nucleic acid to site-directed polypeptide in the RNP can be 1:1. For example, the weight ratio of sgRNA to Cas9 endonuclease in the RNP can be 1:1.

Target Sequence Selection

Shifts in the location of the 5' boundary and/or the 3' boundary relative to particular reference loci can be used to facilitate or enhance particular applications of gene editing, which depend in part on the endonuclease system selected for the editing, as further described and illustrated herein.

In a first non-limiting example of such target sequence selection, many endonuclease systems have rules or criteria that can guide the initial selection of potential target sites for cleavage, such as the requirement of a PAM sequence motif in a particular position adjacent to the DNA cleavage sites in the case of CRISPR Type II or Type V endonucleases.

In another nonlimiting example of target sequence selection or optimization, the frequency of off-target activity for a particular combination of target sequence and gene editing endonuclease (i.e. the frequency of DSBs occurring at sites other than the selected target sequence) can be assessed relative to the frequency of on-target activity. In some cases, cells that have been correctly edited at the desired locus can have a selective advantage relative to other cells. Illustrative, but nonlimiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly edited at the desired locus can be positively selected for by one or more screening methods used to identify, sort or otherwise select for cells that have been correctly edited. Both selective advantage and directed selection methods can take advantage of the phenotype associated with the correction. In some cases, cells can be edited two or more times in order to create a second modification that creates a new phenotype that is used to select or purify the intended population of cells. Such a second modification could be created by adding a second gRNA for a selectable or screenable marker. In some cases, cells can be correctly edited at the desired locus using a DNA fragment that contains the cDNA and also a selectable marker.

Whether any selective advantage is applicable or any directed selection is to be applied in a particular case, target sequence selection can also be guided by consideration of off-target frequencies in order to enhance the effectiveness of the application and/or reduce the potential for undesired alterations at sites other than the desired target. As described further and illustrated herein and in the art, the occurrence of off-target activity can be influenced by a number of factors including similarities and dissimilarities between the target site and various off-target sites, as well as the particular endonuclease used. Bioinformatics tools are available that assist in the prediction of off-target activity, and frequently such tools can also be used to identify the most likely sites of off-target activity, which can then be assessed in experimental settings to evaluate relative frequencies of off-target to on-target activity, thereby allowing the selection of sequences that have higher relative on-target activities. Illustrative examples of such techniques are provided herein, and others are known in the art.

Another aspect of target sequence selection relates to homologous recombination events. Sequences sharing regions of homology can serve as focal points for homologous recombination events that result in deletion of intervening sequences. Such recombination events occur during the normal course of replication of chromosomes and other DNA sequences, and also at other times when DNA sequences are being synthesized, such as in the case of repairs of double-strand breaks (DSBs), which occur on a regular basis during the normal cell replication cycle but can also be enhanced by the occurrence of various events (such as UV light and other inducers of DNA breakage) or the presence of certain agents (such as various chemical inducers). Many such inducers cause DSBs to occur indiscriminately in the genome, and DSBs can be regularly induced and repaired in normal cells. During repair, the original sequence can be reconstructed with complete fidelity, however, in some cases, small insertions or deletions (referred to as "indels") are introduced at the DSB site.

DSBs can also be specifically induced at particular locations, as in the case of the endonucleases systems described herein, which can be used to cause directed or preferential gene modification events at selected chromosomal locations. The tendency for homologous sequences to be subject to recombination in the context of DNA repair (as well as replication) can be taken advantage of in a number of circumstances, and is the basis for one application of gene editing systems, such as CRISPR, in which homology directed repair is used to insert a sequence of interest, provided through use of a "donor" polynucleotide, into a desired chromosomal location.

Regions of homology between particular sequences, which can be small regions of "microhomology" that can comprise as few as ten base pairs or less, can also be used to bring about desired deletions. For example, a single DSB can be introduced at a site that exhibits microhomology with a nearby sequence. During the normal course of repair of such DSB, a result that occurs with high frequency is the deletion of the intervening sequence as a result of recombination being facilitated by the DSB and concomitant cellular repair process.

In some circumstances, however, selecting target sequences within regions of homology can also give rise to much larger deletions, including gene fusions (when the deletions are in coding regions), which may or may not be desired given the particular circumstances.

The examples provided herein further illustrate the selection of various target regions for the creation of DSBs designed to induce replacements that result in restoration of RHO protein activity, as well as the selection of specific target sequences within such regions that are designed to minimize off-target events relative to on-target events.

Homology Direct Repair (HDR)/Donor Nucleotides

Homology direct repair is a cellular mechanism for repairing double-stranded breaks (DSBs). The most common form is homologous recombination. There are additional pathways for HDR, including single-strand annealing and alternative-HDR. Genome engineering tools allow researchers to manipulate the cellular homologous recombination pathways to create site-specific modifications to the genome. It has been found that cells can repair a double-stranded break using a synthetic donor molecule provided in trans. Therefore, by introducing a double-stranded break near a specific mutation and providing a suitable donor, targeted changes can be made in the genome. Specific cleavage increases the rate of HDR more than 1,000 fold above the rate of 1 in $10^6$ cells receiving a homologous donor alone. The rate of homology directed repair (HDR) at a particular nucleotide is a function of the distance to the cut site, so choosing overlapping or nearest target sites is important. Gene editing offers the advantage over gene addition, as correcting in situ leaves the rest of the genome unperturbed.

Supplied donors for editing by HDR vary markedly but can contain the intended sequence with small or large flanking homology arms to allow annealing to the genomic DNA. The homology regions flanking the introduced genetic changes can be 30 bp or smaller, or as large as a multi-kilobase cassette that can contain promoters, cDNAs, etc. Both single-stranded and double-stranded oligonucleotide donors have been used. These oligonucleotides range in size from less than 100 nt to over many kb, though longer ssDNA can also be generated and used. Double-stranded donors can be used, including PCR amplicons, plasmids, and mini-circles. In general, it has been found that an AAV vector can be a very effective means of delivery of a donor template, though the packaging limits for individual donors is <5 kb. Active transcription of the donor increased HDR three-fold, indicating the inclusion of promoter may increase conversion. Conversely, CpG methylation of the donor decreased gene expression and HDR.

Donor nucleotides for correcting mutations often are small (<300 bp). This is advantageous, as HDR efficiencies may be inversely related to the size of the donor molecule. Also, it is expected that the donor templates can fit into size constrained AAV molecules, which have been shown to be an effective means of donor template delivery.

In addition to wildtype endonucleases, such as Cas9, nickase variants exist that have one or the other nuclease domain inactivated resulting in cutting of only one DNA strand. HDR can be directed from individual Cas nickases or using pairs of nickases that flank the target area. Donors can be single-stranded, nicked, or dsDNA.

The donor DNA can be supplied with the nuclease or independently by a variety of different methods, for example by transfection, nanoparticle, microinjection, or viral transduction. A range of tethering options has been proposed to increase the availability of the donors for HDR. Examples include attaching the donor to the nuclease, attaching to DNA binding proteins that bind nearby, or attaching to proteins that are involved in DNA end binding or repair.

The repair pathway choice can be guided by a number of culture conditions, such as those that influence cell cycling, or by targeting of DNA repair and associated proteins. For example, to increase HDR, key NHEJ molecules can be suppressed, such as KU70, KU80 or DNA ligase IV.

Without a donor present, the ends from a DNA break or ends from different breaks can be joined using the several non-homologous repair pathways in which the DNA ends are joined with little or no base-pairing at the junction. In addition to canonical NHEJ, there are similar repair mechanisms, such as ANHEJ. If there are two breaks, the intervening segment can be deleted or inverted. NHEJ repair pathways can lead to insertions, deletions or mutations at the joints. NHEJ was used to insert a 15-kb inducible gene expression cassette into a defined locus in human cell lines after nuclease cleavage. The methods of insertion of large inducible gene expression cassettes have been described [Maresca, M., Lin, V. G., Guo, N. & Yang, Y., *Genome Res* 23, 539-546 (2013), Suzuki et al. *Nature,* 540, 144-149 (2016)].

In addition to genome editing by NHEJ or HDR, site-specific gene insertions have been conducted that use both the NHEJ pathway and HDR. A combination approach can be applicable in certain settings, possibly including intron/ exon borders. NHEJ may prove effective for ligation in the intron, while the error-free HDR may be better suited in the coding region.

Illustrative modifications within the RHO gene include replacements within or near (proximal) to the mutations referred to above, such as within the region of less than 3 kb, less than 2 kb, less than 1 kb, less than 0.5 kb upstream or downstream of the specific mutation. Given the relatively wide variations of mutations in the RHO gene, it will be appreciated that numerous variations of the replacements referenced above (including without limitation larger as well as smaller deletions), would be expected to result in restoration of the RHO protein activity.

Such variants can include replacements that are larger in the 5' and/or 3' direction than the specific mutation in question, or smaller in either direction. Accordingly, by "near" or "proximal" with respect to specific replacements, it is intended that the SSB or DSB locus associated with a desired replacement boundary (also referred to herein as an endpoint) can be within a region that is less than about 3 kb from the reference locus, e.g., the mutation site. The SSB or DSB locus can be more proximal and within 2 kb, within 1 kb, within 0.5 kb, or within 0.1 kb. In the case of a small replacement, the desired endpoint can be at or "adjacent to" the reference locus, by which it is intended that the endpoint can be within 100 bp, within 50 bp, within 25 bp, or less than about 10 bp to 5 bp from the reference locus.

Larger or smaller replacements can provide the same benefit, as long as the RHO protein activity is restored. It is thus expected that many variations of the replacements described and illustrated herein can be effective for ameliorating retinitis pigmentosa (RP).

The terms "near" or "proximal" with respect to the SSBs or DSBs refer to the SSBs or DSBs being within 2 kb, within 1 kb, within 0.5 kb, within 0.25 kb, within 0.2 kb, or within 0.1 kb of the P23H mutation.

Nucleic Acid Modifications (Chemical and Structural Modifications)

In some cases, polynucleotides introduced into cells can comprise one or more modifications that can be used individually or in combination, for example, to enhance activity, stability or specificity, alter delivery, reduce innate immune responses in host cells, or for other enhancements, as further described herein and known in the art.

In certain examples, modified polynucleotides can be used in the CRISPR/Cas9/Cpf1 system, in which case the guide RNAs (either single-molecule guides or double-molecule guides) and/or a DNA or an RNA encoding a Cas or Cpf1 endonuclease introduced into a cell can be modified, as described and illustrated below. Such modified polynucleotides can be used in the CRISPR/Cas9/Cpf1 system to edit any one or more genomic loci.

Using the CRISPR/Cas9/Cpf1 system for purposes of non-limiting illustrations of such uses, modifications of guide RNAs can be used to enhance the formation or stability of the CRISPR/Cas9/Cpf1 genome editing complex comprising guide RNAs, which can be single-molecule guides or double-molecule, and a Cas or Cpf1 endonuclease. Modifications of guide RNAs can also or alternatively be used to enhance the initiation, stability or kinetics of interactions between the genome editing complex with the target sequence in the genome, which can be used, for example, to enhance on-target activity. Modifications of guide RNAs can also or alternatively be used to enhance specificity, e.g., the relative rates of genome editing at the on-target site as compared to effects at other (off-target) sites.

Modifications can also or alternatively be used to increase the stability of a guide RNA, e.g., by increasing its resistance to degradation by ribonucleases (RNases) present in a cell, thereby causing its half-life in the cell to be increased. Modifications enhancing guide RNA half-life can be particularly useful in aspects in which a Cas or Cpf1 endonuclease is introduced into the cell to be edited via an RNA that needs to be translated in order to generate endonuclease, because increasing the half-life of guide RNAs introduced at the same time as the RNA encoding the endonuclease can be used to increase the time that the guide RNAs and the encoded Cas or Cpf1 endonuclease co-exist in the cell.

Modifications can also or alternatively be used to decrease the likelihood or degree to which RNAs introduced into cells elicit innate immune responses. Such responses, which have been well characterized in the context of RNA interference (RNAi), including small-interfering RNAs (siRNAs), as described below and in the art, tend to be associated with reduced half-life of the RNA and/or the elicitation of cytokines or other factors associated with immune responses.

One or more types of modifications can also be made to RNAs encoding an endonuclease that are introduced into a cell, including, without limitation, modifications that enhance the stability of the RNA (such as by increasing its degradation by RNAses present in the cell), modifications that enhance translation of the resulting product (i.e. the endonuclease), and/or modifications that decrease the likelihood or degree to which the RNAs introduced into cells elicit innate immune responses.

Combinations of modifications, such as the foregoing and others, can likewise be used. In the case of CRISPR/Cas9/Cpf1, for example, one or more types of modifications can be made to guide RNAs (including those exemplified above), and/or one or more types of modifications can be made to RNAs encoding Cas endonuclease (including those exemplified above).

By way of illustration, guide RNAs used in the CRISPR/Cas9/Cpf1 system, or other smaller RNAs can be readily synthesized by chemical means, enabling a number of modifications to be readily incorporated, as illustrated below and described in the art. While chemical synthetic procedures are continually expanding, purifications of such RNAs by procedures such as high-performance liquid chromatography (HPLC, which avoids the use of gels such as PAGE) tends to become more challenging as polynucleotide lengths increase significantly beyond a hundred or so nucleotides. One approach that can be used for generating chemically modified RNAs of greater length is to produce two or more molecules that are ligated together. Much longer RNAs, such as those encoding a Cas9 endonuclease, are more readily generated enzymatically. While fewer types of modifications are available for use in enzymatically produced RNAs, there are still modifications that can be used to, e.g., enhance stability, reduce the likelihood or degree of innate immune response, and/or enhance other attributes, as described further below and in the art; and new types of modifications are regularly being developed.

By way of illustration of various types of modifications, especially those used frequently with smaller chemically synthesized RNAs, modifications can comprise one or more nucleotides modified at the 2' position of the sugar, in some aspects a 2'-O-alkyl, 2'-O-alkyl-O-alkyl, or 2'-fluoro-modified nucleotide. In some examples, RNA modifications can comprise 2'-fluoro, 2'-amino or 2'-O-methyl modifications on the ribose of pyrimidines, abasic residues, or an inverted base at the 3' end of the RNA. Such modifications can be routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligonucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Some oligonucleotides are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH); amide backbones [see De Mesmaeker et al., Ace. Chem. Res., 28:366-374 (1995)]; morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Braasch and David Corey, Biochemistry, 41(14): 4503-4510 (2002); Genesis, Volume 30, Issue 3, (2001); Heasman, Dev. Biol., 243: 209-214 (2002); Nasevicius et al., Nat. Genet., 26:216-220 (2000); Lacerra et al., Proc. Natl. Acad. Sci., 97: 9591-9596 (2000); and U.S. Pat. No. 5,034,506, issued Jul. 23, 1991.

Cyclohexenyl nucleic acid oligonucleotide mimetics are described in Wang et al., J. Am. Chem. Soc., 122: 8595-8602 (2000).

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

One or more substituted sugar moieties can also be included, e.g., one of the following at the 2' position: OH, SH, $SCH_3$, F, OCN, $OCH_3$ $OCH_3$, $OCH_3$ O($CH_2$)n $CH_3$, O($CH_2$)n $NH_2$, or O($CH_2$)n $CH_3$, where n is from 1 to about 10; C1 to C10 lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. In some aspects, a modification includes 2'-methoxyethoxy (2'-O—$CH_2CH_2OCH_3$, also known as 2'-O-(2-methoxyethyl)) (Martin et al, Helv. Chim. Acta, 1995, 78, 486). Other modifications include 2'-methoxy (2'-O—$CH_3$), 2'-propoxy (2'-$OCH_2$ $CH_2CH_3$) and 2'-fluoro (2'-F). Similar modifications can also be made at other positions on the oligonucleotide, particularly the 3' position of the sugar on the 3' terminal nucleotide and the 5' position of 5' terminal nucleotide. Oligonucleotides can also have sugar mimetics, such as cyclobutyls in place of the pentofuranosyl group.

In some examples, both a sugar and an internucleoside linkage, i.e., the backbone, of the nucleotide units can be replaced with novel groups. The base units can be maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide can be replaced with an amide containing backbone, for example, an aminoethylglycine backbone. The nucleobases can be retained and bound directly or indirectly to aza nitrogen atoms of the amide portion of the backbone. Representative U.S. patents that teach the preparation of PNA compounds comprise, but are not limited to, U.S. Pat. Nos. 5,539,082; 5,714,331; and 5,719,262. Further teaching of PNA compounds can be found in Nielsen et al, Science, 254: 1497-1500 (1991).

Guide RNAs can also include, additionally or alternatively, nucleobase (often referred to in the art simply as "base") modifications or substitutions. As used herein, "unmodified" or "natural" nucleobases include adenine (A), guanine (G), thymine (T), cytosine (C), and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino) adenine, 2-(imidazolylalkyl)adenine, 2-(aminoalklyamino) adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl) adenine, and 2,6-diaminopurine. Kornberg, A., DNA Replication, W. H. Freeman & Co., San Francisco, pp. 75-77 (1980); Gebeyehu et al., Nucl. Acids Res. 15:4513 (1997). A "universal" base known in the art, e.g., inosine, can also be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are aspects of base substitutions.

Modified nucleobases can comprise other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine, and 3-deazaguanine and 3-deazaadenine.

Further, nucleobases can comprise those disclosed in U.S. Pat. No. 3,687,808, those disclosed in 'The Concise Encyclopedia of Polymer Science and Engineering', pages 858-859, Kroschwitz, J. I., ed. John Wiley & Sons, 1990, those disclosed by Englisch et al., Angewandle Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are aspects of base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,681,941; 5,750,692; 5,763,588; 5,830,653; 6,005,096; and U.S. Patent Application Publication 2003/0158403.

Thus, the term "modified" refers to a non-natural sugar, phosphate, or base that is incorporated into a guide RNA, an endonuclease, or both a guide RNA and an endonuclease. It is not necessary for all positions in a given oligonucleotide to be uniformly modified, and in fact more than one of the aforementioned modifications can be incorporated in a single oligonucleotide, or even in a single nucleoside within an oligonucleotide.

The guide RNAs and/or mRNA (or DNA) encoding an endonuclease can be chemically linked to one or more moieties or conjugates that enhance the activity, cellular distribution, or cellular uptake of the oligonucleotide. Such moieties comprise, but are not limited to, lipid moieties such as a cholesterol moiety [Letsinger et al., Proc. Natl. Acad. Sci. USA, 86: 6553-6556 (1989)]; cholic acid [Manoharan et al., Bioorg. Med. Chem. Let., 4: 1053-1060 (1994)]; a thioether, e.g., hexyl-S-tritylthiol [Manoharan et al, Ann. N. Y. Acad. Sci., 660: 306-309 (1992) and Manoharan et al., Bioorg. Med. Chem. Let., 3: 2765-2770 (1993)]; a thiocholesterol [Oberhauser et al., Nucl. Acids Res., 20: 533-538 (1992)]; an aliphatic chain, e.g., dodecandiol or undecyl residues [Kabanov et al., FEBS Lett., 259: 327-330 (1990) and Svinarchuk et al., Biochimie, 75: 49-54 (1993)]; a phospholipid, e.g., di-hexadecyl-rac-glycerol or triethylammonium 1,2-di-O-hexadecyl-rac-glycero-3-H-phosphonate [Manoharan et al., Tetrahedron Lett., 36: 3651-3654 (1995) and Shea et al., Nucl. Acids Res., 18: 3777-3783 (1990)]; a polyamine or a polyethylene glycol chain [Mancharan et al., Nucleosides & Nucleotides, 14: 969-973 (1995)]; adamantane acetic acid [Manoharan et al., Tetrahedron Lett., 36: 3651-3654 (1995)]; a palmityl moiety [(Mishra et al., Biochim. Biophys. Acta, 1264: 229-237 (1995)]; or an octadecylamine or hexylamino-carbonyl-t oxycholesterol moiety [Crooke et al., J. Pharmacol. Exp. Ther., 277: 923-937 (1996)]. See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599, 928 and 5,688,941.

Sugars and other moieties can be used to target proteins and complexes comprising nucleotides, such as cationic polysomes and liposomes, to particular sites. For example, hepatic cell directed transfer can be mediated via asialoglycoprotein receptors (ASGPRs); see, e.g., Hu, et al., Protein Pept Lett. 21(10):1025-30 (2014). Other systems known in the art and regularly developed can be used to target biomolecules of use in the present case and/or complexes thereof to particular target cells of interest.

These targeting moieties or conjugates can include conjugate groups covalently bound to functional groups, such as primary or secondary hydroxyl groups. Conjugate groups of the present disclosure include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this present disclosure, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present disclosure. Representative conjugate groups are disclosed in International Patent Application No. PCT/US92/09196, filed Oct. 23, 1992 (published as WO1993007883), and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O- hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Longer polynucleotides that are less amenable to chemical synthesis and are typically produced by enzymatic synthesis can also be modified by various means. Such modifications can include, for example, the introduction of certain nucleotide analogs, the incorporation of particular sequences or other moieties at the 5' or 3' ends of molecules, and other modifications. By way of illustration, the mRNA encoding Cas9 is approximately 4 kb in length and can be synthesized by in vitro transcription. Modifications to the mRNA can be applied to, e.g., increase its translation or stability (such as by increasing its resistance to degradation with a cell), or to reduce the tendency of the RNA to elicit an innate immune response that is often observed in cells following introduction of exogenous RNAs, particularly longer RNAs such as that encoding Cas9.

Numerous such modifications have been described in the art, such as polyA tails, 5' cap analogs (e.g., Anti Reverse Cap Analog (ARCA) or m7G(5')ppp(5')G (mCAP)), modified 5' or 3' untranslated regions (UTRs), use of modified bases (such as Pseudo-UTP, 2-Thio-UTP, 5-Methylcytidine-5'-Triphosphate (5-Methyl-CTP) or N6-Methyl-ATP), or treatment with phosphatase to remove 5' terminal phosphates. These and other modifications are known in the art, and new modifications of RNAs are regularly being developed.

There are numerous commercial suppliers of modified RNAs, including for example, TriLink Biotech, AxoLabs, Bio-Synthesis Inc., Dharmacon and many others. As described by TriLink, for example, 5-Methyl-CTP can be used to impart desirable characteristics, such as increased nuclease stability, increased translation or reduced interaction of innate immune receptors with in vitro transcribed RNA. 5-Methylcytidine-5'-Triphosphate (5-Methyl-CTP), N6-Methyl-ATP, as well as Pseudo-UTP and 2-Thio-UTP, have also been shown to reduce innate immune stimulation in culture and in vivo while enhancing translation, as illustrated in publications by Kormann et al. and Warren et al. referred to below.

It has been shown that chemically modified mRNA delivered in vivo can be used to achieve improved therapeutic effects; see, e.g., Kormann et al., Nature Biotechnology 29, 154-157 (2011). Such modifications can be used, for example, to increase the stability of the RNA molecule and/or reduce its immunogenicity. Using chemical modifications such as Pseudo-U, N6-Methyl-A, 2-Thio-U and 5-Methyl-C, it was found that substituting just one quarter of the uridine and cytidine residues with 2-Thio-U and 5-Methyl-C respectively resulted in a significant decrease in toll-like receptor (TLR) mediated recognition of the mRNA in mice. By reducing the activation of the innate immune system, these modifications can be used to effectively increase the stability and longevity of the mRNA in vivo; see, e.g., Kormann et al., supra.

It has also been shown that repeated administration of synthetic messenger RNAs incorporating modifications designed to bypass innate anti-viral responses can reprogram differentiated human cells to pluripotency. See, e.g., Warren, et al., Cell Stem Cell, 7(5):618-30 (2010). Such modified mRNAs that act as primary reprogramming proteins can be an efficient means of reprogramming multiple human cell types. Such cells are referred to as induced pluripotency stem cells (iPSCs), and it was found that enzymatically synthesized RNA incorporating 5-Methyl-CTP, Pseudo-UTP and an Anti Reverse Cap Analog (ARCA) could be used to effectively evade the cell's antiviral response; see, e.g., Warren et al., supra.

Other modifications of polynucleotides described in the art include, for example, the use of polyA tails, the addition of 5' cap analogs such as (m7G(5')ppp(5')G (mCAP)), modifications of 5' or 3' untranslated regions (UTRs), or treatment with phosphatase to remove 5' terminal phosphates—and new approaches are regularly being developed.

A number of compositions and techniques applicable to the generation of modified RNAs for use herein have been developed in connection with the modification of RNA interference (RNAi), including small-interfering RNAs (siRNAs). siRNAs present particular challenges in vivo because their effects on gene silencing via mRNA interference are generally transient, which can require repeat administration. In addition, siRNAs are double-stranded RNAs (dsRNA) and mammalian cells have immune responses that have evolved to detect and neutralize dsRNA, which is often a by-product of viral infection. Thus, there are mammalian enzymes such as PKR (dsRNA-responsive kinase), and potentially retinoic acid-inducible gene I (RIG-I), that can mediate cellular responses to dsRNA, as well as Toll-like receptors (such as TLR3, TLR7 and TLR8) that can trigger the induction of cytokines in response to such molecules; see, e.g., the reviews by Angart et al., Pharmaceuticals (Basel) 6(4): 440-468 (2013); Kanasty et al., Molecular Therapy 20(3): 513-524 (2012); Burnett et al., Biotechnol J. 6(9):1130-46 (2011); Judge and MacLachlan, Hum Gene Ther 19(2):111-24 (2008).

A large variety of modifications have been developed and applied to enhance RNA stability, reduce innate immune responses, and/or achieve other benefits that can be useful in connection with the introduction of polynucleotides into human cells, as described herein; see, e.g., the reviews by Whitehead K A et al., Annual Review of Chemical and Biomolecular Engineering, 2: 77-96 (2011); Gaglione and Messere, Mini Rev Med Chem, 10(7):578-95 (2010); Chernolovskaya et al, Curr Opin Mol Ther., 12(2):158-67 (2010); Deleavey et al., Curr Protoc Nucleic Acid Chem Chapter 16:Unit 16.3 (2009); Behlke, Oligonucleotides 18(4):305-19 (2008); Fucini et al., Nucleic Acid Ther 22(3): 205-210 (2012); Bremsen et al., Front Genet 3:154 (2012).

As noted above, there are a number of commercial suppliers of modified RNAs, many of which have specialized in modifications designed to improve the effectiveness of siRNAs. A variety of approaches are offered based on various findings reported in the literature. For example, Dharmacon notes that replacement of a non-bridging oxygen with sulfur (phosphorothioate, PS) has been extensively used to improve nuclease resistance of siRNAs, as reported by Kole, Nature Reviews Drug Discovery 11:125-140 (2012). Modifications of the 2'-position of the ribose have been reported to improve nuclease resistance of the internucleotide phosphate bond while increasing duplex stability (Tm), which has also been shown to provide protection from immune activation. A combination of moderate PS backbone modifications with small, well-tolerated 2'-substitutions (2'-O-Methyl, 2'-Fluoro, 2'-Hydro) have been associated with highly stable siRNAs for applications in vivo, as reported by Soutschek et al. Nature 432:173-178 (2004); and 2'-O-Methyl modifications have been reported to be effective in improving stability as reported by Volkov, Oligonucleotides 19:191-202 (2009). With respect to decreasing the induction of innate immune responses, modifying specific sequences with 2'-O-Methyl, 2'-Fluoro, 2'-Hydro have been reported to reduce TLR7/TLR8 interaction while generally preserving silencing activity; see, e.g., Judge et al., Mol. Ther. 13:494-505 (2006); and Cekaite et al., J. Mol. Biol. 365:90-108 (2007). Additional modifications, such as 2-thiouracil, pseudouracil, 5-methylcytosine, 5-methyluracil, and N6-methyladenosine have also been shown to minimize the immune effects mediated by TLR3, TLR7, and TLR8; see, e.g., Kariko, K. et al., Immunity 23:165-175 (2005).

As is also known in the art, and commercially available, a number of conjugates can be applied to polynucleotides, such as RNAs, for use herein that can enhance their delivery and/or uptake by cells, including for example, cholesterol, tocopherol and folic acid, lipids, peptides, polymers, linkers and aptamers; see, e.g., the review by Winkler, Ther. Deliv. 4:791-809 (2013).

Codon-Optimization

A polynucleotide encoding a site-directed polypeptide can be codon-optimized according to methods standard in the art for expression in the cell containing the target DNA of interest. For example, if the intended target nucleic acid is in a human cell, a human codon-optimized polynucleotide encoding Cas9 is contemplated for use for producing the Cas9 polypeptide.

Nucleic Acids Encoding System Components

The present disclosure provides a nucleic acid comprising a nucleotide sequence encoding a genome-targeting nucleic acid of the disclosure, a site-directed polypeptide of the disclosure, and/or any nucleic acid or proteinaceous molecule necessary to carry out the aspects of the methods of the disclosure.

The nucleic acid encoding a genome-targeting nucleic acid of the disclosure, a site-directed polypeptide of the disclosure, and/or any nucleic acid or proteinaceous molecule necessary to carry out the aspects of the methods of the disclosure can comprise a vector (e.g., a recombinant expression vector).

The term "vector" refers to a nucleic acid molecule capable of transporting another nucleic acid to which it has been linked. One type of vector is a "plasmid", which refers to a circular double-stranded DNA loop into which additional nucleic acid segments can be ligated. Another type of vector is a viral vector, wherein additional nucleic acid segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome.

In some examples, vectors can be capable of directing the expression of nucleic acids to which they are operatively linked. Such vectors are referred to herein as "recombinant expression vectors", or more simply "expression vectors", which serve equivalent functions.

The term "operably linked" means that the nucleotide sequence of interest is linked to regulatory sequence(s) in a manner that allows for expression of the nucleotide sequence. The term "regulatory sequence" is intended to include, for example, promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a nucleotide sequence in many types of host cells, and those that direct expression of the nucleotide sequence only in certain host cells (e.g., tissue-specific regulatory sequences). It will be appreciated by those skilled in the art that the design of the expression vector can depend on such factors as the choice of the target cell, the level of expression desired, and the like.

Expression vectors contemplated include, but are not limited to, viral vectors based on vaccinia virus, poliovirus, adenovirus, adeno-associated virus, SV40, herpes simplex virus, human immunodeficiency virus, retrovirus (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus) and other recombinant vectors. Other vectors contemplated for eukaryotic target cells include, but are not limited to, the vectors pXT1, pSG5, pSVK3, pBPV, pMSG, and pSVLSV40 (Pharmacia). Additional vectors contemplated for eukaryotic target cells include, but are not limited to, the vectors pCTx-1, pCTx-2, and pCTx-3. Other vectors can be used so long as they are compatible with the host cell.

In some examples, a vector can comprise one or more transcription and/or translation control elements. Depending on the host/vector system utilized, any of a number of suitable transcription and translation control elements, including constitutive and inducible promoters, transcription enhancer elements, transcription terminators, etc. can be used in the expression vector. The vector can be a self-inactivating vector that either inactivates the viral sequences or the components of the CRISPR machinery or other elements.

Non-limiting examples of suitable eukaryotic promoters (i.e., promoters functional in a eukaryotic cell) include those from cytomegalovirus (CMV) immediate early, herpes simplex virus (HSV) thymidine kinase, early and late SV40, long terminal repeats (LTRs) from retrovirus, human elongation factor-1 promoter (EF1), a hybrid construct comprising the cytomegalovirus (CMV) enhancer fused to the chicken beta-actin promoter (CAG), murine stem cell virus promoter (MSCV), phosphoglycerate kinase-1 locus promoter (PGK), and mouse metallothionein-I.

For expressing small RNAs, including guide RNAs used in connection with Cas endonuclease, various promoters such as RNA polymerase III promoters, including for example U6 and H1, can be advantageous. Descriptions of and parameters for enhancing the use of such promoters are known in art, and additional information and approaches are regularly being described; see, e.g., Ma, H. et al., *Molecular Therapy—Nucleic Acids* 3, e161 (2014) doi:10.1038/mtna.2014.12.

The expression vector can also contain a ribosome binding site for translation initiation and a transcription terminator. The expression vector can also comprise appropriate sequences for amplifying expression. The expression vector can also include nucleotide sequences encoding non-native tags (e.g., histidine tag, hemagglutinin tag, green fluorescent protein, etc.) that are fused to the site-directed polypeptide, thus resulting in a fusion protein.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The nucleic acid encoding a genome-targeting nucleic acid of the disclosure and/or a site-directed polypeptide can be packaged into or on the surface of delivery vehicles for delivery to cells. Delivery vehicles contemplated include, but are not limited to, nanospheres, liposomes, quantum dots, nanoparticles, polyethylene glycol particles, hydrogels, and micelles. As described in the art, a variety of targeting moieties can be used to enhance the preferential interaction of such vehicles with desired cell types or locations.

Introduction of the complexes, polypeptides, and nucleic acids of the disclosure into cells can occur by viral or bacteriophage infection, transfection, conjugation, protoplast fusion, lipofection, electroporation, nucleofection, calcium phosphate precipitation, polyethyleneimine (PEI)-mediated transfection, DEAE-dextran mediated transfection, liposome-mediated transfection, particle gun technology, calcium phosphate precipitation, direct micro-injection, nanoparticle-mediated nucleic acid delivery, and the like.

microRNA (miRNA)

Another class of gene regulatory regions is microRNA (miRNA) binding sites. miRNAs are non-coding RNAs that play key roles in post-transcriptional gene regulation. miRNAs can regulate the expression of 30% of all mammalian protein-encoding genes. Specific and potent gene silencing by double stranded RNA (RNAi) was discovered, plus additional small noncoding RNA (Canver, M. C. et al., Nature (2015)). The largest class of non-coding RNAs important for gene silencing is miRNAs. In mammals, miRNAs are first transcribed as long RNA transcripts, which can be separate transcriptional units, part of protein introns, or other transcripts. The long transcripts are called primary miRNA (pri-miRNA) that include imperfectly base-paired hairpin structures. These pri-miRNA can be cleaved into one or more shorter precursor miRNAs (pre-miRNAs) by Microprocessor, a protein complex in the nucleus, involving Drosha.

Pre-miRNAs are short stem loops ~70 nucleotides in length with a 2-nucleotide 3'-overhang that are exported into the mature 19-25 nucleotide miRNA:miRNA* duplexes. The miRNA strand with lower base pairing stability (the guide strand) can be loaded onto the RNA-induced silencing complex (RISC). The passenger guide strand (marked with *), can be functional, but is usually degraded. The mature miRNA tethers RISC to partly complementary sequence motifs in target mRNAs predominantly found within the 3' untranslated regions (UTRs) and induces posttranscriptional gene silencing (Bartel, D. P. Cell 136, 215-233 (2009); Saj, A. & Lai, E. C. Curr Opin Genet Dev 21, 504-510 (2011)).

miRNAs can be important in development, differentiation, cell cycle and growth control, and in virtually all biological pathways in mammals and other multicellular organisms. miRNAs can also be involved in cell cycle control, apoptosis and stem cell differentiation, hematopoiesis, hypoxia, muscle development, neurogenesis, insulin secretion, cholesterol metabolism, aging, viral replication and immune responses.

A single miRNA can target hundreds of different mRNA transcripts, while an individual transcript can be targeted by many different miRNAs. More than 28645 miRNAs have been annotated in the latest release of miRBase (v.21). Some miRNAs can be encoded by multiple loci, some of which can be expressed from tandemly co-transcribed clusters. The features allow for complex regulatory networks with multiple pathways and feedback controls. miRNAs can be integral parts of these feedback and regulatory circuits and can help regulate gene expression by keeping protein production within limits (Herranz, H. & Cohen, S. M. Genes Dev 24, 1339-1344 (2010); Posadas, D. M. & Carthew, R. W. Curr Opin Genet Dev 27, 1-6 (2014)).

miRNAs can also be important in a large number of human diseases that are associated with abnormal miRNA expression. This association underscores the importance of the miRNA regulatory pathway. Recent miRNA deletion studies have linked miRNAs with regulation of the immune responses (Stern-Ginossar, N. et al., Science 317, 376-381 (2007)).

miRNAs also have a strong link to cancer and can play a role in different types of cancer. miRNAs have been found to be downregulated in a number of tumors. miRNAs can be important in the regulation of key cancer-related pathways, such as cell cycle control and the DNA damage response, and can therefore be used in diagnosis and can be targeted clinically. miRNAs can delicately regulate the balance of angiogenesis, such that experiments depleting all miRNAs suppress tumor angiogenesis (Chen, S. et al., Genes Dev 28, 1054-1067 (2014)).

As has been shown for protein coding genes, miRNA genes can also be subject to epigenetic changes occurring with cancer. Many miRNA loci can be associated with CpG islands increasing their opportunity for regulation by DNA methylation (Weber, B., Stresemann, C., Brueckner, B. & Lyko, F. Cell Cycle 6, 1001-1005 (2007)). The majority of studies have used treatment with chromatin remodeling drugs to reveal epigenetically silenced miRNAs.

In addition to their role in RNA silencing, miRNAs can also activate translation (Posadas, D. M. & Carthew, R. W. Curr Opin Genet Dev 27, 1-6 (2014)). Knocking out these sites can lead to decreased expression of the targeted gene, while introducing these sites can increase expression.

Individual miRNAs can be knocked out most effectively by mutating the seed sequence (bases 2-8 of the miRNA), which can be important for binding specificity. Cleavage in this region, followed by mis-repair by NHEJ can effectively abolish miRNA function by blocking binding to target sites. miRNAs could also be inhibited by specific targeting of the special loop region adjacent to the palindromic sequence. Catalytically inactive Cas9 can also be used to inhibit shRNA expression (Zhao, Y. et al., Sci Rep 4, 3943 (2014)). In addition to targeting the miRNA, the binding sites can also be targeted and mutated to prevent the silencing by miRNA.

According to the present disclosure, any of the miRNAs or their binding sites can be incorporated into the compositions of the invention.

The compositions can have a region such as, but not limited to, a region comprising the sequence of any of the miRNAs listed in SEQ ID NOs: 613-4696, the reverse complement of the miRNAs listed in SEQ ID NOs: 613-4696, or the miRNA anti-seed region of any of the miRNAs listed in SEQ ID NOs: 613-4696.

The compositions of the invention can comprise one or more miRNA target sequences, miRNA sequences, or miRNA seeds. Such sequences can correspond to any known miRNA such as those taught in US Publication No. 2005/0261218 and US Publication No. 2005/0059005. As a non-limiting example, known miRNAs, their sequences, and their binding site sequences in the human genome are listed in SEQ ID NOs: 613-4696.

A miRNA sequence comprises a "seed" region, i.e., a sequence in the region of positions 2-8 of the mature miRNA, which sequence has perfect Watson-Crick complementarity to the miRNA target sequence. A miRNA seed can comprise positions 2-8 or 2-7 of the mature miRNA. In some examples, a miRNA seed can comprise 7 nucleotides (e.g., nucleotides 2-8 of the mature miRNA), wherein the seed-complementary site in the corresponding miRNA target is flanked by an adenine (A) opposed to miRNA position 1. In some examples, a miRNA seed can comprise 6 nucleotides (e.g., nucleotides 2-7 of the mature miRNA), wherein the seed-complementary site in the corresponding miRNA target is flanked by an adenine (A) opposed to miRNA position 1. See for example, Grimson A, Farh K K, Johnston W K, Garrett-Engele P, Lim L P, Bartel D P; Mol Cell. 2007 Jul. 6; 27(1):91-105. The bases of the miRNA seed have complete complementarity with the target sequence.

Identification of miRNA, miRNA target regions, and their expression patterns and role in biology have been reported (Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403.

For example, if the composition is not intended to be delivered to the liver but ends up there, then miR-122, a miRNA abundant in liver, can inhibit the expression of the sequence delivered if one or multiple target sites of miR-122 are engineered into the polynucleotide encoding that target sequence. Introduction of one or multiple binding sites for different miRNA can be engineered to further decrease the longevity, stability, and protein translation hence providing an additional layer of tenability.

As used herein, the term "miRNA site" refers to a miRNA target site or a miRNA recognition site, or any nucleotide sequence to which a miRNA binds or associates. It should be understood that "binding" can follow traditional Watson-Crick hybridization rules or can reflect any stable association of the miRNA with the target sequence at or adjacent to the miRNA site.

Conversely, for the purposes of the compositions of the present disclosure, miRNA binding sites can be engineered out of (i.e. removed from) sequences in which they naturally occur in order to increase protein expression in specific tissues. For example, miR-122 binding sites can be removed to improve protein expression in the liver.

Specifically, miRNAs are known to be differentially expressed in immune cells (also called hematopoietic cells), such as antigen presenting cells (APCs) (e.g. dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in the immune cells, particularly abundant in myeloid dendritic cells. Introducing the miR-142 binding site into the 3'-UTR of a polypeptide of the present disclosure can selectively suppress the gene expression in the antigen presenting cells through miR-142 mediated mRNA degradation, limiting antigen presentation in professional APCs (e.g. dendritic cells) and thereby preventing antigen-mediated immune response after gene delivery (see, Annoni A et al., blood, 2009, 114, 5152-5161.

In one example, miRNAs binding sites that are known to be expressed in immune cells, in particular, the antigen presenting cells, can be engineered into the polynucleotides to suppress the expression of the polynucleotide in APCs through miRNA mediated RNA degradation, subduing the antigen-mediated immune response, while the expression of the polynucleotide is maintained in non-immune cells where the immune cell specific miRNAs are not expressed.

Many miRNA expression studies have been conducted, and are described in the art, to profile the differential expression of miRNAs in various cancer cells/tissues and other diseases. Some miRNAs are abnormally over-expressed in certain cancer cells and others are under-expressed. For example, miRNAs are differentially expressed in cancer cells (WO2008/154098, US2013/0059015, US2013/0042333, WO2011/157294); cancer stem cells (US2012/0053224); pancreatic cancers and diseases (US2009/0131348, US2011/0171646, US2010/0286232, U.S. Pat. No. 8,389,210); asthma and inflammation (U.S. Pat. No. 8,415,096); prostate cancer (US2013/0053264); hepatocellular carcinoma (WO2012/151212, US2012/0329672, WO2008/054828, U.S. Pat. No. 8,252,538); lung cancer cells (WO2011/076143, WO2013/033640, WO2009/070653, U52010/0323357); cutaneous T-cell lymphoma (WO2013/011378); colorectal cancer cells (WO2011/0281756, WO2011/076142); cancer positive lymph nodes (WO2009/100430, US2009/0263803); nasopharyngeal carcinoma (EP2112235); chronic obstructive pulmonary disease (US2012/0264626, US2013/0053263); thyroid cancer (WO2013/066678); ovarian cancer cells (US2012/0309645, WO2011/095623); breast cancer cells (WO2008/154098, WO2007/081740, US2012/0214699), leukemia and lymphoma (WO2008/073915, US2009/0092974, US2012/0316081, US2012/0283310, WO2010/018563.

Human Cells

For ameliorating retinitis pigmentosa (RP) or any disorder associated with RHO, as described and illustrated herein, the principal targets for gene editing are human cells. For example, in the ex vivo methods, the human cells can be somatic cells, which after being modified using the techniques as described, can give rise to differentiated cells, e.g., photoreceptor cells or retinal progenitor cells. For example, in the in vivo methods, the human cells can be photoreceptor cells or retinal progenitor cells.

By performing gene editing in autologous cells that are derived from and therefore already completely matched with the patient in need, it is possible to generate cells that can be safely re-introduced into the patient, and effectively give rise to a population of cells that can be effective in ameliorating one or more clinical conditions associated with the patient's disease.

Progenitor cells (also referred to as stem cells herein) are capable of both proliferation and giving rise to more progenitor cells, these in turn having the ability to generate a large number of mother cells that can in turn give rise to differentiated or differentiable daughter cells. The daughter cells themselves can be induced to proliferate and produce progeny that subsequently differentiate into one or more mature cell types, while also retaining one or more cells with parental developmental potential. The term "stem cell" refers then, to a cell with the capacity or potential, under particular circumstances, to differentiate to a more specialized or differentiated phenotype, and which retains the capacity, under certain circumstances, to proliferate without substantially differentiating. In one aspect, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell can derive from a multipotent cell that itself is derived from a multipotent cell, and so on. While each of these multipotent cells can be considered stem cells, the range of cell types that each can give rise to can vary considerably. Some differentiated cells also have the capacity to give rise to cells of greater developmental potential. Such capacity can be natural or can be induced artificially upon treatment with various factors. In many biological instances, stem cells can also be "multipotent" because they can produce progeny of more than one distinct cell type, but this is not required for "stem-ness."

Self-renewal can be another important aspect of the stem cell. In theory, self-renewal can occur by either of two major mechanisms. Stem cells can divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Generally, "progenitor cells" have a cellular phenotype that is more primitive (i.e., is at an earlier step along a developmental pathway or progression than is a fully differentiated cell). Often, progenitor cells also have significant or very high proliferative potential. Progenitor cells can give rise to multiple distinct differentiated cell types or to a single differentiated cell type, depending on the developmental pathway and on the environment in which the cells develop and differentiate.

In the context of cell ontogeny, the adjective "differentiated," or "differentiating" is a relative term. A "differentiated cell" is a cell that has progressed further down the developmental pathway than the cell to which it is being compared. Thus, stem cells can differentiate into lineage-restricted precursor cells (such as a myocyte progenitor cell), which in turn can differentiate into other types of precursor cells further down the pathway (such as a myocyte precursor), and then to an end-stage differentiated cell, such as a myocyte, which plays a characteristic role in a certain tissue type, and can or cannot retain the capacity to proliferate further.

Induced Pluripotent Stem Cells

The genetically engineered human cells described herein can be induced pluripotent stem cells (iPSCs). An advantage of using iPSCs is that the cells can be derived from the same subject to which the progenitor cells are to be administered. That is, a somatic cell can be obtained from a subject, reprogrammed to an induced pluripotent stem cell, and then re-differentiated into a progenitor cell to be administered to the subject (e.g., autologous cells). Because the progenitors are essentially derived from an autologous source, the risk of engraftment rejection or allergic response can be reduced compared to the use of cells from another subject or group of subjects. In addition, the use of iPSCs negates the need for cells obtained from an embryonic source. Thus, in one aspect, the stem cells used in the disclosed methods are not embryonic stem cells.

Although differentiation is generally irreversible under physiological contexts, several methods have been recently developed to reprogram somatic cells to iPSCs. Exemplary methods are known to those of skill in the art and are described briefly herein below.

The term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. Reprogramming can encompasse complete reversion of the differentiation state of a differentiated cell (e.g., a somatic cell) to a pluripotent state or a multipotent state. Reprogramming can encompasse complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain examples described herein, reprogramming of a differentiated cell (e.g., a somatic cell) can cause the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a myogenic stem cell). Reprogramming is also distinct from promoting the self-renewal or proliferation of cells that are already pluripotent or multipotent, although the compositions and methods described herein can also be of use for such purposes, in some examples.

Many methods are known in the art that can be used to generate pluripotent stem cells from somatic cells. Any such method that reprograms a somatic cell to the pluripotent phenotype would be appropriate for use in the methods described herein.

Reprogramming methodologies for generating pluripotent cells using defined combinations of transcription factors have been described. Mouse somatic cells can be converted to ES cell-like cells with expanded developmental potential by the direct transduction of Oct4, Sox2, Klf4, and c-Myc; see, e.g., Takahashi and Yamanaka, Cell 126(4): 663-76 (2006). iPSCs resemble ES cells, as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission [see, e.g., Maherali and Hochedlinger, Cell Stem Cell. 3(6):595-605 (2008)], and tetraploid complementation.

Human iPSCs can be obtained using similar transduction methods, and the transcription factor trio, OCT4, SOX2, and NANOG, has been established as the core set of transcription factors that govern pluripotency; see, e.g., Budniatzky and Gepstein, Stem Cells Transl Med. 3(4):448-57 (2014); Barrett et al., Stem Cells Trans Med 3:1-6 sctm.2014-0121 (2014); Focosi et al., Blood Cancer Journal 4: e211 (2014). The production of iPSCs can be achieved by the introduction of nucleic acid sequences encoding stem cell-associated genes into an adult, somatic cell, historically using viral vectors.

iPSCs can be generated or derived from terminally differentiated somatic cells, as well as from adult stem cells, or somatic stem cells. That is, a non-pluripotent progenitor cell can be rendered pluripotent or multipotent by reprogramming. In such instances, it cannot be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 7(5):618-30 (2010). Reprogramming can be achieved by introducing a combination of nucleic acids encoding stem cell-associated genes, including, for example, Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. Reprogramming using the methods and compositions described herein can further comprise introducing one or more of Oct-3/4, a member of the Sox family, a member of the Klf family, and a member of the Myc family to a somatic cell. The methods and compositions described herein can further comprise introducing one or more of each of Oct-4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one aspect the reprogramming is not effected by a method that alters the genome. Thus, in such examples, reprogramming can be achieved, e.g., without the use of viral or plasmid vectors.

The efficiency of reprogramming (i.e., the number of reprogrammed cells) derived from a population of starting cells can be enhanced by the addition of various agents, e.g., small molecules, as shown by Shi et al., Cell-Stem Cell 2:525-528 (2008); Huangfu et al., Nature Biotechnology 26(7):795-797 (2008) and Marson et al., Cell-Stem Cell 3: 132-135 (2008). Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide, hydroxamic acid (SAHA), vitamin C, and trichostatin (TSA), among others.

Other non-limiting examples of reprogramming enhancing agents include: Suberoylanilide Hydroxamic Acid (SAHA (e.g., MK0683, vorinostat) and other hydroxamic acids), BML-210, Depudecin (e.g., (-)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Titan Pharmaceuticals, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one case, for example, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. Detection can involve not only RT-PCR, but can also include detection of protein markers. Intracellular markers can be best identified via RT-PCR, or protein detection methods such as immunocytochemistry, while cell surface markers are readily identified, e.g., by immunocytochemistry.

The pluripotent stem cell character of isolated cells can be confirmed by tests evaluating the ability of the iPSCs to differentiate into cells of each of the three germ layers. As one example, teratoma formation in nude mice can be used to evaluate the pluripotent character of the isolated clones. The cells can be introduced into nude mice and histology and/or immunohistochemistry can be performed on a tumor arising from the cells. The growth of a tumor comprising cells from all three germ layers, for example, further indicates that the cells are pluripotent stem cells.

Retinal Progenitor Cells and Photoreceptor Cells

In some examples, the genetically engineered human cells described herein are photoreceptor cells or retinal progenitor cells (RPCs). RPCs are multipotent progenitor cells that can give rise to all the six neurons of the retina as well as the Müller glia. Müller glia are a type of retinal glial cells and are the major glial component of the retina. Their function is to support the neurons of the retina and to maintain retinal homeostasis and integrity. Müller glia isolated from adult human retinas have been shown to differentiate into rod photoreceptors. Functional characterization of such Müller glia-derived photoreceptors by patch-clamp recordings has revealed that their electrical properties are comparable to those of adult rods (Giannelli et al., 2011, Stem Cells, (2):344-56). RPCs are gradually specified into lineage-restricted precursor cells during retinogenesis, which then mature into the terminally differentiated neurons or Müuller glia. Fetal-derived human retinal progenitor cells (hRPCs) exhibit molecular characteristics indicative of a retinal progenitor state up to the sixth passage. They demonstrate a gradual decrease in the percentages of KI67-, SOX2-, and vimentin-positive cells from passages 1 to 6, whereas a sustained expression of nestin and PAX6 is seen through passage 6. Microarray analysis of passage 1 hRPCs demonstrate the expression of early retinal developmental genes: VIM (vimentin), KI67, NES (nestin), PAX6, SOX2, HESS, GNL3, OTX2, DACH1, SIX6, and CHX10 (VSX2). The hRPCs are functional in nature and respond to excitatory neurotransmitters (Schmitt et al., 2009, Investigative Ophthalmology and Visual Sciences. 2009; 50(12):5901-8). The outermost region of the retina contains a supportive retinal pigment epithelium (RPE) layer, which maintains photoreceptor health by transporting nutrients and recycling shed photoreceptor parts. The RPE is attached to Bruch's membrane, an extracellular matrix structure at the interface between the choroid and retina. On the other side of the RPE, moving inwards towards the interior of the eye, there are three layers of neurons: lightsensing rod and cone photoreceptors, a middle layer of connecting neurons (amacrine, bipolar and horizontal cells) and the innermost layer of ganglion cells, which transmit signals originating in the photoreceptor layer through the optic nerve and into the brain. In some aspects, the genetically engineered human cells described herein are photoreceptor cells, which are specialized types of neurons found in the retina. Photoreceptors convert light into signals that are able to stimulate biological processes and are responsible for sight. Rods and cones are the two classic photoreceptor cells that contribute information to the visual system.

Isolating a Retinal Progenitor Cell and Photoreceptor Cell

Retinal cells, including progenitor cells may be isolated according to any method known in the art. For example, human retinal cells are isolated from fresh surgical specimens. The retinal pigment epithelium (RPE) is separated from the choroid by digesting the tissue with type IV collagenase and the retinal pigment epithelium patches are cultured. Following the growth of 100-500 cells from the explant, the primary cultures are passaged (Ishida M. et al., Current Eye Research 1998; 17(4):392-402) and characterized for expression of RPE markers. Rods are isolated by disruption of the biopsied retina using papain. Precautions are taken to avoid a harsh disruption and improve cell yield. The isolated cells are sorted to yield a population of pure rod cells and characterized further by immunostaining (Feodorova et al., MethodsX 2015; 2:39-46).

In order to isolate cones, neural retina is identified, cut-out, and placed on 10% gelatin. The inner retinal layers are isolated using a laser. The isolated cone monolayers are cultured for 18 hours and compared with untreated retinas by light microscopy and transmission microscopy to check for any structural damage. The cells are characterized for expression of cone-specific markers (Salchow et al., Current Eye Research 2001; 22).

In order to isolate retinal progenitor cells, the biopsied retina is minced with dual scalpels and digested enzymatically in an incubator at 37° C. The supernatants of the digested cells are centrifuged and the cells are resuspended in cell-free retinal progenitor-conditioned medium. The cells are transferred to fibronectin-coated tissue culture flasks containing fresh media and cultured (Klassen et al., Journal of Neuroscience Research 2004; 77:334-343).

Creating Patient Specific iPSCs

One step of the ex vivo methods of the present disclosure can involve creating a patient-specific iPS cell, patient-specific iPS cells, or a patient-specific iPS cell line. There are many established methods in the art for creating patient specific iPS cells, as described in Takahashi and Yamanaka 2006; Takahashi, Tanabe et al. 2007. For example, the creating step can comprise: a) isolating a somatic cell, such as a skin cell or fibroblast, from the patient; and b) introducing a set of pluripotency-associated genes into the somatic cell in order to induce the cell to become a pluripotent stem cell. The set of pluripotency-associated genes can be one or more of the genes selected from the group consisting of OCT4, SOX1, SOX2, SOX3, SOX15, SOX18, NANOG, KLF1, KLF2, KLF4, KLF5, c-MYC, n-MYC, REM2, TERT and LIN28.

Performing a Biopsy or Aspirate of the Patient's Bone Marrow

A biopsy or aspirate is a sample of tissue or fluid taken from the body. There are many different kinds of biopsies or aspirates. Nearly all of them involve using a sharp tool to remove a small amount of tissue. If the biopsy will be on the skin or other sensitive area, numbing medicine can be applied first. A biopsy or aspirate can be performed according to any of the known methods in the art. For example, in a bone marrow aspirate, a large needle is used to enter the pelvis bone to collect bone marrow.

Isolating a Mesenchymal Stem Cell

Mesenchymal stem cells can be isolated according to any method known in the art, such as from a patient's bone marrow or peripheral blood. For example, marrow aspirate can be collected into a syringe with heparin. Cells can be washed and centrifuged on a Percoll™ density gradient. Cells, such as blood cells, liver cells, interstitial cells, macrophages, mast cells, and thymocytes, can be separated using density gradient centrifugation media, Percoll™. The cells can then be cultured in Dulbecco's modified Eagle's medium (DMEM) (low glucose) containing 10% fetal bovine serum (FBS) (Pittinger M F, Mackay A M, Beck S C et al., Science 1999; 284:143-147).

Differentiation of Genome-Edited iPSCs into Other Cell Types

Another step of the ex vivo methods of the present disclosure can comprise differentiating the genome-edited iPSCs into photoreceptor cells or retinal progenitor cells. The differentiating step may be performed according to any method known in the art. For example, iPSCs can be used to generate retinal organioids and photoreceptors as described in the art (Phillips et al., Stem Cells, June 2014, 32(6): pgs. 1480-1492; Zhong et al. Nat. Commun., 2014, 5: pg 4047; Tucker et al., PLoS One, April 2011, 6(4): e18992). For example, hiPSC are differentiated into retinal progenitor cells using various treatments, including Wnt, Nodal, and Notch pathway inhibitors (Noggin, Dk1, LeftyA, and DAPT) and other growth factors. The retinal progenitor cells are further differentiated into photoreceptor cells, the treatment including: exposure to native retinal cells in coculture systems, RX+ or Mitf+ by subsequent treatment with retinoic acid and taurine, or exposure to several exogenous factors including Noggin, Dkk1, DAPT, and insulin-like growth factor (Yang et al., Stem Cells International 2016).

Differentiation of Genome-Edited Mesenchymal Stem Cells into Photoreceptor Cells or Retinal Progenitor Cells Another step of the ex vivo methods of the present disclosure can comprise differentiating the genome-edited mesenchymal stem cells into photoreceptor cells or retinal progenitor cells. The differentiating step can be performed according to any method known in the art.

Implanting Cells into Patients

Another step of the ex vivo methods of the present disclosure can comprise implanting the photoreceptor cells or retinal progenitor cells into patients. This implanting step can be accomplished using any method of implantation known in the art. For example, the genetically modified cells can be injected directly in the patient's blood or otherwise administered to the patient.

Another step of the ex vivo methods of the invention involves implanting the photoreceptor cells or retinal progenitor cells into patients. This implanting step can be accomplished using any method of implantation known in the art. For example, the genetically modified cells can be injected directly in the patient's eye or otherwise administered to the patient.

Genetically Modified Cells

The term "genetically modified cell" refers to a cell that comprises at least one genetic modification introduced by genome editing (e.g., using the CRISPR/Cas9/Cpf1 system). In some ex vivo examples herein, the genetically modified cell can be genetically modified progenitor cell. In some in vivo examples herein, the genetically modified cell can be a genetically modified photoreceptor cell or retinal progenitor cell. A genetically modified cell comprising an exogenous genome-targeting nucleic acid and/or an exogenous nucleic acid encoding a genome-targeting nucleic acid is contemplated herein.

The term "control treated population" describes a population of cells that has been treated with identical media, viral induction, nucleic acid sequences, temperature, confluency, flask size, pH, etc., with the exception of the addition of the genome editing components. Any method known in the art can be used to measure restoration of RHO gene or protein expression or activity, for example Western Blot analysis of the RHO protein or real time PCR for quantifying RHO mRNA.

The term "isolated cell" refers to a cell that has been removed from an organism in which it was originally found, or a descendant of such a cell. Optionally, the cell can be cultured in vitro, e.g., under defined conditions or in the presence of other cells. Optionally, the cell can be later introduced into a second organism or re-introduced into the organism from which it (or the cell from which it is descended) was isolated.

The term "isolated population" with respect to an isolated population of cells refers to a population of cells that has been removed and separated from a mixed or heterogeneous population of cells. In some cases, the isolated population can be a substantially pure population of cells, as compared to the heterogeneous population from which the cells were isolated or enriched. In some cases, the isolated population can be an isolated population of human progenitor cells, e.g., a substantially pure population of human progenitor cells, as compared to a heterogeneous population of cells comprising human progenitor cells and cells from which the human progenitor cells were derived.

The term "substantially enhanced," with respect to a particular cell population, refers to a population of cells in which the occurrence of a particular type of cell is increased relative to pre-existing or reference levels, by at least 2-fold, at least 3-, at least 4-, at least 5-, at least 6-, at least 7-, at least 8-, at least 9, at least 10-, at least 20-, at least 50-, at least 100-, at least 400-, at least 1000-, at least 5000-, at least 20000-, at least 100000- or more fold depending, e.g., on the desired levels of such cells for ameliorating retinitis pigmentosa (RP).

The term "substantially enriched" with respect to a particular cell population, refers to a population of cells that is at least about 10%, about 20%, about 30%, about 40%, about 50%, about 60%, about 70% or more with respect to the cells making up a total cell population.

The terms "substantially pure" with respect to a particular cell population, refers to a population of cells that is at least about 75%, at least about 85%, at least about 90%, or at least about 95% pure, with respect to the cells making up a total cell population. That is, the terms "substantially pure" or "essentially purified," with regard to a population of progenitor cells, refers to a population of cells that contain fewer than about 20%, about 15%, about 10%, about 9%, about 8%, about 7%, about 6%, about 5%, about 4%, about 3%, about 2%, about 1%, or less than 1%, of cells that are not progenitor cells as defined by the terms herein.

Delivery

Guide RNA polynucleotides (RNA or DNA) and/or endonuclease polynucleotide(s) (RNA or DNA) can be delivered by viral or non-viral delivery vehicles known in the art. Alternatively, endonuclease polypeptide(s) can be delivered by viral or non-viral delivery vehicles known in the art, such as electroporation or lipid nanoparticles. In further alternative aspects, the DNA endonuclease can be delivered as one or more polypeptides, either alone or pre-complexed with one or more guide RNAs, or one or more crRNA together with a tracrRNA.

Polynucleotides can be delivered by non-viral delivery vehicles including, but not limited to, nanoparticles, liposomes, ribonucleoproteins, positively charged peptides, small molecule RNA-conjugates, aptamer-RNA chimeras, and RNA-fusion protein complexes. Some exemplary non-viral delivery vehicles are described in Peer and Lieberman, Gene Therapy, 18: 1127-1133 (2011) (which focuses on non-viral delivery vehicles for siRNA that are also useful for delivery of other polynucleotides).

Polynucleotides, such as guide RNA, sgRNA, and mRNA encoding an endonuclease, can be delivered to a cell or a patient by a lipid nanoparticle (LNP).

A LNP refers to any particle having a diameter of less than 1000 nm, 500 nm, 250 nm, 200 nm, 150 nm, 100 nm, 75 nm, 50 nm, or 25 nm. Alternatively, a nanoparticle can range in size from 1-1000 nm, 1-500 nm, 1-250 nm, 25-200 nm, 25-100 nm, 35-75 nm, or 25-60 nm.

LNPs can be made from cationic, anionic, or neutral lipids. Neutral lipids, such as the fusogenic phospholipid DOPE or the membrane component cholesterol, can be included in LNPs as 'helper lipids' to enhance transfection activity and nanoparticle stability. Limitations of cationic lipids include low efficacy owing to poor stability and rapid clearance, as well as the generation of inflammatory or anti-inflammatory responses.

LNPs can also be comprised of hydrophobic lipids, hydrophilic lipids, or both hydrophobic and hydrophilic lipids.

Any lipid or combination of lipids that are known in the art can be used to produce a LNP. Examples of lipids used to produce LNPs are: DOTMA, DOSPA, DOTAP, DMRIE, DC-cholesterol, DOTAP-cholesterol, GAP-DMORIE-DPyPE, and GL67A-DOPE-DMPE-polyethylene glycol (PEG). Examples of cationic lipids are: 98N12-5, C12-200, DLin-KC2-DMA (KC2), DLin-MC3-DMA (MC3), XTC, MD1, and 7C1. Examples of neutral lipids are: DPSC, DPPC, POPC, DOPE, and SM. Examples of PEG-modified lipids are: PEG-DMG, PEG-CerC14, and PEG-CerC20.

The lipids can be combined in any number of molar ratios to produce a LNP. In addition, the polynucleotide(s) can be combined with lipid(s) in a wide range of molar ratios to produce a LNP.

As stated previously, the site-directed polypeptide and genome-targeting nucleic acid can each be administered separately to a cell or a patient. On the other hand, the site-directed polypeptide can be pre-complexed with one or more guide RNAs, or one or more crRNA together with a tracrRNA. The pre-complexed material can then be administered to a cell or a patient. Such pre-complexed material is known as a ribonucleoprotein particle (RNP).

RNA is capable of forming specific interactions with RNA or DNA. While this property is exploited in many biological processes, it also comes with the risk of promiscuous interactions in a nucleic acid-rich cellular environment. One solution to this problem is the formation of ribonucleoprotein particles (RNPs), in which the RNA is pre-complexed with an endonuclease. Another benefit of the RNP is protection of the RNA from degradation.

The endonuclease in the RNP can be modified or unmodified. Likewise, the gRNA, crRNA, tracrRNA, or sgRNA can be modified or unmodified. Numerous modifications are known in the art and can be used.

The endonuclease and sgRNA can be generally combined in a 1:1 molar ratio. Alternatively, the endonuclease, crRNA and tracrRNA can be generally combined in a 1:1:1 molar ratio. However, a wide range of molar ratios can be used to produce a RNP.

AAV (Adeno Associated Virus)

A recombinant adeno-associated virus (AAV) vector can be used for delivery.

Techniques to produce rAAV particles, in which an AAV genome to be packaged that includes the polynucleotide to be delivered, rep and cap genes, and helper virus functions are provided to a cell are standard in the art. Production of rAAV typically requires that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes described herein. Production of pseudotyped rAAV is disclosed in, for example, international patent application publication number WO 01/83692.

AAV sequences disclosed herein can comprise sgRNAs that target the P23H mutation within the RHO gene. For example, pSIA010 comprises an AAV sequence (SEQ ID NO: 5339) that encodes a sgRNA that targets the P23H mutation within the RHO gene. The sgRNA comprises SEQ ID NOs: 5290 (sgRNA protospacer sequence) and SEQ ID NO: 5327 (sgRNA backbone sequence). pSIA011 comprises an AAV sequence (SEQ ID NO: 5340) that encodes a sgRNA that targets the P23H mutation within the RHO gene. The sgRNA comprises SEQ ID NOs: 5291 (sgRNA protospacer sequence) and SEQ ID NO: 5327 (sgRNA backbone sequence).

AAV Serotypes

AAV particles packaging polynucleotides encoding compositions of the present disclosure, e.g., endonucleases, donor sequences, or RNA guide molecules, of the present disclosure can comprise or be derived from any natural or recombinant AAV serotype. According to the present disclosure, the AAV particles can utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAV5, AAV52.1/hu.20, AAV52/hu.19, AAV5-22/rh.58, AAV5-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In some examples, the AAV serotype can be, or have, a mutation in the AAV9 sequence as described by N Pulicherla et al. (Molecular Therapy 19(6):1070-1078 (2011), such as but not limited to, AAV9.9, AAV9.11, AAV9.13, AAV9.16, AAV9.24, AAV9.45, AAV9.47, AAV9.61, AAV9.68, AAV9.84.

In some examples, the AAV serotype can be, or have, a sequence as described in U.S. Pat. No. 6,156,303, such as, but not limited to, AAV3B (SEQ ID NO: 1 and 10 of U.S. Pat. No. 6,156,303), AAV6 (SEQ ID NO: 2, 7 and 11 of U.S. Pat. No. 6,156,303), AAV2 (SEQ ID NO: 3 and 8 of U.S. Pat. No. 6,156,303), AAV3A (SEQ ID NO: 4 and 9, of U.S. Pat. No. 6,156,303), or derivatives thereof.

In some examples, the serotype can be AAVDJ or a variant thereof, such as AAVDJ8 (or AAV-DJ8), as described by Grimm et al. (Journal of Virology 82(12): 5887-5911 (2008)). The amino acid sequence of AAVDJ8 can comprise two or more mutations in order to remove the heparin binding domain (HBD). As a non-limiting example, the AAV-DJ sequence described as SEQ ID NO: 1 in U.S. Pat. No. 7,588,772, can comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, can comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some examples, the AAV serotype can be, or have, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use can be from a variety of species. In one example, the AAV can be an avian AAV (AAAV). The AAAV serotype can be, or have, a sequence as described in U.S. Pat. No. 9,238,800, such as, but not limited to, AAAV (SEQ ID NO: 1, 2, 4, 6, 8, 10, 12, and 14 of U.S. Pat. No. 9,238,800), or variants thereof.

In one example, the AAV can be a bovine AAV (BAAV). The BAAV serotype can be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype can be or have a sequence as described in U.S. Pat. No. 7,427,396, such as, but not limited to, BAAV (SEQ ID NO: 5 and 6 of U.S. Pat. No. 7,427,396), or variants thereof.

In one example, the AAV can be a caprine AAV. The caprine AAV serotype can be, or have, a sequence as described in U.S. Pat. No. 7,427,396, such as, but not limited to, caprine AAV (SEQ ID NO: 3 of U.S. Pat. No. 7,427,396), or variants thereof.

In other examples the AAV can be engineered as a hybrid AAV from two or more parental serotypes. In one example, the AAV can be AAV2G9 which comprises sequences from AAV2 and AAV9. The AAV2G9 AAV serotype can be, or have, a sequence as described in United States Patent Publication No. US20160017005.

In one example, the AAV can be a serotype generated by the AAV9 capsid library with mutations in amino acids 390-627 (VP1 numbering) as described by Pulicherla et al. (Molecular Therapy 19(6):1070-1078 (2011). The serotype and corresponding nucleotide and amino acid substitutions can be, but is not limited to, AAV9.1 (G1594C; D532H), AAV6.2 (T1418A and T1436X; V473D and I479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V6061), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T582I), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, 5469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A; G481R), AAV9.83 (C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In one example, the AAV can be a serotype comprising at least one AAV capsid CD8+ T-cell epitope. As a non-limiting example, the serotype can be AAV1, AAV2 or AAV8.

In one example, the AAV can be a variant, such as PHP.A or PHP.B as described in Deverman. 2016. Nature Biotechnology. 34(2): 204-209.

In one example, the AAV can be a serotype selected from any of those found in SEQ ID NOs: 4697-5265 and Table 4.

In one example, the AAV can be encoded by a sequence, fragment or variant as described in SEQ ID NOs: 4697-5265 and Table 4.

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595.

AAV vector serotypes can be matched to target cell types. For example, the following exemplary cell types can be transduced by the indicated AAV serotypes among others.

TABLE 4

Tissue/Cell Types and Serotypes

| Tissue/Cell Type | Serotype |
| --- | --- |
| Liver | AAV3, AA5, AAV8, AAV9 |
| Skeletal muscle | AAV1, AAV7, AAV6, AAV8, AAV9 |
| Central nervous system | AAV1, AAV4, AAV5, AAV8, AAV9 |
| RPE | AAV5, AAV4, AAV2, AAV8, AAV9 AAVrh8r |
| Photoreceptor cells | AAV5, AAV8, AAV9, AAVrh8R |
| Lung | AAV9, AAV5 |
| Heart | AAV8 |
| Pancreas | AAV8 |
| Kidney | AAV2, AAV8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirusr, poxvirus, vaccinia virus, and herpes simplex virus.

In some cases, Cas9 mRNA, sgRNA targeting one or two loci in RHO gene, and donor DNA can each be separately formulated into lipid nanoparticles, or are all co-formulated into one lipid nanoparticle.

In some cases, Cas9 mRNA can be formulated in a lipid nanoparticle, while sgRNA and donor DNA can be delivered in an AAV vector.

Options are available to deliver the Cas9 nuclease as a DNA plasmid, as mRNA or as a protein. The guide RNA can be expressed from the same DNA, or can also be delivered as an RNA. The RNA can be chemically modified to alter or improve its half-life, or decrease the likelihood or degree of immune response. The endonuclease protein can be complexed with the gRNA prior to delivery. Viral vectors allow efficient delivery; split versions of Cas9 and smaller orthologs of Cas9 can be packaged in AAV, as can donors for HDR. A range of non-viral delivery methods also exist that can deliver each of these components, or non-viral and viral methods can be employed in tandem. For example, nanoparticles can be used to deliver the protein and guide RNA, while AAV can be used to deliver a donor DNA.

Self-Inactivating (SIN) CRISPR-Cas Systems

Disclosed herein are "self-inactivating" (SIN) CRISPR-Cas systems. The SIN CRISPR-Cas system can comprise one or more segments. The SIN CRISPR-Cas system can be an AAV system. The SIN CRISPR-Cas system can be an AAV5 system.

A first segment can comprise a nucleotide sequence that encodes one or more polypeptide inducing site-directed mutagenesis (e.g. Cas9 or Cpf1). The first segment can further comprise a start codon, a stop codon, a poly (A) termination site, and an intron. Such a polypeptide can be Streptococcus pyogenes Cas9 (SpCas9), Staphylococcus aureus Cas9 (SaCas9), or any variants thereof. A nucleotide sequence functioning as a promoter can be operably linked to the first segment. The promoter can be a spatially-restricted promoter, bidirectional promoter driving sgRNA in one direction and Cas9 in the opposite orientation, or an inducible promoter. The spatially-restricted promoter can be selected from the group consisting of: any ubiquitous promoter, any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a retinal pigment epithelial (RPE) selective promoter. The promoter can be a sEF1α promoter or GRK1 promoter.

A second segment can comprise a nucleotide sequence that encodes a sgRNA. The sgRNA can comprise any of SEQ ID NOs: 5287-5291 (FIG. 2B), 5319-5322 (FIG. 2E), 5358 (FIG. 2H), 5302-5304, 5351-5356, and 5360. The sgRNAs can be substantially complementary to a SIN site and a genomic target sequence. By "hybridizable" or "complementary" or "substantially complementary" it is meant that a nucleic acid (e.g. RNA) comprises a sequence of nucleotides that enables it to non-covalently bind, e.g.: form Watson-Crick base pairs, "anneal", or "hybridize," to another nucleic acid in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C) [DNA, RNA]. In some examples, the sgRNAs may be fully complementary to the nucleotide sequence of the SIN site except for in at least one location. In some examples, the sgRNAs may be fully complementary to the nucleotide sequence of the SIN site except for in at least two locations.

One or more third segments can be located at a 5' end of the first segment (upstream of the start codon and/or downstream of the transcriptional start site), within an intron (natural or chimeric) dividing the first segment, or at a 3' end of a first segment (between the stop codon and poly (A) termination site). In another example, the one or more third segments can be located at the 5' end of the first segment and within an intron (natural or chimeric) dividing the first segment. The third segment can be less than 100 nucleotides in length. For example, the third segment can be 20-99, 30-99, 40-99, 50-99, 60-99, 70-99, 80-99, and 90-99 nucleotides in length. The third segment can be less than 50 nucleotides in length. For example, the third segment can be 20-49, 25-49, 30-49, 35-49, 40-49, and 45-49 nucleotides in length.

The one or more third segments can comprise a self-inactivating (SIN) site. The SIN site or P23H target site, as used herein, is a 20-50 nucleotide sequence of the RHO gene comprising the P23H mutation (SEQ ID NO: 5313 and 5314) (Table 5). The SIN site comprises protospacer adjacent motifs (PAMs).

sequence. In these examples, the SIN sites may be more than 20 nucleotides in length or less than 20 nucleotides in length.

In the SIN-AAV system, the endonuclease can be guided by one or more sgRNAs to one or more genomic target sequences. The one or more genomic target sequences can be a P23H mutation within the RHO gene. The endonuclease can be further guided to the SIN-AAV system that is expressing the endonuclease and the system's components. Examples of SIN-AAV system components that can be targeted include: essential sequences of a vector of the SIN-AAV system (e.g. viral inverted terminal repeats), promoters driving expression of genes important for editing (e.g. sgRNA or endonuclease genes), the open reading frame (ORF) of Cas9 or Cpf1, introns dividing encoded genes, or non-coding regions (SIN sites) located 5' or 3' of the Cas9 or Cpf1 ORF or located in an intron. This leads to self-limiting editing activity which results in editing of one or

TABLE 5

| SIN-AAV SaCas9 ver. 1 & 2 | SEQ ID NO: | Sequence | RHO allele |
|---|---|---|---|
| 5' SIN site | 5313 | ggtagtactgtgggtactcgaagtggctgcgtaccacacccgtcgcat | P23H |
| 3' SIN site | 5314 | atgcgacgggtgtggtacgcagccacttcgagtacccacagtactacc | P23H |

The spacer sequence of a gRNA or sgRNA hybridizes to the strand complementary to the protospacer sequence located within the SIN site, which leads to editing by the gRNA-endonuclease complex or the sgRNA-endonuclease complex and eventually results in inactivation of the endonuclease (e.g. Cas9 or Cpf1). SIN sites that comprise a 20-50 nucleotide sequence of the RHO gene comprising the P23H mutation can be targeted with any of the sgRNAs comprising SEQ ID NOs: 5287-5291 (FIG. 2B), 5319-5322 (FIG. 2E), and 5358 (FIG. 2H) even though one or more of the sgRNAs may not be fully complementary to the nucleotide sequence of the SIN site in at least 1-2 locations.

In other examples, the SIN site can be shorter in length compared to the sequences listed in Table 5. For example, the SIN site can be any one of the sequences in SEQ ID NOs: 5277-5281 (FIG. 2A) and a PAM. The SIN site can be any one of the sequences in SEQ ID NOs: 5315-5318 (FIG. 2D) and a PAM. The SIN site can be SEQ ID NO: 5357 (FIG. 2G) and a PAM. The SIN site can be any one of the sequences in SEQ ID NOs: 5297-5301 (FIG. 2C) and a PAM. The SIN site can be any one of the sequences in SEQ ID NOs: 5323-5326 (FIG. 2F) and a PAM. The SIN site can be SEQ ID NO: 5359 (FIG. 2I) and a PAM.

In other examples, the SIN site can be shorter than the corresponding protospacer sequence of the sgRNA. For example, a protospacer sequence for a sgRNA may be 24 nucleotides in length whereas the corresponding SIN site may contain a shorter protospacer (only 23, 22, 21, 20, 19, 18, or 17 nucleotides in length) and a PAM. This shortened SIN site (that still corresponds to the protospacer sequence of the sgRNA) will allow the genomic target sequence to be cleaved more efficiently than the shortened SIN site. For this reason, any one of the sequences in SEQ ID NOs: 5277-5281 (FIG. 2A), 5315-5318 (FIG. 2D), and 5357 (FIG. 2G) or in SEQ ID NOs: 5297-5301 (FIG. 2C), 5323-5326 (FIG. 2F), and 5359 (FIG. 2I) can be shortened by 1, 2, 3, 4, 5, 6, or 7 nucleotides and used as a SIN site along with a PAM more target genomic loci, and, thereafter, reduced or eliminated expression of the endonuclease and/or other essential components of the system (e.g. sgRNAs). This self-limited expression of genes in the SIN-AAV system can result in reduced off-target editing and reduced risk of successfully edited cells being targeted by the patient's immune system.

One or more vectors can encode the disclosed SIN-AAV systems. If only one vector encodes the entire SIN-AAV system, then the system is referred to as an "all-in-one" SIN system. For example, the first segment, second segment, and third segment can be provided together in an "all-in-one" SIN AAV system. If two vectors encode the entire SIN-AAV system, then the system is referred to as an "all-in-two" SIN system. For example, the first segment and third segment can be provided in a first vector and the second segment can be provided in a second vector for an "all-in-two" SIN AAV system.

All-in-One SIN-AAV Systems

In one example, an all-in-one SIN system can comprise a vector comprising an endonuclease ORF and a sgRNA gene. The vector can further comprise SIN sites at locations 5' and 3' of the endonuclease ORF, and within an intron dividing an endonuclease ORF. The sgRNA can be substantially complementary to the SIN site. The sgRNA can also be substantially complementary to a genomic target sequence. Thus, the sequence of the sgRNA is such that it can hybridize with both the SIN sites on the vector and with one or more genomic target sequences. When hybridizing with the one or more genomic targets or with the SIN sites, the sgRNA may comprise one or more mismatched bases. The system can lead to self-limited editing at the targeted genomic loci, followed by excision and/or inactivation of the endonuclease gene.

In another example, an all-in-one SIN system can comprise a vector comprising an endonuclease ORF, a first sgRNA gene, and a second sgRNA gene. The vector can further comprise SIN sites at one or more of the following locations: 5' of the endonuclease ORF, 3' of the endonuclease ORF, or within an intron dividing an endonuclease ORF. The sequence of the first sgRNA is such that it can hybridize with one or more genomic target sequences. The sequence of the second sgRNA is such that it can hybridize with the SIN sites on the vector. When hybridizing with the one or more genomic targets or with the SIN sites, the sgRNAs can comprise one or more mismatched bases. Additional sgRNAs can be incorporated into the system to allow for editing of additional genomic or SIN system targets. The system can lead to self-limited editing at the targeted genomic loci, followed by excision and/or inactivation of the endonuclease gene.

In another example, an all-in-one SIN system can comprise a vector comprising an endonuclease ORF, a first sgRNA gene, and a second sgRNA gene. The sequence of the first sgRNA is such that it can hybridize with one or more genomic target sequences. The sequence of the second sgRNA is such that it can hybridize within or near the endonuclease ORF (Cas9 or Cpf1) on the vector, leading to inactivation of the endonuclease gene via indel generation. Additional sgRNAs can be incorporated into the system to allow for editing of additional genomic or SIN system targets. When hybridizing with the one or more genomic targets or the endonuclease ORF, the two or more sgRNAs may comprise one or more mismatched bases. The system can lead to self-limited editing at the targeted genomic loci, followed by inactivation of the endonuclease gene.

In all-in-one systems such as those described above, production of appropriate viral vectors can be challenging due to inactivation of the endonuclease gene that occurs earlier than desired and accumulation of mutagenized SIN sites on DNA packaged in AAV capsids (e.g. during production and packaging of the viral vector in a cell line of choice). To solve this problem, the endonuclease ORF and/or the sgRNA genes that direct editing at the endonuclease gene locus can be expressed from one or more cell/tissue-specific promoters. The cell/tissue specific promoters can be active in the cells where editing is desired and inactive earlier in the cells used for production and packaging of the vectors. In addition, one or more inducible promoter systems can be used to control expression of genes of interest, such as tetracycline-controlled transcriptional activation (i.e. tet-ON or tet-OFF). Other solutions to the premature inactivation problem include regulating gene expression with miRNAs, small interfering RNAs, short hairpin RNAs, or other antisense oligonucleotides, blocking transcription of sgRNA (e.g. the use of a tet-OFF system), or inhibiting sgRNA loading onto Cas9.

All-in-Two SIN-AAV Systems

Figure 5D:
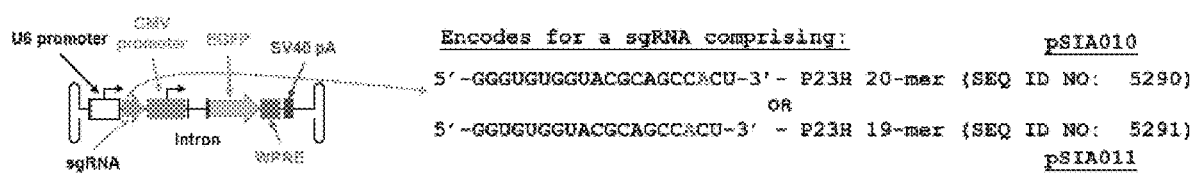

In one example, an all-in-two SIN system can comprise a first vector to provide an ORF encoding an endonuclease (FIGS. 5A-B). SIN sites can be located 5' of the endonuclease ORF and within an intron dividing the endonuclease ORF on the first vector (FIG. 5A-B). The SIN site can be any one of SEQ ID NOs: 5313-5314, as shown in Table 5. The SIN site can be shorter in length compared to the sequences listed in Table 5. For example, the SIN site can be any one of the sequences in SEQ ID NOs: 5277-5281 (FIG. 2A) and a PAM. The SIN site can be any one of the sequences in SEQ ID NOs: 5315-5318 (FIG. 2D) and a PAM. The SIN site can be SEQ ID NO: 5357 (FIG. 2G) and a PAM. The SIN site can be any one of the sequences in SEQ ID NOs: 5297-5301 (FIG. 2C) and a PAM. The SIN site can be any one of the sequences in SEQ ID NOs: 5323-5326 (FIG. 2F) and a PAM. The SIN site can be SEQ ID NO: 5359 (FIG. 2I) and a PAM. In other examples, the SIN site can be shorter than the corresponding protospacer sequence of the sgRNA. For example, a protospacer sequence for a sgRNA may be 24 nucleotides in length whereas the corresponding SIN site may contain a shorter protospacer (only 23, 22, 21, 20, 19, 18, or 17 nucleotides in length) and a PAM. By using a shortened (or truncated) SIN site (that still corresponds to the protospacer sequence of the sgRNA), this will allow the RNP complex to more efficiently cleave the genomic target sequence compared to the shortened SIN site itself. For this reason, any one of the sequences in SEQ ID NOs: 5277-5281 (FIG. 2A), 5315-5318 (FIG. 2D), and 5357 (FIG. 2G) or in SEQ ID NOs: 5297-5301 (FIG. 2C), 5323-5326 (FIG. 2F), and 5359 (FIG. 2I) can be shortened by 1, 2, 3, 4, 5, 6, or 7 nucleotides and used as a SIN site along with a PAM sequence. In a second vector, a single sgRNA can be encoded (FIG. 5D). The sgRNA can comprise any of SEQ ID NOs: 5287-5291 (FIG. 2B), 5319-5322 (FIG. 2E), 5358 (FIG. 2H), 5302-5304, 5351-5356, and 5360. The sgRNA can be substantially complementary to the SIN site. The sgRNA can also be substantially complementary to a genomic target sequence. Thus, the sequence of the sgRNA can be such that it can hybridize with both the SIN sites on the first vector and with one or more genomic target sequences (e.g. the P23H mutation within the RHO gene). When hybridizing with the one or more genomic targets or with the SIN sites, the sgRNA may comprise one or more mismatched bases. The system can lead to self-limited editing at the targeted genomic loci, followed by excision and/or inactivation of the endonuclease gene.

In another example, an all-in-two SIN system can comprise a first vector to provide an ORF encoding an endonuclease. SIN sites can be located 5' of the endonuclease ORF and within an intron dividing the endonuclease ORF on the first vector. The SIN site can be any one of SEQ ID NOs: 5313-5314, as shown in Table 5. The SIN site can be shorter in length compared to the sequences listed in Table 5. For example, the SIN site can be any one of the sequences in SEQ ID NOs: 5277-5281 (FIG. 2A) and a PAM. The SIN site can be any one of the sequences in SEQ ID NOs: 5315-5318 (FIG. 2D) and a PAM. The SIN site can be SEQ ID NO: 5357 (FIG. 2G) and a PAM. The SIN site can be any one of the sequences in SEQ ID NOs: 5297-5301 (FIG. 2C) and a PAM. The SIN site can be any one of the sequences in SEQ ID NOs: 5323-5326 (FIG. 2F) and a PAM. The SIN site can be SEQ ID NO: 5359 (FIG. 2I) and a PAM. In other examples, the SIN site can be shorter than the corresponding protospacer sequence of the sgRNA. For example, a protospacer sequence for a sgRNA may be 24 nucleotides in length whereas the corresponding SIN site may contain a shorter protospacer (only 23, 22, 21, 20, 19, 18, or 17 nucleotides in length) and a PAM. By using a shortened (or truncated) SIN site (that still corresponds to the protospacer sequence of the sgRNA), this will allow the RNP complex to more efficiently cleave the genomic target sequence compared to the shortened SIN site itself. For this reason, any one of the sequences in SEQ ID NOs: 5277-5281 (FIG. 2A), 5315-5318 (FIG. 2D), and 5357 (FIG. 2G) or in SEQ ID NOs: 5297-5301 (FIG. 2C), 5323-5326 (FIG. 2F), and 5359 (FIG. 2I) can be shortened by 1, 2, 3, 4, 5, 6, or 7 nucleotides and used as a SIN site along with a PAM sequence. The all-in-two system can further comprise a second vector, comprising two sgRNA genes. When expressed from the second vector, a first sgRNA can bind with an endonuclease molecule and direct editing at one or more genomic target loci (e.g. the P23H mutation within the RHO gene). The first sgRNA can comprise any of SEQ ID NOs: 5287-5291 (FIG. 2B), 5319-5322 (FIG. 2E), 5358 (FIG. 2H), 5302-5304, 5351-5356, and 5360. When expressed from the second vector, a second sgRNA can bind with an endonuclease molecule and directly edit at the SIN sites. Additional sgRNAs can be incorporated into the system to allow for editing of additional genomic or SIN system targets. When hybridizing with the one or more genomic targets or with the SIN sites, the two or more sgRNAs may comprise one or more mismatched bases. In some examples, the one or more sgRNAs that target genomic loci may be encoded on the first vector, or a combination of both the first and second vectors. The system can lead to self-limited editing at the targeted genomic loci, followed by excision and/or inactivation of the endonuclease gene.

In another example, an all-in-two SIN system can comprise a first vector comprising an endonuclease ORF, and a second vector comprising two sgRNA genes. When expressed from the second vector, a first sgRNA can bind with an endonuclease molecule and direct editing at one or more genomic target loci (e.g. the P23H mutation within the RHO gene). The sgRNA can comprise any of SEQ ID NOs: 5287-5291 (FIG. 2B), 5319-5322 (FIG. 2E), 5358 (FIG. 2H), 5302-5304, 5351-5356, and 5360. When expressed from the second vector, a second sgRNA can bind with an endonuclease molecule and direct editing within or near the endonuclease ORF (Cas9 or Cpf1) on the first vector, leading to inactivation of the endonuclease gene via indel generation. Additional sgRNAs can be incorporated into the system to allow for editing of additional genomic or SIN system targets. When hybridizing with the one or more genomic targets or within or near the endonuclease ORF, the two or more sgRNAs may comprise one or more mismatched bases. In some examples, the one or more sgRNAs that target genomic loci may be encoded on the first vector, or a combination of both the first and second vectors. The system can lead to self-limited editing at the targeted genomic loci, followed by inactivation of the endonuclease gene.

Lentivirus

In some aspects, lentiviral vectors or particles can be used as delivery vehicles. Lentiviruses are subgroup of the Retroviridae family of viruses. Lentiviral particles are able to integrate their genetic material into the genome of a target/host cell. Examples of lentivirus include the Human Immunodeficiency Viruses: HIV-1 and HIV-2, Jembrana Disease Virus (JDV), equine infectious anemia virus (EIAV), equine infectious anemia virus, visna-maedi and caprine arthritis encephalitis virus (CAEV), the Simian Immunodeficiency Virus (SIV), feline immunodeficiency virus (Hy), bovine immunodeficiency virus (BIV). LV's are capable of infecting both dividing and non-dividing cells due to their unique ability to pass through a target cell's intact nuclear membrane Greenberg et al., University of Berkeley, Calif.; 2006). Lentiviral particles that form the gene delivery vehicle are replication defective and are generated by attenuating the HIV virulence genes. For example, the genes Vpu, Vpr, Nef, Env, and Tat are excised making the vector biologically safe. Lentiviral vehicles, for example, derived from HIV-1/HIV-2 can mediate the efficient delivery, integration and long-term expression of transgenes into non-dividing cells. As used herein, the term "recombinant" refers to a vector or other nucleic acid containing both lentiviral sequences and non-lentiviral retroviral sequences.

In order to produce a lentivirus that is capable of infecting host cells, three types of vectors need to be co-expressed in virus producing cells: a backbone vector containing the transgene of interests and self-inactivating 3'-LTR regions, one construct expressing viral structure proteins, and one vector encoding vesicular stomatitis virus glycoprotein (VSVG) for encapsulation (Naldini, L. et al., Science 1996; 272, 263-267). Separation of the Rev gene from other structural genes further increases the biosafety by reducing the possibility of reverse recombination. Cell lines that can be used to produce high-titer lentiviral particles may include, but are not limited to 293T cells, 293FT cells, and 293 SF-3F6 cells (Witting et al., Human Gene Therapy, 2012; 23: 243-249; Ansorge et al., Journal of Genetic Medicine, 2009; 11: 868-876).

Methods for generating recombinant lentiviral particles are discussed in the art, for example, WO 2013076309 (PCT/EP2012/073645); WO 2009153563 (PCT/GB2009/001527); U.S. Pat. Nos. 7,629,153; and 6, 808, 905.

Cell types such as photoreceptors, retinal pigment epithelium, and ganglion cells have been successfully targeted with lentivirus (LV) vector. The efficiency of delivery to photoreceptors and ganglion cells is significantly higher with AAV than LV vectors.

Pharmaceutically Acceptable Carriers

The ex vivo methods of administering progenitor cells to a subject contemplated herein involve the use of therapeutic compositions comprising progenitor cells.

Therapeutic compositions can contain a physiologically tolerable carrier together with the cell composition, and optionally at least one additional bioactive agent as described herein, dissolved or dispersed therein as an active ingredient. In some cases, the therapeutic composition is not substantially immunogenic when administered to a mammal or human patient for therapeutic purposes, unless so desired.

In general, the progenitor cells described herein can be administered as a suspension with a pharmaceutically acceptable carrier. One of skill in the art will recognize that a pharmaceutically acceptable carrier to be used in a cell composition will not include buffers, compounds, cryopreservation agents, preservatives, or other agents in amounts that substantially interfere with the viability of the cells to be delivered to the subject. A formulation comprising cells can include e.g., osmotic buffers that permit cell membrane integrity to be maintained, and optionally, nutrients to maintain cell viability or enhance engraftment upon administration. Such formulations and suspensions are known to those of skill in the art and/or can be adapted for use with the progenitor cells, as described herein, using routine experimentation.

A cell composition can also be emulsified or presented as a liposome composition, provided that the emulsification procedure does not adversely affect cell viability. The cells and any other active ingredient can be mixed with excipients that are pharmaceutically acceptable and compatible with the active ingredient, and in amounts suitable for use in the therapeutic methods described herein.

Additional agents included in a cell composition can include pharmaceutically acceptable salts of the components therein. Pharmaceutically acceptable salts include the acid addition salts (formed with the free amino groups of the polypeptide) that are formed with inorganic acids, such as, for example, hydrochloric or phosphoric acids, or such organic acids as acetic, tartaric, mandelic and the like. Salts formed with the free carboxyl groups can also be derived from inorganic bases, such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active compound used in the cell compositions that is effective in the treatment of a particular disorder or condition can depend on the nature of the disorder or condition, and can be determined by standard clinical techniques.

Guide RNA Formulation

Guide RNAs of the present disclosure can be formulated with pharmaceutically acceptable excipients such as carriers, solvents, stabilizers, adjuvants, diluents, etc., depending upon the particular mode of administration and dosage form. Guide RNA compositions can be formulated to achieve a physiologically compatible pH, and range from a pH of about 3 to a pH of about 11, about pH 3 to about pH 7, depending on the formulation and route of administration. In some cases, the pH can be adjusted to a range from about pH 5.0 to about pH 8. In some cases, the compositions can comprise a therapeutically effective amount of at least one compound as described herein, together with one or more pharmaceutically acceptable excipients. Optionally, the compositions can comprise a combination of the compounds described herein, or can include a second active ingredient useful in the treatment or prevention of bacterial growth (for example and without limitation, anti-bacterial or anti-microbial agents), or can include a combination of reagents of the present disclosure.

Suitable excipients include, for example, carrier molecules that include large, slowly metabolized macromolecules such as proteins, polysaccharides, polylactic acids, polyglycolic acids, polymeric amino acids, amino acid copolymers, and inactive virus particles. Other exemplary excipients can include antioxidants (for example and without limitation, ascorbic acid), chelating agents (for example and without limitation, EDTA), carbohydrates (for example and without limitation, dextrin, hydroxyalkylcellulose, and hydroxyalkylmethylcellulose), stearic acid, liquids (for example and without limitation, oils, water, saline, glycerol and ethanol), wetting or emulsifying agents, pH buffering substances, and the like.

Administration & Efficacy

The terms "administering," "introducing" and "transplanting" can be used interchangeably in the context of the placement of cells, e.g., progenitor cells, into a subject, by a method or route that results in at least partial localization of the introduced cells at a desired site, such as a site of injury or repair, such that a desired effect(s) is produced. The cells e.g., progenitor cells, or their differentiated progeny can be administered by any appropriate route that results in delivery to a desired location in the subject where at least a portion of the implanted cells or components of the cells remain viable. The period of viability of the cells after administration to a subject can be as short as a few hours, e.g., twenty-four hours, to a few days, to as long as several years, or even the life time of the patient, i.e., long-term engraftment. For example, in some aspects described herein, an effective amount of photoreceptor cells or retinal progenitor cells is administered via a systemic route of administration, such as an intraperitoneal or intravenous route.

The terms "administering," "introducing" and "transplanting" can also be used interchangeably in the context of the placement of at least one of a gRNA, sgRNA, and an endonuclease into a subject, by a method or route that results in at least partial localization of the introduced gRNA, sgRNA, and/or endonuclease at a desired site, such as a site of injury or repair, such that a desired effect(s) is produced. The gRNA, sgRNA, and/or endonuclease can be administered by any appropriate route that results in delivery to a desired location in the subject.

The terms "individual," "subject," "host" and "patient" are used interchangeably herein and refer to any subject for whom diagnosis, treatment or therapy is desired. In some aspects, the subject is a mammal. In some aspects, the subject is a human being.

When provided prophylactically, progenitor cells described herein can be administered to a subject in advance of any symptom of autosomal dominant RP. Accordingly, the prophylactic administration of a progenitor cell population serves to prevent autosomal dominant RP.

A progenitor cell population being administered according to the methods described herein can comprise allogeneic progenitor cells obtained from one or more donors. Such progenitors can be of any cellular or tissue origin, e.g., liver, muscle, cardiac, etc. "Allogeneic" refers to a progenitor cell or biological samples comprising progenitor cells obtained from one or more different donors of the same species, where the genes at one or more loci are not identical. For example, a photoreceptor or retinal progenitor cell population being administered to a subject can be derived from one more unrelated donor subjects, or from one or more non-identical siblings. In some cases, syngeneic progenitor cell populations can be used, such as those obtained from genetically identical animals, or from identical twins. The progenitor cells can be autologous cells; that is, the progenitor cells are obtained or isolated from a subject and administered to the same subject, i.e., the donor and recipient are the same.

The term "effective amount" refers to the amount of a population of progenitor cells or their progeny needed to prevent or alleviate at least one or more signs or symptoms of autosomal dominant RP, and relates to a sufficient amount of a composition to provide the desired effect, e.g., to treat a subject having autosomal dominant RP. The term "therapeutically effective amount" therefore refers to an amount of progenitor cells or a composition comprising progenitor cells that is sufficient to promote a particular effect when administered to a typical subject, such as one who has or is at risk for autosomal dominant RP. An effective amount would also include an amount sufficient to prevent or delay the development of a symptom of the disease, alter the course of a symptom of the disease (for example but not limited to, slow the progression of a symptom of the disease), or reverse a symptom of the disease. It is understood that for any given case, an appropriate "effective amount" can be determined by one of ordinary skill in the art using routine experimentation.

For use in the various aspects described herein, an effective amount of progenitor cells comprises at least $10^2$ progenitor cells, at least $5 \times 10^2$ progenitor cells, at least $10^3$ progenitor cells, at least $5 \times 10^3$ progenitor cells, at least $10^4$ progenitor cells, at least $5 \times 10^4$ progenitor cells, at least $10^5$ progenitor cells, at least $2 \times 10^5$ progenitor cells, at least $3 \times 10^5$ progenitor cells, at least $4 \times 10^5$ progenitor cells, at least $5 \times 10^5$ progenitor cells, at least $6 \times 10^5$ progenitor cells, at least $7 \times 10^5$ progenitor cells, at least $8 \times 10^5$ progenitor cells, at least $9 \times 10^5$ progenitor cells, at least $1 \times 10^6$ progenitor cells, at least $2 \times 10^6$ progenitor cells, at least $3 \times 10^6$ progenitor cells, at least $4 \times 10^6$ progenitor cells, at least $5\times10^6$ progenitor cells, at least $6\times10^6$ progenitor cells, at least $7\times10^6$ progenitor cells, at least $8\times10^6$ progenitor cells, at least $9\times10^6$ progenitor cells, or multiples thereof. The progenitor cells can be derived from one or more donors, or can be obtained from an autologous source. In some examples described herein, the progenitor cells can be expanded in culture prior to administration to a subject in need thereof.

Modest and incremental increases in the levels of functional RHO protein expressed in cells of patients having autosomal dominant RP can be beneficial for ameliorating one or more symptoms of the disease, for increasing long-term survival, and/or for reducing side effects associated with other treatments. Upon administration of such cells to human patients, the presence of progenitors that are producing increased levels of functional RHO protein is beneficial. In some cases, effective treatment of a subject gives rise to at least about 3%, 5% or 7% functional RHO protein relative to total RHO in the treated subject. In some examples, functional RHO will be at least about 10% of total RHO. In some examples, functional RHO protein will be at least about 20% to 30% of total RHO protein. Similarly, the introduction of even relatively limited subpopulations of cells having significantly elevated levels of functional RHO protein can be beneficial in various patients because in some situations normalized cells will have a selective advantage relative to diseased cells. However, even modest levels of progenitors with elevated levels of functional RHO protein can be beneficial for ameliorating one or more aspects of autosomal dominant RP in patients. In some examples, about 10%, about 20%, about 30%, about 40%, about 50%, about 60%, about 70%, about 80%, about 90% or more of the photoreceptor cells or retinal progenitor cells in patients to whom such cells are administered are producing increased levels of functional RHO protein.

"Administered" refers to the delivery of a progenitor cell composition into a subject by a method or route that results in at least partial localization of the cell composition at a desired site. A cell composition can be administered by any appropriate route that results in effective treatment in the subject, i.e. administration results in delivery to a desired location in the subject where at least a portion of the composition delivered, i.e. at least $1\times10^4$ cells are delivered to the desired site for a period of time.

In one aspect of the method, the pharmaceutical composition can be administered via a route such as, but not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedullaris), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration, which is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

Modes of administration include injection, infusion, instillation, and/or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

The cells can be administered systemically. The phrases "systemic administration," "administered systemically", "peripheral administration" and "administered peripherally" refer to the administration of a population of progenitor cells other than directly into a target site, tissue, or organ, such that it enters, instead, the subject's circulatory system and, thus, is subject to metabolism and other like processes.

The efficacy of a treatment comprising a composition for the treatment of autosomal dominant RP can be determined by the skilled clinician. However, a treatment is considered "effective treatment," if any one or all of the signs or symptoms of, as but one example, levels of functional autosomal dominant RP are altered in a beneficial manner (e.g., increased by at least 10%), or other clinically accepted symptoms or markers of disease are improved or ameliorated. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of symptoms; or (2) relieving the disease, e.g., causing regression of symptoms; and (3) preventing or reducing the likelihood of the development of symptoms.

The treatment according to the present disclosure can ameliorate one or more symptoms associated with autosomal dominant RP by increasing, decreasing or altering the amount of functional RHO in the individual. Signs typically associated with autosomal dominant RP include for example, night blindness, visual acuity, fundus appearance, posterior subcapsular cataracts, dust-like particles in the vitreous, white dots deep in the retina, hyaline bodies of the optic nerve head, exudative vasculopathy, and sector autosomal dominant RP.

Kits

The present disclosure provides kits for carrying out the methods described herein. A kit can include one or more of a genome-targeting nucleic acid, a polynucleotide encoding a genome-targeting nucleic acid, a site-directed polypeptide, a polynucleotide encoding a site-directed polypeptide, and/or any nucleic acid or proteinaceous molecule necessary to carry out the aspects of the methods described herein, or any combination thereof.

A kit can comprise: (1) a vector comprising a nucleotide sequence encoding a genome-targeting nucleic acid, (2) the site-directed polypeptide or a vector comprising a nucleotide sequence encoding the site-directed polypeptide, and (3) a reagent for reconstitution and/or dilution of the vector(s) and or polypeptide.

A kit can comprise: (1) a vector comprising (i) a nucleotide sequence encoding a genome-targeting nucleic acid, and (ii) a nucleotide sequence encoding the site-directed polypeptide; and (2) a reagent for reconstitution and/or dilution of the vector.

In any of the above kits, the kit can comprise a single-molecule guide genome-targeting nucleic acid. In any of the above kits, the kit can comprise a double-molecule genome-targeting nucleic acid. In any of the above kits, the kit can comprise two or more double-molecule guides or single-molecule guides. The kits can comprise a vector that encodes the nucleic acid targeting nucleic acid.

In any of the above kits, the kit can further comprise a polynucleotide to be inserted to effect the desired genetic modification.

Components of a kit can be in separate containers, or combined in a single container.

Any kit described above can further comprise one or more additional reagents, where such additional reagents are selected from a buffer, a buffer for introducing a polypeptide or polynucleotide into a cell, a wash buffer, a control reagent, a control vector, a control RNA polynucleotide, a reagent for in vitro production of the polypeptide from DNA, adaptors for sequencing and the like. A buffer can be a stabilization buffer, a reconstituting buffer, a diluting buffer, or the like. A kit can also comprise one or more components that can be used to facilitate or enhance the on-target binding or the cleavage of DNA by the endonuclease, or improve the specificity of targeting.

In addition to the above-mentioned components, a kit can further comprise instructions for using the components of the kit to practice the methods. The instructions for practicing the methods can be recorded on a suitable recording medium. For example, the instructions can be printed on a substrate, such as paper or plastic, etc. The instructions can be present in the kits as a package insert, in the labeling of the container of the kit or components thereof (i.e., associated with the packaging or sub packaging), etc. The instructions can be present as an electronic storage data file present on a suitable computer readable storage medium, e.g. CD-ROM, diskette, flash drive, etc. In some instances, the actual instructions are not present in the kit, but means for obtaining the instructions from a remote source (e.g. via the Internet), can be provided. An example of this case is a kit that comprises a web address where the instructions can be viewed and/or from which the instructions can be downloaded. As with the instructions, this means for obtaining the instructions can be recorded on a suitable substrate.

Other Possible Therapeutic Approaches

Gene editing can be conducted using nucleases engineered to target specific sequences. To date there are four major types of nucleases: meganucleases and their derivatives, zinc finger nucleases (ZFNs), transcription activator like effector nucleases (TALENs), and CRISPR-Cas9 nuclease systems. The nuclease platforms vary in difficulty of design, targeting density and mode of action, particularly as the specificity of ZFNs and TALENs is through protein-DNA interactions, while RNA-DNA interactions primarily guide Cas9. Cas9 cleavage also requires an adjacent motif, the PAM, which differs between different CRISPR systems. Cas9 from *Streptococcus pyogenes* cleaves using a NGG PAM, CRISPR from *Neisseria meningitidis* can cleave at sites with PAMs including NNNNGATT, NNNNNGTTT and NNNNGCTT. A number of other Cas9 orthologs target protospacer adjacent to alternative PAMs.

CRISPR endonucleases, such as Cas9, can be used in the methods of the present disclosure. However, the teachings described herein, such as therapeutic target sites, could be applied to other forms of endonucleases, such as ZFNs, TALENs, HEs, or MegaTALs, or using combinations of nucleases. However, in order to apply the teachings of the present disclosure to such endonucleases, one would need to, among other things, engineer proteins directed to the specific target sites.

Additional binding domains can be fused to the Cas9 protein to increase specificity. The target sites of these constructs would map to the identified gRNA specified site, but would require additional binding motifs, such as for a zinc finger domain. In the case of Mega-TAL, a meganuclease can be fused to a TALE DNA-binding domain. The meganuclease domain can increase specificity and provide the cleavage. Similarly, inactivated or dead Cas9 (dCas9) can be fused to a cleavage domain and require the sgRNA/Cas9 target site and adjacent binding site for the fused DNA-binding domain. This likely would require some protein engineering of the dCas9, in addition to the catalytic inactivation, to decrease binding without the additional binding site.

Zinc Finger Nucleases

Zinc finger nucleases (ZFNs) are modular proteins comprised of an engineered zinc finger DNA binding domain linked to the catalytic domain of the type II endonuclease FokI. Because FokI functions only as a dimer, a pair of ZFNs must be engineered to bind to cognate target "half-site" sequences on opposite DNA strands and with precise spacing between them to enable the catalytically active FokI dimer to form. Upon dimerization of the FokI domain, which itself has no sequence specificity per se, a DNA double-strand break is generated between the ZFN half-sites as the initiating step in genome editing.

The DNA binding domain of each ZFN is typically comprised of 3-6 zinc fingers of the abundant Cys2-His2 architecture, with each finger primarily recognizing a triplet of nucleotides on one strand of the target DNA sequence, although cross-strand interaction with a fourth nucleotide also can be important. Alteration of the amino acids of a finger in positions that make key contacts with the DNA alters the sequence specificity of a given finger. Thus, a four-finger zinc finger protein will selectively recognize a 12 bp target sequence, where the target sequence is a composite of the triplet preferences contributed by each finger, although triplet preference can be influenced to varying degrees by neighboring fingers. An important aspect of ZFNs is that they can be readily re-targeted to almost any genomic address simply by modifying individual fingers, although considerable expertise is required to do this well. In most applications of ZFNs, proteins of 4-6 fingers are used, recognizing 12-18 bp respectively. Hence, a pair of ZFNs will typically recognize a combined target sequence of 24-36 bp, not including the typical 5-7 bp spacer between half-sites. The binding sites can be separated further with larger spacers, including 15-17 bp. A target sequence of this length is likely to be unique in the human genome, assuming repetitive sequences or gene homologs are excluded during the design process. Nevertheless, the ZFN protein-DNA interactions are not absolute in their specificity so off-target binding and cleavage events do occur, either as a heterodimer between the two ZFNs, or as a homodimer of one or the other of the ZFNs. The latter possibility has been effectively eliminated by engineering the dimerization interface of the FokI domain to create "plus" and "minus" variants, also known as obligate heterodimer variants, which can only dimerize with each other, and not with themselves. Forcing the obligate heterodimer prevents formation of the homodimer. This has greatly enhanced specificity of ZFNs, as well as any other nuclease that adopts these FokI variants.

A variety of ZFN-based systems have been described in the art, modifications thereof are regularly reported, and numerous references describe rules and parameters that are used to guide the design of ZFNs; see, e.g., Segal et al., Proc Natl Acad Sci USA 96(6):2758-63 (1999); Dreier B et al., J Mol Biol. 303(4):489-502 (2000); Liu Q et al., J Biol Chem. 277(6):3850-6 (2002); Dreier et al., J Biol Chem 280(42): 35588-97 (2005); and Dreier et al., J Biol Chem. 276(31): 29466-78 (2001).

Transcription Activator-Like Effector Nucleases (TALENs)

Transcription Activator-Like Effector Nucleases (TALENs) represent another format of modular nucleases whereby, as with ZFNs, an engineered DNA binding domain is linked to the FokI nuclease domain, and a pair of TALENs operates in tandem to achieve targeted DNA cleavage. The major difference from ZFNs is the nature of the DNA binding domain and the associated target DNA sequence recognition properties. The TALEN DNA binding domain derives from TALE proteins, which were originally described in the plant bacterial pathogen *Xanthomonas* sp. TALEs are comprised of tandem arrays of 33-35 amino acid repeats, with each repeat recognizing a single base pair in the target DNA sequence that is typically up to 20 bp in length, giving a total target sequence length of up to 40 bp. Nucleotide specificity of each repeat is determined by the repeat variable diresidue (RVD), which includes just two amino acids at positions 12 and 13. The bases guanine, adenine, cytosine and thymine are predominantly recognized by the four RVDs: Asn-Asn, Asn-Ile, His-Asp and Asn-Gly, respectively. This constitutes a much simpler recognition code than for zinc fingers, and thus represents an advantage over the latter for nuclease design. Nevertheless, as with ZFNs, the protein-DNA interactions of TALENs are not absolute in their specificity, and TALENs have also benefited from the use of obligate heterodimer variants of the FokI domain to reduce off-target activity.

Additional variants of the FokI domain have been created that are deactivated in their catalytic function. If one half of either a TALEN or a ZFN pair contains an inactive FokI domain, then only single-strand DNA cleavage (nicking) will occur at the target site, rather than a DSB. The outcome is comparable to the use of CRISPR/Cas9/Cpf1 "nickase" mutants in which one of the Cas9 cleavage domains has been deactivated. DNA nicks can be used to drive genome editing by HDR, but at lower efficiency than with a DSB. The main benefit is that off-target nicks are quickly and accurately repaired, unlike the DSB, which is prone to NHEJ-mediated mis-repair.

A variety of TALEN-based systems have been described in the art, and modifications thereof are regularly reported; see, e.g., Boch, Science 326(5959):1509-12 (2009); Mak et al., Science 335(6069):716-9 (2012); and Moscou et al., Science 326(5959):1501 (2009). The use of TALENs based on the "Golden Gate" platform, or cloning scheme, has been described by multiple groups; see, e.g., Cermak et al., Nucleic Acids Res. 39(12):e82 (2011); Li et al., Nucleic Acids Res. 39(14):6315-25(2011); Weber et al., PLoS One. 6(2): e16765 (2011); Wang et al., J Genet Genomics 41(6): 339-47, Epub 2014 May 17 (2014); and Cermak T et al., Methods Mol Biol. 1239:133-59 (2015).

Homing Endonucleases

Homing endonucleases (HEs) are sequence-specific endonucleases that have long recognition sequences (14-44 base pairs) and cleave DNA with high specificity—often at sites unique in the genome. There are at least six known families of HEs as classified by their structure, including LAGLIDADG (SEQ ID NO: 5271), GIY-YIG, His-Cis box, H-N-H, PD-(D/E)xK, and Vsr-like that are derived from a broad range of hosts, including eukarya, protists, bacteria, archaea, cyanobacteria and phage. As with ZFNs and TALENs, HEs can be used to create a DSB at a target locus as the initial step in genome editing. In addition, some natural and engineered HEs cut only a single strand of DNA, thereby functioning as site-specific nickases. The large target sequence of HEs and the specificity that they offer have made them attractive candidates to create site-specific DSBs.

A variety of HE-based systems have been described in the art, and modifications thereof are regularly reported; see, e.g., the reviews by Steentoft et al., Glycobiology 24(8):

663-80 (2014); Belfort and Bonocora, Methods Mol Biol. 1123:1-26 (2014); Hafez and Hausner, Genome 55(8):553-69 (2012).

MegaTAL/Tev-mTALEN/MegaTev

As further examples of hybrid nucleases, the MegaTAL platform and Tev-mTALEN platform use a fusion of TALE DNA binding domains and catalytically active HEs, taking advantage of both the tunable DNA binding and specificity of the TALE, as well as the cleavage sequence specificity of the HE; see, e.g., Boissel et al., NAR 42: 2591-2601 (2014); Kleinstiver et al., G3 4:1155-65 (2014); and Boissel and Scharenberg, Methods Mol. Biol. 1239: 171-96 (2015).

In a further variation, the MegaTev architecture is the fusion of a meganuclease (Mega) with the nuclease domain derived from the GIY-YIG homing endonuclease I-TevI (Tev). The two active sites are positioned ~30 bp apart on a DNA substrate and generate two DSBs with non-compatible cohesive ends; see, e.g., Wolfs et al., NAR 42, 8816-29 (2014). It is anticipated that other combinations of existing nuclease-based approaches will evolve and be useful in achieving the targeted genome modifications described herein.

dCas9-FokI or dCpf1-FokI and Other Nucleases

Combining the structural and functional properties of the nuclease platforms described above offers a further approach to genome editing that can potentially overcome some of the inherent deficiencies. As an example, the CRISPR genome editing system typically uses a single Cas9 endonuclease to create a DSB. The specificity of targeting is driven by a 20 or 24 nucleotide sequence in the guide RNA that undergoes Watson-Crick base-pairing with the target DNA (plus an additional 2 bases in the adjacent NAG or NGG PAM sequence in the case of Cas9 from *S. pyogenes*). Such a sequence is long enough to be unique in the human genome, however, the specificity of the RNA/DNA interaction is not absolute, with significant promiscuity sometimes tolerated, particularly in the 5' half of the target sequence, effectively reducing the number of bases that drive specificity. One solution to this has been to completely deactivate the Cas9 or Cpf1 catalytic function—retaining only the RNA-guided DNA binding function—and instead fusing a FokI domain to the deactivated Cas9; see, e.g., Tsai et al., Nature Biotech 32: 569-76 (2014); and Guilinger et al., Nature Biotech. 32: 577-82 (2014). Because FokI must dimerize to become catalytically active, two guide RNAs are required to tether two FokI fusions in close proximity to form the dimer and cleave DNA. This essentially doubles the number of bases in the combined target sites, thereby increasing the stringency of targeting by CRISPR-based systems.

As further example, fusion of the TALE DNA binding domain to a catalytically active HE, such as I-TevI, takes advantage of both the tunable DNA binding and specificity of the TALE, as well as the cleavage sequence specificity of I-TevI, with the expectation that off-target cleavage can be further reduced.

Methods and Compositions of the Invention

Accordingly, the present disclosure relates in particular to the following non-limiting inventions:

In a first method, Method 1, the present disclosure provides a method for editing a RHO gene in a human cell, the method comprising: introducing into the human cell one or more DNA endonucleases to effect one or more SSBs or DSBs within or near the RHO gene or other DNA sequences that encode regulatory elements of the RHO gene that results in a permanent deletion, insertion, correction, or modulation of expression or function of one or more mutations within or near or affecting the expression or function of the RHO gene thereby creating an edited human cell.

In another method, Method 2, the present disclosure provides a method for editing a P23H mutation in a RHO gene in a human cell, the method comprising: introducing into the human cell one or more DNA endonucleases to effect one or more SSBs or DSBs within or near the P23H mutation in a RHO gene that results in a permanent deletion, insertion, correction, or modulation of expression or function of the P23H mutation thereby creating an edited human cell.

In another method, Method 3, the present disclosure provides an in vivo method for treating a patient with autosomal dominant RP, the method comprising: editing a P23H mutation in a RHO gene in a cell of the patient.

In another method, Method 4, the present disclosure provides an in vivo method for treating a patient with autosomal dominant RP as provided in Method 3, wherein the editing comprises: introducing into the cell one or more DNA endonucleases to effect one or more SSBs or DSBs within or near the P23H mutation in a RHO gene that results in a permanent deletion, insertion, correction, or modulation of expression or function of the P23H mutation and results in restoration of RHO protein activity.

In another method, Method 5, the present disclosure provides an in vivo method for treating a patient with autosomal dominant RP as provided in any of Methods 1-2 or 4, wherein the one or more DNA endonucleases is a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

In another method, Method 6, the present disclosure provides an in vivo method for treating a patient with autosomal dominant RP as provided in Method 5, wherein the method comprises introducing into the cell one or more polynucleotides encoding the one or more DNA endonucleases.

In another method, Method 7, the present disclosure provides an in vivo method for treating a patient with autosomal dominant RP as provided in Method 5, wherein the method comprises introducing into the cell one or more RNAs encoding the one or more DNA endonucleases.

In another method, Method 8, the present disclosure provides an in vivo method for treating a patient with autosomal dominant RP as provided in any of Methods 6 or 7, wherein the one or more polynucleotides or one or more RNAs is one or more modified polynucleotides or one or more modified RNAs.

In another method, Method 9, the present disclosure provides an in vivo method for treating a patient with autosomal dominant RP as provided in Method 5, wherein the DNA endonuclease is one or more proteins or polypeptides.

In another method, Method 10, the present disclosure provides an in vivo method for treating a patient with autosomal dominant RP as provided in any of Methods 1-9, wherein the method further comprises: introducing into the cell one or more gRNAs.

In another method, Method 11, the present disclosure provides an in vivo method for treating a patient with autosomal dominant RP as provided in Method 10, wherein the one or more gRNAs are sgRNAs.

In another method, Method 12, the present disclosure provides an in vivo method for treating a patient with autosomal dominant RP as provided in any of Methods 10-11, wherein the one or more gRNAs or one or more sgRNAs is one or more modified gRNAs or one or more modified sgRNAs.

In another method, Method 13, the present disclosure provides an in vivo method for treating a patient with autosomal dominant RP as provided in any of Methods 9-11, wherein the one or more DNA endonucleases is pre-complexed with one or more gRNAs or one or more sgRNAs.

In another method, Method 14, the present disclosure provides an in vivo method for treating a patient with autosomal dominant RP as provided in any of Methods 1-13 further comprising: introducing into the cell a polynucleotide donor template comprising at least a portion of the wild-type RHO gene, or cDNA.

In another method, Method 15, the present disclosure provides an in vivo method for treating a patient with autosomal dominant RP as provided in Method 14, wherein the at least a portion of the wild-type RHO gene or cDNA is exon 1, exon 2, exon 3, exon 4, exon 5, intronic regions, fragments or combinations thereof, or the entire RHO gene or cDNA.

In another method, Method 16, the present disclosure provides an in vivo method for treating a patient with autosomal dominant RP as provided in any of Methods 14-15, wherein the donor template is either a single or double stranded polynucleotide.

In another method, Method 17, the present disclosure provides an in vivo method for treating a patient with autosomal dominant RP as provided in any of Methods 14-15, wherein the donor template has homologous arms to the 3q22.1 region.

In another method, Method 18, the present disclosure provides an in vivo method for treating a patient with autosomal dominant RP as provided in any of Methods 2 or 4, further comprising: introducing into the cell one gRNA and a polynucleotide donor template comprising at least a portion of the wild-type RHO gene; wherein the one or more DNA endonucleases is one or more Cas9 or Cpf1 endonucleases that effect one SSB or DSB at a locus located within or near the P23H mutation in a RHO gene that facilitates insertion of a new sequence from the polynucleotide donor template into the chromosomal DNA at the locus that results in a permanent insertion or correction of the P23H mutation in a RHO gene; and wherein the gRNA comprises a spacer sequence that is complementary to a segment of the locus located within or near the P23H mutation in a RHO gene.

In another method, Method 19, the present disclosure provides an in vivo method for treating a patient with autosomal dominant RP as provided in any of Methods 2 or 4, further comprising: introducing into the cell one or more gRNAs and a polynucleotide donor template comprising at least a portion of the wild-type RHO gene; wherein the one or more DNA endonucleases is one or more Cas9 or Cpf1 endonucleases that effect a pair of single-strand breaks (SSBs) or double-strand breaks (DSBs), the first at a 5' locus and the second at a 3' locus, within or near the P23H mutation in a RHO gene that facilitates insertion of a new sequence from the polynucleotide donor template into the chromosomal DNA between the 5' locus and the 3' locus that results in a permanent insertion or correction of the chromosomal DNA between the 5' locus and the 3' locus within or near the P23H mutation in a RHO gene; and wherein the first guide RNA comprises a spacer sequence that is complementary to a segment of the 5' locus and the second guide RNA comprises a spacer sequence that is complementary to a segment of the 3' locus.

In another method, Method 20, the present disclosure provides an in vivo method for treating a patient with autosomal dominant RP as provided in any of Methods 18-19, wherein the one or more gRNAs are one or more sgRNAs.

In another method, Method 21, the present disclosure provides an in vivo method for treating a patient with autosomal dominant RP as provided in any of Methods 18-20, wherein the one or more gRNAs or one or more sgRNAs is one or more modified gRNAs or one or more modified sgRNAs.

In another method, Method 22, the present disclosure provides an in vivo method for treating a patient with autosomal dominant RP as provided in any of Methods 18-21, wherein the one or more DNA endonucleases is pre-complexed with one or more gRNAs or one or more sgRNAs.

In another method, Method 23, the present disclosure provides an in vivo method for treating a patient with autosomal dominant RP as provided in any of Methods 18-22, wherein the at least a portion of the wild-type RHO gene or cDNA is exon 1, exon 2, exon 3, exon 4, exon 5, intronic regions, fragments or combinations thereof, or the entire RHO gene or cDNA.

In another method, Method 24, the present disclosure provides an in vivo method for treating a patient with autosomal dominant RP as provided in any of Methods 18-23, wherein the donor template is either a single or double stranded polynucleotide.

In another method, Method 25, the present disclosure provides an in vivo method for treating a patient with autosomal dominant RP as provided in any of Methods 18-24, wherein the donor template has homologous arms to the 3q22.1 region.

In another method, Method 26, the present disclosure provides an in vivo method for treating a patient with autosomal dominant RP as provided in any of Methods 18-25, wherein the SSB or DSB are in the first exon, second exon, third exon, fourth exon, fifth exon, or combinations thereof of the RHO gene.

In another method, Method 27, the present disclosure provides an in vivo method for treating a patient with autosomal dominant RP as provided in any of Methods 10-13 or 20-22, wherein the gRNA or sgRNA is directed to a pathological variant P23H.

In another method, Method 28, the present disclosure provides an in vivo method for treating a patient with autosomal dominant RP as provided in any of Methods 1-2 or 4-27, wherein the insertion or correction is by HDR.

In another method, Method 29, the present disclosure provides an in vivo method for treating a patient with autosomal dominant RP as provided in any of Methods 18-19, wherein the donor template has homologous arms to a pathological variant P23H.

In another method, Method 30, the present disclosure provides an in vivo method for treating a patient with autosomal dominant RP as provided in any of Methods 2 or 4, further comprising: introducing into the cell two gRNAs and a polynucleotide donor template comprising at least a portion of the wild-type RHO gene; wherein the one or more DNA endonucleases is one or more Cas9 or Cpf1 endonucleases that effect a pair of DSBs, the first at a 5' DSB locus and the second at a 3' DSB locus, within or near the P23H mutation in a RHO gene that causes a deletion of the chromosomal DNA between the 5' DSB locus and the 3' DSB locus that results in a permanent deletion of the chromosomal DNA between the 5' DSB locus and the 3' DSB locus within or near the P23H mutation in a RHO gene; and wherein the first guide RNA comprises a spacer sequence that is complementary to a segment of the 5' DSB locus and the second guide RNA comprises a spacer sequence that is complementary to a segment of the 3' DSB locus.

In another method, Method 31, the present disclosure provides an in vivo method for treating a patient with autosomal dominant RP as provided in Method 30, wherein the two gRNAs are two sgRNAs.

In another method, Method 32, the present disclosure provides an in vivo method for treating a patient with autosomal dominant RP as provided in any of Methods 30-31, wherein the two gRNAs or two sgRNAs are two modified gRNAs or two modified sgRNAs.

In another method, Method 33, the present disclosure provides an in vivo method for treating a patient with autosomal dominant RP as provided in any of Methods 30-32, wherein the one or more DNA endonucleases is pre-complexed with two gRNAs or two sgRNAs.

In another method, Method 34, the present disclosure provides an in vivo method for treating a patient with autosomal dominant RP as provided in any of Methods 30-33, wherein both the 5' DSB and 3' DSB are in or near either the first exon, first intron, second exon, second intron, third exon, third intron, fourth exon, fourth intron, fifth exon, fifth intron, or combinations thereof, of the RHO gene.

In another method, Method 35, the present disclosure provides an in vivo method for treating a patient with autosomal dominant RP as provided in any of Methods 30-34, wherein the deletion is a deletion of 1 kb or less.

In another method, Method 36, the present disclosure provides an in vivo method for treating a patient with autosomal dominant RP as provided in any of Methods 18-19 and 30, wherein the Cas9 or Cpf1 mRNA, gRNA, and donor template are either each formulated into separate lipid nanoparticles or all co-formulated into a lipid nanoparticle.

In another method, Method 37, the present disclosure provides an in vivo method for treating a patient with autosomal dominant RP as provided in any of Methods 18-19 and 30, wherein the Cas9 or Cpf1 mRNA, gRNA, and donor template are either each formulated into separate AAV vectors or all co-formulated into an AAV vector.

In another method, Method 38, the present disclosure provides an in vivo method for treating a patient with autosomal dominant RP as provided in any of Methods 18-19 and 30, wherein the Cas9 or Cpf1 mRNA is formulated into a lipid nanoparticle, and both the gRNA and donor template are delivered to the cell by an AAV vector.

In another method, Method 39, the present disclosure provides an in vivo method for treating a patient with autosomal dominant RP as provided in any of Methods 18-19 and 30, wherein the Cas9 or Cpf1 mRNA is formulated into a lipid nanoparticle, and the gRNA is delivered to the cell by electroporation and donor template is delivered to the cell by an AAV vector.

In another method, Method 40, the present disclosure provides an in vivo method for treating a patient with autosomal dominant RP as provided in any of Methods 37-39, wherein the AAV vector is a self-inactivating AAV vector.

In another method, Method 41, the present disclosure provides an in vivo method for treating a patient with autosomal dominant RP as provided in any of Methods 1-40, wherein the RHO gene is located on Chromosome 3: 129,528,640-129,535,169 (Genome Reference Consortium—GRCh38/hg38).

In another method, Method 42, the present disclosure provides an in vivo method for treating a patient with autosomal dominant RP as provided in any of Methods 2 or 4-41, wherein the restoration of RHO protein activity is compared to wild-type or normal RHO protein activity.

In another method, Method 43, the present disclosure provides a method for editing a RHO gene in a human cell by genome editing as provided in Method 14, wherein the polynucleotide donor template comprises exon 1 of RHO and is up to 5 KB.

In another method, Method 44, the present disclosure provides a method for editing a RHO gene in a human cell by genome editing as provided in Method 43, wherein the polynucleotide donor template is delivered by AAV.

In another method, Method 45, the present disclosure provides a method for editing a RHO gene in a human cell by genome editing as provided in any of Methods 1-2, wherein the human cell is a photoreceptor cell, retinal progenitor cell, or induced pluripotent stem cell (iPSC).

In another method, Method 46, the present disclosure provides an in vivo method for treating a patient with autosomal dominant RP as provided in any of Methods 3-42, wherein the cell is a photoreceptor cell, retinal progenitor cell, or induced pluripotent stem cell (iPSC).

In another method, Method 47, the present disclosure provides a method for editing a P23H mutation within a RHO gene, the method comprising administering a gRNA or sgRNA comprising SEQ ID NO: 5290.

In another method, Method 48, the present disclosure provides a method for editing a P23H mutation within a RHO gene, the method comprising administering a gRNA or sgRNA comprising SEQ ID NO: 5291.

In another method, Method 49, the present disclosure provides a method for editing a P23H mutation within a RHO gene, the method comprising administering a gRNA or sgRNA comprising SEQ ID NO: 5319.

In another method, Method 50, the present disclosure provides a method for editing a P23H mutation within a RHO gene, the method comprising administering a gRNA or sgRNA comprising SEQ ID NO: 5320.

In another method, Method 51, the present disclosure provides a method for editing a P23H mutation within a RHO gene, the method comprising administering a gRNA or sgRNA comprising SEQ ID NO: 5321.

In another method, Method 52, the present disclosure provides a method for editing a P23H mutation within a RHO gene, the method comprising administering a gRNA or sgRNA comprising SEQ ID NO: 5322.

In another method, Method 53, the present disclosure provides a method for editing a P23H mutation within a RHO gene, the method comprising administering a gRNA or sgRNA comprising SEQ ID NO: 5358.

In another method, Method 54, the present disclosure provides a method for editing a P23H mutation within a RHO gene, the method comprising administering a gRNA or sgRNA comprising SEQ ID NO: 5290 and any one of SEQ ID NOs: 5327-5338.

In another method, Method 55, the present disclosure provides a method for editing an P23H mutation within a RHO gene, the method comprising administering a gRNA or sgRNA comprising SEQ ID NO: 5291 and any one of SEQ ID NOs: 5327-5338.

In another method, Method 56, the present disclosure provides a method for editing a P23H mutation within a RHO gene, the method comprising administering a gRNA or sgRNA comprising SEQ ID NO: 5319 and any one of SEQ ID NOs: 5327-5338.

In another method, Method 57, the present disclosure provides a method for editing a P23H mutation within a RHO gene, the method comprising administering a gRNA or sgRNA comprising SEQ ID NO: 5320 and any one of SEQ ID NOs: 5327-5338.

In another method, Method 58, the present disclosure provides a method for editing a P23H mutation within a RHO gene, the method comprising administering a gRNA or sgRNA comprising SEQ ID NO: 5321 and any one of SEQ ID NOs: 5327-5338.

In another method, Method 59, the present disclosure provides a method for editing a P23H mutation within a RHO gene, the method comprising administering a gRNA or sgRNA comprising SEQ ID NO: 5322 and any one of SEQ ID NOs: 5327-5338.

In another method, Method 60, the present disclosure provides a method for editing a P23H mutation within a RHO gene, the method comprising administering a gRNA or sgRNA comprising SEQ ID NO: 5358 and any one of SEQ ID NOs: 5327-5338.

In another method, Method 61, the present disclosure provides a method for treating a patient with a P23H mutation within a RHO gene, the method comprising administering a gRNA or sgRNA comprising SEQ ID NO: 5290 to the patient.

In another method, Method 62, the present disclosure provides a method for treating a patient with a P23H mutation within a RHO gene, the method comprising administering a gRNA or sgRNA comprising SEQ ID NO: 5291 to the patient.

In another method, Method 63, the present disclosure provides a method for treating a patient with a P23H mutation within a RHO gene, the method comprising administering a gRNA or sgRNA comprising SEQ ID NO: 5319 to the patient.

In another method, Method 64, the present disclosure provides a method for treating a patient with a P23H mutation within a RHO gene, the method comprising administering a gRNA or sgRNA comprising SEQ ID NO: 5320 to the patient.

In another method, Method 65, the present disclosure provides a method for treating a patient with a P23H mutation within a RHO gene, the method comprising administering a gRNA or sgRNA comprising SEQ ID NO: 5321 to the patient.

In another method, Method 66, the present disclosure provides a method for treating a patient with a P23H mutation within a RHO gene, the method comprising administering a gRNA or sgRNA comprising SEQ ID NO: 5322 to the patient.

In another method, Method 67, the present disclosure provides a method for treating a patient with a P23H mutation within a RHO gene, the method comprising administering a gRNA or sgRNA comprising SEQ ID NO: 5358 to the patient.

In another method, Method 68, the present disclosure provides a method for treating a patient with a P23H mutation within a RHO gene, the method comprising administering a gRNA or sgRNA to the patient, wherein the sgRNA comprises SEQ ID NO: 5290 and any one of SEQ ID NOs: 5327-5338.

In another method, Method 69, the present disclosure provides a method for treating a patient with a P23H mutation within a RHO gene, the method comprising administering a sgRNA to the patient, wherein the gRNA or sgRNA comprises SEQ ID NO: 5291 and any one of SEQ ID NOs: 5327-5338.

In another method, Method 70, the present disclosure provides a method for treating a patient with a P23H mutation within a RHO gene, the method comprising administering a sgRNA to the patient, wherein the gRNA or sgRNA comprises SEQ ID NO: 5319 and any one of SEQ ID NOs: 5327-5338.

In another method, Method 71, the present disclosure provides a method for treating a patient with a P23H mutation within a RHO gene, the method comprising administering a gRNA or sgRNA to the patient, wherein the sgRNA comprises SEQ ID NO: 5320 and any one of SEQ ID NOs: 5327-5338.

In another method, Method 72, the present disclosure provides a method for treating a patient with a P23H mutation within a RHO gene, the method comprising administering a sgRNA to the patient, wherein the gRNA or sgRNA comprises SEQ ID NO: 5321 and any one of SEQ ID NOs: 5327-5338.

In another method, Method 73, the present disclosure provides a method for treating a patient with a P23H mutation within a RHO gene, the method comprising administering a sgRNA to the patient, wherein the gRNA or sgRNA comprises SEQ ID NO: 5322 and any one of SEQ ID NOs: 5327-5338.

In another method, Method 74, the present disclosure provides a method for treating a patient with a P23H mutation within a RHO gene, the method comprising administering a sgRNA to the patient, wherein the gRNA or sgRNA comprises SEQ ID NO: 5358 and any one of SEQ ID NOs: 5327-5338.

In another method, Method 75, the present disclosure provides a method for editing a P23H mutation within a RHO gene, the method comprising administering a gRNA or sgRNA comprising SEQ ID NO: 5287.

In another method, Method 76, the present disclosure provides a method for editing a P23H mutation within a RHO gene, the method comprising administering a gRNA or sgRNA comprising SEQ ID NO: 5288.

In another method, Method 77, the present disclosure provides a method for editing a P23H mutation within a RHO gene, the method comprising administering a gRNA or sgRNA comprising SEQ ID NO: 5289.

In another method, Method 78, the present disclosure provides a method for treating a patient with a P23H mutation within a RHO gene, the method comprising administering a gRNA or sgRNA comprising SEQ ID NO: 5287 to the patient.

In another method, Method 79, the present disclosure provides a method for treating a patient with a P23H mutation within a RHO gene, the method comprising administering a gRNA or sgRNA comprising SEQ ID NO: 5288 to the patient.

In another method, Method 80, the present disclosure provides a method for treating a patient with a P23H mutation within a RHO gene, the method comprising administering a gRNA or sgRNA comprising SEQ ID NO: 5289 to the patient.

In another method, Method 81, the present disclosure provides a method for editing a P23H mutation within a RHO gene, the method comprising administering the self-inactivating CRISPR-Cas system of any of Self-inactivating CRISPR-Cas systems 1-36.

In another method, Method 82, the present disclosure provides a method for treating a patient with a P23H mutation within a RHO gene, the method comprising administering the self-inactivating CRISPR-Cas system of any of Self-inactivating CRISPR-Cas systems 1-36.

In another method, Method 83, the present disclosure provides a method of controlling Cas9 expression in a cell comprising: contacting the cell with the self-inactivating CRISPR-Cas system of any of Self-inactivating CRISPR-Cas systems 1-36.

In another method, Method 84, the present disclosure provides a method for editing a RHO gene in a human cell as provided in Method 1, wherein the human cell has defective activity and the edited human cell expresses a functional RHO.

In another method, Method 85, the present disclosure provides a method for editing a P23H mutation in a RHO gene in a human cell as provided in Method 2, wherein the human cell has defective activity and the edited human cell expresses a functional RHO.

In a first composition, Composition 1, the present disclosure provides one or more gRNAs for editing a P23H mutation in a RHO gene in a cell from a patient with autosomal dominant RP, the one or more gRNAs comprising a spacer sequence selected from the group consisting of nucleic acid sequences in SEQ ID NOs: 5287-5291, 5319-5322, and 5358 of the Sequence Listing.

In another composition, Composition 2, the present disclosure provides one or more gRNAs of Composition 1, wherein the one or more gRNAs are one or more sgRNAs.

In another composition, Composition 3, the present disclosure provides one or more gRNAs of any of Compositions 1-2, wherein the one or more gRNAs or one or more sgRNAs is one or more modified gRNAs or one or more modified sgRNAs.

In another composition, Composition 4, the present disclosure provides one or more gRNAs of any of Compositions 1-3, wherein the cell is a photoreceptor cell, retinal progenitor cell, or induced pluripotent stem cell (iPSC).

In another composition, Composition 5, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5290.

In another composition, Composition 6, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5291.

In another composition, Composition 7, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5319.

In another composition, Composition 8, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5320.

In another composition, Composition 9, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5321.

In another composition, Composition 10, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5322.

In another composition, Composition 11, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5358.

In another composition, Composition 12, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5290 and any one of SEQ ID NOs: 5327-5338.

In another composition, Composition 13, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5291 and any one of SEQ ID NOs: 5327-5338.

In another composition, Composition 14, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5319 and any one of SEQ ID NOs: 5327-5338.

In another composition, Composition 15, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5320 and any one of SEQ ID NOs: 5327-5338.

In another composition, Composition 16, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5321 and any one of SEQ ID NOs: 5327-5338.

In another composition, Composition 17, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5322 and any one of SEQ ID NOs: 5327-5338.

In another composition, Composition 18, the present disclosure provides a single-molecule guide RNA (sgRNA) for editing a P23H mutation in a RHO gene in a cell from a patient with autosomal dominant CORD, the sgRNA comprising the nucleic acid sequence of SEQ ID NO: 5358 and any one of SEQ ID NOs: 5327-5338.

In another composition, Composition 19, the present disclosure provides one or more gRNAs for editing a P23H mutation in a RHO gene, the one or more gRNAs comprising a spacer sequence selected from the group consisting of SEQ ID NOs: 5287-5291, 5319-5322, and 5358 of the Sequence Listing.

In a first therapeutic, Therapeutic 1, the present disclosure provides a therapeutic for treating a patient with autosomal dominant Retinitis Pigmentosa, the therapeutic comprising at least one or more gRNAs for editing a P23H mutation in a RHO gene, the one or more gRNAs comprising a spacer sequence selected from the group consisting of nucleic acid sequences in SEQ ID NOs: 5287-5291, 5319-5322, and 5358 of the Sequence Listing.

In another therapeutic, Therapeutic 2, the present disclosure provides the therapeutic of Therapeutic 2, wherein the one or more gRNAs are one or more sgRNAs.

In another therapeutic, Therapeutic 3, the present disclosure provides the therapeutic of any of Therapeutics 1 or 2, wherein the one or more gRNAs or one or more sgRNAs is one or more modified gRNAs or one or more modified sgRNAs.

In another therapeutic, Therapeutic 4, the present disclosure provides a therapeutic for treating a patient with autosomal dominant RP, the therapeutic formed by the method comprising: introducing one or more DNA endonucleases; introducing one or more gRNA or one or more sgRNA for editing a P23H mutation in a RHO gene; and optionally introducing one or more donor template; wherein the one or more gRNAs or sgRNAs comprise a spacer sequence selected from the group consisting of nucleic acid sequences in SEQ ID NOs: 5287-5291, 5319-5322, and 5358 of the Sequence Listing.

In another therapeutic, Therapeutic 5, the present disclosure provides a therapeutic comprising the self-inactivating CRISPR-Cas system of any of Self-inactivating CRISPR-Cas systems 1-36.

In another therapeutic, Therapeutic 6, the present disclosure provides the therapeutic of Therapeutic 5, wherein the therapeutic is sterile.

In a first kit, Kit 1, the present disclosure provides a kit for treating a patient with autosomal dominant RP in vivo, the kit comprising one or more gRNAs or sgRNAs for editing a P23H mutation in a RHO gene wherein the one or more gRNAs or sgRNAs comprise a spacer sequence selected from the group consisting of nucleic acid sequences in SEQ ID NOs: 5287-5291, 5319-5322, and 5358 of the Sequence Listing; one or more DNA endonucleases; and optionally, one or more donor template.

In another kit, Kit 2, the present disclosure provides the kit of Kit 1, wherein the one or more DNA endonucleases is a Cas1, Cas1B, Cas2, Cas3, Cas4, Cas5, Cash, Cas7, Cas8, Cas9 (also known as Csn1 and Csx12), Cas100, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or Cpf1 endonuclease; a homolog thereof, a recombination of the naturally occurring molecule thereof, codon-optimized thereof, or modified versions thereof, and combinations thereof.

In another kit, Kit 3, the present disclosure provides the kit of any of Kits 1 or 2, comprising one or more donor template.

In another kit, Kit 4, the present disclosure provides the kit of Kit 3, wherein the donor template has homologous arms to the 3q22.1 region.

In another kit, Kit 5, the present disclosure provides the kit of Kit 3, wherein the donor template has homologous arms to a pathological variant P23H.

In another kit, Kit 6, the present disclosure provides a kit for treating a patient with autosomal dominant RP in vivo, the kit comprising: any one of Self-inactivating CRISPR-Cas systems 1-36; and optionally, one or more donor template.

In another kit, Kit 7, the present disclosure provides the kit of Kit 6, comprising one or more donor template.

In another kit, Kit 8, the present disclosure provides the kit of Kit 7, wherein the donor template has homologous arms to the 3q22.1 region.

In another kit, Kit 9, the present disclosure provides the kit of Kit 7, wherein the donor template has homologous arms to a pathological variant P23H.

In a first self-inactivating CRISPR-Cas system, Self-inactivating CRISPR-Cas system 1, the present disclosure provides a self-inactivating CRISPR-Cas system comprising: a first segment comprising a nucleotide sequence that encodes a polypeptide inducing site-directed mutagenesis; a second segment comprising a nucleotide sequence that encodes a guide RNA (gRNA) or a single-molecule guide RNA (sgRNA) wherein the gRNA or sgRNA comprise SEQ ID NO: 5290; and one or more third segments comprising a self-inactivating (SIN) site; wherein the gRNA or sgRNA is substantially complementary to the SIN site; wherein the gRNA or sgRNA is substantially complementary to a genomic target sequence.

In another self-inactivating CRISPR-Cas system, Self-inactivating CRISPR-Cas system 2, the present disclosure provides a self-inactivating CRISPR-Cas system comprising a first segment comprising a nucleotide sequence that encodes a polypeptide inducing site-directed mutagenesis; a second segment comprising a nucleotide sequence that encodes a guide RNA (gRNA) or a single-molecule guide RNA (sgRNA) wherein the gRNA or sgRNA comprise SEQ ID NO: 5291; and one or more third segments comprising a self-inactivating (SIN) site; wherein the gRNA or sgRNA is substantially complementary to the SIN site; wherein the gRNA or sgRNA is substantially complementary to a genomic target sequence.

In another self-inactivating CRISPR-Cas system, Self-inactivating CRISPR-Cas system 3, the present disclosure provides the self-inactivating CRISPR-Cas system of Self-inactivating CRISPR-Cas systems 1 or 2, wherein the polypeptide inducing site-directed mutagenesis is *Staphylococcus aureus* Cas9 (SaCas9) or any variants thereof.

In another self-inactivating CRISPR-Cas system, Self-inactivating CRISPR-Cas system 4, the present disclosure provides the self-inactivating CRISPR-Cas system of Self-inactivating CRISPR-Cas systems 1-3, wherein the polypeptide inducing site-directed mutagenesis is SaCas9 or any variants thereof; and wherein the SIN site is a 5' SIN site located 5' of a SaCas9 open reading frame (ORF) or a 3' SIN site located within a naturally occurring or chimeric inserted intron located within the SaCas9 ORF.

In another self-inactivating CRISPR-Cas system, Self-inactivating CRISPR-Cas system 5, the present disclosure provides the self-inactivating CRISPR-Cas system of Self-inactivating CRISPR-Cas system 4, wherein the 5' SIN site comprises SEQ ID NO: 5300.

In another self-inactivating CRISPR-Cas system, Self-inactivating CRISPR-Cas system 6, the present disclosure provides the self-inactivating CRISPR-Cas system of Self-inactivating CRISPR-Cas systems 4-5, wherein the 3' SIN site comprises SEQ ID NO: 5280.

In another self-inactivating CRISPR-Cas system, Self-inactivating CRISPR-Cas system 7, the present disclosure provides the self-inactivating CRISPR-Cas system of Self-inactivating CRISPR-Cas system 4, wherein the 5' SIN site comprises SEQ ID NO: 5301.

In another self-inactivating CRISPR-Cas system, Self-inactivating CRISPR-Cas system 8, the present disclosure provides the self-inactivating CRISPR-Cas system of Self-inactivating CRISPR-Cas systems 4 and 7, wherein the 3' SIN site comprises SEQ ID NO: 5281.

In another self-inactivating CRISPR-Cas system, Self-inactivating CRISPR-Cas system 9, the present disclosure provides the self-inactivating CRISPR-Cas system of Self-inactivating CRISPR-Cas systems 4-5 and 7, wherein the 5' SIN site is located upstream of the SaCas9 open reading frame (ORF) and downstream of a SV40 nuclear localization signal (NLS).

In another self-inactivating CRISPR-Cas system, Self-inactivating CRISPR-Cas system 10, the present disclosure provides the self-inactivating CRISPR-Cas system of Self-inactivating CRISPR-Cas systems 4-5 and 7, wherein the 5' SIN site is located upstream of the SaCas9 open reading frame (ORF) and upstream of a SV40 nuclear localization signal (NLS) within a 5' untranslated region (UTR).

In another self-inactivating CRISPR-Cas system, Self-inactivating CRISPR-Cas system 11, the present disclosure provides the self-inactivating CRISPR-Cas system of Self-inactivating CRISPR-Cas systems 4, 6 and 8, wherein the 3' SIN site is located within a naturally occurring or chimeric inserted intron located within the SaCas9 ORF.

In another self-inactivating CRISPR-Cas system, Self-inactivating CRISPR-Cas system 12, the present disclosure provides the self-inactivating CRISPR-Cas system of Self-inactivating CRISPR-Cas systems 1-11, where the SIN site comprises a protospacer adjacent motif (PAM).

In another self-inactivating CRISPR-Cas system, Self-inactivating CRISPR-Cas system 13, the present disclosure provides the self-inactivating CRISPR-Cas system of Self-inactivating CRISPR-Cas system 12, wherein the PAM is NNGRRT or any variants thereof.

In another self-inactivating CRISPR-Cas system, Self-inactivating CRISPR-Cas system 14, the present disclosure provides the self-inactivating CRISPR-Cas system of Self-inactivating CRISPR-Cas systems 1-13, wherein the genomic target sequence is a P23H mutation in a rhodopsin (RHO) gene.

In another self-inactivating CRISPR-Cas system, Self-inactivating CRISPR-Cas system 15, the present disclosure provides the self-inactivating CRISPR-Cas system of Self-inactivating CRISPR-Cas systems 1-14, wherein the first segment comprising a nucleotide sequence that encodes a polypeptide inducing site-directed mutagenesis, further comprises a start codon, a stop codon, and a poly(A) termination site.

In another self-inactivating CRISPR-Cas system, Self-inactivating CRISPR-Cas system 16, the present disclosure provides the self-inactivating CRISPR-Cas system of Self-inactivating CRISPR-Cas systems 1-15, wherein the first segment and the third segment are provided together in a first vector and the second segment is provided in a second vector.

In another self-inactivating CRISPR-Cas system, Self-inactivating CRISPR-Cas system 17, the present disclosure provides the self-inactivating CRISPR-Cas system of Self-inactivating CRISPR-Cas systems 1-15, wherein the first segment, second segment, and third segment are provided together in a vector.

In another self-inactivating CRISPR-Cas system, Self-inactivating CRISPR-Cas system 18, the present disclosure provides the self-inactivating CRISPR-Cas system of Self-inactivating CRISPR-Cas systems 16-17, wherein the third segment is present in the first or second vector at a location 5' of the first segment.

In another self-inactivating CRISPR-Cas system, Self-inactivating CRISPR-Cas system 19, the present disclosure provides the self-inactivating CRISPR-Cas system of Self-inactivating CRISPR-Cas systems 16-17, wherein the third segment is present in the first or second vector at a location 3' of the first segment.

In another self-inactivating CRISPR-Cas system, Self-inactivating CRISPR-Cas system 20, the present disclosure provides the self-inactivating CRISPR-Cas system of Self-inactivating CRISPR-Cas systems 16-17, wherein the one or more third segments are present in the first or second vector at the 5' and 3' ends of the first segment.

In another self-inactivating CRISPR-Cas system, Self-inactivating CRISPR-Cas system 21, the present disclosure provides the self-inactivating CRISPR-Cas system of Self-inactivating CRISPR-Cas system 16, wherein the first vector comprises SEQ ID NO: 5341 and the second vector comprises SEQ ID NO: 5339.

In another self-inactivating CRISPR-Cas system, Self-inactivating CRISPR-Cas system 22, the present disclosure provides the self-inactivating CRISPR-Cas system of Self-inactivating CRISPR-Cas system 16, wherein the first vector comprises SEQ ID NO: 5341 and the second vector comprises SEQ ID NO: 5340.

In another self-inactivating CRISPR-Cas system, Self-inactivating CRISPR-Cas system 23, the present disclosure provides the self-inactivating CRISPR-Cas system of Self-inactivating CRISPR-Cas system 16, wherein the first vector comprises SEQ ID NO: 5342 and the second vector comprises SEQ ID NO: 5339.

In another self-inactivating CRISPR-Cas system, Self-inactivating CRISPR-Cas system 24, the present disclosure provides the self-inactivating CRISPR-Cas system of Self-inactivating CRISPR-Cas system 16, wherein the first vector comprises SEQ ID NO: 5342 and the second vector comprises SEQ ID NO: 5340.

In another self-inactivating CRISPR-Cas system, Self-inactivating CRISPR-Cas system 25, the present disclosure provides the self-inactivating CRISPR-Cas system of Self-inactivating CRISPR-Cas systems 1-24, wherein the third segment is less than 100 nucleotides in length.

In another self-inactivating CRISPR-Cas system, Self-inactivating CRISPR-Cas system 26, the present disclosure provides the self-inactivating CRISPR-Cas system of Self-inactivating CRISPR-Cas system 25, wherein the third segment is less than 50 nucleotides in length.

In another self-inactivating CRISPR-Cas system, Self-inactivating CRISPR-Cas system 27, the present disclosure provides the self-inactivating CRISPR-Cas system of Self-inactivating CRISPR-Cas systems 1-26, wherein the gRNA or sgRNA is fully complementary to the nucleotide sequence of the SIN site except for in at least one location.

In another self-inactivating CRISPR-Cas system, Self-inactivating CRISPR-Cas system 28, the present disclosure provides the self-inactivating CRISPR-Cas system of Self-inactivating CRISPR-Cas systems 1-27, wherein the gRNA or sgRNA is fully complementary to the nucleotide sequence of the SIN site except for in at least two locations.

In another self-inactivating CRISPR-Cas system, Self-inactivating CRISPR-Cas system 29, the present disclosure provides the self-inactivating CRISPR-Cas system of Self-inactivating CRISPR-Cas systems 1-28, wherein a nucleic acid sequence encoding a promoter is operably linked to the first segment.

In another self-inactivating CRISPR-Cas system, Self-inactivating CRISPR-Cas system 30, the present disclosure provides the self-inactivating CRISPR-Cas system of Self-inactivating CRISPR-Cas system 29, wherein the promoter is a spatially-restricted promoter, bidirectional promoter driving gRNA or sgRNA in one direction and SaCas9 in the opposite orientation, or an inducible promoter.

In another self-inactivating CRISPR-Cas system, Self-inactivating CRISPR-Cas system 31, the present disclosure provides the self-inactivating CRISPR-Cas system of Self-inactivating CRISPR-Cas system 30, wherein the spatially-restricted promoter is selected from the group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a retinal pigment epithelial (RPE) selective promoter.

In another self-inactivating CRISPR-Cas system, Self-inactivating CRISPR-Cas system 32, the present disclosure provides the self-inactivating CRISPR-Cas system of Self-inactivating CRISPR-Cas systems 16-17, wherein the vector is one or more adeno-associated virus (AAV) vectors.

In another self-inactivating CRISPR-Cas system, Self-inactivating CRISPR-Cas system 33, the present disclosure provides the self-inactivating CRISPR-Cas system of Self-inactivating CRISPR-Cas system 32, wherein the adeno-associated virus (AAV) vector is an AAV5 serotype capsid vector.

In another self-inactivating CRISPR-Cas system, Self-inactivating CRISPR-Cas system 34, the present disclosure provides a self-inactivating CRISPR-Cas system comprising: a first segment comprising a nucleotide sequence that encodes a SaCas9 or any variants thereof; a second segment comprising a nucleotide sequence that encodes a guide RNA (gRNA) or a single-molecule guide RNA (sgRNA); and one or more third segments comprising a self-inactivating (SIN) site; wherein the gRNA or sgRNA is substantially complementary to the SIN site; wherein the gRNA or sgRNA is substantially complementary to a genomic target sequence; wherein the SIN site comprises a sequence selected from the group consisting of SEQ ID NOs: 5313-5314.

In another self-inactivating CRISPR-Cas system, Self-inactivating CRISPR-Cas system 35, the present disclosure provides a self-inactivating CRISPR-Cas system comprising: a first segment comprising a nucleotide sequence that encodes a SpCas9 or any variants thereof; a second segment comprising a nucleotide sequence that encodes a guide RNA (gRNA) or a single-molecule guide RNA (sgRNA); and one or more third segments comprising a self-inactivating (SIN) site; wherein the gRNA or sgRNA is substantially complementary to the SIN site; wherein the gRNA or sgRNA is substantially complementary to a genomic target sequence; wherein the SIN site comprises a sequence selected from the group consisting of SEQ ID NOs: 5277-5279 or SEQ ID NOs: 5297-5299.

In another self-inactivating CRISPR-Cas system, Self-Inactivating CRISPR-Cas system 36, the present disclosure provides a self-inactivating CRISPR-Cas system of Self-inactivating CRISPR-Cas system 35, wherein the SIN site comprises a sequence 1, 2, 3, 4, 5, 6, or 7 nucleotides shorter than any one of the sequences selected from the group consisting of SEQ ID NOs: 5277-5279 or SEQ ID NOs: 5297-5299.

In another self-inactivating CRISPR-Cas system, Self-inactivating CRISPR-Cas system 35, the present disclosure provides a self-inactivating CRISPR-Cas system comprising: a first segment comprising a nucleotide sequence that encodes a SaCas9 or any variants thereof; a second segment comprising a nucleotide sequence that encodes a guide RNA (gRNA) or a single-molecule guide RNA (sgRNA); and one or more third segments comprising a self-inactivating (SIN) site; wherein the gRNA or sgRNA is substantially complementary to the SIN site; wherein the gRNA or sgRNA is substantially complementary to a genomic target sequence; wherein the SIN site comprises a sequence selected from the group consisting of SEQ ID NOs: 5280-5281, 5315-5318, and 5357 or SEQ ID NOs: 5300-5301, 5323-5326, and 5359.

In another self-inactivating CRISPR-Cas system, Self-Inactivating CRISPR-Cas system 36, the present disclosure provides a self-inactivating CRISPR-Cas system of Self-inactivating CRISPR-Cas system 35, wherein the SIN site comprises a sequence 1, 2, 3, 4, 5, 6, or 7 nucleotides shorter than any one of the sequences selected from the group consisting of SEQ ID NOs: 5280-5281, 5315-5318, and 5357 or SEQ ID NOs: 5300-5301, 5323-5326, and 5359.

In a first genetically modified cell, Genetically Modified Cell 1, the present disclosure provides a genetically modified cell comprising the self-inactivating CRISPR-Cas system of any of Self-inactivating CRISPR-Cas systems 1-36.

In another genetically modified cell, Genetically Modified Cell 2, the present disclosure provides the genetically modified cell of Genetically Modified Cell 1, wherein the cell is selected from the group consisting of: an archaeal cell, a bacterial cell, a eukaryotic cell, a eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, and a human cell.

In a first nucleic acid, Nucleic Acid 1, the present disclosure provides a nucleic acid encoding a gRNA comprising a spacer sequence selected from the group consisting of SEQ ID NOs: 5287-5291, 5319-5322, and 5358.

In another nucleic acid, Nucleic Acid 2, the present disclosure provides the nucleic acid of Nucleic Acid 1, wherein the gRNA is a sgRNA.

In a first vector, Vector 1, the present disclosure provides a vector encoding a gRNA comprising a spacer sequence selected from the group consisting of SEQ ID NOs: 5287-5291, 5319-5322, and 5358.

In another vector, Vector 2, the present disclosure provides the vector of Vector 1, wherein the gRNA is a sgRNA.

In another vector, Vector 3, the present disclosure provides the vector of any one of Vectors 1 or 2, wherein the vector is an AAV.

In another vector, Vector 4, the present disclosure provides the vector of any one of Vectors 1-3, wherein the vector is an AAV5 sertoype capsid vector.

Definitions

In addition to the definitions previously set forth herein, the following definitions are relevant to the present disclosure:

The term "alteration" or "alteration of genetic information" refers to any change in the genome of a cell. In the context of treating genetic disorders, alterations may include, but are not limited to, insertion, deletion and correction.

The term "insertion" refers to an addition of one or more nucleotides in a DNA sequence. Insertions can range from small insertions of a few nucleotides to insertions of large segments such as a cDNA or a gene.

The term "deletion" refers to a loss or removal of one or more nucleotides in a DNA sequence or a loss or removal of the function of a gene. In some cases, a deletion can include, for example, a loss of a few nucleotides, an exon, an intron, a gene segment, or the entire sequence of a gene. In some cases, deletion of a gene refers to the elimination or reduction of the function or expression of a gene or its gene product. This can result from not only a deletion of sequences within or near the gene, but also other events (e.g., insertion, nonsense mutation) that disrupt the expression of the gene.

The term "correction" as used herein, refers to a change of one or more nucleotides of a genome in a cell, whether by insertion, deletion or substitution. Such correction may result in a more favorable genotypic or phenotypic outcome, whether in structure or function, to the genomic site which was corrected. One non-limiting example of a "correction" includes the correction of a mutant or defective sequence to a wild-type sequence which restores structure or function to a gene or its gene product(s). Depending on the nature of the mutation, correction may be achieved via various strategies disclosed herein. In one non-limiting example, a missense mutation may be corrected by replacing the region containing the mutation with its wild-type counterpart. As another example, duplication mutations (e.g., repeat expansions) in a gene may be corrected by removing the extra sequences.

The term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a cDNA encoding the wild-type protein may be inserted into the genome of a cell carrying a mutant gene. Knock-in strategies need not replace the defective gene, in whole or in part. In some cases, a knock-in strategy may further involve substitution of an existing sequence with the provided sequence, e.g., substitution of a mutant allele with a wild-type copy. On the other hand, the term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. Finally, the term "knock-down" as used herein refers to reduction in the expression of a gene or its gene product(s). As a result of a gene knock-down, the protein activity or function may be attenuated or the protein levels may be reduced or eliminated.

The term "comprising" or "comprises" is used in reference to compositions, therapeutics, kits, methods, and respective component(s) thereof, that are essential to the present disclosure, yet open to the inclusion of unspecified elements, whether essential or not.

The term "consisting essentially of" refers to those elements required for a given aspect. The term permits the presence of additional elements that do not materially affect the basic and novel or functional characteristic(s) of that aspect of the present disclosure.

The term "consisting of" refers to compositions, therapeutics, kits, methods, and respective components thereof as described herein, which are exclusive of any element not recited in that description of the aspect.

The singular forms "a," "an," and "the" include plural references, unless the context clearly dictates otherwise.

Any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will comply with written description, sufficiency of description, and added matter requirements, including the requirements under 35 U.S.C. § 112(a) and Article 123(2) EPC. Also, unless expressly specified or otherwise required by context, all numerical parameters described in this specification (such as those expressing values, ranges, amounts, percentages, and the like) may be read as if prefaced by the word "about," even if the word "about" does not expressly appear before a number. Additionally, numerical parameters described in this specification should be construed in light of the number of reported significant digits, numerical precision, and by applying ordinary rounding techniques. It is also understood that numerical parameters described in this specification will necessarily possess the inherent variability characteristic of the underlying measurement techniques used to determine the numerical value of the parameter.

Any patent, publication, or other disclosure material identified herein is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is said to be incorporated by reference into this specification, but which conflicts with existing definitions, statements, or other disclosure material set forth herein, is only incorporated to the extent that no conflict arises between that incorporated material and the existing disclosure material. Applicants reserve the right to amend this specification to expressly recite any subject matter, or portion thereof, incorporated by reference herein.

The details of one or more aspects of the present disclosure are set forth in the accompanying examples below. Although any materials and methods similar or equivalent to those described herein can be used in the practice or testing of the present disclosure, specific examples of the materials and methods contemplated are now described. Other features, objects and advantages of the present disclosure will be apparent from the description. In the description examples, the singular forms also include the plural unless the context clearly dictates otherwise. Unless defined otherwise, all technical and scientific terms used herein have the same meaning as commonly understood by one of ordinary skill in the art to which this present disclosure belongs. In the case of conflict, the present description will control.

EXAMPLES

The present disclosure will be more fully understood by reference to the following examples, which provide illustrative non-limiting aspects of the invention.

The examples describe the use of the CRISPR system as an illustrative genome editing technique to create defined therapeutic genomic deletions, insertions, or replacements, termed "genomic modifications" herein, within or near the P23H mutation in the RHO gene that lead to a frameshift and silencing of the expression of the mutant gene or permanent correction of the P23H mutation in the genomic locus, or expression at a heterologous locus, that restore RHO protein activity. Introduction of the defined therapeutic modifications represents a novel therapeutic strategy for the potential amelioration of retinitis pigmentosa (RP), as described and illustrated herein.

Example 1

CRISPR/*S. pyogenes*(Sp)Cas9 PAM Sites for the P23H Mutation in the RHO Gene The P23H mutation in the RHO gene was scanned for SpCas9 protospacer adjacent motifs (PAMs). The area was scanned for PAMs having the sequence NRG. gRNA spacer sequences (17-24 bps) located upstream to the NRG PAM were then identified.

Example 2

CRISPR/*S. aureus*(Sa)Cas9 PAM sites for the P23H mutation in the RHO gene

The P23H mutation in the RHO gene was scanned for SaCas9 PAMs. The area was scanned for PAMs having the sequence NNGRRT. gRNA spacer sequences (17-24 bps) located upstream to the NNGRRT PAM were then identified.

Example 3

CRISPR/*S. thermophilus*(St)Cas9 PAM Sites for the P23H Mutation in the RHO Gene The P23H mutation in the RHO gene was scanned for StCas9 PAMs. The area was scanned for PAMs having the sequence NNAGAAW. gRNA spacer sequences (17-24 bps) located upstream to the NNAGAAW PAM were then identified.

Example 4

CRISPR/*T. denticola*(Td)Cas9 PAM Sites for the P23H Mutation in the RHO Gene The P23H mutation in the RHO gene was scanned for TdCas9 PAMs. The area was scanned for PAMs having the sequence NAAAAC. gRNA spacer sequences (17-24 bps) located upstream to the NAAAAC PAM were then identified.

Example 5

CRISPR/*N. meningitides*(Nm)Cas9 PAM Sites for the P23H Mutation in the RHO Gene The P23H mutation in the RHO gene was scanned for NmCas9 PAMs. The area was scanned for PAMs having the sequence NNNNGHTT. gRNA spacer sequences (17-24 bps) located upstream to the NNNNGHTT PAM were then identified.

Example 6

CRISPR/Cpf1 PAM Sites for the P23H Mutation in the RHO Gene

The P23H mutation in the RHO gene was scanned for Cpf-1 PAMs. The area was scanned for PAMs having the sequence YTN. gRNA spacer sequences (17-24 bps) located upstream to the YTN PAM were then identified.

Example 7

Bioinformatics Analysis of the Guide Strands

A gRNA or sgRNA is capable of directing a RNP complex to an on-target site such as a genomic sequence for which editing is desired or an off-target site for which editing is not desired. To learn more about which candidate gRNAs or sgRNAs were likely to have on-target and/or off-target activity, candidate guides were screened and selected in a single process or multi-step process that involves both theoretical binding and experimentally assessed activity at both on-target and off-target sites. These processes allow for selection of high specificity gRNAs or sgRNAs for further development.

By way of illustration, candidate guides having sequences that match a particular on-target site, such as a site within or near the P23H mutation in the RHO gene, with adjacent PAM were assessed for their potential to cleave at off-target sites having similar sequences, using one or more of a variety of bioinformatics tools available for assessing off-target binding, as described and illustrated in more detail below, in order to assess the likelihood of effects at chromosomal positions other than those intended.

Candidates predicted to have relatively lower potential for off-target activity were then assessed experimentally to measure their on-target activity, and then off-target activities at various sites. Guides having sufficiently high on-target activity to achieve desired levels of gene editing at the selected locus, and relatively lower off-target activity to reduce the likelihood of alterations at other chromosomal loci were preferred. The ratio of on-target to off-target activity is referred to as the "specificity" of a guide.

For initial screening of predicted off-target activities, there were a number of bioinformatics tools known and publicly available that were used to predict the most likely off-target sites; and since binding to target sites in the CRISPR/Cas9/Cpf1 nuclease system is driven by Watson-Crick base pairing between complementary sequences, the degree of dissimilarity (and therefore reduced potential for off-target binding) was essentially related to primary sequence differences: mismatches and bulges, i.e. bases that were changed to a non-complementary base, and insertions or deletions of bases in the potential off-target site relative to the target site. An exemplary bioinformatics tool called COSMID (CRISPR Off-target Sites with Mismatches, Insertions and Deletions) (available on the web at crispr.bme.gatech.edu) compiled such similarities. Other bioinformatics tools include, but are not limited to autoCOSMID and CCTop.

Bioinformatics was used to minimize off-target cleavage in order to reduce the detrimental effects of mutations and chromosomal rearrangements. Studies on CRISPR/Cas9 systems suggested the possibility of off-target activity due to non-specific hybridization of the guide strand to DNA sequences with base pair mismatches and/or bulges, particularly at positions distal from the PAM region. Therefore, it was important to have a bioinformatics tool that identified potential off-target sites that have insertions and/or deletions between the RNA guide strand and genomic sequences, in addition to base-pair mismatches. Bioinformatics tools based upon the off-target prediction algorithm CCTop were used to search genomes for potential CRISPR off-target sites (CCTop is available on the web at crispr.cos.uni-heidelberg.de/). The output ranked lists of the potential off-target sites based on the number and location of mismatches, allowing more informed choice of target sites, and avoiding the use of sites with more likely off-target cleavage.

Additional bioinformatics pipelines were employed that weigh the estimated on- and/or off-target activity of gRNA targeting sites in a region. Other features that were used to predict activity include information about the cell type in question, DNA accessibility, chromatin state, transcription factor binding sites, transcription factor binding data, and other CHIP-seq data. Additional factors were weighed that predict editing efficiency, such as relative positions and directions of pairs of gRNAs, local sequence features and micro-homologies.

Example 8

Testing of Guides in Cells for On-Target and Off-Target Activity

In order to further evaluate the specificity of guide RNAs investigated previously, select guide RNAs that were predicted to have the lowest off-target activity were tested for on-target and off-target activity in genetically engineered K562 cells by evaluating indel frequency using TIDE analysis. The data obtained provide evidence that the selected guide RNAs effectively edit the mutant P23H RHO gene while minimizing off-target activity.

The genome of the K562 cells contains two wild-type alleles of the human rhodopsin (RHO) gene, and the cells were engineered to stably express Staphylococcus aureus Cas9 endonuclease. These cells were transfected with either gRNAs that target the wild-type RHO gene or gRNAs that target the mutant P23H RHO gene. The gRNAs that target the wild-type RHO gene include: Human Rhodopsin WT 20mer (SEQ ID NO: 5285) and Human Rhodopsin WT 19mer (SEQ ID NO: 5286). The gRNAs that target the mutant P23H RHO gene include: Human Rhodopsin P23H 20mer (SEQ ID NO: 5290) and Human Rhodopsin P23H 19mer (SEQ ID NO: 5291) (FIG. 2B). The transfected K562 cells were compared to control cells, which were K562 cells expressing S. aureus Cas9 protein, but not transfected with any guide RNA.

Figure 3:
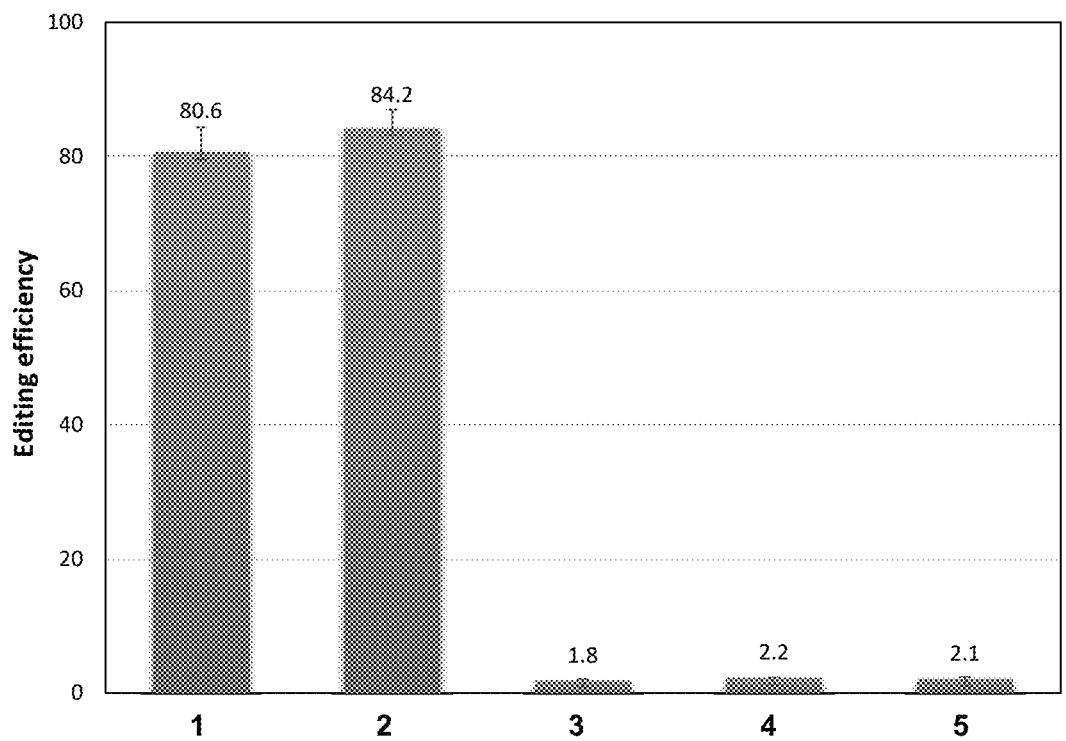
FIG. 3 describes the on-target editing efficiency of gRNAs targeting the wild-type rhodopsin gene and the off-target editing efficiency of sgRNAs targeting the mutant P23H rhodopsin gene.

Genomic DNA was harvested from the cells 48-72 hours after transfection and PCR amplified around codon 23 of the RHO gene. A forward primer located in the non-coding upstream region of the first exon of the RHO gene and a reverse primer localized in the coding region was used to amplify the wild-type RHO gene from genomic DNA. Because the genome of the K562 cells contain only the wild-type version of the RHO gene, these K562 cells were used to measure on-target editing efficiency for the gRNAs targeting the wild-type RHO gene and off-target editing efficiency for the gRNAs targeting the mutant P23H RHO gene. The on-target and off-target activity was measured by the rate of insertions, deletions and mutations introduced by NHEJ repair of the free DNA ends. Sequence analysis revealed that for the gRNAs targeting the wild-type RHO gene (SEQ ID NOs: 5285-5286), greater than 80% of loci were successfully edited (FIG. 3). For the gRNAs targeting the mutated P23H RHO gene (SEQ ID NOs: 5290-5291), it was found that off-target editing was low and similar to background levels in the control cells (FIG. 3).

In order to test the on- and off-target editing efficiency of gRNAs targeting the mutant P23H RHO gene (SEQ ID NOs: 5290-5291), K562 cells expressing S. aureus Cas9 protein were transfected with gRNAs that target the mutant P23H RHO gene and transfected with a plasmid encoding either the P23H mutant RHO gene or the wild-type RHO gene. Because the genetically engineered K562 cells have only the wild-type version of the RHO gene in their genomes, the plasmid was used to introduce an exogenous copy of the RHO gene (either a P23H mutated version of the RHO gene or a wild-type version of the RHO gene). These transfected K562 cells were compared to control cells. The control cells were K562 cells expressing S. aureus Cas9 protein and transfected with plasmid, but not transfected with any guide RNA. When analyzing the resulting sequences from transfected K562 cells, only the plasmid DNA (and not the genomic DNA) in these cells was used to establish the on- and off-target editing efficiencies for the gRNAs targeting the mutant P23H RHO gene (SEQ ID NOs: 5290-5291). For example, K562 cells were transfected with gRNAs that target the mutant P23H RHO gene and transfected with a plasmid encoding a P23H mutated version of the RHO gene in order to test the on-target activity for the gRNAs that target the mutant P23H RHO gene. In separate experiments, K562 cells were transfected with gRNAs that target the mutant P23H RHO gene and transfected with a plasmid containing a wild-type version of the RHO gene in order to test the off-target activity for the gRNAs that target the mutant P23H RHO gene. A forward primer located in the promoter region of the plasmid (which is not the natural RHO promoter) and a reverse primer in the RHO gene was used to amplify a DNA product from either RHO-encoding plasmid. Neither plasmid contained an upstream non-coding region of the RHO gene and thus could not produce a PCR product with primers used to amplify the genomic DNA surrounding codon 23 of the RHO gene. The resulting plasmid- or genome-specific PCR products were then sequenced with a primer located internally in the respective amplified PCR product and subjected to a TIDE analysis, a web tool used to rapidly assess genome editing of a target locus by CRISPR-Cas9 and a guide RNA (gRNA or sgRNA). Based on quantitative sequence trace data from two standard capillary sequencing reactions, the TIDE software quantifies the editing efficacy and identifies the predominant types of insertions and deletions (indels) in the DNA of a targeted cell pool. See Brinkman et al, Nucl. Acids Res. (2014) for a detailed explanation and examples. This technology allows DNA and RNA to be sequenced much more quickly and cheaply than the previously used Sanger sequencing, and as such have revolutionized the study of genomics and molecular biology.

Figure 4:
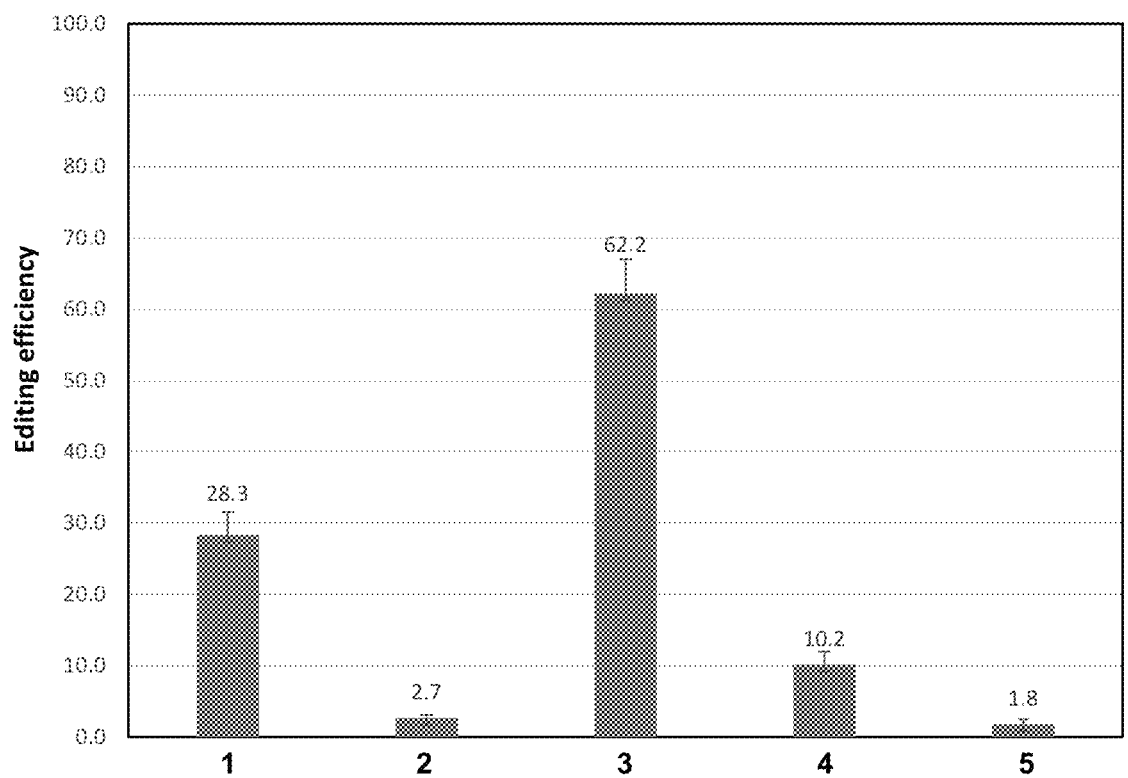
FIG. 4 describes the on-target and off-target editing efficiency of sgRNAs targeting the mutant P23H rhodopsin gene.

Sequence analysis revealed that the 19mer gRNA targeting the mutant P23H RHO gene (SEQ ID NO: 5291) was found to cause on-target editing ~15-fold greater than the control cells, and the 20mer gRNA targeting the mutant P23H RHO gene (SEQ ID NO: 5290) was found to cause on-target editing ~34-fold greater than the control cells (FIG. 4). The 19mer gRNA showed off-target editing that was similar to the control cells, while the 20mer showed off-target editing that was slightly increased compared to the control cells (FIG. 4). These data provide evidence that the selected guide RNAs (SEQ ID NOs: 5290-5291) effectively edit the mutant P23H RHO gene while minimizing off-target activity.

The gRNAs with significant editing activity can be followed up in cultured cells to measure the frameshift or correction of the P23H mutation in the RHO gene. Off-target events can be followed again. A variety of cells can be transfected and the level of gene correction and possible off-target events measured. These experiments allow optimization of nuclease and donor design and delivery.

Example 9

Testing of Guides in Cells for Off-Target Activity

To determine the extent of off-target editing on a genomic level, the gRNAs (or sgRNAs) having the best on-target activity will then be tested for targeted-genome-wide off-target editing using GUIDE-seq, Amplicon-seq, and/or Digenome-seq. Off-target effects will be tested on human cells.

Example 10

Testing Different Approaches for HDR Gene Editing

After testing the gRNAs for both on-target activity and off-target activity, mutation correction and knock-in strategies will be tested for HDR gene editing. These tests will allow for optimization of the various HDR gene editing strategies and comparisons based on their respective effectiveness will be made.

For the mutation correction approach, donor DNA template will be provided as a short single-stranded oligonucleotide, a short double-stranded oligonucleotide (PAM sequence intact/PAM sequence mutated), a long single-stranded DNA molecule (PAM sequence intact/PAM sequence mutated) or a long double-stranded DNA molecule (PAM sequence intact/PAM sequence mutated). In addition, the donor DNA template will be delivered by AAV.

For the cDNA knock-in approach, a single-stranded or double-stranded DNA having homologous arms to the RHO chromosomal region can include more than 40 nt of the first exon (the first coding exon) of the RHO gene, the complete CDS of the RHO gene and 3' UTR of the RHO gene, and at least 40 nt of the following intron. The single-stranded or double-stranded DNA having homologous arms to the RHO chromosomal region can include more than 80 nt of the first exon of the RHO gene, the complete CDS of the RHO gene and 3' UTR of the RHO gene, and at least 80 nt of the following intron. The single-stranded or double-stranded DNA having homologous arms to the RHO chromosomal region can include more than 100 nt of the first exon of the RHO gene, the complete CDS of the RHO gene and 3' UTR of the RHO gene, and at least 100 nt of the following intron. The single-stranded or double-stranded DNA having homologous arms to the RHO chromosomal region can include more than 150 nt of the first exon of the RHO gene, the complete CDS of the RHO gene and 3' UTR of the RHO gene, and at least 150 nt of the following intron. The single-stranded or double-stranded DNA having homologous arms to the RHO chromosomal region can include more than 300 nt of the first exon of the RHO gene, the complete CDS of the RHO gene and 3' UTR of the RHO gene, and at least 300 nt of the following intron. The single-stranded or double-stranded DNA having homologous arms to the RHO chromosomal region can include more than 400 nt of the first exon of the RHO gene, the complete CDS of the RHO gene and 3' UTR of the RHO gene, and at least 400 nt of the following intron.

Alternatively, the DNA template will be delivered by a recombinant AAV particle such as those taught herein.

A knock-in of RHO cDNA can be performed into any selected chromosomal location or in one of the "safe-harbor" locus, i.e., albumin gene, an AAVS 1 gene, an HRPT gene, a CCR5 gene, a globin gene, TTR gene, TF gene, F9 gene, Alb gene, Gys2 gene and PCSK9 gene. Assessment of efficiency of HDR mediated knock-in of cDNA into the first exon can utilize cDNA knock-in into "safe harbor" sites such as: single-stranded or double-stranded DNA having homologous arms to one of the following regions, for example: AAVS1 19q13.4-qter, HRPT 1q31.2, CCR5 3p21.31, Globin 11p15.4, TTR 18q12.1, TF 3q22.1, F9 Xq27.1, Alb 4q13.3, Gys2 12p12.1, PCSK9 1p32.3; 5'UTR correspondent to RHO or alternative 5' UTR, complete CDS of RHO and 3' UTR of RHO or modified 3' UTR and at least 80 nt of the first intron, alternatively same DNA template sequence will be delivered by AAV.

Example 11

Re-Assessment of Lead CRISPR-Cas9/DNA Donor Combinations

After testing the different strategies for gene editing, the lead CRISPR-Cas9/DNA donor combinations will be re-assessed in cells for efficiency of deletion, recombination, and off-target specificity. Cas9 mRNA or RNP will be formulated into lipid nanoparticles for delivery, sgRNAs will be formulated into nanoparticles or delivered as a recombinant AAV particle, and donor DNA will be formulated into nanoparticles or delivered as recombinant AAV particle.

Example 12

Self-Inactivating (SIN) CRISPR-Cas Systems

When nucleic acids encoding Cas9 and/or guide RNA are delivered via viral vector, it can be advantageous to use a SIN vector to deliver at least one of the nucleic acids. Experiments were performed in order to further investigate the ability of various SIN vectors to edit targeted nucleic acids with specificity.

Two reporter cell lines were generated that contain a Cas9 target site fused to a blue fluorescence protein (BFP) at the beta-tubulin gene locus. The first reporter cell line has a wild-type RHO gene (Cas9 target site) fused to a BFP at the beta-tubulin gene locus. The second reporter cell line has a RHO gene comprising a P23H mutation (Cas9 target site) fused to a BFP at the beta-tubulin gene locus. Thus, the Cas9 target site-BFP gene fusions comprised by the reporter cell lines can be used to report on editing activity at the Cas9 target site. The editing activity can cause loss of the BFP signal via a frameshit mutation. It was found that various combinations of Cas9 vectors and guide RNAs according to the present disclosure were effective in editing targeted RHO P23H mutant Cas9 target sites. The various combinations were also specific such that editing of the wild-type RHO Cas9 target sites was minimal and similar to background levels of BFP signal loss.

Figure 8:
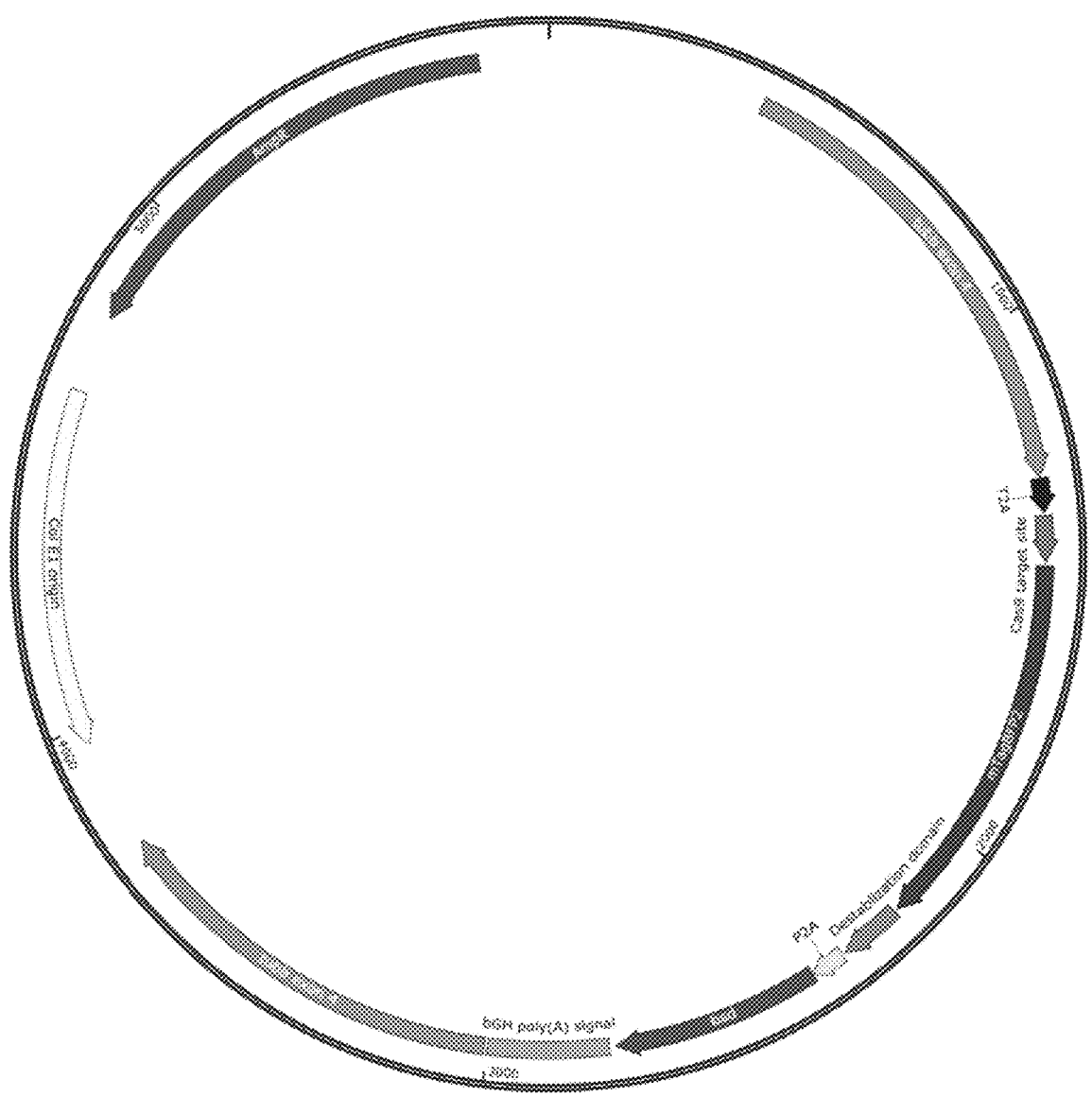
FIG. 8 depicts a donor plasmid comprising a Cas9 target site (either a wild-type RHO gene or a RHO gene comprising a P23H mutation) fused to a blue fluorescence protein.

To generate these two reporter cell lines pDL124 and a donor plasmid were used. pDL124 contains a SpCas9 ORF under CMV promoter and a U6 promoter-driven sgRNA and was built by Gibson assembly. The U6 promoter-driven sgRNA can cut the codon corresponding to the third residue from the C-terminus of beta-tubulin. A donor plasmid (FIG. 8) comprises a Cas9 target site (either a wild-type RHO gene or a RHO gene comprising a P23H mutation). Each of these 2 donor plasmids was synthesized using GeneArt service (ThermoFisher Scientific). HEK 293FT cells (200,000 cells) were transfected with 0.5 µg of pDL124 and 0.5 µg of donor plasmid by nucleofection under the program DN-100. pDL124 was used to generate a double-strand break at the beta-tubulin gene locus of the HEK 293FT cells in order to integrate the Cas9 target site (i.e. the wild-type RHO gene or the RHO gene comprising the P23H mutation) from the donor plasmid and into the beta-tubulin gene locus of the HEK 293FT cells between the two homologous arms (tubb exon 4). Homologous recombination leads to expression of beta-tubulin fused to T2A peptide. The Cas9 target site includes no stop codon, and blue fluorescence protein (mTagBFP2) and blasticidin selection marker (bsd) are encoded in the same reading frame as for beta-tubulin. Cells with a Cas9 target site integrated correctly were enriched in 10% FBS/DMEM supplemented with 2-5 µg/ml blasticidin, and isolated by cell sorting. Each of the reporter cell lines was seeded in 2.5 ml of 10% FBS/DMEM at 500,000 cells per well in 6-well plates 24 hours before transfection.

FIG. 6A shows results obtained when the reporter cell line having a wild-type RHO gene (Cas9 target site) fused to a blue fluorescence protein at the beta-tubulin gene locus was transfected with 1.25 μg SIN-AAV SaCas9 ver. 1 (FIG. 5A) and 1.25 μg pSIA010 (FIG. 5D) using Lipofectamine 3000. pSIA010 is a plasmid comprising an AAV sequence (SEQ ID NO: 5339) that encodes for P23H 20-mer sgRNA (a sgRNA comprising SEQ ID NO: 5290) and EGFP. SIN-AAV SaCas9 ver. 1 encodes SaCas9 and includes a SIN site (also called P23H target site) located 5' of the SaCas9 ORF (SEQ ID NO: 5313) and a 3' SIN site located within a naturally occurring or chimeric inserted intron located within the SaCas9 ORF (SEQ ID NO: 5314). The 5' SIN site (SEQ ID NO: 5313) in SIN-AAV SaCas9 ver. 1 comprises SEQ ID NO: 5300, which is targeted by sgRNA comprising SEQ ID NO: 5290. The 3' SIN site (SEQ ID NO: 5314) in SIN-AAV SaCas9 ver. 1 comprises SEQ ID NO: 5280, which is also targeted by sgRNA comprising SEQ ID NO: 5290 (Table 6).

TABLE 6

SIN-AAV SaCas9 version 1 & 2 comprising two SIN sites targeted by an sgRNA comprising SEQ ID NO: 5290

| Sequence type | SEQ ID NO: | Sequence |
| --- | --- | --- |
| 5' SIN site sequence | 5313 | ggtagtactgtgggtactcgaagtggctgcgtaccacacccgtcgcat |
| Target sequence | 5300 | agtggctgcgtaccacaccc |
| 3' SIN site sequence | 5314 | atgcgacgggtgtggtacgcagccacttcgagtacccacagtactacc |
| Target sequence | 5280 | gggtgtggtacgcagccact |

The reporter cell line having a RHO gene comprising a P23H mutation (Cas9 target site) fused to a blue fluorescence protein at the beta-tubulin gene locus was transfected with 1.25 μg SIN-AAV SaCas9 ver. 1 and 1.25 μg pSIA010 using Lipofectamine 3000 (FIG. 6C).

FIG. 6B shows results obtained when the reporter cell line having a wild-type RHO gene (Cas9 target site) fused to a blue fluorescence protein at the beta-tubulin gene locus was transfected with 1.25 μg SIN-AAV SaCas9 ver. 1 (FIG. 5A) and 1.25 μg pSIA011 (FIG. 5D) using Lipofectamine 3000. pSIA011 is a plasmid comprising an AAV sequence (SEQ ID NO: 5340) that encodes for P23H 19-mer sgRNA (a sgRNA comprising SEQ ID NO: 5291) and EGFP. SIN-AAV SaCas9 ver. 1 encodes SaCas9 and includes a SIN site (also called a P23H target site) located 5' of the SaCas9 ORF (SEQ ID NO: 5313) and a 3' SIN site located within a naturally occurring or chimeric inserted intron located within the SaCas9 ORF (SEQ ID NO: 5314). The 5' SIN site (SEQ ID NO: 5313) in SIN-AAV SaCas9 ver. 1 comprises SEQ ID NO: 5301, which is targeted by sgRNA comprising SEQ ID NO: 5291. The 3' SIN site (SEQ ID NO: 5314) in SIN-AAV SaCas9 ver. 1 comprises SEQ ID NO: 5281, which is targeted by sgRNA comprising SEQ ID NO: 5291 (Table 7).

TABLE 7

SIN-AAV SaCas9 version 1 & 2 comprising two SIN sites targeted by an sgRNA comprising SEQ ID NO: 5291

| Sequence type | SEQ ID NO: | Sequence |
| --- | --- | --- |
| 5' SIN site sequence | 5313 | ggtagtactgtgggtactcgaagtggctgcgtaccacacccgtcgcat |
| Target sequence | 5301 | agtggctgcgtaccacacc |
| 3' SIN site sequence | 5314 | atgcgacgggtgtggtacgcagccacttcgagtacccacagtactacc |
| Target sequence | 5281 | ggtgtggtacgcagccact |

The reporter cell line having a RHO gene comprising a P23H mutation (Cas9 target site) fused to a blue fluorescence protein at the beta-tubulin gene locus was transfected with 1.25 µg SIN-AAV SaCas9 ver. 1 and 1.25 µg pSIA011 using Lipofectamine 3000 (FIG. 6D).

FIG. 6E shows results obtained when the reporter cell line having a wild-type RHO gene (Cas9 target site) fused to a blue fluorescence protein at the beta-tubulin gene locus was transfected with 1.25 µg SIN-AAV SaCas9 ver. 2 (FIG. 5B) and 1.25 µg pSIA010 (FIG. 5D) using Lipofectamine 3000. SIN-AAV SaCas9 ver. 2 encodes SaCas9 and includes a SIN site (also called P23H target site) located 5' of the SaCas9 ORF (SEQ ID NO: 5313) and a 3' SIN site located within a naturally occurring or chimeric inserted intron located within the SaCas9 ORF (SEQ ID NO: 5314). The 5' SIN site (SEQ ID NO: 5313) in SIN-AAV SaCas9 ver. 2 comprises SEQ ID NO: 5300, which is targeted by sgRNA comprising SEQ ID NO: 5290. The 3' SIN site (SEQ ID NO: 5314) in SIN-AAV SaCas9 ver. 2 comprises SEQ ID NO: 5280, which is also targeted by sgRNA comprising SEQ ID NO: 5290 (Table 6).

The reporter cell line having a RHO gene comprising a P23H mutation (Cas9 target site) fused to a blue fluorescence protein at the beta-tubulin gene locus was transfected with 1.25 µg SIN-AAV SaCas9 ver. 2 and 1.25 µg pSIA010 using Lipofectamine 3000 (FIG. 6G).

FIG. 6F shows results obtained when the reporter cell line having a wild-type RHO gene (Cas9 target site) fused to a blue fluorescence protein at the beta-tubulin gene locus was transfected with 1.25 µg SIN-AAV SaCas9 ver. 2 (FIG. 5B) and 1.25 µg pSIA011 (FIG. 5D) using Lipofectamine 3000. SIN-AAV SaCas9 ver. 2 encodes SaCas9 and includes a SIN site (also called a P23H target site) located 5' of the SaCas9 ORF (SEQ ID NO: 5313) and a 3' SIN site located within a naturally occurring or chimeric inserted intron located within the SaCas9 ORF (SEQ ID NO: 5314). The 5' SIN site (SEQ ID NO: 5313) in SIN-AAV SaCas9 ver. 2 comprises SEQ ID NO: 5301, which is targeted by sgRNA comprising SEQ ID NO: 5291. The 3' SIN site (SEQ ID NO: 5314) in SIN-AAV SaCas9 ver. 2 comprises SEQ ID NO: 5281, which is targeted by sgRNA comprising SEQ ID NO: 5291 (Table 7).

The reporter cell line having a RHO gene comprising a P23H mutation (Cas9 target site) fused to a blue fluorescence protein at the beta-tubulin gene locus was transfected with 1.25 µg SIN-AAV SaCas9 ver. 2 and 1.25 µg pSIA011 using Lipofectamine 3000 (FIG. 6H).

FIG. 6I shows results obtained when the reporter cell line having a wild-type RHO gene (Cas9 target site) fused to a blue fluorescence protein at the beta-tubulin gene locus was transfected with 1.25 µg Non-SIN-AAV SaCas9 (FIG. 5C) and 1.25 µg pSIA010 (FIG. 5D) using Lipofectamine 3000. Non-SIN-AAV SaCas9 encodes SaCas9 and includes no SIN sites (also called P23H target sites).

The reporter cell line having a RHO gene comprising a P23H mutation (Cas9 target site) fused to a blue fluorescence protein at the beta-tubulin gene locus was transfected with 1.25 µg Non-SIN-AAV SaCas9 and 1.25 µg pSIA010 using Lipofectamine 3000 (FIG. 6L).

FIG. 6J shows results obtained when the reporter cell line having a wild-type RHO gene (Cas9 target site) fused to a blue fluorescence protein at the beta-tubulin gene locus was transfected with 1.25 µg Non-SIN-AAV SaCas9 (FIG. 5C) and 1.25 µg pSIA011 (FIG. 5D) using Lipofectamine 3000.

The reporter cell line having a RHO gene comprising a P23H mutation (Cas9 target site) fused to a blue fluorescence protein at the beta-tubulin gene locus was transfected with 1.25 µg Non-SIN-AAV SaCas9 and 1.25 µg pSIA011 using Lipofectamine 3000 (FIG. 6M).

The reporter cell line having a wild-type RHO gene (Cas9 target site) fused to a blue fluorescence protein at the beta-tubulin gene locus was transfected with only transfection reagent (no DNA) using Lipofectamine 3000 (FIG. 6K).

The reporter cell line having a RHO gene comprising a P23H mutation (Cas9 target site) fused to a blue fluorescence protein at the beta-tubulin gene locus was transfected with only transfection reagent (no DNA) using Lipofectamine 3000 (FIG. 6N).

At 72 hours post-transfection, reporter cells were dissociated from the plates by incubation with trypsin-EDTA, and analyzed for blue fluorescence (BFP) and green fluorescence (GFP) by flow cytometry. A frame-shift induced by genome editing at a Cas9 target site (whether the Cas9 target site is the wild-type RHO gene or the RHO gene comprising the P23H mutation) of the HEK 293FT cell results in loss of BFP. EGFP and sgRNA are encoded on the same vector and the EGFP serves as a transfection marker. Therefore, HEK 293FT cells transfected with pSIA010 (which comprises an AAV sequence that encodes P23H 20-mer sgRNA—a sgRNA comprising SEQ ID NO: 5290) or pSIA011 (which comprises an AAV sequence that encodes P23H 19-mer sgRNA—a sgRNA comprising SEQ ID NO: 5291) are GFP positive.

Gene editing in the transfected cells was estimated in the cell populations plotted within a gate (FIGS. 6A-6N). The bolded percentages in FIGS. 6A-6N indicate BFP negative and GFP positive cells within the gate. BFP negative means that gene editing occurred at the Cas9 target site of these transfected HEK 293FT cells. GFP positive means that these transfected HEK 293FT cells contain a plasmid that encodes EGFP and sgRNA.

FIG. 6A shows that of the transfected HEK 293FT reporter cells that have the wild-type RHO gene as the Cas9 target site in the gate, ~0% of these cells had the wild-type RHO gene edited when transfected with SIN-AAV SaCas9 ver. 1 and pSIA010, which encodes P23H 20-mer sgRNA (sgRNA comprising SEQ ID NO: 5290).

FIG. 6B shows that of the transfected HEK 293FT reporter cells that have the wild-type RHO gene as the Cas9 target site in the gate, ~0% of these cells had the wild-type RHO gene edited when transfected with SIN-AAV SaCas9 ver. 1 and pSIA011, which encodes P23H 19-mer sgRNA (sgRNA comprising SEQ ID NO: 5291).

FIG. 6C shows that of the transfected HEK 293FT reporter cells that have the P23H mutation as the Cas9 target site in the gate, 42.41% of these cells had the P23H mutation edited when transfected with SIN-AAV SaCas9 ver. 1 and pSIA010.

FIG. 6D shows that of the transfected HEK 293FT reporter cells that have the P23H mutation as the Cas9 target site in the gate, 19.42% of these cells had the P23H mutation edited when transfected with SIN-AAV SaCas9 ver. 1 and pSIA011.

FIG. 6E shows that of the transfected HEK 293FT reporter cells that have the wild-type RHO gene as the Cas9 target site in the gate, ~0% of these cells had the wild-type RHO gene edited when transfected with SIN-AAV SaCas9 ver. 2 and pSIA010.

FIG. 6F shows that of the transfected HEK 293FT reporter cells that have the wild-type RHO gene as the Cas9 target site in the gate, ~0% of these cells had the wild-type RHO gene edited when transfected with SIN-AAV SaCas9 ver. 2 and pSIA011.

FIG. 6G shows that of the transfected HEK 293FT reporter cells that have the P23H mutation as the Cas9 target site in the gate, 46.23% of these cells had the P23H mutation edited when transfected with SIN-AAV SaCas9 ver. 2 and pSIA010.

FIG. 6H shows that of the transfected HEK 293FT reporter cells that have the P23H mutation as the Cas9 target site in the gate, 18.58% of these cells had the P23H mutation edited when transfected with SIN-AAV SaCas9 ver. 2 and pSIA011.

FIG. 6I shows that of the transfected HEK 293FT reporter cells that have the wild-type RHO gene as the Cas9 target site in the gate, ~0% of these cells had the wild-type RHO gene edited when transfected with Non-SIN-AAV SaCas9 and pSIA010.

FIG. 6J shows that of the transfected HEK 293FT reporter cells that have the wild-type RHO gene as the Cas9 target site in the gate, ~0% of these cells had the wild-type RHO gene edited when transfected with Non-SIN-AAV SaCas9 and pSIA011.

FIG. 6K shows that of the transfected HEK 293FT reporter cells that have the wild-type RHO gene as the Cas9 target site in the gate, 0% of these cells had the wild-type RHO gene edited when no DNA was used.

FIG. 6L shows that of the transfected HEK 293FT reporter cells that have the P23H mutation as the Cas9 target site in the gate, 49.97% of these cells had the P23H mutation edited when transfected with Non-SIN-AAV SaCas9 and pSIA010.

FIG. 6M shows that of the transfected HEK 293FT reporter cells that have the P23H mutation as the Cas9 target site in the gate, 26.30% of these cells had the P23H mutation edited when transfected with Non-SIN-AAV SaCas9 and pSIA011.

FIG. 6N shows that of the transfected HEK 293FT reporter cells that have the P23H mutation as the Cas9 target site in the gate, 0% of these cells had the P23H mutation edited when no DNA was used.

Since no genome editing was induced in mock transfected cells, the vast majority of mock transfected cells are BFP positive (FIGS. 6K and 6N).

To determine the ability of SIN vectors to limit Cas9 expression, the expression levels of Cas9 protein were measured by immunoblot (FIGS. 7A-B) for the cells used in the experiments described by FIG. 6A-N. SIN Cas9 vectors showed decreased expression of Cas9 in both reporter cell lines when targeted by either a guide RNA comprising SEQ ID NO: 5290 or 5291.

At 72 hours post-transfection, reporter cells were also harvested in PBS, and total protein was extracted in 0.1% Triton X-100/TBS (25 mM Tris-HCl (pH 7.5) and 150 mM NaCl). Five micrograms of total protein was separated on NUPAGE 4-12% polyacrylamide/Tris-Bis gels, and transferred onto nitrocellulose membranes. SaCas9, EGFP (as a transfection control) and beta actin (as an internal control) were detected using a Cas9 monoclonal antibody, GFP Tag polyclonal antibody, and beta actin loading control monoclonal antibody, respectively.

Figure 7A:
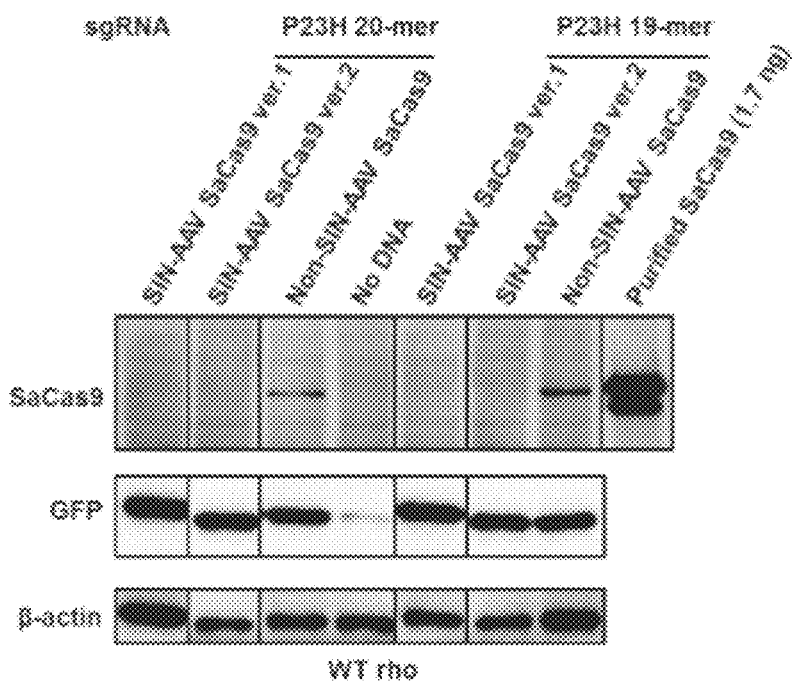
FIGS. 7A-B show western blot data for 2 different HEK 293FT reporter cell lines that are co-transfected with pSIA010, a plasmid comprising an AAV sequence that encodes P23H 20-mer sgRNA (a sgRNA comprising SEQ ID NO: 5290) or pSIA011, a plasmid comprising an AAV sequence that encodes P23H 19-mer sgRNA (a sgRNA comprising SEQ ID NO: 5291), and either (1) a SIN-AAV SaCas9 version 1 (sEF1α promoter), (2) a SIN-AAV SaCas9 version 2 (sEF1α promoter), or (3) a Non-SIN-AAV SaCas9 (sEF1α promoter).

FIG. 7A (lane 1) shows Cas9 inactivation in HEK 293FT reporter cells that have the wild-type RHO gene as the Cas9 target site and that were transfected with SIN-AAV SaCas9 ver. 1 (FIG. 5A) and pSIA010, which encodes P23H 20-mer sgRNA (sgRNA comprising SEQ ID NO: 5290).

FIG. 7A (lane 2) shows Cas9 inactivation in HEK 293FT reporter cells that have the wild-type RHO gene as the Cas9 target site and that were transfected with SIN-AAV SaCas9 ver. 2 (FIG. 5B) and pSIA010.

FIG. 7A (lane 3) shows Cas9 expression in HEK 293FT reporter cells that have the wild-type RHO gene as the Cas9 target site and that were transfected with Non-SIN-AAV SaCas9 (FIG. 5C) and pSIA010.

FIG. 7A (lane 4) shows no Cas9 expression in HEK 293FT reporter cells that have the wild-type RHO gene as the Cas9 target site and that were not transfected with any DNA.

FIG. 7A (lane 5) shows Cas9 inactivation in HEK 293FT reporter cells that have the wild-type RHO gene as the Cas9 target site and that were transfected with SIN-AAV SaCas9 ver. 1 (FIG. 5A) and pSIA011, which encodes P23H 19-mer sgRNA sgRNA (sgRNA comprising SEQ ID NO: 5291).

FIG. 7A (lane 6) shows Cas9 inactivation in HEK 293FT reporter cells that have the wild-type RHO gene as the Cas9 target site and that were transfected with SIN-AAV SaCas9 ver. 2 (FIG. 5B) and pSIA011.

FIG. 7A (lane 7) shows Cas9 expression in HEK 293FT reporter cells that have the wild-type RHO gene as the Cas9 target site and that were transfected with Non-SIN-AAV SaCas9 (FIG. 5C) and pSIA011.

Figure 7B:
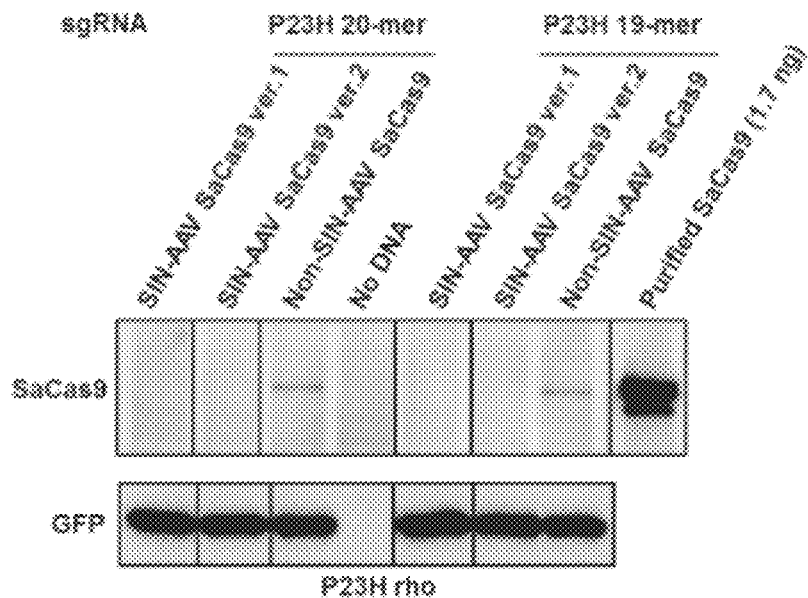

FIG. 7B (lane 1) shows Cas9 inactivation in HEK 293FT reporter cells that have the P23H mutation as the Cas9 target site and that were transfected with SIN-AAV SaCas9 ver. 1 (FIG. 5A) and pSIA010, which encodes P23H 20-mer sgRNA sgRNA (sgRNA comprising SEQ ID NO: 5290).

FIG. 7B (lane 2) shows Cas9 inactivation in HEK 293FT reporter cells that have the P23H mutation as the Cas9 target site and that were transfected with SIN-AAV SaCas9 ver. 2 (FIG. 5B) and pSIA010.

FIG. 7B (lane 3) shows Cas9 expression in HEK 293FT reporter cells that have the P23H mutation as the Cas9 target site and that were transfected with Non-SIN-AAV SaCas9 (FIG. 5C) and pSIA010.

FIG. 7B (lane 4) shows no Cas9 expression in HEK 293FT reporter cells that have the P23H mutation as the Cas9 target site and that were not transfected with any DNA.

FIG. 7B (lane 5) shows Cas9 inactivation in HEK 293FT reporter cells that have the P23H mutation as the Cas9 target site and that were transfected with SIN-AAV SaCas9 ver. 1 (FIG. 5A) and pSIA011, which encodes P23H 19-mer sgRNA sgRNA (sgRNA comprising SEQ ID NO: 5291).

FIG. 7B (lane 6) shows Cas9 inactivation in HEK 293FT reporter cells that have the P23H mutation as the Cas9 target site and that were transfected with SIN-AAV SaCas9 ver. 2 (FIG. 5B) and pSIA011.

FIG. 7B (lane 7) shows Cas9 expression in HEK 293FT reporter cells that have the P23H mutation as the Cas9 target site and that were transfected with Non-SIN-AAV SaCas9 (FIG. 5C) and pSIA011.

As discussed above, two versions of self-inactivating (SIN) AAV vectors that limit their own expression of Cas9 after transfection were created. An example of a version 1 vector is depicted in FIG. 5A. An example of a version 2 vector is depicted in FIG. 5B. Both version 1 and version 2 vectors comprise two SIN sites (also called P23H target sites), which are vulnerable to cutting by Cas9-sgRNA RNPs. Cas9-mediated double strand breaks at one of these sites could lead to removal of either a promoter or polyadenylation signal in the Cas9 gene. Cas9-mediated double strand breaks at both of these sites occurring contemporaneously could lead to deletion of the Cas9 gene. Both possibilities would inhibit Cas9 expression.

It has been observed that version 1 vectors lead to more efficient self-inactivation than version 2 vectors. Version 1 vectors comprise a 5' SIN site (P23H target site) that is located upstream of the Cas9 open reading frame (ORF) and downstream of a SV40 nuclear localization signal (NLS). Version 2 vectors comprise a 5' SIN site (P23H target site) that is located upstream of the Cas9 open reading frame (ORF) and upstream of a SV40 nuclear localization signal (NLS) within a 5' untranslated region (UTR). In a version 1 vector, mutations resulting from non-homologous end-joining could create frame-shifts, which cause introduction of premature stop codons in the Cas9 gene ORF. In a version 2 vector, such mutations would be unlikely to create such changes in the Cas9 ORF since the SIN site (P23H target site) is in the 5' UTR, outside of the ORF. These mutations could still disrupt transcription initiation, but their overall effect on Cas9 expression is likely to be less than the mutations in a version 1 vector. Furthermore, once a mutation is created in either vector, a second is unlikely since the site will no longer share sufficient homology with the sgRNA spacer sequence for efficient additional editing. It is important that the editing which does occur is likely to inhibit expression. For at least these reasons, there is a disparity in SIN efficiency observed between the two vector versions.

To confirm that introduced SIN sites do not influence transcription and translation of Cas9, HEK 293FT cells were transfected with 1.25 µg of pDL107 (which encodes GFP and does not encode sgRNA) and either (1) SIN-AAV SaCas9 ver. 1, (2) SIN-AAV SaCas9 ver. 2, or (3) Non-SIN-AAV SaCas9. Cells were seeded in 2.5 ml of 10% FBS/DMEM at 500,000 cells per well in 6-well plates at 24 hours before transfection. At 72 hours after transfection, GFP expression of all the transfected cells were analyzed by flow cytometry, and total protein was extracted in 0.1% Triton X-100/TBS (25 mM Tris-HCl (pH 7.5) and 150 mM NaCl). Five micrograms of total protein was separated on a NUPAGE 4-12% polyacrylamide/Tris-Bis gel, and transferred onto nitrocellulose membranes. SaCas9, EGFP (as a transfection control) and beta actin (as an internal control) were detected using a Cas9 monoclonal antibody, GFP Tag polyclonal antibody and beta actin loading control monoclonal antibody, respectively. Results showed that there was equal SaCas9 expression in HEK 293FT cells transfected with (1) SIN-AAV SaCas9 ver. 1, (2) SIN-AAV SaCas9 ver. 2, and (3) Non-SIN-AAV SaCas9 (Data not shown).

Example 13

Generation of a P2311 Mutant RHO Cell Line

In order to allow for on-target testing of guide RNAs that target the P23H mutant RHO gene sequence in the context of genomic DNA (as opposed to the plasmid DNA used in Example 8), a K562 cell line with a homozygote g.129528801C>A mutation (P23H mutant RHO cell line) was generated using wild-type K562 cells. Wild-type K562 cells contain two wild-type alleles of the human rhodopsin gene. The wild-type K562 cells that were used to generate the P23H mutant RHO cell line were also previously engineered to stably express *Staphylococcus aureus* Cas9 endonuclease under a doxycycline inducible promoter.

The wild-type K562 cells were transfected with Lonza's Nucleofector™ kit, ribonucleoproteins (RNPs), and single-stranded DNA oligos (3-6 µg) using Lonza's nucleofector machine and the recommended program for K562 cells.

Figure 9A:
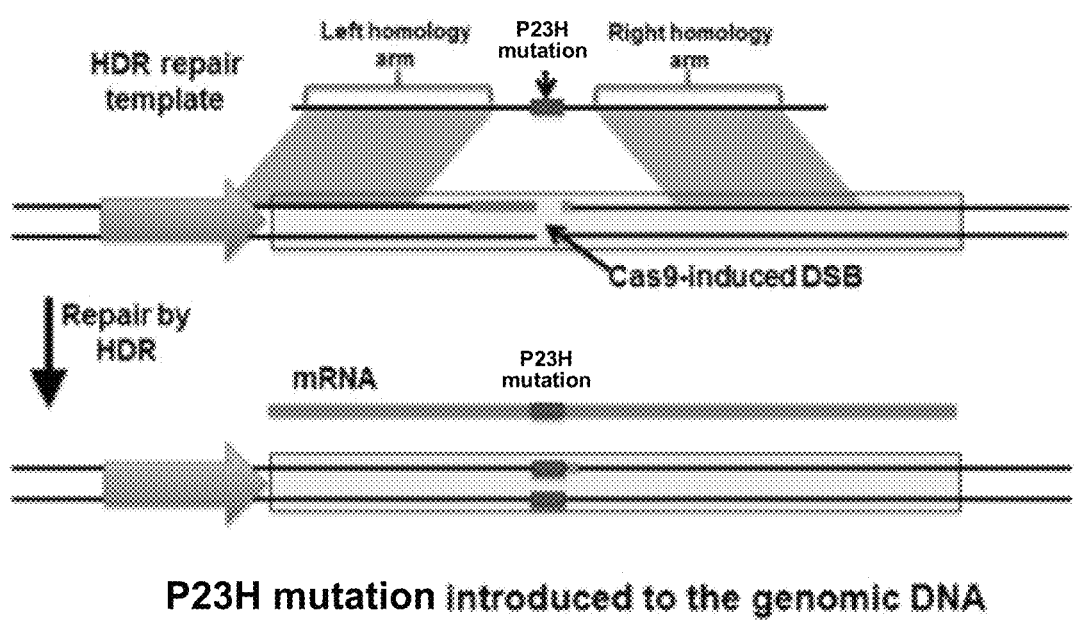
FIGS. 9A-B show a P23H mutation introduced into genomic DNA via homology directed repair (HDR) and a single nucleotide mutation in codon 23 of the human rhodopsin gene.
Figure 9B:
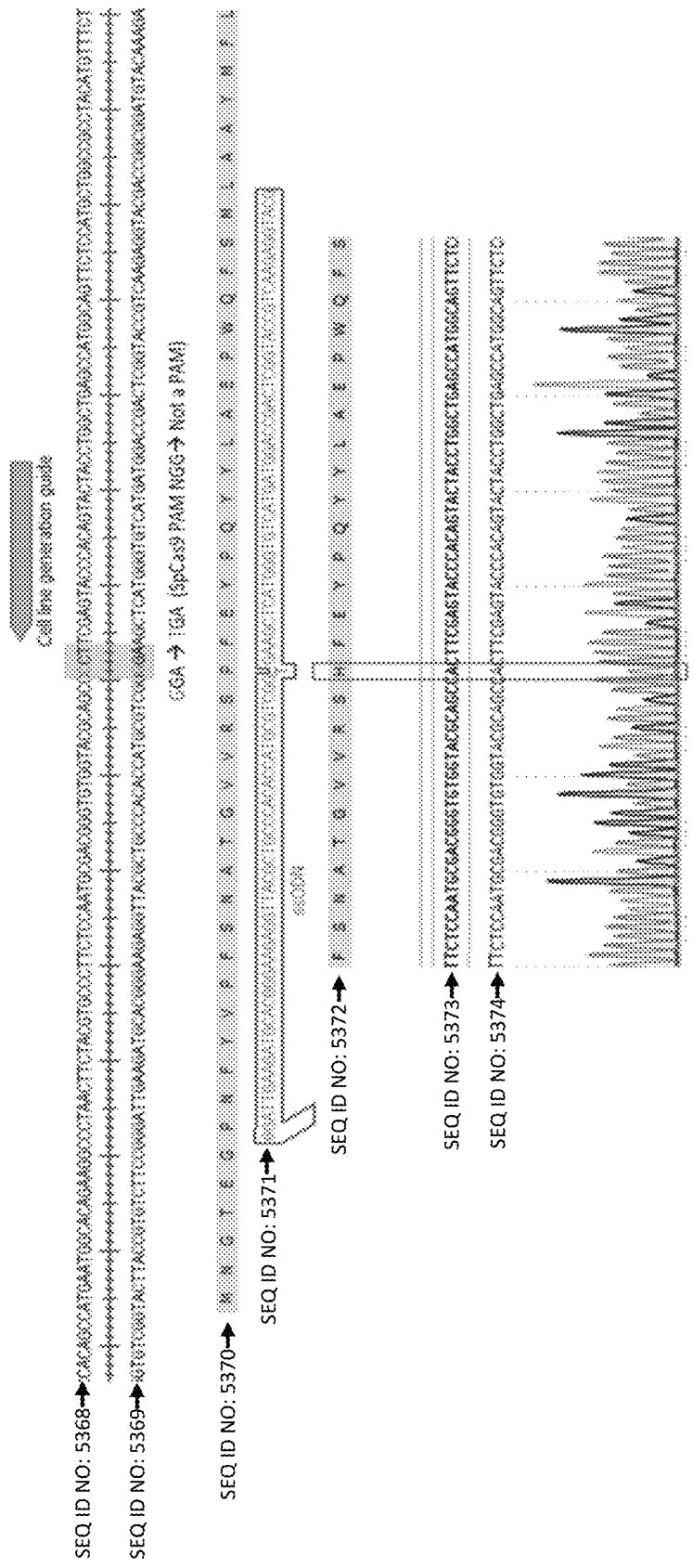

Ribonucleoproteins (RNPs) were made with 2.5 µg TrueCut™ Cas9 Protein v2 (ThermoFisher Scientific) and a 1 µg (~25 pM) synthetic gRNA (ThermoFisher Scientific). The synthetic gRNA comprised the following unmodified protospacer region: UAGUACUGUGGGUACUCGA (SEQ ID NO: 5343) and ThermoFisher's proprietary tracrRNA sequence. The synthetic gRNA used to introduce a double break in the wild-type K562 genome was designed so that the PAM sequence recognized by the RNP would no longer serve as a PAM sequence once the desired P23H mutation was introduced to the genome, thus preventing further editing of the genomes of cells that have undergone successful HDR (FIG. 9B).

The single stranded DNA oligo used as a template for HDR was:

(SEQ ID NO: 5346)
AGTTGATGGGGAAGCCCAGCACGATCAGCAGAAACATGTAGGCGGCCAGC

ATGGAGAACTGCCATGGCTCAGCCAGGTAGTACTGTGGGTACTCGAAGTG

GCTGCGTACCACACCCGTCGCATTGGAGAAGGGCACGTAGAAGTTAGGGC

CTTCTGTGCCATTCATGGCTGTGGCCCTTGTGGCTGACCCGTGGCT.

The transfected cells were allowed to recover in culture for 3-7 days post-transfection. Single cells were automatically sorted into 96-well plates and colonies originated from the single cells. Genomic DNA was isolated from each colony of cells and sequenced for the presence of the desired single nucleotide mutation in codon 23 of the human rhodopsin gene. Several clones were isolated that had the P23H mutation introduced into both alleles (FIGS. 9A-B).

Example 14

Testing of Synthetic Guide RNAs in P2311 Mutant RHO Cells for On-/Off-Target Activity The cell line constructed in Example 13 (as well as a pre-existing wild-type RHO cell line) was used to test select guide RNAs for on-/off-target activity by evaluating indel frequency using TIDE analysis. In these experiments, synthetic guide RNAs were used to target the P23H mutation within RHO, rather than guide RNAs that were transcribed from a viral or plasmid vector as in previous experiments. Additionally, the RHO gene DNA sequence as encoded in the genomic DNA was targeted. It was found that under these conditions, guide RNAs of the present disclosure exhibited specific editing of the mutant P23H RHO locus.

Wild-type RHO cells and P23H mutant RHO cells were first treated with Doxycycline for 48 hours prior to transfection in order to induce SaCas9 expression.

After 48 hours, both cell types (200,000 per well) were separately transfected with either 1 µg of synthetic sgRNA that targets the wild-type RHO gene or 1 µg of synthetic sgRNA that targets the P23H mutant RHO gene. The wild-type RHO cells and P23H mutant RHO cells were transfected using Lonza's nucleofector machine and the recommended program for K562 cells. The sgRNAs that target the P23H mutant RHO gene comprise: Human Rhodopsin P23H 20mer (SEQ ID NO: 5290) and Human Rhodopsin P23H 19mer (SEQ ID NO: 5291) (FIG. 2B). The sgRNAs that target the wild-type RHO gene comprise: Human Rhodopsin WT 20mer (SEQ ID NO: 5285) and Human Rhodopsin WT 19mer (SEQ ID NO: 5286) (FIG. 2B). The transfected K562 cells (wild-type RHO cells or P23H mutant RHO cells) were compared to control cells, which were K562 cells expressing *S. aureus* Cas9 protein, but not transfected with any guide RNA.

Genomic DNA was harvested from the cells 48-72 hours after transfection and PCR amplified around codon 23 of the RHO gene. A forward primer located in the non-coding upstream region of the first exon of the RHO gene (SEQ ID NO: 5347) and a reverse primer located in the coding region (SEQ ID NO: 5348) was used for the PCR amplification.

Because the genome of the wild-type RHO cells contains only the wild-type version of the RHO gene, and not the P23H mutant allele, these wild-type RHO cells were used to measure on-target editing efficiency for the gRNAs targeting the wild-type RHO gene and off-target editing efficiency for the gRNAs targeting the P23H mutant RHO gene. Because the genome of the P23H mutant RHO cells contains only the P23H mutant version of the RHO gene, and not the wild-type allele, these P23H mutant RHO cells were used to measure on-target editing efficiency for the gRNAs targeting the P23H mutant RHO gene and off-target editing efficiency for the gRNAs targeting the wild-type RHO gene. The on-target and off-target activity was measured by the rate of insertions, deletions and mutations introduced by NHEJ repair of the free DNA ends produced when the RNP created a DSB at the edit site.

Figure 10:
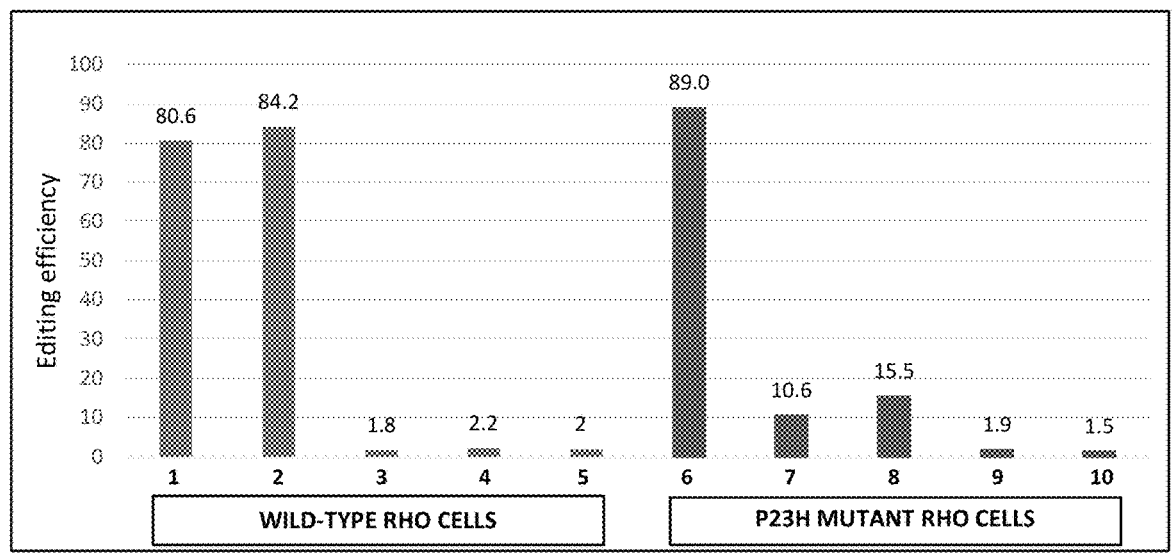
FIG. 10 describes the on-/off-target editing efficiency of synthetic sgRNAs targeting the wild-type rhodopsin gene and the on-/off-target editing efficiency of synthetic sgRNAs targeting the P23H mutant rhodopsin gene.

Sequence analysis revealed that for sgRNA comprising SEQ ID NO: 5290, which targets the P23H mutant RHO gene, 89% of the P23H mutant RHO loci were successfully edited (FIG. 10, sample 6) and the off-target editing was low (FIG. 10, sample 3) and similar to background levels in the control cells (FIG. 10, sample 5).

Sequence analysis revealed that for sgRNA comprising SEQ ID NO: 5291, which targets the P23H mutant RHO gene, 10.6% of the P23H mutant RHO loci were successfully edited (FIG. 10, sample 7) and the off-target editing was low (FIG. 10, sample 4) and similar to background levels in the control cells (FIG. 10, sample 5).

Sequence analysis revealed that for sgRNA comprising SEQ ID NO: 5285, which targets the wild-type RHO gene, 80.6% of the wild-type RHO loci were successfully edited (FIG. 10, sample 1) and the off-target editing was 15.5% (FIG. 10, sample 8).

Sequence analysis revealed that for sgRNA comprising SEQ ID NO: 5286, which targets the wild-type RHO gene, 84.2% of the wild-type RHO loci were successfully edited (FIG. 10, sample 2) and the off-target editing was low (FIG. 10, sample 9) and similar to background levels in the control cells (FIG. 10, sample 10).

Example 15

Testing of Plasmid Encoded sgRNAs for On-/Off-Target Activity

The ability of sgRNAs encoded by a transfected plasmid to edit targeted genomic P23H mutant RHO gene DNA with specificity was also tested. Using the same two cell lines as in Example 14, it was found that sgRNAs of the present disclosure were able to direct editing of targeted P23H mutant DNA with specificity.

Plasmid encoded sgRNAs that target the P23H mutant RHO gene were constructed by cloning DNA inserts of 18-24 nucleotides (Table 8) into a plasmid under a U6 promoter, such that the DNA insert would be transcribed into a sgRNA by RNA Polymerase III. In addition to the U6 promoter, the plasmids also include green fluorescent protein driven by a CMV promoter.

The U6 promoter/RNA Polymerase III used to drive sgRNA expression from each plasmid added a guanine (G) nucleotide at the 5' end of the sgRNA. For example, a cloned DNA insert that encodes for a sgRNA that is 19 nucleotides in length (19 mer) becomes 20 nucleotides (20 mer) after the 5'G is added. For many of the sgRNAs that target the P23H mutant RHO gene, the extra G is part of the natural sequence of the rhodopsin gene (SEQ ID NOs: 5315, 5317, 5281, and 5357), while for other sgRNAs that target the P23H mutant RHO gene, the 5' G is a mismatched nucleotide (i.e., a "hanging 5' G") (SEQ ID NOs: 5316, 5318, and 5280) (Table 8).

TABLE 8

Plasmid encoded sgRNAs that target the P23H mutant RHO gene

| Guide Name | DNA insert | SEQ ID NO: (DNA insert) | Sequence match to RHO gene after adding G | Encoded sgRNA comprises SEQ ID NO: | SEQ ID NO: (Plasmid comprising DNA insert) |
|---|---|---|---|---|---|
| Rho-P23HMut-24mer | CGACGGGTGTGGTACGCAGCCACT | 5315 | perfect match | 5319 | 5367 |
| Rho-P23HMut-23mer | GACGGGTGTGGTACGCAGCCACT | 5316 | hanging 5' G | 5320 | 5366 |
| Rho-P23HMut-22mer | ACGGGTGTGGTACGCAGCCACT | 5317 | perfect match | 5321 | 5365 |
| Rho-P23HMut-21mer | CGGGTGTGGTACGCAGCCACT | 5318 | hanging 5' G | 5322 | 5364 |
| Human Rhodopsin P23H 20mer | GGGTGTGGTACGCAGCCACT | 5280 | hanging 5' G | 5290 | 5363 |
| Human Rhodopsin P23H 19mer | GGTGTGGTACGCAGCCACT | 5281 | perfect match | 5291 | 5362 |
| Rho-P23HMut-18mer | GTGTGGTACGCAGCCACT | 5357 | perfect match | 5358 | 5361 |

Wild-type RHO cells and P23H mutant RHO cells were first treated with 1-10 µg/mL Doxycycline for 48 hours prior to transfection in order to induce SaCas9 expression.

After 48 hours, both cell types (200,000 per well) were transfected with 1 µg plasmid encoding a sgRNA that targets the P23H mutant RHO gene (Table 8: SEQ ID NO: 5361, 5362, 5363, 5364, 5365, 5366, or 5367). The wild-type RHO cells and P23H mutant RHO cells were transfected using Lonza's nucleofector machine and the recommended program for K562 cells. The transfected K562 cells (wild-type RHO cells or P23H mutant RHO cells) were compared to control cells, which were K562 cells expressing *S. aureus* Cas9 protein, but not transfected with any guide RNA.

The treatment with 1-10 µg/mL Doxycycline was resumed for 48-72 hours post-transfection. Genomic DNA was then harvested from the cells 48-72 hours after transfection and PCR amplified around codon 23 of the RHO gene. A forward primer located in the non-coding upstream region of the first exon of the RHO gene (SEQ ID NO: 5347) and a reverse primer located in the coding region (SEQ ID NO: 5348) was used for the PCR amplification.

Because the genome of the wild-type RHO cells contains only the wild-type version of the RHO gene, and not the P23H mutant allele, the wild-type RHO cells were used to measure off-target editing efficiency for the sgRNAs targeting the P23H mutant RHO gene. Because the genome of the P23H mutant RHO cells contains only the P23H mutant version of the RHO gene, and not the wild-type allele, these P23H mutant RHO cells were used to measure on-target editing efficiency for the sgRNAs targeting the P23H mutant RHO gene.

Figure 11:
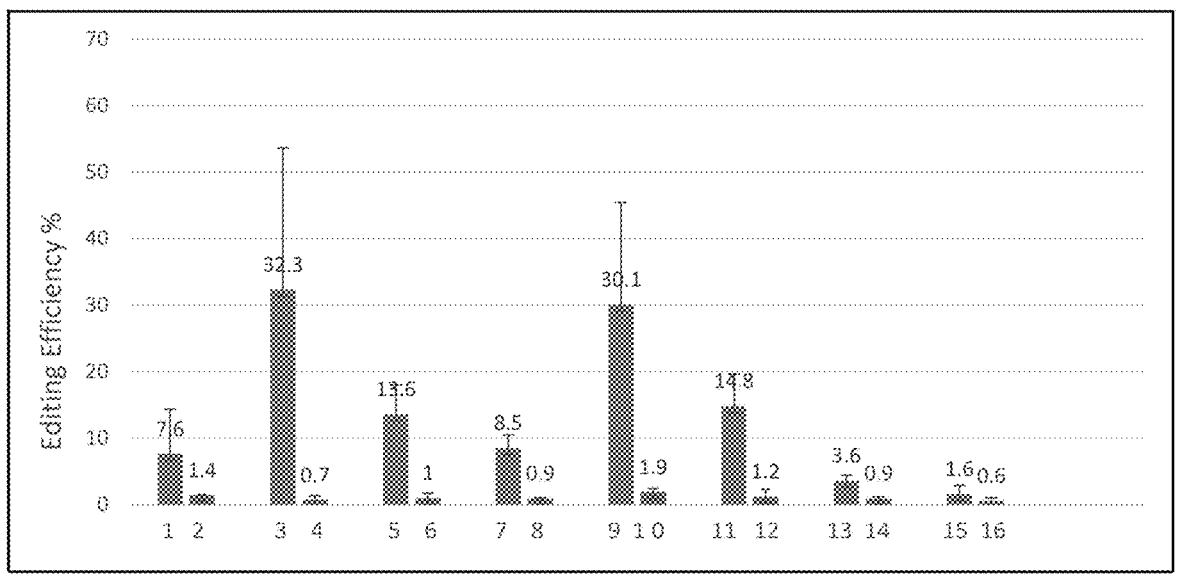
FIG. 11 describes the on-/off-target editing efficiency of plasmid encoded sgRNAs targeting the P23H mutant rhodopsin gene.

Sequence analysis revealed that for cells transfected with a plasmid that encodes for a sgRNA comprising SEQ ID NO: 5358, which targets the P23H mutant RHO gene, 7.6% of the P23H mutant RHO loci were successfully edited (FIG. 11, sample 1) and the off-target editing was low (FIG. 11, sample 2) and similar to background levels in control cells (FIG. 11, sample 16).

Sequence analysis revealed that for cells transfected with a plasmid that encodes for a sgRNA comprising SEQ ID NO: 5291, which targets the P23H mutant RHO gene, 32.3% of the P23H mutant RHO loci were successfully edited (FIG. 11, sample 3) and the off-target editing was low (FIG. 11, sample 4) and similar to background levels in control cells (FIG. 11, sample 16).

Sequence analysis revealed that for cells transfected with a plasmid that encodes for a sgRNA comprising SEQ ID NO: 5290, which targets the P23H mutant RHO gene, 13.6% of the P23H mutant RHO loci were successfully edited (FIG. 11, sample 5) and the off-target editing was low (FIG. 11, sample 6) and similar to background levels in control cells (FIG. 11, sample 16).

Sequence analysis revealed that for cells transfected with a plasmid that encodes for a sgRNA comprising SEQ ID NO: 5322, which targets the P23H mutant RHO gene, 8.5% of the P23H mutant RHO loci were successfully edited (FIG. 11, sample 7) and the off-target editing was low (FIG. 11, sample 8) and similar to background levels in control cells (FIG. 11, sample 16).

Sequence analysis revealed that for cells transfected with a plasmid that encodes for a sgRNA comprising SEQ ID NO: 5321, which targets the P23H mutant RHO gene, 30.1% of the P23H mutant RHO loci were successfully edited (FIG. 11, sample 9) and the off-target editing was low (FIG. 11, sample 10) and similar to background levels in control cells (FIG. 11, sample 16).

Sequence analysis revealed that for cells transfected with a plasmid that encodes for a sgRNA comprising SEQ ID NO: 5320, which targets the P23H mutant RHO gene, 14.8% of the P23H mutant RHO loci were successfully edited (FIG. 11, sample 11) and the off-target editing was low (FIG. 11, sample 12) and similar to background levels in control cells (FIG. 11, sample 16).

Sequence analysis revealed that for cells transfected with a plasmid that encodes for a sgRNA comprising SEQ ID NO: 5319, which targets the P23H mutant RHO gene, 3.6% of the P23H mutant RHO loci were successfully edited (FIG. 11, sample 13) and the off-target editing was low (FIG. 11, sample 14) and similar to background levels in control cells (FIG. 11, sample 16).

Figure 12:
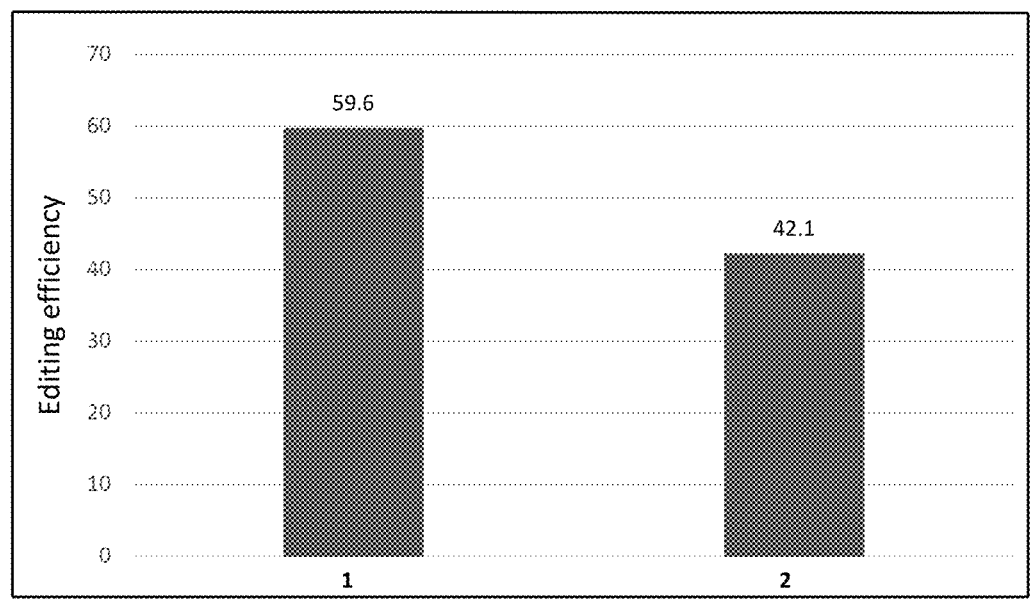
FIG. 12 describes the on-/off-target editing efficiency of plasmid encoded sgRNAs targeting the P23H mutant rhodopsin gene.

Sequence analysis from a second experiment revealed that for cells transfected with a plasmid that encodes for sgRNA comprising SEQ ID NO: 5291, which targets the P23H mutant RHO gene, 59.6% of the P23H mutant RHO loci were successfully edited (FIG. 12, sample 1).

Sequence analysis from a second experiment revealed that for cells transfected with a plasmid that encodes for a sgRNA comprising SEQ ID NO: 5321, which targets the P23H mutant RHO gene, 42.1% of the P23H mutant RHO loci were successfully edited (FIG. 12, sample 2).

Example 16

In Vivo Testing

Two different RHO knock-in mouse lines were used to further demonstrate the capability of a Cas9-sgRNA system to specifically cut a P23H mutant allele within the human RHO gene, introduce a frameshift mutation into the P23H mutant RHO allele, and suppress expression of the P23H mutant RHO allele in an in vivo system.

In a first RHO knock-in mouse line, referred to as: hRHO-GFP mice, both mouse copies of the RHO gene were substituted with wild-type human RHO genes (including all introns and exons) and fused to green fluorescent protein (GFP) creating a homozygote mouse with two hRHO-GFP alleles and no remaining mouse RHO alleles.

In a second RHO knock-in mouse line, referred to as: P23H-hRHO-RFP mice, one mouse copy of the RHO gene was substituted with a P23H mutant human RHO gene (including all introns and exons) and fused to red fluorescent protein (RFP) creating a heterozygote mouse with one P23H-hRHO-RFP mutant allele and one mouse RHO allele.

Both RHO knock-in mouse lines were obtained from the laboratory of Dr. Theodore Wensel where the mouse lines were generated at Baylor College of Medicine (Houston, Tex.; United States).

Fusion of a fluorescent tag (e.g., GFP or RFP) to the RHO protein in these mouse lines allows for the monitoring of protein distribution within cells, and monitoring of levels of RHO protein expression. Fluorescent tagging of the two human alleles using distinct fluorescent proteins also allows for discrimination between the wild-type RHO protein and the P23H mutant RHO protein, whose native sequences only differ by one amino acid and are indistinguishable from one another when using antibodies to detect the native protein.

A dual vector system comprising Non-SIN AAV-SaCas9 (FIG. 5C) and pSIA010 (FIG. 5D) was used for the in vivo experiments. The Non-SIN AAV-SaCas9 that was used is identical to the Non-SIN AAV-SaCas9 depicted in FIG. 5C except that the present vector comprises a photoreceptor cell specific human Rhodopsin Kinase promoter to drive SaCas9 expression (instead of a sEF1α promoter). pSIA010 encodes an sgRNA, which is driven by a U6 promoter (a RNA polymerase III promoter). The sgRNA comprises SEQ ID NO: 5290, which targets the P23H mutation within the human RHO gene. The pSIA010 that was used is identical to the pSIA010 depicted in FIG. 5D except that the present vector encodes a blue fluorescent protein (BFP), driven by a cytomegalovirus (CMV) promoter (instead of an EGFP driven by CMV promoter). The BFP provides a fluorescent label that allows for separation of cells that were transduced by pSIA010 from cells that were not transduced. Both AAV vectors (Non-SIN AAV-SaCas9 and pSIA010) were serotype AAV5, which is an AAV serotype suitable for transducing photoreceptor cells in vivo.

Non-SIN AAV-SaCas9 and pSIA010 were delivered into P23H-hRHO-RFP mice (FIG. 13, sample 1) and control hRHO-GFP mice (FIG. 13, sample 2) at postnatal day 14 to 29 by sub-retinal injection using a 1:1 ratio for the SaCas9-encoding vector (Non-SIN AAV-SaCas9) and the sgRNA-encoding vector (pSIA010). Each vector had a dosage of either $2.5 \times 10^9$ or $5 \times 10^9$ vector genome particles. Three or eight weeks after transduction, retinas were dissected and digested with a mixture of proteolytic enzymes (pronase) to achieve a single cell suspension, followed by fluorescence-activated cell sorting (FACS) to sort transduced and non-transduced cells.

Genomic DNA was isolated from transduced cells for subsequent quantitative analysis of the SaCas9/sgRNA-induced editing using next generation deep sequencing. For the sequencing, primers that specifically amplify only human RHO sequences were used. As a control for primer specificity, PCR using the sequencing primers generated a 200 bp band for genomic DNA samples comprising human RHO sequences. The 200 bp band was not generated for genomic DNA samples comprising mouse RHO sequences, but not human RHO sequences.

Figure 13:
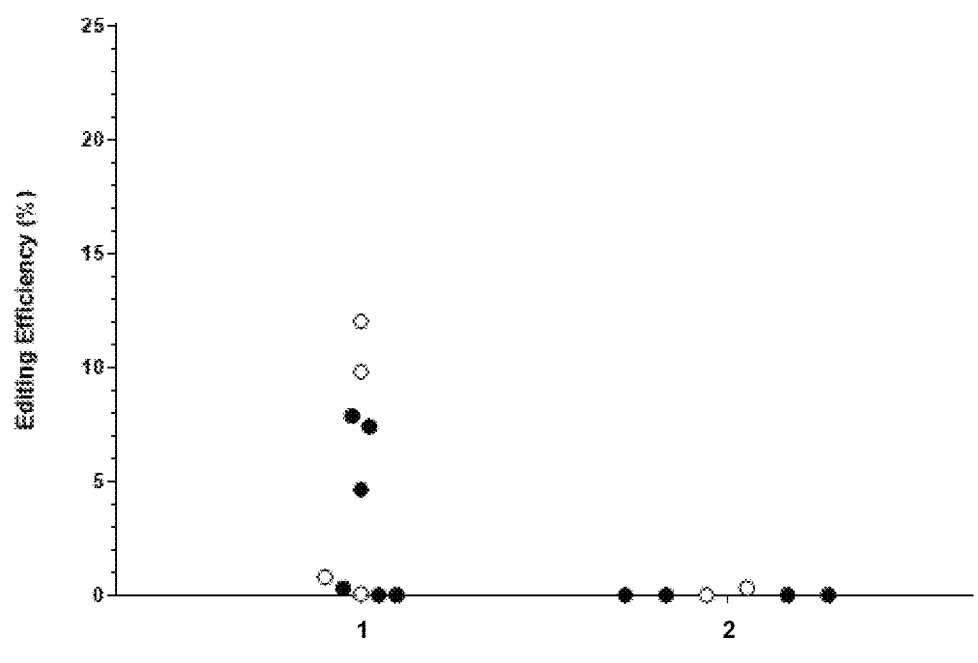
FIG. 13 shows an in vivo experiment in which Non-SIN AAV-SaCas9 and pSIA010 were delivered into P23H-hRHO-RFP mice and control hRHO-GFP mice via subretinal injection.

Allele-specific, on-target editing of the P23H mutant human RHO allele was observed when using the pSIA010 AAV vector that encodes a sgRNA comprising SEQ ID NO: 5290 (FIG. 13, sample 1; and Table 9, rows 1-10). The sgRNA comprising SEQ ID NO: 5290 has full complementarity to the P23H mutant human RHO allele, and one mismatch to the wild-type human RHO allele.

Minimal off-target editing of the wild-type RHO gene was observed when using the same pSIA010 AAV vector that encodes a sgRNA comprising SEQ ID NO: 5290 (FIG. 13, sample 2; and Table 9, rows 11-16).

TABLE 9

| Mouse genotype | # Weeks between injection and analysis | AAV vector encoding SaCas9 | pSIA010 encoding a sgRNA comprising SEQ ID NO: | Editing Efficiency (percent of transduced cells edited) |
| --- | --- | --- | --- | --- |
| hP23H-RHO-RFP/mRho | 3 | Non-SIN AAV SaCas9 | 5290 | 7.4 |
| hP23H-RHO-RFP/mRho | 3 | Non-SIN AAV SaCas9 | 5290 | 7.86 |
| hP23H-RHO-RFP/mRho | 3 | Non-SIN AAV SaCas9 | 5290 | 0.00 |
| hP23H-RHO-RFP/mRho | 3 | Non-SIN AAV SaCas9 | 5290 | 0.3 |
| hP23H-RHO-RFP/mRho | 3 | Non-SIN AAV SaCas9 | 5290 | 0.00 |
| hP23H-RHO-RFP/mRho | 3 | Non-SIN AAV SaCas9 | 5290 | 4.64 |
| hP23H-RHO-RFP/mRho | 8 | Non-SIN AAV SaCas9 | 5290 | 0.06 |
| hP23H-RHO-RFP/mRho | 8 | Non-SIN AAV SaCas9 | 5290 | 9.81 |
| hP23H-RHO-RFP/mRho | 8 | Non-SIN AAV SaCas9 | 5290 | 12.03 |
| hP23H-RHO-RFP/mRho | 8 | Non-SIN AAV SaCas9 | 5290 | 0.79 |
| hRHO-GFP/hRHO-GFP | 3 | Non-SIN AAV SaCas9 | 5290 | 0.00 |
| hRHO-GFP/hRHO-GFP | 3 | Non-SIN AAV SaCas9 | 5290 | 0.00 |
| hRHO-GFP/hRHO-GFP | 3 | Non-SIN AAV SaCas9 | 5290 | 0.00 |
| hRHO-GFP/hRHO-GFP | 3 | Non-SIN AAV SaCas9 | 5290 | 0.00 |
| hRHO-GFP/hRHO-GFP | 8 | Non-SIN AAV SaCas9 | 5290 | 0.00 |
| hRHO-GFP/hRHO-GFP | 8 | Non-SIN AAV SaCas9 | 5290 | 0.31 |

NOTE REGARDING ILLUSTRATIVE EXAMPLES

While the present disclosure provides descriptions of various specific aspects for the purpose of illustrating various examples of the present disclosure and/or its potential applications, it is understood that variations and modifications will occur to those skilled in the art. Accordingly, the invention or inventions described herein should be understood to be at least as broad as they are claimed, and not as more narrowly defined by particular illustrative examples provided herein.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10662425B2). An electronic copy of the "Sequence Listing" will also be available from the USPTO upon request and payment of the fee set forth in 37 CFR 1.19(b)(3).

What is claimed is:

1. A self-inactivating CRISPR-Cas system comprising:
   a first segment comprising a nucleotide sequence that encodes Cas9;
   a second segment comprising a nucleotide sequence that encodes a guide RNA (gRNA) or a single-molecule guide RNA (sgRNA) wherein the gRNA or the sgRNA comprises SEQ ID NO: 5290 or 5291; and
   one or more third segments comprising a self-inactivating (SIN) site, wherein the SIN site is:
   a 5' SIN site located upstream of the nucleotide sequence that encodes Cas9 and downstream of a SV40 nuclear localization signal (NLS); or
   a 3' SIN site located within a naturally occurring or chimeric inserted intron located within the nucleotide sequence that encodes Cas9;
   wherein the gRNA or sgRNA is complementary to the SIN site;
   wherein the gRNA or sgRNA is complementary to a genomic target sequence.

2. The self-inactivating CRISPR-Cas system of claim 1, wherein the Cas9 is *Staphylococcus aureus* Cas9 (SaCas9).

3. The self-inactivating CRISPR-Cas system of claim 1, wherein the 5' SIN site comprises SEQ ID NO: 5300 or 5301.

4. The self-inactivating CRISPR-Cas system of claim 1, wherein the 3' SIN site comprises SEQ ID NO: 5280 or 5281.

5. The self-inactivating CRISPR-Cas system of claim 1, where the SIN site comprises a protospacer adjacent motif (PAM).

6. The self-inactivating CRISPR-Cas system of claim 5, wherein the PAM is NNGRRT.

7. The self-inactivating CRISPR-Cas system of claim 1, wherein the genomic target sequence is a P23H mutation in a rhodopsin (RHO) gene.

8. The self-inactivating CRISPR-Cas system of claim 1, wherein the first segment comprising a nucleotide sequence that encodes Cas9, further comprises a start codon, a stop codon, and a poly(A) termination site.

9. The self-inactivating CRISPR-Cas system of claim 1, wherein the first segment and the third segment are provided together in a first vector and the second segment is provided in a second vector.

10. The self-inactivating CRISPR-Cas system of claim 1, wherein the first segment, second segment, and third segment are provided together in a vector.

11. The self-inactivating CRISPR-Cas system of claim 9, wherein the first vector comprises SEQ ID NO: 5341 or 5342.

12. The self-inactivating CRISPR-Cas system of claim 9, wherein the second vector comprises SEQ ID NO: 5339 or 5340.

13. The self-inactivating CRISPR-Cas system of claim 1, wherein the third segment is less than 100 nucleotides in length.

14. The self-inactivating CRISPR-Cas system of claim 1, wherein the gRNA or the sgRNA is complementary to the nucleotide sequence of the SIN site except for in at least one location.

15. The self-inactivating CRISPR-Cas system of claim 1, wherein a nucleic acid sequence encoding a promoter is operably linked to the first segment.

16. The self-inactivating CRISPR-Cas system of claim 15, wherein the promoter is a spatially-restricted promoter, bidirectional promoter, or an inducible promoter.

17. The self-inactivating CRISPR-Cas system of claim 16, wherein the spatially-restricted promoter is selected from the group consisting of: any tissue or cell type specific promoter, a hepatocyte-specific promoter, a neuron-specific promoter, an adipocyte-specific promoter, a cardiomyocyte-specific promoter, a skeletal muscle-specific promoter, lung progenitor cell specific promoter, a photoreceptor-specific promoter, and a retinal pigment epithelial (RPE) selective promoter.

18. The self-inactivating CRISPR-Cas system of claim 9, wherein the first vector and the second vector are adeno-associated virus (AAV) vectors.

19. The self-inactivating CRISPR-Cas system of claim 18, wherein the AAV vectors are AAV5 serotype capsid vectors.

20. The self-inactivating CRISPR-Cas system of claim 10, wherein the vector is an AAV vector.

21. The self-inactivating CRISPR-Cas system of claim 20, wherein the AAV vector is an AAV5 serotype capsid vector.

22. A kit for treating a patient with autosomal dominant Retinitis Pigmentosa in vivo, the kit comprising:
   the self-inactivating CRISPR-Cas system of claim 1; and
   optionally, one or more donor template.

23. A therapeutic for treating a patient with autosomal dominant Retinitis Pigmentosa, the therapeutic comprising the self-inactivating CRISPR-Cas system of claim 1.

24. The self-inactivating CRISPR-Cas system of claim 1, wherein the gRNA or the sgRNA is complementary to the genomic target sequence except for in at least one location.

25. A self-inactivating CRISPR-Cas system comprising:
   a first segment comprising a nucleotide sequence that encodes Cas9;
   a second segment comprising a nucleotide sequence that encodes a gRNA or a sgRNA wherein the gRNA or the sgRNA comprises SEQ ID NO: 5290 or 5291; and
   one or more third segments comprising a SIN site, wherein the SIN site is:
      a 5' SIN site located upstream of the nucleotide sequence that encodes Cas9 and upstream of a SV40 NLS within a 5' UTR; or
      a 3' SIN site located within a naturally occurring or chimeric inserted intron located within the nucleotide sequence that encodes Cas9;
   wherein the gRNA or sgRNA is complementary to the SIN site; wherein the gRNA or sgRNA is complementary to a genomic target sequence.

26. The self-inactivating CRISPR-Cas system of claim 25, wherein the gRNA or the sgRNA is complementary to the nucleotide sequence of the SIN site except for in at least one location.

27. The self-inactivating CRISPR-Cas system of claim 25, wherein the gRNA or the sgRNA is complementary to the genomic target sequence except for in at least one location.

28. A method for editing a P23H mutation within a RHO gene, the method comprising: administering the self-inactivating CRISPR-Cas system of claim 1.

29. A method for treating a patient with a P23H mutation within a RHO gene, the method comprising: administering the self-inactivating CRISPR-Cas system of claim 1.

30. A method of controlling Cas9 expression in a cell comprising: contacting the cell with the self-inactivating CRISPR-Cas system of claim 1.

* * * * *

UNITED STATES PATENT AND TRADEMARK OFFICE
CERTIFICATE OF CORRECTION

PATENT NO. : 10,662,425 B2
APPLICATION NO. : 16/198361
DATED : May 26, 2020
INVENTOR(S) : Albena Kantardzhieva et al.

Page 1 of 1

It is certified that error appears in the above-identified patent and that said Letters Patent is hereby corrected as shown below:

In the Claims

At Column 122, Claim number 19, Line number 54, delete "AAVS" and insert --AAV5--

Signed and Sealed this
Thirtieth Day of June, 2020

Andrei Iancu
*Director of the United States Patent and Trademark Office*